US012766191B2

(12) United States Patent
Nelson et al.

(10) Patent No.: US 12,766,191 B2
(45) Date of Patent: Oct. 20, 2026

(54) PEPTIDE THERAPEUTICS AGAINST SARS-COV-2 SPIKE PROTEIN

(71) Applicant: NantCell, Inc., Culver City, CA (US)

(72) Inventors: Jay Gardner Nelson, Sherman Oaks, CA (US); Oleksandr Buzko, Oak Park, CA (US); Wendy M. Higashide, Rosemead, CA (US); Kayvan Niazi, Agoura Hills, CA (US); Clifford Anders Olson, Long Beach, CA (US); Patrick Soon-Shiong, Los Angeles, CA (US); Shiho Tanaka, Redondo Beach, CA (US)

(73) Assignee: NantCell, Inc., Culver City, CA (US)

( * ) Notice: Subject to any disclaimer, the term of this patent is extended or adjusted under 35 U.S.C. 154(b) by 930 days.

(21) Appl. No.: 17/929,805

(22) Filed: Sep. 6, 2022

(65) Prior Publication Data

US 2023/0218743 A1 Jul. 13, 2023

Related U.S. Application Data

(63) Continuation-in-part of application No. PCT/US2021/021819, filed on Mar. 11, 2021, which is a continuation of application No. 16/880,804, filed on May 21, 2020, now abandoned.

(60) Provisional application No. 63/121,102, filed on Dec. 3, 2020, provisional application No. 63/117,847, filed on Nov. 24, 2020, provisional application No. 63/082,145, filed on Sep. 23, 2020, provisional application No. 63/080,887, filed on Sep. 21, 2020, provisional application No. 63/036,445, filed on Jun. 9, 2020, provisional application No. 63/022,146, filed on May 8, 2020, provisional application No. 63/016,048, filed on Apr. 27, 2020, provisional application No. 63/016,241, filed on Apr. 27, 2020, provisional application No. 62/991,504, filed on Mar. 18, 2020, provisional application No. 62/988,328, filed on Mar. 11, 2020.

(51) Int. Cl.

| | |
|---|---|
| ***A61K 39/42*** | (2006.01) |
| ***A61K 38/20*** | (2006.01) |
| ***A61K 39/215*** | (2006.01) |
| ***C07K 14/005*** | (2006.01) |
| ***C07K 14/165*** | (2006.01) |
| ***C07K 16/104*** | (2026.01) |
| ***C12N 15/86*** | (2006.01) |
| *A61K 39/235* | (2006.01) |
| *C07K 14/81* | (2006.01) |

(52) U.S. Cl.

CPC .......... *A61K 39/42* (2013.01); *A61K 38/2013* (2013.01); *A61K 38/2086* (2013.01); *A61K 39/215* (2013.01); *C07K 14/005* (2013.01); *C07K 14/165* (2013.01); *C07K 16/104* (2026.01); *C12N 15/86* (2013.01); *A61K 39/235* (2013.01); *C07K 14/8103* (2013.01); *C07K 2317/52* (2013.01); *C07K 2317/55* (2013.01); *C07K 2317/76* (2013.01); *C07K 2317/92* (2013.01); *C07K 2319/01* (2013.01); *C07K 2319/06* (2013.01); *C12N 2710/10341* (2013.01); *C12N 2770/20022* (2013.01); *C12N 2770/20034* (2013.01); *C12Y 304/17023* (2013.01)

(58) Field of Classification Search

CPC ................ C07K 14/165; C07K 16/104; C12N 2770/20022; A61K 39/42

See application file for complete search history.

(56) References Cited

U.S. PATENT DOCUMENTS

2012/0288502 A1 11/2012 Diskin et al.

FOREIGN PATENT DOCUMENTS

WO WO-2018140456 A1 8/2018

OTHER PUBLICATIONS

Sela-Culang, I., et al., Oct. 2013, The structural basis of antibody-antigen recognition, Front. Immunol. 4, Article 302, 1-13.*

Xiang, J., et al., 1999, Light-chain framework region residue Tyr71 of chimeric B72.3 antibody plays an important role in influencing the TAG72 antigen binding, Prot. Eng. 12(5):417-421.*

Tiller, K. E., et al., Sep. 2017, Facile affinity maturation of antibody variable domains using natural diversity mutagenesis, Front. Immunol. 8, Article 986, 1-16.*

Yuan, W., and C. R. Parrish, 2000, Comparison of two single-chain antibodies that neutralize canine parvovirus: Analysis of an antibody-combining site and mechanisms of neutralization, Virol. 269:471-480.*

International Search Report from corresponding PCT Application No. PCT/US2021/021819 dated Jun. 21, 2021.

Written Opinion from corresponding PCT Application No. PCT/US2021/021819 dated Jun. 21, 2021.

(Continued)

*Primary Examiner* — Jeffrey S Parkin

(74) *Attorney, Agent, or Firm* — Harness Dickey & Pierce P.L.C.

(57) ABSTRACT

Proteinaceous therapeutics, such as antibodies and fusion proteins, for preventing, reducing the occurrence of, and/or treating a SARS-CoV-2 infection in a subject are provided herein. The methods provided herein include administering to a subject an antigen binding fragments (Fab fragment) or antibody that binds to the SARS-CoV-2 Spike protein, ACE2 decoy peptides that bind to the SARS-CoV-2 Spike protein, and/or a DNA construct encoding an anti-Spike Fab fragment or ACE2 decoy peptide.

24 Claims, 39 Drawing Sheets

Specification includes a Sequence Listing.

(56) References Cited

OTHER PUBLICATIONS

Ng, O.W., et al., "Substitution at Aspartic Acid 1128 in the SARS Coronavirus Spike Glycoprotein Mediates Escape from a S2 Domain-Targeting Neutralizing Monoclonal Antibody," PLOS One, 9(7): e102415 (2014).

Pak, J.E., et al., "Structural Insights into Immune Recognition of the Severe Acute Respiratory Syndrome Coronavirus S Protein Receptor Binding Domain," J. Mol. Biol., 388: 815-823 (2009).

Park, T., et al., "Spike protein binding prediction with neutralizing antibodies of SARS-CoV-2," bioRxi, pp. 1-22 (2020).

Tripp, R.A., et al., "Monoclonal antibodies to SARS-associated coronavirus (SARS-CoV): Identification of neutralizing and antibodies reactive to S, N, M and E viral proteins," Journal of Virological Methods, 128: 21-28 (2005).

Zheng, Z., et al., "Monoclonal antibodies for the S2 subunit of spike of SARS-CoV-1 cross-react with the newly-emerged SARS-CoV-2," Eurosurveillance, 25(28): 19-28 (2020).

Batlle, D., et al., "Soluble angiotensin-converting enzyme 2: a potential approach for coronavirus infection therapy?," Clinical Science, 134: 543-545 (2020).

Jiang, S., et al., "Neutralizing Antibodies against SARS-CoV-2 and Other Human Coronaviruses," Trends in Immunology, 41(5): 355-359 (2020).

Esvelt, K., "Designing virus-specific sACE2 mimics for competitive inhibition of SARS-CoV-2," COVID-19 HPC Consortium, 2020.

* cited by examiner

SEQUENCE LISTING

```
Sequence total quantity: 245
SEQ ID NO: 1            moltype = AA  length = 327
FEATURE                 Location/Qualifiers
REGION                  1..327
                        note = Receptor binding domain of SARS-CoV-2 Spike, fused
                         to anendosomal targeting sequence
source                  1..327
                        mol_type = protein
                        organism = synthetic construct
SEQUENCE: 1
MLLLPFQLLA VLFPGGNSER VQPTESIVRF PNITNLCPFG EVFNATRFAS VYAWNRKRIS  60
NCVADYSVLY NSASFSTFKC YGVSPTKLND LCFTNVYADS FVIRGDEVRQ IAPGQTGKIA  120
DYNYKLPDDF TGCVIAWNSN NLDSKVGGNY NYLYRLFRKS NLKPFERDIS TEIYQAGSTP  180
CNGVEGFNCY FPLQSYGFQP TNGVGYQPYR VVVLSFELLH APATVCGPKK STNLVKNKCV  240
NFNFNGLTGT GVLTESNKKF LPFQQFGRDI ADTTDAVRDP QTLEILDITP CSMLIPIAVG  300
GALAGLVLIV LIAYLIGKKH CSYQDIL                                    327

SEQ ID NO: 2            moltype = AA  length = 516
FEATURE                 Location/Qualifiers
REGION                  1..516
                        note = SARS-CoV-2 N protein, fused to endosomal targeting
                         sequence
source                  1..516
                        mol_type = protein
                        organism = synthetic construct
SEQUENCE: 2
MLLLPFQLLA VLFPGGNSED YKDDDDKGGG SGGGSGGGSG GGSMSDNGPQ NQRNAPRITF  60
GGPSDSTGSN QNGERSGARS KQRRPQGLPN NTASWFTALT QHGKEDLKFP RGQGVPINTN  120
SSPDDQIGYY RRATRRIRGG DGKMKDLSPR WYFYYLGTGP EAGLPYGANK DGIIWVATEG  180
ALNTPKDHIG TRNPANNAAI VLQLPQGTTL PKGFYAEGSR GGSQASSRSS SRSRNSSRNS  240
TPGSSRGTSP ARMAGNGGDA ALALLLLDRL NQLESKMSGK GQQQQGQTVT KKSAAEASKK  300
PRQKRTATKA YNVTQAFGRR GPEQTQGNFG DQELIRQGTD YKHWPQIAQF APSASAFFGM  360
SRIGMEVTPS GTWLTYTGAI KLDDKDPNFK DQVILLNKHI DAYKTFPPTE PKKDKKKKAD  420
ETQALPQRQK KQQTVTLLPA ADLDDFSKQL QQSMSSADST QAGPGPGNLV PMVATVGPGP  480
GMLIPIAVGG ALAGLVLIVL IAYLIGKKHC SYQDIL                          516

SEQ ID NO: 3            moltype = AA  length = 6
FEATURE                 Location/Qualifiers
REGION                  1..6
                        note = Anti-Spike Group 1, CDR-H1
source                  1..6
                        mol_type = protein
                        organism = synthetic construct
SEQUENCE: 3
SSYTMH                                                           6

SEQ ID NO: 4            moltype = AA  length = 10
FEATURE                 Location/Qualifiers
REGION                  1..10
                        note = Anti-Spike Group 1, CDR-H2
source                  1..10
                        mol_type = protein
                        organism = synthetic construct
SEQUENCE: 4
AISGSGGSTY                                                       10

SEQ ID NO: 5            moltype = AA  length = 7
FEATURE                 Location/Qualifiers
REGION                  1..7
                        note = Anti-Spike Group 1, CDR-H3
source                  1..7
                        mol_type = protein
                        organism = synthetic construct
SEQUENCE: 5
DLFDFWG                                                          7

SEQ ID NO: 6            moltype = AA  length = 6
FEATURE                 Location/Qualifiers
REGION                  1..6
                        note = Anti-Spike Group 1, CDR-L3
```

```
source                1..6
                      mol_type = protein
                      organism = synthetic construct
SEQUENCE: 6
DYGFPL                                                                6

SEQ ID NO: 7          moltype = AA  length = 6
FEATURE               Location/Qualifiers
REGION                1..6
                      note = Anti-Spike Group 2, CDR-H1
source                1..6
                      mol_type = protein
                      organism = synthetic construct
SEQUENCE: 7
SNYAMH                                                                6

SEQ ID NO: 8          moltype = AA  length = 10
FEATURE               Location/Qualifiers
REGION                1..10
                      note = Anti-Spike Group 2, CDR-H2
source                1..10
                      mol_type = protein
                      organism = synthetic construct
SEQUENCE: 8
AISGNGGSTG                                                            10

SEQ ID NO: 9          moltype = AA  length = 8
FEATURE               Location/Qualifiers
REGION                1..8
                      note = Anti-Spike Group 2, CDR-H3
source                1..8
                      mol_type = protein
                      organism = synthetic construct
SEQUENCE: 9
DRWYVKNA                                                              8

SEQ ID NO: 10         moltype = AA  length = 6
FEATURE               Location/Qualifiers
REGION                1..6
                      note = Anti-Spike Group 2, CDR-L3
source                1..6
                      mol_type = protein
                      organism = synthetic construct
SEQUENCE: 10
LDGTPF                                                                6

SEQ ID NO: 11         moltype = AA  length = 6
FEATURE               Location/Qualifiers
REGION                1..6
                      note = Anti-Spike Group 3, CDR-H1
source                1..6
                      mol_type = protein
                      organism = synthetic construct
SEQUENCE: 11
SSYAMH                                                                6

SEQ ID NO: 12         moltype = AA  length = 10
FEATURE               Location/Qualifiers
REGION                1..10
                      note = Anti-Spike Group 3, CDR-H2
source                1..10
                      mol_type = protein
                      organism = synthetic construct
SEQUENCE: 12
AIYGNGGSTD                                                            10

SEQ ID NO: 13         moltype = AA  length = 8
FEATURE               Location/Qualifiers
REGION                1..8
                      note = Anti-Spike Group 3, CDR-H3
source                1..8
                      mol_type = protein
                      organism = synthetic construct
SEQUENCE: 13
DRYMLWMA                                                              8

SEQ ID NO: 14         moltype = AA  length = 6
FEATURE               Location/Qualifiers
REGION                1..6
```

```
                        note = Anti-Spike Group 3, CDR-L3
source                  1..6
                        mol_type = protein
                        organism = synthetic construct
SEQUENCE: 14
DTDDPL                                                          6

SEQ ID NO: 15           moltype = AA  length = 6
FEATURE                 Location/Qualifiers
REGION                  1..6
                        note = Anti-Spike Group 4, CDR-H1
source                  1..6
                        mol_type = protein
                        organism = synthetic construct
SEQUENCE: 15
SSYAMS                                                          6

SEQ ID NO: 16           moltype = AA  length = 10
FEATURE                 Location/Qualifiers
REGION                  1..10
                        note = Anti-Spike Group 4, CDR-H2
source                  1..10
                        mol_type = protein
                        organism = synthetic construct
SEQUENCE: 16
IISGSGGSTY                                                      10

SEQ ID NO: 17           moltype = AA  length = 8
FEATURE                 Location/Qualifiers
REGION                  1..8
                        note = Anti-Spike Group 4, CDR-H3
source                  1..8
                        mol_type = protein
                        organism = synthetic construct
SEQUENCE: 17
DLYGLWNA                                                        8

SEQ ID NO: 18           moltype = AA  length = 6
FEATURE                 Location/Qualifiers
REGION                  1..6
                        note = Anti-Spike Group 4, CDR-L3
source                  1..6
                        mol_type = protein
                        organism = synthetic construct
SEQUENCE: 18
DSADPR                                                          6

SEQ ID NO: 19           moltype = AA  length = 6
FEATURE                 Location/Qualifiers
REGION                  1..6
                        note = Anti-Spike Group 5, CDR-H1
source                  1..6
                        mol_type = protein
                        organism = synthetic construct
SEQUENCE: 19
SSYAMS                                                          6

SEQ ID NO: 20           moltype = AA  length = 10
FEATURE                 Location/Qualifiers
REGION                  1..10
                        note = Anti-Spike Group 5, CDR-H2
source                  1..10
                        mol_type = protein
                        organism = synthetic construct
SEQUENCE: 20
AIRGSGGSTY                                                      10

SEQ ID NO: 21           moltype = AA  length = 8
FEATURE                 Location/Qualifiers
REGION                  1..8
                        note = Anti-Spike Group 5, CDR-H3
source                  1..8
                        mol_type = protein
                        organism = synthetic construct
SEQUENCE: 21
DRWCRCIA                                                        8

SEQ ID NO: 22           moltype = AA  length = 6
FEATURE                 Location/Qualifiers
```

```
REGION                  1..6
                        note = Anti-Spike Group 5, CDR-L3
source                  1..6
                        mol_type = protein
                        organism = synthetic construct
SEQUENCE: 22
VAANPY                                                                   6

SEQ ID NO: 23           moltype = AA  length = 6
FEATURE                 Location/Qualifiers
REGION                  1..6
                        note = Anti-Spike Group 6, CDR-H1
source                  1..6
                        mol_type = protein
                        organism = synthetic construct
SEQUENCE: 23
SSYAMS                                                                   6

SEQ ID NO: 24           moltype = AA  length = 10
FEATURE                 Location/Qualifiers
REGION                  1..10
                        note = Anti-Spike Group 6, CDR-H2
source                  1..10
                        mol_type = protein
                        organism = synthetic construct
SEQUENCE: 24
AISGSGGSTN                                                               10

SEQ ID NO: 25           moltype = AA  length = 8
FEATURE                 Location/Qualifiers
REGION                  1..8
                        note = Anti-Spike Group 6, CDR-H3
source                  1..8
                        mol_type = protein
                        organism = synthetic construct
SEQUENCE: 25
DLWGLAFA                                                                 8

SEQ ID NO: 26           moltype = AA  length = 6
FEATURE                 Location/Qualifiers
REGION                  1..6
                        note = Anti-Spike Group 6, CDR-L3
source                  1..6
                        mol_type = protein
                        organism = synthetic construct
SEQUENCE: 26
DSSNPW                                                                   6

SEQ ID NO: 27           moltype = AA  length = 6
FEATURE                 Location/Qualifiers
REGION                  1..6
                        note = Anti-Spike Group 7, CDR-H1
source                  1..6
                        mol_type = protein
                        organism = synthetic construct
SEQUENCE: 27
SSYYMH                                                                   6

SEQ ID NO: 28           moltype = AA  length = 10
FEATURE                 Location/Qualifiers
REGION                  1..10
                        note = Anti-Spike Group 7, CDR-H2
source                  1..10
                        mol_type = protein
                        organism = synthetic construct
SEQUENCE: 28
AISGSGGYTY                                                               10

SEQ ID NO: 29           moltype = AA  length = 9
FEATURE                 Location/Qualifiers
REGION                  1..9
                        note = Anti-Spike Group 7, CDR-H3
source                  1..9
                        mol_type = protein
                        organism = synthetic construct
SEQUENCE: 29
DRDHAYDWG                                                                9

SEQ ID NO: 30           moltype = AA  length = 6
```

```
FEATURE                 Location/Qualifiers
REGION                  1..6
                        note = Anti-Spike Group 7, CDR-L3
source                  1..6
                        mol_type = protein
                        organism = synthetic construct
SEQUENCE: 30
WADWPL                                                                      6

SEQ ID NO: 31           moltype = AA  length = 6
FEATURE                 Location/Qualifiers
REGION                  1..6
                        note = Anti-Spike Group 8, CDR-H1
source                  1..6
                        mol_type = protein
                        organism = synthetic construct
SEQUENCE: 31
SSYAMH                                                                      6

SEQ ID NO: 32           moltype = AA  length = 10
FEATURE                 Location/Qualifiers
REGION                  1..10
                        note = Anti-Spike Group 8, CDR-H2
source                  1..10
                        mol_type = protein
                        organism = synthetic construct
SEQUENCE: 32
AISWSGRSTY                                                                  10

SEQ ID NO: 33           moltype = AA  length = 9
FEATURE                 Location/Qualifiers
REGION                  1..9
                        note = Anti-Spike Group 8, CDR-H3
source                  1..9
                        mol_type = protein
                        organism = synthetic construct
SEQUENCE: 33
DLSSNWGCG                                                                   9

SEQ ID NO: 34           moltype = AA  length = 6
FEATURE                 Location/Qualifiers
REGION                  1..6
                        note = Anti-Spike Group 8, CDR-L3
source                  1..6
                        mol_type = protein
                        organism = synthetic construct
SEQUENCE: 34
SADTPF                                                                      6

SEQ ID NO: 35           moltype = AA  length = 6
FEATURE                 Location/Qualifiers
REGION                  1..6
                        note = Anti-Spike Group 9, CDR-H1
source                  1..6
                        mol_type = protein
                        organism = synthetic construct
SEQUENCE: 35
SSYAMT                                                                      6

SEQ ID NO: 36           moltype = AA  length = 10
FEATURE                 Location/Qualifiers
REGION                  1..10
                        note = Anti-Spike Group 9, CDR-H2
source                  1..10
                        mol_type = protein
                        organism = synthetic construct
SEQUENCE: 36
YISGSGGGTY                                                                  10

SEQ ID NO: 37           moltype = AA  length = 9
FEATURE                 Location/Qualifiers
REGION                  1..9
                        note = Anti-Spike Group 9, CDR-H3
source                  1..9
                        mol_type = protein
                        organism = synthetic construct
SEQUENCE: 37
DRWASGWLA                                                                   9
```

-continued

```
SEQ ID NO: 38           moltype = AA  length = 6
FEATURE                 Location/Qualifiers
REGION                  1..6
                        note = Anti-Spike Group 9, CDR-L3
source                  1..6
                        mol_type = protein
                        organism = synthetic construct
SEQUENCE: 38
AYAYPL                                                                   6

SEQ ID NO: 39           moltype = AA  length = 6
FEATURE                 Location/Qualifiers
REGION                  1..6
                        note = Anti-Spike Group 10, CDR-H1
source                  1..6
                        mol_type = protein
                        organism = synthetic construct
SEQUENCE: 39
SSYYMH                                                                   6

SEQ ID NO: 40           moltype = AA  length = 10
FEATURE                 Location/Qualifiers
REGION                  1..10
                        note = Anti-Spike Group 10, CDR-H2
source                  1..10
                        mol_type = protein
                        organism = synthetic construct
SEQUENCE: 40
AISGSGGYTY                                                               10

SEQ ID NO: 41           moltype = AA  length = 9
FEATURE                 Location/Qualifiers
REGION                  1..9
                        note = Anti-Spike Group 10, CDR-H3
source                  1..9
                        mol_type = protein
                        organism = synthetic construct
SEQUENCE: 41
DLWGSGFFA                                                                9

SEQ ID NO: 42           moltype = AA  length = 6
FEATURE                 Location/Qualifiers
REGION                  1..6
                        note = Anti-Spike Group 10, CDR-L3
source                  1..6
                        mol_type = protein
                        organism = synthetic construct
SEQUENCE: 42
DAGTPL                                                                   6

SEQ ID NO: 43           moltype = AA  length = 6
FEATURE                 Location/Qualifiers
REGION                  1..6
                        note = Anti-Spike Group 11, CDR-H1
source                  1..6
                        mol_type = protein
                        organism = synthetic construct
SEQUENCE: 43
SSYAMS                                                                   6

SEQ ID NO: 44           moltype = AA  length = 10
FEATURE                 Location/Qualifiers
REGION                  1..10
                        note = Anti-Spike Group 11, CDR-H2
source                  1..10
                        mol_type = protein
                        organism = synthetic construct
SEQUENCE: 44
LISGSGGSTY                                                               10

SEQ ID NO: 45           moltype = AA  length = 9
FEATURE                 Location/Qualifiers
REGION                  1..9
                        note = Anti-Spike Group 11, CDR-H3
source                  1..9
                        mol_type = protein
                        organism = synthetic construct
SEQUENCE: 45
DLWGSGFFA                                                                9
```

```
SEQ ID NO: 46          moltype = AA  length = 6
FEATURE                Location/Qualifiers
REGION                 1..6
                       note = Anti-Spike Group 11, CDR-L3
source                 1..6
                       mol_type = protein
                       organism = synthetic construct
SEQUENCE: 46
DAGTPL                                                              6

SEQ ID NO: 47          moltype = AA  length = 6
FEATURE                Location/Qualifiers
REGION                 1..6
                       note = Anti-Spike Group 12, CDR-H1
source                 1..6
                       mol_type = protein
                       organism = synthetic construct
SEQUENCE: 47
SSYAMH                                                              6

SEQ ID NO: 48          moltype = AA  length = 10
FEATURE                Location/Qualifiers
REGION                 1..10
                       note = Anti-Spike Group 12, CDR-H2
source                 1..10
                       mol_type = protein
                       organism = synthetic construct
SEQUENCE: 48
LISGSGGSTD                                                          10

SEQ ID NO: 49          moltype = AA  length = 9
FEATURE                Location/Qualifiers
REGION                 1..9
                       note = Anti-Spike Group 12, CDR-H3
source                 1..9
                       mol_type = protein
                       organism = synthetic construct
SEQUENCE: 49
DLVVPYGPG                                                           9

SEQ ID NO: 50          moltype = AA  length = 6
FEATURE                Location/Qualifiers
REGION                 1..6
                       note = Anti-Spike Group 12, CDR-L3
source                 1..6
                       mol_type = protein
                       organism = synthetic construct
SEQUENCE: 50
STDGPL                                                              6

SEQ ID NO: 51          moltype = AA  length = 6
FEATURE                Location/Qualifiers
REGION                 1..6
                       note = Anti-Spike Group 13, CDR-H1
source                 1..6
                       mol_type = protein
                       organism = synthetic construct
SEQUENCE: 51
SSYAMS                                                              6

SEQ ID NO: 52          moltype = AA  length = 10
FEATURE                Location/Qualifiers
REGION                 1..10
                       note = Anti-Spike Group 13, CDR-H2
source                 1..10
                       mol_type = protein
                       organism = synthetic construct
SEQUENCE: 52
AISGSGGSTS                                                          10

SEQ ID NO: 53          moltype = AA  length = 9
FEATURE                Location/Qualifiers
REGION                 1..9
                       note = Anti-Spike Group 13, CDR-H3
source                 1..9
                       mol_type = protein
                       organism = synthetic construct
SEQUENCE: 53
```

```
DLFMEFMWA                                                          9

SEQ ID NO: 54          moltype = AA  length = 6
FEATURE                Location/Qualifiers
REGION                 1..6
                       note = Anti-Spike Group 13, CDR-L3
source                 1..6
                       mol_type = protein
                       organism = synthetic construct
SEQUENCE: 54
WANLPY                                                             6

SEQ ID NO: 55          moltype = AA  length = 6
FEATURE                Location/Qualifiers
REGION                 1..6
                       note = Anti-Spike Group 14, CDR-H1
source                 1..6
                       mol_type = protein
                       organism = synthetic construct
SEQUENCE: 55
SSYAMT                                                             6

SEQ ID NO: 56          moltype = AA  length = 10
FEATURE                Location/Qualifiers
REGION                 1..10
                       note = Anti-Spike Group 14, CDR-H2
source                 1..10
                       mol_type = protein
                       organism = synthetic construct
SEQUENCE: 56
AISGSGGSTY                                                         10

SEQ ID NO: 57          moltype = AA  length = 10
FEATURE                Location/Qualifiers
REGION                 1..10
                       note = Anti-Spike Group 14, CDR-H3
source                 1..10
                       mol_type = protein
                       organism = synthetic construct
SEQUENCE: 57
DRWWDSLWVG                                                         10

SEQ ID NO: 58          moltype = AA  length = 6
FEATURE                Location/Qualifiers
REGION                 1..6
                       note = Anti-Spike Group 14, CDR-L3
source                 1..6
                       mol_type = protein
                       organism = synthetic construct
SEQUENCE: 58
TDDNPF                                                             6

SEQ ID NO: 59          moltype = AA  length = 6
FEATURE                Location/Qualifiers
REGION                 1..6
                       note = Anti-Spike Group 15, CDR-H1
source                 1..6
                       mol_type = protein
                       organism = synthetic construct
SEQUENCE: 59
SSYAMS                                                             6

SEQ ID NO: 60          moltype = AA  length = 10
FEATURE                Location/Qualifiers
REGION                 1..10
                       note = Anti-Spike Group 15, CDR-H2
source                 1..10
                       mol_type = protein
                       organism = synthetic construct
SEQUENCE: 60
AISNSGGETY                                                         10

SEQ ID NO: 61          moltype = AA  length = 10
FEATURE                Location/Qualifiers
REGION                 1..10
                       note = Anti-Spike Group 15, CDR-H3
source                 1..10
                       mol_type = protein
                       organism = synthetic construct
```

```
SEQUENCE: 61
DLWVENLWWG                                                        10

SEQ ID NO: 62           moltype = AA  length = 6
FEATURE                 Location/Qualifiers
REGION                  1..6
                        note = Anti-Spike Group 15, CDR-L3
source                  1..6
                        mol_type = protein
                        organism = synthetic construct
SEQUENCE: 62
TDDIPF                                                            6

SEQ ID NO: 63           moltype = AA  length = 6
FEATURE                 Location/Qualifiers
REGION                  1..6
                        note = Anti-Spike Group 16, CDR-H1
source                  1..6
                        mol_type = protein
                        organism = synthetic construct
SEQUENCE: 63
SSYTMH                                                            6

SEQ ID NO: 64           moltype = AA  length = 10
FEATURE                 Location/Qualifiers
REGION                  1..10
                        note = Anti-Spike Group 16, CDR-H2
source                  1..10
                        mol_type = protein
                        organism = synthetic construct
SEQUENCE: 64
AISGSGGYTY                                                        10

SEQ ID NO: 65           moltype = AA  length = 10
FEATURE                 Location/Qualifiers
REGION                  1..10
                        note = Anti-Spike Group 16, CDR-H3
source                  1..10
                        mol_type = protein
                        organism = synthetic construct
SEQUENCE: 65
DRDLLWMGWA                                                        10

SEQ ID NO: 66           moltype = AA  length = 6
FEATURE                 Location/Qualifiers
REGION                  1..6
                        note = Anti-Spike Group 16, CDR-L3
source                  1..6
                        mol_type = protein
                        organism = synthetic construct
SEQUENCE: 66
YANWPL                                                            6

SEQ ID NO: 67           moltype = AA  length = 6
FEATURE                 Location/Qualifiers
REGION                  1..6
                        note = Anti-Spike Group 17, CDR-H1
source                  1..6
                        mol_type = protein
                        organism = synthetic construct
SEQUENCE: 67
SSYAMH                                                            6

SEQ ID NO: 68           moltype = AA  length = 10
FEATURE                 Location/Qualifiers
REGION                  1..10
                        note = Anti-Spike Group 17, CDR-H2
source                  1..10
                        mol_type = protein
                        organism = synthetic construct
SEQUENCE: 68
AIWGSGSNTY                                                        10

SEQ ID NO: 69           moltype = AA  length = 11
FEATURE                 Location/Qualifiers
REGION                  1..11
                        note = Anti-Spike Group 17, CDR-H3
source                  1..11
                        mol_type = protein
```

```
                        organism = synthetic construct
SEQUENCE: 69
GRDLAAFTKT A                                                 11

SEQ ID NO: 70           moltype = AA  length = 6
FEATURE                 Location/Qualifiers
REGION                  1..6
                        note = Anti-Spike Group 17, CDR-L3
source                  1..6
                        mol_type = protein
                        organism = synthetic construct
SEQUENCE: 70
HDALPW                                                       6

SEQ ID NO: 71           moltype = AA  length = 6
FEATURE                 Location/Qualifiers
REGION                  1..6
                        note = Anti-Spike Group 18, CDR-H1
source                  1..6
                        mol_type = protein
                        organism = synthetic construct
SEQUENCE: 71
NSYAMH                                                       6

SEQ ID NO: 72           moltype = AA  length = 10
FEATURE                 Location/Qualifiers
REGION                  1..10
                        note = Anti-Spike Group 18, CDR-H2
source                  1..10
                        mol_type = protein
                        organism = synthetic construct
SEQUENCE: 72
AISGSGGRTY                                                   10

SEQ ID NO: 73           moltype = AA  length = 12
FEATURE                 Location/Qualifiers
REGION                  1..12
                        note = Anti-Spike Group 18, CDR-H3
source                  1..12
                        mol_type = protein
                        organism = synthetic construct
SEQUENCE: 73
DLRSSWVFYT LA                                                12

SEQ ID NO: 74           moltype = AA  length = 6
FEATURE                 Location/Qualifiers
REGION                  1..6
                        note = Anti-Spike Group 18, CDR-L3
source                  1..6
                        mol_type = protein
                        organism = synthetic construct
SEQUENCE: 74
GYTIPL                                                       6

SEQ ID NO: 75           moltype = AA  length = 6
FEATURE                 Location/Qualifiers
REGION                  1..6
                        note = Anti-Spike Group 19, CDR-H1
source                  1..6
                        mol_type = protein
                        organism = synthetic construct
SEQUENCE: 75
SNYAMH                                                       6

SEQ ID NO: 76           moltype = AA  length = 10
FEATURE                 Location/Qualifiers
REGION                  1..10
                        note = Anti-Spike Group 19, CDR-H2
source                  1..10
                        mol_type = protein
                        organism = synthetic construct
SEQUENCE: 76
AISGSGGSTY                                                   10

SEQ ID NO: 77           moltype = AA  length = 13
FEATURE                 Location/Qualifiers
REGION                  1..13
                        note = Anti-Spike Group 19, CDR-H3
source                  1..13
```

```
                        mol_type = protein
                        organism = synthetic construct
SEQUENCE: 77
DLSFWLTYHL ASA                                                    13

SEQ ID NO: 78           moltype = AA  length = 6
FEATURE                 Location/Qualifiers
REGION                  1..6
                        note = Anti-Spike Group 19, CDR-L3
source                  1..6
                        mol_type = protein
                        organism = synthetic construct
SEQUENCE: 78
SYSDPL                                                            6

SEQ ID NO: 79           moltype = AA  length = 6
FEATURE                 Location/Qualifiers
REGION                  1..6
                        note = Anti-Spike Group 20, CDR-H1
source                  1..6
                        mol_type = protein
                        organism = synthetic construct
SEQUENCE: 79
SSYAMH                                                            6

SEQ ID NO: 80           moltype = AA  length = 10
FEATURE                 Location/Qualifiers
REGION                  1..10
                        note = Anti-Spike Group 20, CDR-H2
source                  1..10
                        mol_type = protein
                        organism = synthetic construct
SEQUENCE: 80
AIDGNGGYTY                                                        10

SEQ ID NO: 81           moltype = AA  length = 13
FEATURE                 Location/Qualifiers
REGION                  1..13
                        note = Anti-Spike Group 20, CDR-H3
source                  1..13
                        mol_type = protein
                        organism = synthetic construct
SEQUENCE: 81
GRVSASWYGA DVG                                                    13

SEQ ID NO: 82           moltype = AA  length = 6
FEATURE                 Location/Qualifiers
REGION                  1..6
                        note = Anti-Spike Group 20, CDR-L3
source                  1..6
                        mol_type = protein
                        organism = synthetic construct
SEQUENCE: 82
SYGIPL                                                            6

SEQ ID NO: 83           moltype = AA  length = 6
FEATURE                 Location/Qualifiers
REGION                  1..6
                        note = Anti-RBD Group 1, CDR-H1
source                  1..6
                        mol_type = protein
                        organism = synthetic construct
SEQUENCE: 83
NSYAMH                                                            6

SEQ ID NO: 84           moltype = AA  length = 10
FEATURE                 Location/Qualifiers
REGION                  1..10
                        note = Anti-RBD Group 1, CDR-H2
source                  1..10
                        mol_type = protein
                        organism = synthetic construct
SEQUENCE: 84
AISGNGGSTY                                                        10

SEQ ID NO: 85           moltype = AA  length = 8
FEATURE                 Location/Qualifiers
REGION                  1..8
                        note = Anti-RBD Group 1, CDR-H3
```

```
source                  1..8
                        mol_type = protein
                        organism = synthetic construct
SEQUENCE: 85
DRCFAIWG                                                                     8

SEQ ID NO: 86           moltype = AA  length = 6
FEATURE                 Location/Qualifiers
REGION                  1..6
                        note = Anti-RBD Group 1, CDR-L3
source                  1..6
                        mol_type = protein
                        organism = synthetic construct
SEQUENCE: 86
YDDHPF                                                                       6

SEQ ID NO: 87           moltype = AA  length = 6
FEATURE                 Location/Qualifiers
REGION                  1..6
                        note = Anti-RBD Group 2, CDR-H1
source                  1..6
                        mol_type = protein
                        organism = synthetic construct
SEQUENCE: 87
SSYAMN                                                                       6

SEQ ID NO: 88           moltype = AA  length = 10
FEATURE                 Location/Qualifiers
REGION                  1..10
                        note = Anti-RBD Group 2, CDR-H2
source                  1..10
                        mol_type = protein
                        organism = synthetic construct
SEQUENCE: 88
AISGSGGSTY                                                                   10

SEQ ID NO: 89           moltype = AA  length = 8
FEATURE                 Location/Qualifiers
REGION                  1..8
                        note = Anti-RBD Group 2, CDR-H3
source                  1..8
                        mol_type = protein
                        organism = synthetic construct
SEQUENCE: 89
GRVWVWVA                                                                     8

SEQ ID NO: 90           moltype = AA  length = 6
FEATURE                 Location/Qualifiers
REGION                  1..6
                        note = Anti-RBD Group 2, CDR-L3
source                  1..6
                        mol_type = protein
                        organism = synthetic construct
SEQUENCE: 90
WDALPR                                                                       6

SEQ ID NO: 91           moltype = AA  length = 6
FEATURE                 Location/Qualifiers
REGION                  1..6
                        note = Anti-RBD Group 3, CDR-H1
source                  1..6
                        mol_type = protein
                        organism = synthetic construct
SEQUENCE: 91
GSYAMH                                                                       6

SEQ ID NO: 92           moltype = AA  length = 10
FEATURE                 Location/Qualifiers
REGION                  1..10
                        note = Anti-RBD Group 3, CDR-H2
source                  1..10
                        mol_type = protein
                        organism = synthetic construct
SEQUENCE: 92
GISGSGGYTY                                                                   10

SEQ ID NO: 93           moltype = AA  length = 8
FEATURE                 Location/Qualifiers
REGION                  1..8
```

```
                        note = Anti-RBD Group 3, CDR-H3
source                  1..8
                        mol_type = protein
                        organism = synthetic construct
SEQUENCE: 93
DRLNMFLA                                                        8

SEQ ID NO: 94           moltype = AA  length = 6
FEATURE                 Location/Qualifiers
REGION                  1..6
                        note = Anti-RBD Group 3, CDR-L3
source                  1..6
                        mol_type = protein
                        organism = synthetic construct
SEQUENCE: 94
DAGTPL                                                          6

SEQ ID NO: 95           moltype = AA  length = 6
FEATURE                 Location/Qualifiers
REGION                  1..6
                        note = Anti-RBD Group 4, CDR-H1
source                  1..6
                        mol_type = protein
                        organism = synthetic construct
SEQUENCE: 95
SSYAMN                                                          6

SEQ ID NO: 96           moltype = AA  length = 10
FEATURE                 Location/Qualifiers
REGION                  1..10
                        note = Anti-RBD Group 4, CDR-H2
source                  1..10
                        mol_type = protein
                        organism = synthetic construct
SEQUENCE: 96
AISGGGGNTY                                                      10

SEQ ID NO: 97           moltype = AA  length = 8
FEATURE                 Location/Qualifiers
REGION                  1..8
                        note = Anti-RBD Group 4, CDR-H3
source                  1..8
                        mol_type = protein
                        organism = synthetic construct
SEQUENCE: 97
DLRCRPGA                                                        8

SEQ ID NO: 98           moltype = AA  length = 6
FEATURE                 Location/Qualifiers
REGION                  1..6
                        note = Anti-RBD Group 4, CDR-L3
source                  1..6
                        mol_type = protein
                        organism = synthetic construct
SEQUENCE: 98
LYSDPY                                                          6

SEQ ID NO: 99           moltype = AA  length = 6
FEATURE                 Location/Qualifiers
REGION                  1..6
                        note = Anti-RBD Group 5, CDR-H1
source                  1..6
                        mol_type = protein
                        organism = synthetic construct
SEQUENCE: 99
SSYAMS                                                          6

SEQ ID NO: 100          moltype = AA  length = 10
FEATURE                 Location/Qualifiers
REGION                  1..10
                        note = Anti-RBD Group 5, CDR-H2
source                  1..10
                        mol_type = protein
                        organism = synthetic construct
SEQUENCE: 100
LISGSGGSTY                                                      10

SEQ ID NO: 101          moltype = AA  length = 9
FEATURE                 Location/Qualifiers
```

```
REGION                1..9
                      note = Anti-RBD Group 5, CDR-H3
source                1..9
                      mol_type = protein
                      organism = synthetic construct
SEQUENCE: 101
DLWGSGFFA                                                                   9

SEQ ID NO: 102        moltype = AA  length = 6
FEATURE               Location/Qualifiers
REGION                1..6
                      note = Anti-RBD Group 5, CDR-L3
source                1..6
                      mol_type = protein
                      organism = synthetic construct
SEQUENCE: 102
DAGTPL                                                                      6

SEQ ID NO: 103        moltype = AA  length = 6
FEATURE               Location/Qualifiers
REGION                1..6
                      note = Anti-RBD Group 6, CDR-H1
source                1..6
                      mol_type = protein
                      organism = synthetic construct
SEQUENCE: 103
SAYAMH                                                                      6

SEQ ID NO: 104        moltype = AA  length = 10
FEATURE               Location/Qualifiers
REGION                1..10
                      note = Anti-RBD Group 6, CDR-H2
source                1..10
                      mol_type = protein
                      organism = synthetic construct
SEQUENCE: 104
AIWGSGGSTY                                                                  10

SEQ ID NO: 105        moltype = AA  length = 9
FEATURE               Location/Qualifiers
REGION                1..9
                      note = Anti-RBD Group 6, CDR-H3
source                1..9
                      mol_type = protein
                      organism = synthetic construct
SEQUENCE: 105
DLWMAMWFG                                                                   9

SEQ ID NO: 106        moltype = AA  length = 6
FEATURE               Location/Qualifiers
REGION                1..6
                      note = Anti-RBD Group 6, CDR-L3
source                1..6
                      mol_type = protein
                      organism = synthetic construct
SEQUENCE: 106
RSTYPL                                                                      6

SEQ ID NO: 107        moltype = AA  length = 6
FEATURE               Location/Qualifiers
REGION                1..6
                      note = Anti-RBD Group 7, CDR-H1
source                1..6
                      mol_type = protein
                      organism = synthetic construct
SEQUENCE: 107
SNYAMH                                                                      6

SEQ ID NO: 108        moltype = AA  length = 10
FEATURE               Location/Qualifiers
REGION                1..10
                      note = Anti-RBD Group 7, CDR-H2
source                1..10
                      mol_type = protein
                      organism = synthetic construct
SEQUENCE: 108
AISWSGGSTY                                                                  10

SEQ ID NO: 109        moltype = AA  length = 9
```

```
FEATURE                 Location/Qualifiers
REGION                  1..9
                        note = Anti-RBD Group 7, CDR-H3
source                  1..9
                        mol_type = protein
                        organism = synthetic construct
SEQUENCE: 109
DRFYIVLLG                                                                9

SEQ ID NO: 110          moltype = AA  length = 6
FEATURE                 Location/Qualifiers
REGION                  1..6
                        note = Anti-RBD Group 7, CDR-L3
source                  1..6
                        mol_type = protein
                        organism = synthetic construct
SEQUENCE: 110
RDAGPF                                                                   6

SEQ ID NO: 111          moltype = AA  length = 6
FEATURE                 Location/Qualifiers
REGION                  1..6
                        note = Anti-RBD Group 8, CDR-H1
source                  1..6
                        mol_type = protein
                        organism = synthetic construct
SEQUENCE: 111
SSYAMS                                                                   6

SEQ ID NO: 112          moltype = AA  length = 10
FEATURE                 Location/Qualifiers
REGION                  1..10
                        note = Anti-RBD Group 8, CDR-H2
source                  1..10
                        mol_type = protein
                        organism = synthetic construct
SEQUENCE: 112
AISSSGGSTN                                                               10

SEQ ID NO: 113          moltype = AA  length = 10
FEATURE                 Location/Qualifiers
REGION                  1..10
                        note = Anti-RBD Group 8, CDR-H3
source                  1..10
                        mol_type = protein
                        organism = synthetic construct
SEQUENCE: 113
DLWSERVWFG                                                               10

SEQ ID NO: 114          moltype = AA  length = 6
FEATURE                 Location/Qualifiers
REGION                  1..6
                        note = Anti-RBD Group 8, CDR-L3
source                  1..6
                        mol_type = protein
                        organism = synthetic construct
SEQUENCE: 114
VDNAPY                                                                   6

SEQ ID NO: 115          moltype = AA  length = 6
FEATURE                 Location/Qualifiers
REGION                  1..6
                        note = Anti-RBD Group 9, CDR-H1
source                  1..6
                        mol_type = protein
                        organism = synthetic construct
SEQUENCE: 115
SSYAMH                                                                   6

SEQ ID NO: 116          moltype = AA  length = 10
FEATURE                 Location/Qualifiers
REGION                  1..10
                        note = Anti-RBD Group 9, CDR-H2
source                  1..10
                        mol_type = protein
                        organism = synthetic construct
SEQUENCE: 116
AIWGSGSNTY                                                               10
```

-continued

```
SEQ ID NO: 117          moltype = AA  length = 11
FEATURE                 Location/Qualifiers
REGION                  1..11
                        note = Anti-RBD Group 9, CDR-H3
source                  1..11
                        mol_type = protein
                        organism = synthetic construct
SEQUENCE: 117
GRDLAAFTKT A                                                              11

SEQ ID NO: 118          moltype = AA  length = 6
FEATURE                 Location/Qualifiers
REGION                  1..6
                        note = Anti-RBD Group 9, CDR-L3
source                  1..6
                        mol_type = protein
                        organism = synthetic construct
SEQUENCE: 118
HDALPW                                                                    6

SEQ ID NO: 119          moltype = AA  length = 6
FEATURE                 Location/Qualifiers
REGION                  1..6
                        note = Anti-RBD Group 10, CDR-H1
source                  1..6
                        mol_type = protein
                        organism = synthetic construct
SEQUENCE: 119
SSYAMN                                                                    6

SEQ ID NO: 120          moltype = AA  length = 10
FEATURE                 Location/Qualifiers
REGION                  1..10
                        note = Anti-RBD Group 10, CDR-H2
source                  1..10
                        mol_type = protein
                        organism = synthetic construct
SEQUENCE: 120
AISGSGGSTY                                                                10

SEQ ID NO: 121          moltype = AA  length = 12
FEATURE                 Location/Qualifiers
REGION                  1..12
                        note = Anti-RBD Group 10, CDR-H3
source                  1..12
                        mol_type = protein
                        organism = synthetic construct
SEQUENCE: 121
DLLWTSKAVW WG                                                             12

SEQ ID NO: 122          moltype = AA  length = 6
FEATURE                 Location/Qualifiers
REGION                  1..6
                        note = Anti-RBD Group 10, CDR-L3
source                  1..6
                        mol_type = protein
                        organism = synthetic construct
SEQUENCE: 122
SATMPW                                                                    6

SEQ ID NO: 123          moltype = AA  length = 6
FEATURE                 Location/Qualifiers
REGION                  1..6
                        note = Anti-RBD Group 11, CDR-H1
source                  1..6
                        mol_type = protein
                        organism = synthetic construct
SEQUENCE: 123
SSYAMT                                                                    6

SEQ ID NO: 124          moltype = AA  length = 10
FEATURE                 Location/Qualifiers
REGION                  1..10
                        note = Anti-RBD Group 11, CDR-H2
source                  1..10
                        mol_type = protein
                        organism = synthetic construct
SEQUENCE: 124
AIDGNGGSTS                                                                10
```

```
SEQ ID NO: 125          moltype = AA  length = 12
FEATURE                 Location/Qualifiers
REGION                  1..12
                        note = Anti-RBD Group 11, CDR-H3
source                  1..12
                        mol_type = protein
                        organism = synthetic construct
SEQUENCE: 125
DLGFMTIVAF AA                                                     12

SEQ ID NO: 126          moltype = AA  length = 6
FEATURE                 Location/Qualifiers
REGION                  1..6
                        note = Anti-RBD Group 11, CDR-L3
source                  1..6
                        mol_type = protein
                        organism = synthetic construct
SEQUENCE: 126
SYDRPW                                                            6

SEQ ID NO: 127          moltype = AA  length = 29
FEATURE                 Location/Qualifiers
source                  1..29
                        mol_type = protein
                        organism = Homo sapiens
SEQUENCE: 127
EVQLVESGGG LVQPGGSLRL SCAASGFTF                                   29

SEQ ID NO: 128          moltype = AA  length = 14
FEATURE                 Location/Qualifiers
source                  1..14
                        mol_type = protein
                        organism = Homo sapiens
SEQUENCE: 128
WVRQAPGKGL EWVS                                                   14

SEQ ID NO: 129          moltype = AA  length = 39
FEATURE                 Location/Qualifiers
source                  1..39
                        mol_type = protein
                        organism = Homo sapiens
SEQUENCE: 129
YADSVKGRFT ISRDNSKNTL YLQMNSLRAE DTAVYYCAR                        39

SEQ ID NO: 130          moltype = AA  length = 14
FEATURE                 Location/Qualifiers
source                  1..14
                        mol_type = protein
                        organism = Homo sapiens
SEQUENCE: 130
FDVWGQGTLV TVSS                                                   14

SEQ ID NO: 131          moltype = AA  length = 90
FEATURE                 Location/Qualifiers
source                  1..90
                        mol_type = protein
                        organism = Homo sapiens
SEQUENCE: 131
DIQMTQSPSS LSASVGDRVT ITCQASQDIS NYLNWYQQKP GKAPKLLIYD ASNLETGVPS  60
RFSGSGSGTD FTFTISSLQP EDIATYYCQQ                                  90

SEQ ID NO: 132          moltype = AA  length = 11
FEATURE                 Location/Qualifiers
source                  1..11
                        mol_type = protein
                        organism = Homo sapiens
SEQUENCE: 132
TFGQGTKVEI K                                                      11

SEQ ID NO: 133          moltype = AA  length = 419
FEATURE                 Location/Qualifiers
source                  1..419
                        mol_type = protein
                        organism = SARS CoV
SEQUENCE: 133
MSDNGPQNQR NAPRITFGGP SDSTGSNQNG ERSGARSKQR RPQGLPNNTA SWFTALTQHG  60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
```

-continued

```
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 134          moltype = AA  length = 422
FEATURE                 Location/Qualifiers
source                  1..422
                        mol_type = protein
                        organism = SARS CoV-2
SEQUENCE: 134
MSDNGPQSNQ RSAPRITFGG PTDSTDNNQN GGRNGARPKQ RRPQGLPNNT ASWFTALTQH  60
GKEELRFPRG QGVPINTNSG PDDQIGYYRR ATRRVRGGDG KMKELSPRWY FYYLGTGPEA  120
SLPYGANKEG IVWVATEGAL NTPKDHIGTR NPNNNAATVL QLPQGTTLPK GFYAEGSRGG  180
SQASSRSSSR SRGNSRNSTP GSSRGNSPAR MASGGGETAL ALLLLDRLNQ LESKVSGKGQ  240
QQQGQTVTKK SAAEASKKPR QKRTATKQYN VTQAFGRRGP EQTQGNFGDQ DLIRQGTDYK  300
HWPQIAQFAP SASAFFGMSR IGMEVTPSGT WLTYHGAIKL DDKDPQFKDN VILLNKHIDA  360
YKTFPPTEPK KDKKKKTDEA QPLPQRQKKQ PTVTLLPAAD MDDFSRQLQN SMSGASADST  420
QA                                                                422

SEQ ID NO: 135          moltype = AA  length = 805
FEATURE                 Location/Qualifiers
source                  1..805
                        mol_type = protein
                        organism = Homo sapiens
SEQUENCE: 135
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 136          moltype = AA  length = 805
FEATURE                 Location/Qualifiers
REGION                  1..805
                        note = Q24 mutant ACE2
VARIANT                 24
                        note = not Q
source                  1..805
                        mol_type = protein
                        organism = synthetic construct
SEQUENCE: 136
MSSSSWLLLS LVAVTAAQST IEEXAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 137          moltype = AA  length = 805
FEATURE                 Location/Qualifiers
REGION                  1..805
                        note = T27 mutant ACE2
VARIANT                 27
                        note = not T
source                  1..805
                        mol_type = protein
                        organism = synthetic construct
SEQUENCE: 137
MSSSSWLLLS LVAVTAAQST IEEQAKXFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
```

```
EEYVVLKNEM ARANHYEDYG DYWRGDYEVN GVDGGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                         805

SEQ ID NO: 138         moltype = AA  length = 805
FEATURE                Location/Qualifiers
REGION                 1..805
                       note = D30 mutant ACE2
VARIANT                30
                       note = not D
source                 1..805
                       mol_type = protein
                       organism = synthetic construct
SEQUENCE: 138
MSSSSWLLLS LVAVTAAQST IEEQAKTFLX KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                         805

SEQ ID NO: 139         moltype = AA  length = 805
FEATURE                Location/Qualifiers
REGION                 1..805
                       note = H34 mutant ACE2
VARIANT                34
                       note = not H
source                 1..805
                       mol_type = protein
                       organism = synthetic construct
SEQUENCE: 139
MSSSSWLLLS LVAVTAAQST IEEQAKTFLD KFNXEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                         805

SEQ ID NO: 140         moltype = AA  length = 805
FEATURE                Location/Qualifiers
REGION                 1..805
                       note = E35 mutant ACE2
VARIANT                35
                       note = not E
source                 1..805
                       mol_type = protein
                       organism = synthetic construct
SEQUENCE: 140
MSSSSWLLLS LVAVTAAQST IEEQAKTFLD KFNHXAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
```

```
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 141          moltype = AA  length = 805
FEATURE                 Location/Qualifiers
REGION                  1..805
                        note = D38 mutant ACE2
VARIANT                 38
                        note = not D
source                  1..805
                        mol_type = protein
                        organism = synthetic construct
SEQUENCE: 141
MSSSSWLLLS LVAVTAAQST IEEQAKTFLD KFNHEAEXLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 142          moltype = AA  length = 805
FEATURE                 Location/Qualifiers
REGION                  1..805
                        note = Y41 mutant ACE2
VARIANT                 41
                        note = not Y
source                  1..805
                        mol_type = protein
                        organism = synthetic construct
SEQUENCE: 142
MSSSSWLLLS LVAVTAAQST IEEQAKTFLD KFNHEAEDLF XQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 143          moltype = AA  length = 805
FEATURE                 Location/Qualifiers
REGION                  1..805
                        note = D355 mutant ACE2
VARIANT                 355
                        note = not D
source                  1..805
                        mol_type = protein
                        organism = synthetic construct
SEQUENCE: 143
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGXFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
```

```
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 144          moltype = AA  length = 805
FEATURE                 Location/Qualifiers
REGION                  1..805
                        note = Mutant ACE2
VARIANT                 24
                        note = not Q
VARIANT                 27
                        note = not T
VARIANT                 30
                        note = not D
VARIANT                 34
                        note = not H
VARIANT                 35
                        note = not E
VARIANT                 38
                        note = not D
VARIANT                 41
                        note = not Y
VARIANT                 273
                        note = not R
VARIANT                 345
                        note = not H
VARIANT                 355
                        note = not D
VARIANT                 374
                        note = not H
VARIANT                 378
                        note = not H
VARIANT                 505
                        note = not H
source                  1..805
                        mol_type = protein
                        organism = synthetic construct
SEQUENCE: 144
MSSSSWLLLS LVAVTAAQST IEEXAKXFLX KFNXXAEXLF XQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGXFWTNLYS LTVPFGQKPN IDVTDAMVDQ  300
AWDAQRIFKE AEKFFVSVGL PNMTQGFWEN SMLTDPGNVQ KAVCXPTAWD LGKGXFRILM  360
CTKVTMDDFL TAHXEMGXIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFXVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                        805

SEQ ID NO: 145          moltype = AA  length = 225
FEATURE                 Location/Qualifiers
source                  1..225
                        mol_type = protein
                        organism = Homo sapiens
SEQUENCE: 145
THTCPPCPAP ELLGGPSVFL FPPKPKDTLM ISRTPEVTCV VVDVSHEDPQ VKFNWYVDGV  60
QVHNAKTKPR EQQYNSTYRV VSVLTVLHQN WLDGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPGK                  225

SEQ ID NO: 146          moltype = AA  length = 275
FEATURE                 Location/Qualifiers
source                  1..275
                        mol_type = protein
                        organism = Homo sapiens
SEQUENCE: 146
MDPKQTTLLC LGDFPMPFIS AKSSPVIPLD GSVKIQCQAI REAYLTQLMI IKNSTYREIG  60
RRLKFWNETD PEFVIDHMDA NKAGRYQCQY RIGHYRFRYS DTLELVVTGL YGKPFLSADR  120
GLVLMPGENI SLTCSSAHIP FDRFSLAKEG ELSLPQHQSG EHPANFSLGP VDLNVSGIYR  180
CYGWYNRSPY LWSFPSNALE LVVTDSIHQD YTTQNLIRMA VAGLVLVALL AILVENWHSH  240
TALNKEASAD VAEPSWSQQM CQPGLTFART PSVCK                             275

SEQ ID NO: 147          moltype = AA  length = 594
FEATURE                 Location/Qualifiers
REGION                  1..594
```

```
                        note = D30E ACE2 mutant
source                  1..594
                        mol_type = protein
                        organism = synthetic construct
SEQUENCE: 147
IEEQAKTFLE KFNHEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 148          moltype = AA  length = 594
FEATURE                 Location/Qualifiers
REGION                  1..594
                        note = D38M ACE2 mutant
source                  1..594
                        mol_type = protein
                        organism = synthetic construct
SEQUENCE: 148
IEEQAKTFLD KFNHEAMDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 149          moltype = AA  length = 594
FEATURE                 Location/Qualifiers
REGION                  1..594
                        note = D38W ACE2 mutant
source                  1..594
                        mol_type = protein
                        organism = synthetic construct
SEQUENCE: 149
IEEQAKTFLD KFNHEAWDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 150          moltype = AA  length = 594
FEATURE                 Location/Qualifiers
REGION                  1..594
                        note = D38Y ACE2 mutant
source                  1..594
                        mol_type = protein
                        organism = synthetic construct
SEQUENCE: 150
IEEQAKTFLD KFNHEAYDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 151          moltype = AA  length = 594
FEATURE                 Location/Qualifiers
REGION                  1..594
                        note = H34E ACE2 mutant
source                  1..594
                        mol_type = protein
```

```
                         organism = synthetic construct
SEQUENCE: 151
IEEQAKTFLD KFNEEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 152           moltype = AA  length = 594
FEATURE                  Location/Qualifiers
REGION                   1..594
                         note = H34F ACE2 mutant
source                   1..594
                         mol_type = protein
                         organism = synthetic construct
SEQUENCE: 152
IEEQAKTFLD KFNFEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 153           moltype = AA  length = 594
FEATURE                  Location/Qualifiers
REGION                   1..594
                         note = H34K ACE2 mutant
source                   1..594
                         mol_type = protein
                         organism = synthetic construct
SEQUENCE: 153
IEEQAKTFLD KFNKEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 154           moltype = AA  length = 594
FEATURE                  Location/Qualifiers
REGION                   1..594
                         note = H34M ACE2 mutant
source                   1..594
                         mol_type = protein
                         organism = synthetic construct
SEQUENCE: 154
IEEQAKTFLD KFNMEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 155           moltype = AA  length = 594
FEATURE                  Location/Qualifiers
REGION                   1..594
                         note = H34W ACE2 mutant
source                   1..594
                         mol_type = protein
                         organism = synthetic construct
SEQUENCE: 155
IEEQAKTFLD KFNWEAEDLF YQSSLASWNY NTNITEENVQ NMNNAGDKWS AFLKEQSTLA  60
```

-continued

```
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 156          moltype = AA  length = 594
FEATURE                 Location/Qualifiers
REGION                  1..594
                        note = H34Y ACE2 mutant
source                  1..594
                        mol_type = protein
                        organism = synthetic construct
SEQUENCE: 156
IEEQAKTFLD KFNFEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 157          moltype = AA  length = 594
FEATURE                 Location/Qualifiers
REGION                  1..594
                        note = T27F ACE2 mutant
source                  1..594
                        mol_type = protein
                        organism = synthetic construct
SEQUENCE: 157
IEEQAKFFLD KFNHEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 158          moltype = AA  length = 594
FEATURE                 Location/Qualifiers
REGION                  1..594
                        note = T27W ACE2 mutant
source                  1..594
                        mol_type = protein
                        organism = synthetic construct
SEQUENCE: 158
IEEQAKWFLD KFNHEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 159          moltype = AA  length = 594
FEATURE                 Location/Qualifiers
REGION                  1..594
                        note = T27Y ACE2 mutant
source                  1..594
                        mol_type = protein
                        organism = synthetic construct
SEQUENCE: 159
IEEQAKYFLD KFNHEAEDLF YQSSLASWNY NTNITEENVQ NMNNAGDKWS AFLKEQSTLA  60
QMYPLQEIQN LTVKLQLQAL QQNGSSVLSE DKSKRLNTIL NTMSTIYSTG KVCNPDNPQE  120
CLLLEPGLNE IMANSLDYNE RLWAWESWRS EVGKQLRPLY EEYVVLKNEM ARANHYEDYG  180
DYWRGDYEVN GVDGYDYSRG QLIEDVEHTF EEIKPLYEHL HAYVRAKLMN AYPSYISPIG  240
```

```
CLPAHLLGDM WGRFWTNLYS LTVPFGQKPN IDVTDAMVDQ AWDAQRIFKE AEKFFVSVGL  300
PNMTQGFWEN SMLTDPGNVQ KAVCHPTAWD LGKGDFRILM CTKVTMDDFL TAHHEMGHIQ  360
YDMAYAAQPF LLRNGANEGF HEAVGEIMSL SAATPKHLKS IGLLSPDFQE DNETEINFLL  420
KQALTIVGTL PFTYMLEKWR WMVFKGEIPK DQWMKKWWEM KREIVGVVEP VPHDETYCDP  480
ASLFHVSNDY SFIRYYTRTL YQFQFQEALC QAAKHEGPLH KCDISNSTEA GQKLFNMLRL  540
GKSEPWTLAL ENVVGAKNMN VRPLLNYFEP LFTWLKDQNK NSFVGWSTDW SPYA        594

SEQ ID NO: 160          moltype = AA  length = 595
FEATURE                 Location/Qualifiers
REGION                  1..595
                        note = ACE2 mutant, Ala inserted at #30
source                  1..595
                        mol_type = protein
                        organism = synthetic construct
SEQUENCE: 160
IEEQAKTFLA DKFNHEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 161          moltype = AA  length = 595
FEATURE                 Location/Qualifiers
REGION                  1..595
                        note = ACE2 mutant, Ala inserted at #31
source                  1..595
                        mol_type = protein
                        organism = synthetic construct
SEQUENCE: 161
IEEQAKTFLD AKFNHEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 162          moltype = AA  length = 595
FEATURE                 Location/Qualifiers
REGION                  1..595
                        note = ACE2 mutant, Ala inserted at #32
source                  1..595
                        mol_type = protein
                        organism = synthetic construct
SEQUENCE: 162
IEEQAKTFLD KAFNHEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 163          moltype = AA  length = 595
FEATURE                 Location/Qualifiers
REGION                  1..595
                        note = ACE2 mutant, Ala insertion at #33
source                  1..595
                        mol_type = protein
                        organism = synthetic construct
SEQUENCE: 163
IEEQAKTFLD KFANHEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
```

-continued

```
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 164          moltype = AA  length = 595
FEATURE                 Location/Qualifiers
REGION                  1..595
                        note = ACE2 mutant, Ala insertion at #34
source                  1..595
                        mol_type = protein
                        organism = synthetic construct
SEQUENCE: 164
IEEQAKTFLD KFNAHEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 165          moltype = AA  length = 595
FEATURE                 Location/Qualifiers
REGION                  1..595
                        note = ACE2 mutant, Ala insertion at #35
source                  1..595
                        mol_type = protein
                        organism = synthetic construct
SEQUENCE: 165
IEEQAKTFLD KFNHAEAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 166          moltype = AA  length = 595
FEATURE                 Location/Qualifiers
REGION                  1..595
                        note = ACE2 mutant, Ala insertion at #36
source                  1..595
                        mol_type = protein
                        organism = synthetic construct
SEQUENCE: 166
IEEQAKTFLD KFNHEAAEDL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595

SEQ ID NO: 167          moltype = AA  length = 595
FEATURE                 Location/Qualifiers
REGION                  1..595
                        note = ACE2 mutant, Ala insertion at #38
source                  1..595
                        mol_type = protein
                        organism = synthetic construct
SEQUENCE: 167
IEEQAKTFLD KFNHEAEADL FYQSSLASWN YNTNITEENV QNMNNAGDKW SAFLKEQSTL  60
AQMYPLQEIQ NLTVKLQLQA LQQNGSSVLS EDKSKRLNTI LNTMSTIYST GKVCNPDNPQ  120
ECLLLEPGLN EIMANSLDYN ERLWAWESWR SEVGKQLRPL YEEYVVLKNE MARANHYEDY  180
GDYWRGDYEV NGVDGYDYSR GQLIEDVEHT FEEIKPLYEH LHAYVRAKLM NAYPSYISPI  240
GCLPAHLLGD MWGRFWTNLY SLTVPFGQKP NIDVTDAMVD QAWDAQRIFK EAEKFFVSVG  300
LPNMTQGFWE NSMLTDPGNV QKAVCHPTAW DLGKGDFRIL MCTKVTMDDF LTAHHEMGHI  360
QYDMAYAAQP FLLRNGANEG FHEAVGEIMS LSAATPKHLK SIGLLSPDFQ EDNETEINFL  420
LKQALTIVGT LPFTYMLEKW RWMVFKGEIP KDQWMKKWWE MKREIVGVVE PVPHDETYCD  480
PASLFHVSND YSFIRYYTRT LYQFQFQEAL CQAAKHEGPL HKCDISNSTE AGQKLFNMLR  540
LGKSEPWTLA LENVVGAKNM NVRPLLNYFE PLFTWLKDQN KNSFVGWSTD WSPYA       595
```

```
SEQ ID NO: 168          moltype = DNA  length = 3596
FEATURE                 Location/Qualifiers
source                  1..3596
                        mol_type = genomic DNA
                        organism = Homo sapiens
SEQUENCE: 168
ggcactcata catacactct ggcaatgagg acactgagct cgcttctgaa atttgacaag  60
ataaccacta aaatctcttt gaattctatg ttgttgtgat cccatggcta cagaggatca  120
ggagttgaca tagatactct ttggatttca taccatgtgg aggctttctt acttccacgt  180
gaccttgact gagttttgaa tagcgcccaa cccaagttca aaggctgata agagagaaaa  240
tctcatgagg aggttttagt ctagggaaag tcattcagtg gatgtgatct tggctcacag  300
gggacgatgt caagctcttc ctggctcctt ctcagccttg ttgctgtaac tgctgctcag  360
tccaccattg aggaacaggc caagacattt ttggacaagt ttaaccacga agccgaagac  420
ctgttctatc aaagttcact tgcttcttgg aattataaca ccaatattac tgaagagaat  480
gtccaaaaca tgaataatgc tggggacaaa tggtctgcct ttttaaagga acagtccaca  540
cttgcccaaa tgtatccact acaagaaatt cagaatctca cagtcaagct tcagctgcag  600
gctcttcagc aaaatgggtc ttcagtgctc tcagaagaca agagcaaacg gttgaacaca  660
attctaaata caatgagcac catctacagt actggaaaag tttgtaaccc agataatcca  720
caagaatgct tattacttga accaggtttg aatgaaataa tggcaaacag tttagactac  780
aatgagaggc tctgggcttg ggaaagctgg agatctgagg tcggcaagca gctgaggcca  840
ttatatgaag agtatgtggt cttgaaaaat gagatggcaa gagcaaatca ttatgaggac  900
tatggggatt attggagagg agactatgaa gtaaatgggg tagatggcta tgactacagc  960
cgcggccagt tgattgaaga tgtggaacat acctttgaag agattaaacc attatatgaa  1020
catcttcatg cctatgtgag ggcaaagttg atgaatgcct atccttccta tatcagtcca  1080
attggatgcc tccctgctca tttgcttggt gatatgtggg gtagattttg gacaaatctg  1140
tactctttga cagttccctt tggacagaaa ccaaacatag atgttactga tgcaatggtg  1200
gaccaggcct gggatgcaca gagaatattc aaggaggccg agaagttctt tgtatctgtt  1260
ggtcttccta atatgactca aggattctgg gaaaattcca tgctaacgga cccaggaaat  1320
gttcagaaag cagtctgcca tcccacagct tgggacctgg ggaagggcga cttcaggatc  1380
cttatgtgca caaaggtgac aatggacgac ttcctgacag ctcatcatga gatggggcat  1440
atccagtatg atatggcata tgctgcacaa ccttttctgc taagaaatgg agctaatgaa  1500
ggattccatg aagctgttgg ggaaatcatg tcactttctg cagccacacc taagcattta  1560
aaatccattg gtcttctgtc acccgatttt caagaagaca atgaaacaga aataaacttc  1620
ctgctcaaac aagcactcac gattgttggg actctgccat ttacttacat gttagagaag  1680
tggaggtgga tggtctttaa aggggaaatt cccaaagacc agtggatgaa aaagtggtgg  1740
gagatgaagc gagagatagt tggggtggtg gaacctgtgc cccatgatga aacatactgt  1800
gaccccgcat ctctgttcca tgtttctaat gattactcat tcattcgata ttacacaagg  1860
acccttttacc aattccagtt tcaagaagca ctttgtcaag cagctaaaca tgaaggccct  1920
ctgcacaaat gtgacatctc aaactctaca gaagctggac agaaactgtt caatatgctg  1980
aggcttggaa aatcagaacc ctggacccta gcattggaaa atgttgtagg agcaaagaac  2040
atgaatgtaa ggccactgct caactacttt gagcccttat ttacctggct gaaagaccag  2100
aacaagaatt cttttgtggg atggagtacc gactggagtc catatgcaga ccaaagcatc  2160
aaagtgagga taagcctaaa atcagctctt ggagataaag catatgaatg gaacgacaat  2220
gaaatgtacc tgttccgatc atctgttgca tatgctatga ggcagtactt tttaaaagta  2280
aaaaatcaga tgattctttt tggggaggag gatgtgcgag tggctaattt gaaaccaaga  2340
atctccttta atttctttgt cactgcacct aaaaatgtgt ctgatatcat tcctagaact  2400
gaagttgaaa aggccatcag gatgtcccgg agccgtatca atgatgcttt ccgtctgaat  2460
gacaacagcc tagagtttct ggggatacag ccaacacttg gacctcctaa ccagcccccct  2520
gtttccatat ggctgattgt ttttggagtt gtgatgggag tgatagtggt tggcattgtc  2580
atcctgatct tcactgggat cagagatcgg aagaagaaaa ataaagcaag aagtggagaa  2640
aatccttatg cctccatcga tattagcaaa ggagaaaata atccaggatt ccaaaacact  2700
gatgatgttc agacctcctt ttagaaaaat ctatgttttt cctcttgagg tgattttgtt  2760
gtatgtaaat gttaatttca tggtatagaa aatataagat gataaagata tcattaaatg  2820
tcaaaactat gactctgttc agaaaaaaaa ttgtccaaag acaacatggc caaggagaga  2880
gcatcttcat tgacattgct ttcagtattt atttctgtct ctggatttga cttctgttct  2940
gtttcttaat aaggattttg tattagagta tattagggaa agtgtgtatt tggtctcaca  3000
ggctgttcag ggataatcta aatgtaaatg tctgttgaat ttctgaagtt gaaaacaagg  3060
atatatcatt ggagcaagtg ttggatcttg tatggaatat ggatggatca cttgtaagga  3120
cagtgcctgg gaactggtgt agctgcaagg attgagaatg gcatgcatta gctcactttc  3180
atttaatcca ttgtcaagga tgacatgctt tcttcacagt aactcagttc aagtactatg  3240
gtgatttgcc tacagtgatg tttggaatcg atcatgcttt cttcaaggtg acaggtctaa  3300
agagagaaga atccagggaa caggtagagg acattgcttt ttcacttcca aggtgcttga  3360
tcaacatctc cctgacaaca caaaactaga gccaggggcc tccgtgaact cccagagcat  3420
gcctgataga aactcatttc tactgttctc taactgtgga gtgaatggaa attccaactg  3480
tatgttcacc ctctgaagtg ggtacccagt ctcttaaatc ttttgtattt gctcacagtg  3540
tttgagcagt gctgagcaca aagcagacac tcaataaatg ctagatttac acactc      3596

SEQ ID NO: 169          moltype = DNA  length = 696
FEATURE                 Location/Qualifiers
source                  1..696
                        mol_type = genomic DNA
                        organism = Homo sapiens
SEQUENCE: 169
gagcccaaat cttgtgacaa aactcacaca tgcccaccgt gcccagcacc tgaactcctg  60
gggggaccgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
```

```
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gaggagatga ccaagaacca ggtcagcctg acctgcctgg tcaaaggctt ctatcccagc  480
gacatcgccg tggagtggga gagcaatggg cagccggaga acaactacaa gaccacgcct  540
cccgtgctgg actccgacgg ctccttcttc ctctatagca agctcaccgt ggacaagagc  600
aggtggcagc aggggaacgt cttctcatgc tccgtgatgc atgaggctct gcacaaccac  660
tacacgcaga agagcctctc cctgtccccg ggtaaa                            696

SEQ ID NO: 170          moltype = DNA  length = 2440
FEATURE                 Location/Qualifiers
source                  1..2440
                        mol_type = genomic DNA
                        organism = Homo sapiens
SEQUENCE: 170
atcctgctaa tgtgcattga aaggagagca acggggctga ggccgtgtca gcacgatgga  60
ccccaaacag accaccctcc tgtgtcttgg ggactttccc atgcctttca tatctgccaa  120
atcgagtcct gtgattccct tggatggatc tgtgaaaatc cagtgccagg ccattcgtga  180
agcttacctg acccagctga tgatcataaa aaactccacg taccgagaga taggcagaag  240
actgaagttt tggaatgaga ctgatcctga gttcgtcatt gaccacatgg acgcaaacaa  300
ggcagggcgc tatcagtgcc aatataggat agggcactac aggttccggt acagtgacac  360
cctggagctg gtagtgacag gcttgtatgg caaacccttc ctctctgcag atcggggtct  420
ggtgttgatg ccaggagaga atatttccct cacgtgcagc tcagcacaca tcccatttga  480
tagattttca ctggccaagg agggagaact ttctctgcca cagcaccaaa gtggggaaca  540
cccggccaac ttctctttgg gtcctgtgga cctcaatgtc tcagggatct acaggtgcta  600
cggttggtac aacaggagcc cctacctgtg gtccttcccc agtaatgcct tggagcttgt  660
ggtcacagac tccatccacc aagattacac gacgcagaac ttgatccgca tggccgtggc  720
aggactggtc ctcgtggctc tcttggccat actggttgaa aattggcaca gccatacggc  780
actgaacaag gaagcctcgg cagatgtggc tgaaccgagc tggagccaac agatgtgtca  840
gccaggattg acctttgcac gaacaccaag tgtctgcaag taaacacctg gaggtgaagg  900
cagagaggag ccaggactgt ggagtccgac aaagctactt gaaggacaca agagagaaaa  960
gctcactaag aagcttgaat ctactttttt tttttttga gacagagtct ggctctgtca  1020
cccaggctgg agtgcagtgg agcaatctcg gctcattgaa cctcttgggt tcaagtgatt  1080
cttgtgcctc agcctcccaa gtagctggaa ttacaggcac ataccactgc acccagctaa  1140
tttttgtatt tttagtagag atggggtttc actgtgttgg ccaggctggt ctcgaactcc  1200
tgacctcagg tgatccaccc accttggcct cccaaagtgc tgagattata ggcatgagcc  1260
accacgcctg gccagatgca tgttcaaacc aatcaaatgg tgttttctta tgcaggactg  1320
atcgatttgc acccaccttt ctgcacataa gttatggttt tccatcttat ctgtcttctg  1380
atttttttata tcctgtttaa tttcttcctt cattgttctt ctcttttttt atttatttta  1440
tttattttta tttttatttt tatttgagac agagtctcac tctgttgccc aggctggagt  1500
gcagtggcac gatctcggct cactgcaacc tctgcctcct gggttcaagt gattctcctg  1560
cctcggcctc ccaagtagct gggattgcag gctcccacca tcacgcccag ctacttttac  1620
agtattttta gtagagacgg ggtttcatca cattggccaa gctggtctca aacttctgac  1680
ctcgtgatct gcccgcctcg gcctcccaaa gtgctgggat tacagatgtg agccactgcg  1740
cccagccttc tttttatatt tttaaatgtg tcttccccaa atataaatgg ttggtaagca  1800
tgccaaatat attcaataac ccccctcctt tattttttttt tgttgaagtg aggctctccc  1860
tatgttgcct aagctggtct tgaactcctg gtctcaagca atcctcctac ctcagcctcc  1920
tgctgtgttc atctacaaat tgataagagt gaaagtcata atcctacagg aggattaccc  1980
tatttatttc acaaacccta tttctaccgg attttcatac aaggaataca ggcatgtgtt  2040
tcacctcatt aatttatttt ttcacttagt tttgatgata ttcacatata ttatcaagtg  2100
tgcaaacatt aaattcttgt gtacaaaact caaatggtct tccaaataat tccccattct  2160
tttttcttat aaactttcac agctttaccc ttgacagact ttactcaagg aaatctaagt  2220
tggtcatatg tggctctttc actgattgct atttacttca ttgtccagta gcttatgtat  2280
gaaaatataa ttataaaatg taagggtcct acttccagtg aaactgaagg gacttaggcc  2340
cacttttatc ctttactgag agcttatctc tacttgataa aatttctact gtattcttgg  2400
cttaactcag gtcctgtgat taaaaaaaaa atgcaaagta                       2440

SEQ ID NO: 171          moltype = DNA  length = 729
FEATURE                 Location/Qualifiers
source                  1..729
                        mol_type = genomic DNA
                        organism = Homo sapiens
SEQUENCE: 171
ccggccatgg ccgaggtgca gctgttggag tctgggggag gcttggtaca gcctgggggg  60
tccctgagac tctcctgtgc agcctctgga ttcaccttta gcagctatgc catgagctgg  120
gtccgccagg ctccagggaa ggggctggag tgggtctcaa ctatttctag taatggtggt  180
tatacatatt acgcagactc cgtgaagggc aggttcacca tctccagaga caattccaag  240
aacacgctgt atctgcaaat gaacagcctg agagccgagg acacggccgt atattactgt  300
gcgaaagctt attctgcttt tgactactgg ggccagggaa ccctggtcac cgtctcgagc  360
ggtggaggcg gttcaggcgg aggtggcagc ggcggtggcg ggtcgacgga catccagatg  420
acccagtctc catcctccct gtctgcatct gtaggagaca gagtcaccat cacttgccgg  480
gcaagtcaga gcattagcag ctatttaaat tggtatcagc agaaaccagg gaaagcccct  540
aagctcctga tctatactgc atccactttg caaagtgggg tcccgtcaag gttcagtggc  600
agtggatctg ggacagattt cactctcacc atcagcagtc tgcaacctga agattttgca  660
acttactact gtcaacagac ttctgctaat cctggtacgt tcggccaagg gaccaaggtg  720
gaaatcaaa                                                          729

SEQ ID NO: 172          moltype = DNA  length = 321
FEATURE                 Location/Qualifiers
source                  1..321
```

```
                        mol_type = genomic DNA
                        organism = Homo sapiens
SEQUENCE: 172
gacatccagt tgacccagtc tccatcctcc ctgtctgcat ctgtaggaga cagagtcacc  60
atcacttgcc aggcgagtca ggacattagc aactatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag tctgcaacct  240
gaagattttg caacttacta ctgtcaacag agttacagtt caccttggac gttcggccaa  300
gggaccaagg tggaaatcaa a                                            321

SEQ ID NO: 173          moltype = AA  length = 6
FEATURE                 Location/Qualifiers
REGION                  1..6
                        note = Anti-Spike Group 21, CDR-H1
source                  1..6
                        mol_type = protein
                        organism = synthetic construct
SEQUENCE: 173
SSYAMS                                                             6

SEQ ID NO: 174          moltype = AA  length = 10
FEATURE                 Location/Qualifiers
REGION                  1..10
                        note = Anti-Spike Group 21, CDR-H2
source                  1..10
                        mol_type = protein
                        organism = synthetic construct
SEQUENCE: 174
AISGSGGSTN                                                         10

SEQ ID NO: 175          moltype = AA  length = 8
FEATURE                 Location/Qualifiers
REGION                  1..8
                        note = Anti-Spike Group 21, CDR-H3
source                  1..8
                        mol_type = protein
                        organism = synthetic construct
SEQUENCE: 175
DLWGLAFA                                                           8

SEQ ID NO: 176          moltype = AA  length = 6
FEATURE                 Location/Qualifiers
REGION                  1..6
                        note = Anti-Spike Group 21, CDR-L3
source                  1..6
                        mol_type = protein
                        organism = synthetic construct
SEQUENCE: 176
DSSNPW                                                             6

SEQ ID NO: 177          moltype = AA  length = 6
FEATURE                 Location/Qualifiers
REGION                  1..6
                        note = Anti-Spike Group 22, CDR-H1
source                  1..6
                        mol_type = protein
                        organism = synthetic construct
SEQUENCE: 177
SSYAMS                                                             6

SEQ ID NO: 178          moltype = AA  length = 10
FEATURE                 Location/Qualifiers
REGION                  1..10
                        note = Anti-Spike Group 22, CDR-H2
source                  1..10
                        mol_type = protein
                        organism = synthetic construct
SEQUENCE: 178
SISGSGGSTD                                                         10

SEQ ID NO: 179          moltype = AA  length = 8
FEATURE                 Location/Qualifiers
REGION                  1..8
                        note = Anti-Spike Group 22, CDR-H3
source                  1..8
                        mol_type = protein
                        organism = synthetic construct
SEQUENCE: 179
DLWGLAMA                                                           8
```

```
SEQ ID NO: 180          moltype = AA  length = 6
FEATURE                 Location/Qualifiers
REGION                  1..6
                        note = Anti-Spike Group 22, CDR-L3
source                  1..6
                        mol_type = protein
                        organism = synthetic construct
SEQUENCE: 180
DNNVPL                                                        6

SEQ ID NO: 181          moltype = AA  length = 6
FEATURE                 Location/Qualifiers
REGION                  1..6
                        note = Anti-Spike Group 23, CDR-H1
source                  1..6
                        mol_type = protein
                        organism = synthetic construct
SEQUENCE: 181
SSYAMH                                                        6

SEQ ID NO: 182          moltype = AA  length = 10
FEATURE                 Location/Qualifiers
REGION                  1..10
                        note = Anti-Spike Group 23, CDR-H2
source                  1..10
                        mol_type = protein
                        organism = synthetic construct
SEQUENCE: 182
AISWSGRSTY                                                    10

SEQ ID NO: 183          moltype = AA  length = 9
FEATURE                 Location/Qualifiers
REGION                  1..9
                        note = Anti-Spike Group 23, CDR-H3
source                  1..9
                        mol_type = protein
                        organism = synthetic construct
SEQUENCE: 183
DLSSNWGAG                                                     9

SEQ ID NO: 184          moltype = AA  length = 6
FEATURE                 Location/Qualifiers
REGION                  1..6
                        note = Anti-Spike Group 23, CDR-L3
source                  1..6
                        mol_type = protein
                        organism = synthetic construct
SEQUENCE: 184
SADTPF                                                        6

SEQ ID NO: 185          moltype = AA  length = 6
FEATURE                 Location/Qualifiers
REGION                  1..6
                        note = Anti-Spike Group 24, CDR-H1
source                  1..6
                        mol_type = protein
                        organism = synthetic construct
SEQUENCE: 185
SSYAMH                                                        6

SEQ ID NO: 186          moltype = AA  length = 10
FEATURE                 Location/Qualifiers
REGION                  1..10
                        note = Anti-Spike Group 24, CDR-H2
source                  1..10
                        mol_type = protein
                        organism = synthetic construct
SEQUENCE: 186
AISWSGRSTY                                                    10

SEQ ID NO: 187          moltype = AA  length = 9
FEATURE                 Location/Qualifiers
REGION                  1..9
                        note = Anti-Spike Group 24, CDR-H3
source                  1..9
                        mol_type = protein
                        organism = synthetic construct
SEQUENCE: 187
```

```
DLSSNWGSG                                                       9

SEQ ID NO: 188          moltype = AA  length = 6
FEATURE                 Location/Qualifiers
REGION                  1..6
                        note = Anti-Spike Group 24, CDR-L3
source                  1..6
                        mol_type = protein
                        organism = synthetic construct
SEQUENCE: 188
SADTPF                                                          6

SEQ ID NO: 189          moltype = AA  length = 6
FEATURE                 Location/Qualifiers
REGION                  1..6
                        note = Anti-Spike Group 25, CDR-H1
source                  1..6
                        mol_type = protein
                        organism = synthetic construct
SEQUENCE: 189
SSYAMH                                                          6

SEQ ID NO: 190          moltype = AA  length = 10
FEATURE                 Location/Qualifiers
REGION                  1..10
                        note = Anti-Spike Group 25, CDR-H2
source                  1..10
                        mol_type = protein
                        organism = synthetic construct
SEQUENCE: 190
IISGSGGSTS                                                      10

SEQ ID NO: 191          moltype = AA  length = 9
FEATURE                 Location/Qualifiers
REGION                  1..9
                        note = Anti-Spike Group 25, CDR-H3
source                  1..9
                        mol_type = protein
                        organism = synthetic construct
SEQUENCE: 191
DLCDCFAVA                                                       9

SEQ ID NO: 192          moltype = AA  length = 6
FEATURE                 Location/Qualifiers
REGION                  1..6
                        note = Anti-Spike Group 25, CDR-L3
source                  1..6
                        mol_type = protein
                        organism = synthetic construct
SEQUENCE: 192
WAARPL                                                          6

SEQ ID NO: 193          moltype = AA  length = 6
FEATURE                 Location/Qualifiers
REGION                  1..6
                        note = Anti-Spike Group 26, CDR-H1
source                  1..6
                        mol_type = protein
                        organism = synthetic construct
SEQUENCE: 193
SAYAMH                                                          6

SEQ ID NO: 194          moltype = AA  length = 10
FEATURE                 Location/Qualifiers
REGION                  1..10
                        note = Anti-Spike Group 26, CDR-H2
source                  1..10
                        mol_type = protein
                        organism = synthetic construct
SEQUENCE: 194
AIWGSGGSTY                                                      10

SEQ ID NO: 195          moltype = AA  length = 9
FEATURE                 Location/Qualifiers
REGION                  1..9
                        note = Anti-Spike Group 26, CDR-H3
source                  1..9
                        mol_type = protein
                        organism = synthetic construct
```

```
SEQUENCE: 195
DLWMAMWFG                                                       9

SEQ ID NO: 196         moltype = AA  length = 6
FEATURE                Location/Qualifiers
REGION                 1..6
                       note = Anti-Spike Group 26, CDR-L3
source                 1..6
                       mol_type = protein
                       organism = synthetic construct
SEQUENCE: 196
RSTYPL                                                          6

SEQ ID NO: 197         moltype = AA  length = 6
FEATURE                Location/Qualifiers
REGION                 1..6
                       note = Anti-Spike Group 27, CDR-H1
source                 1..6
                       mol_type = protein
                       organism = synthetic construct
SEQUENCE: 197
SSYAMS                                                          6

SEQ ID NO: 198         moltype = AA  length = 10
FEATURE                Location/Qualifiers
REGION                 1..10
                       note = Anti-Spike Group 27, CDR-H2
source                 1..10
                       mol_type = protein
                       organism = synthetic construct
SEQUENCE: 198
AISGSGGSTS                                                      10

SEQ ID NO: 199         moltype = AA  length = 10
FEATURE                Location/Qualifiers
REGION                 1..10
                       note = Anti-Spike Group 27, CDR-H3
source                 1..10
                       mol_type = protein
                       organism = synthetic construct
SEQUENCE: 199
DLIYDTVWWG                                                      10

SEQ ID NO: 200         moltype = AA  length = 6
FEATURE                Location/Qualifiers
REGION                 1..6
                       note = Anti-Spike Group 27, CDR-L3
source                 1..6
                       mol_type = protein
                       organism = synthetic construct
SEQUENCE: 200
DTNVPY                                                          6

SEQ ID NO: 201         moltype = AA  length = 805
FEATURE                Location/Qualifiers
REGION                 1..805
                       note = R273 mutant ACE2
VARIANT                273
                       note = not R
source                 1..805
                       mol_type = protein
                       organism = synthetic construct
SEQUENCE: 201
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGXFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                     805

SEQ ID NO: 202         moltype = AA  length = 805
```

```
FEATURE                 Location/Qualifiers
REGION                  1..805
                        note = H345 mutant ACE2
VARIANT                 345
                        note = not H
source                  1..805
                        mol_type = protein
                        organism = synthetic construct
SEQUENCE: 202
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCXPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 203          moltype = AA  length = 805
FEATURE                 Location/Qualifiers
REGION                  1..805
                        note = H374 mutant ACE2
VARIANT                 374
                        note = not H
source                  1..805
                        mol_type = protein
                        organism = synthetic construct
SEQUENCE: 203
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHXEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 204          moltype = AA  length = 805
FEATURE                 Location/Qualifiers
REGION                  1..805
                        note = H378 mutant ACE2
VARIANT                 378
                        note = not H
source                  1..805
                        mol_type = protein
                        organism = synthetic construct
SEQUENCE: 204
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGXIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 205          moltype = AA  length = 805
FEATURE                 Location/Qualifiers
REGION                  1..805
                        note = H505 mutant ACE2
VARIANT                 505
```

```
                        note = not H
source                  1..805
                        mol_type = protein
                        organism = synthetic construct
SEQUENCE: 205
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFXVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADQSIKV RISLKSALGD KAYEWNDNEM YLFRSSVAYA MRQYFLKVKN  660
QMILFGEEDV RVANLKPRIS FNFFVTAPKN VSDIIPRTEV EKAIRMSRSR INDAFRLNDN  720
SLEFLGIQPT LGPPNQPPVS IWLIVFGVVM GVIVVGIVIL IFTGIRDRKK KNKARSGENP  780
YASIDISKGE NNPGFQNTDD VQTSF                                       805

SEQ ID NO: 206          moltype = AA  length = 615
FEATURE                 Location/Qualifiers
REGION                  1..615
                        note = T27Y H34A R273K ACE2 mutant
source                  1..615
                        mol_type = protein
                        organism = synthetic construct
SEQUENCE: 206
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGKFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 207          moltype = AA  length = 615
FEATURE                 Location/Qualifiers
REGION                  1..615
                        note = T27Y H34A R273L ACE2 mutant
source                  1..615
                        mol_type = protein
                        organism = synthetic construct
SEQUENCE: 207
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGLFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 208          moltype = AA  length = 615
FEATURE                 Location/Qualifiers
REGION                  1..615
                        note = T27Y H34A H505L ACE2 mutant
source                  1..615
                        mol_type = protein
                        organism = synthetic construct
SEQUENCE: 208
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFLVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615
```

```
SEQ ID NO: 209          moltype = AA  length = 615
FEATURE                 Location/Qualifiers
REGION                  1..615
                        note = T27Y H34A H374N ACE2 mutant
source                  1..615
                        mol_type = protein
                        organism = synthetic construct
SEQUENCE: 209
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHNEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 210          moltype = AA  length = 615
FEATURE                 Location/Qualifiers
REGION                  1..615
                        note = T27Y H34A H378N ACE2 mutant
source                  1..615
                        mol_type = protein
                        organism = synthetic construct
SEQUENCE: 210
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGNIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYAD                                                  615

SEQ ID NO: 211          moltype = AA  length = 614
FEATURE                 Location/Qualifiers
REGION                  1..614
                        note = T27Y H34A H345A ACE2 mutant
source                  1..614
                        mol_type = protein
                        organism = synthetic construct
SEQUENCE: 211
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCAPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYA                                                   614

SEQ ID NO: 212          moltype = AA  length = 615
FEATURE                 Location/Qualifiers
REGION                  1..615
                        note = T27Y H34A R273Q ACE2 mutant
source                  1..615
                        mol_type = protein
                        organism = synthetic construct
SEQUENCE: 212
MSSSSWLLLS LVAVTAAQST IEEQAKYFLD KFNAEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGQFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
```

```
NSFVGWSTDW SPYAD                                                  615

SEQ ID NO: 213          moltype = DNA  length = 1845
FEATURE                 Location/Qualifiers
misc_feature            1..1845
                        note = CDS for T27Y H34A R273K ACE2 mutant
source                  1..1845
                        mol_type = other DNA
                        organism = synthetic construct
SEQUENCE: 213
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggaaagt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtcaccctac cgcttgggac cttgggaaag gtgactttcg aatcttgatg  1080
tgtaccaagg tgacaatgga tgactttctt acagcccatc atgaaatggg tcacatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tccacgttag caatgactat tcatttatac gttattacac tcgcactctt  1560
taccagtttc aatttcagga ggctctgtgt caggctgcca agcatgaggg acccttcac  1620
aagtgtgata ttagtaacag tactgaggca ggccaaaaac tgttcaatat gttgaggctt  1680
ggcaaaagcg agccatggac tctcgccttg gaaaatgttg tcggggctaa aaacatgaat  1740
gtacgccctc tgcttaacta ttttgagccc ctttttacat ggctcaagga ccagaataag  1800
aactcctttg tcggctggtc aacagactgg tctccctatg cagac                 1845

SEQ ID NO: 214          moltype = DNA  length = 1845
FEATURE                 Location/Qualifiers
misc_feature            1..1845
                        note = CDS for T27Y H34A R273L ACE2 mutant
source                  1..1845
                        mol_type = other DNA
                        organism = synthetic construct
SEQUENCE: 214
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggactgt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtcaccctac cgcttgggac cttgggaaag gtgactttcg aatcttgatg  1080
tgtaccaagg tgacaatgga tgactttctt acagcccatc atgaaatggg tcacatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tccacgttag caatgactat tcatttatac gttattacac tcgcactctt  1560
taccagtttc aatttcagga ggctctgtgt caggctgcca agcatgaggg acccttcac  1620
aagtgtgata ttagtaacag tactgaggca ggccaaaaac tgttcaatat gttgaggctt  1680
ggcaaaagcg agccatggac tctcgccttg gaaaatgttg tcggggctaa aaacatgaat  1740
```

```
gtacgccctc tgcttaacta ttttgagccc ctttttacat ggctcaagga ccagaataag  1800
aactcctttg tcggctggtc aacagactgg tctccctatg cagac                  1845

SEQ ID NO: 215         moltype = DNA  length = 1845
FEATURE                Location/Qualifiers
misc_feature           1..1845
                       note = CDS for T27Y H34A H505L ACE2 mutant
source                 1..1845
                       mol_type = other DNA
                       organism = synthetic construct
SEQUENCE: 215
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggacgtt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtcaccctac cgcttgggac cttgggaaag gtgactttcg aatcttgatg  1080
tgtaccaagg tgacaatgga tgactttctt acagcccatc atgaaatggg tcacatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tcctggttag caatgactat tcatttatac gttattacac tcgcactctt  1560
taccagtttc aatttcagga ggctctgtgt caggctgcca agcatgaggg accccttcac  1620
aagtgtgata ttagtaacag tactgaggca ggccaaaaac tgttcaatat gttgaggctt  1680
ggcaaaagcg agccatggac tctcgccttg gaaaatgttg tcggggctaa aaacatgaat  1740
gtacgccctc tgcttaacta ttttgagccc ctttttacat ggctcaagga ccagaataag  1800
aactcctttg tcggctggtc aacagactgg tctccctatg cagac                  1845

SEQ ID NO: 216         moltype = DNA  length = 1845
FEATURE                Location/Qualifiers
misc_feature           1..1845
                       note = CDS for T27Y H34A H374N ACE2 mutant
source                 1..1845
                       mol_type = other DNA
                       organism = synthetic construct
SEQUENCE: 216
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggacgtt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtcaccctac cgcttgggac cttgggaaag gtgactttcg aatcttgatg  1080
tgtaccaagg tgacaatgga tgactttctt acagcccata atgaaatggg tcacatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tccacgttag caatgactat tcatttatac gttattacac tcgcactctt  1560
taccagtttc aatttcagga ggctctgtgt caggctgcca agcatgaggg accccttcac  1620
aagtgtgata ttagtaacag tactgaggca ggccaaaaac tgttcaatat gttgaggctt  1680
```

```
ggcaaaagcg agccatggac tctcgccttg gaaaatgttg tcggggctaa aaacatgaat  1740
gtacgccctc tgcttaacta ttttgagccc ctttttacat ggctcaagga ccagaataag  1800
aactcctttg tcggctggtc aacagactgg tctccctatg cagac                  1845

SEQ ID NO: 217         moltype = DNA  length = 1845
FEATURE                Location/Qualifiers
misc_feature           1..1845
                       note = CDS for T27Y H34A H378N ACE2 mutant
source                 1..1845
                       mol_type = other DNA
                       organism = synthetic construct
SEQUENCE: 217
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggacgtt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtcaccctac cgcttgggac cttgggaaag gtgactttcg aatcttgatg  1080
tgtaccaagg tgacaatgga tgactttctt acagcccatc atgaaatggg taatatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tccacgttag caatgactat tcatttatac gttattacac tcgcactctt  1560
taccagtttc aatttcagga ggctctgtgt caggctgcca agcatgaggg accccttcac  1620
aagtgtgata ttagtaacag tactgaggca ggccaaaaac tgttcaatat gttgaggctt  1680
ggcaaaagcg agccatggac tctcgccttg gaaaatgttg tcggggctaa aaacatgaat  1740
gtacgccctc tgcttaacta ttttgagccc ctttttacat ggctcaagga ccagaataag  1800
aactcctttg tcggctggtc aacagactgg tctccctatg cagac                  1845

SEQ ID NO: 218         moltype = DNA  length = 1845
FEATURE                Location/Qualifiers
misc_feature           1..1845
                       note = CDS for T27Y H34A H345A ACE2 mutant
source                 1..1845
                       mol_type = other DNA
                       organism = synthetic construct
SEQUENCE: 218
atgagcagca gtagttggct tctcttgagt ttggtggcag tgacagcagc ccagagtact  60
atcgaggagc aggctaaata ctttctggat aagtttaacg ccgaggccga agacttgttc  120
tatcaatctt ctctcgcttc atggaattac aatactaaca tcactgagga gaacgtccag  180
aatatgaaca atgctggcga caaatggagc gccttcttga aggagcagtc tacccttgca  240
caaatgtatc cactgcagga gatacagaac cttacagtaa agttgcagct ccaggctctc  300
cagcagaacg gatctagcgt gctttcagag gataaaagca aaaggctgaa caccatactt  360
aataccatgt ccacaattta ctctactggt aaagtatgta accccgacaa ccctcaagaa  420
tgcctccttc ttgagccagg cctcaatgag atcatggcta atagtctgga ctataatgaa  480
agactgtggg catgggagtc ctggagatct gaagtaggga agcaactgag gcccctttat  540
gaagagtacg tcgtacttaa gaatgaaatg gcccgcgcta accactacga ggattacggc  600
gattactggc gtggggacta tgaagtaaat ggtgtagatg gatacgacta tagtcgtggg  660
caattgattg aggatgtgga gcacactttt gaggagataa aaccactcta tgagcatctt  720
cacgcatatg tgagagctaa actgatgaac gcctacccaa gttacatcag tccaatcgga  780
tgtctcccag ctcacctcct tggcgacatg tggggacgtt tctggaccaa tctgtattcc  840
ctcacagtcc ctttcgggca aaagcctaat atagacgtga cagacgcaat ggttgatcag  900
gcttgggatg ctcaaaggat ttttaaggaa gctgagaagt tttttgtgtc agtcggtttg  960
ccaaatatga cacaaggctt ctgggaaaat agcatgttga ctgatcccgg taatgttcaa  1020
aaggctgtgt gtgcccctac cgcttgggac cttgggaaag gtgactttcg aatcttgatg  1080
tgtaccaagg tgacaatgga tgactttctt acagcccatc atgaaatggg tcacatccag  1140
tatgatatgg cttatgcagc tcaacctttc ctcttgagaa atggtgcaaa tgaaggtttt  1200
catgaagctg taggggaaat aatgtccctg agtgctgcaa ccccaaagca tctcaagagt  1260
atcggattgt tgagcccaga ttttcaagaa gataacgaga ccgaaatcaa cttccttctg  1320
aaacaagccc tcacaatagt tggtactctt ccattcacat acatgctgga gaaatggcgt  1380
tggatggttt ttaaggggga gatacctaaa gatcagtgga tgaaaaagtg gtgggagatg  1440
aagcgtgaga tcgtaggggt cgtggagcca gtgcctcatg atgagactta ctgtgaccca  1500
gcatcactct tccacgttag caatgactat tcatttatac gttattacac tcgcactctt  1560
taccagtttc aatttcagga ggctctgtgt caggctgcca agcatgaggg accccttcac  1620
```

aagtgtgata ttagtaacag tactgaggca ggccaaaaac tgttcaatat gttgaggctt 1680
ggcaaaagcg agccatggac tctcgccttg gaaaatgttg tcggggctaa aaacatgaat 1740
gtacgccctc tgcttaacta ttttgagccc ctttttacat ggctcaagga ccagaataag 1800
aactcctttg tcggctggtc aacagactgg tctccctatg cagac 1845

SEQ ID NO: 219 moltype = DNA length = 1845
FEATURE Location/Qualifiers
misc_feature 1..1845
note = CDS for T27Y H34A R273Q ACE2 mutant
source 1..1845
mol_type = other DNA
organism = synthetic construct
SEQUENCE: 219
atgagcagca gtagttggct tctcttgagt ttggtggcag tgacagcagc ccagagtact 60
atcgaggagc aggctaaata ctttctggat aagtttaacg ccgaggccga agacttgttc 120
tatcaatctt ctctcgcttc atggaattac aatactaaca tcactgagga gaacgtccag 180
aatatgaaca atgctggcga caaatggagc gccttcttga aggagcagtc taccettgca 240
caaatgtatc cactgcagga gatacagaac cttacagtaa agttgcagct ccaggctctc 300
cagcagaacg gatctagcgt gctttcagag gataaaagca aaaggctgaa caccatactt 360
aataccatgt ccacaattta ctctactggt aaagtatgta accccgacaa ccctcaagaa 420
tgcctccttc ttgagccagg cctcaatgag atcatggcta atagtctgga ctataatgaa 480
agactgtggg catgggagtc ctggagatct gaagtaggga agcaactgag gcccctttat 540
gaagagtacg tcgtacttaa gaatgaaatg gcccgcgcta accactacga ggattacggc 600
gattactggc gtggggacta tgaagtaaat ggtgtagatg gatacgacta tagtcgtggg 660
caattgattg aggatgtgga gcacactttt gaggagataa aaccactcta tgagcatctt 720
cacgcatatg tgagagctaa actgatgaac gcctacccaa gttacatcag tccaatcgga 780
tgtctcccag ctcacctcct tggcgacatg tggggacagt tctggaccaa tctgtattcc 840
ctcacagtcc ctttcgggca aaagcctaat atagacgtga cagacgcaat ggttgatcag 900
gcttgggatg ctcaaaggat ttttaaggaa gctgagaagt tttttgtgtc agtcggtttg 960
ccaaatatga cacaaggctt ctgggaaaat agcatgttga ctgatcccgg taatgttcaa 1020
aaggctgtgt gtcaccctac cgcttgggac cttgggaaag gtgactttcg aatcttgatg 1080
tgtaccaagg tgacaatgga tgactttctt acagcccatc atgaaatggg tcacatccag 1140
tatgatatgg cttatgcagc tcaacctttc ctcttgagaa atggtgcaaa tgaaggtttt 1200
catgaagctg taggggaaat aatgtccctg agtgctgcaa ccccaaagca tctcaagagt 1260
atcggattgt tgagcccaga ttttcaagaa gataacgaga ccgaaatcaa cttccttctg 1320
aaacaagccc tcacaatagt tggtactctt ccattcacat acatgctgga gaaatggcgt 1380
tggatggttt ttaaggggga gatacctaaa gatcagtgga tgaaaaagtg gtgggagatg 1440
aagcgtgaga tcgtaggggt cgtggagcca gtgcctcatg atgagactta ctgtgaccca 1500
gcatcactct tccacgttag caatgactat tcatttatac gttattacac tcgcactctt 1560
taccagtttc aatttcagga ggctctgtgt caggctgcca agcatgaggg acccccttcac 1620
aagtgtgata ttagtaacag tactgaggca ggccaaaaac tgttcaatat gttgaggctt 1680
ggcaaaagcg agccatggac tctcgccttg gaaaatgttg tcggggctaa aaacatgaat 1740
gtacgccctc tgcttaacta ttttgagccc ctttttacat ggctcaagga ccagaataag 1800
aactcctttg tcggctggtc aacagactgg tctccctatg cagac 1845

SEQ ID NO: 220 moltype = DNA length = 38496
FEATURE Location/Qualifiers
misc_feature 1..38496
note = vector for IgA against T27Y H34A R273K ACE2 mutant
source 1..38496
mol_type = other DNA
organism = synthetic construct
SEQUENCE: 220
tattattgat gatgttaatt aacatgcatg gatcctacgt ctcgaccgat gcccttgaga 60
gccttcaacc cagtcagctc cttccggtgg gcgcggggca tgactatcgt cgccgcactt 120
atgactgtct tctttatcat gcaactcgta ggacaggtgc cggcagcgct ctgggtcatt 180
ttcggcgagg accgctttcg ctggagcgcg acgatgatcg gcctgtcgct tgcggtattc 240
ggaatcttgc acgccctcgc tcaagccttc gtcactggtc ccgccaccaa acgtttcggc 300
gagaagcagg ccattatcgc cggcatggcg gccgacgcgc tgggctacgt cttgctggcg 360
ttcgcgacgc gaggctggat ggccttcccc attatgattc ttctcgcttc cggcggcatc 420
gggatgcccg cgttgcaggc catgctgtcc aggcaggtag atgacgacca tcagggacag 480
cttcaaggat cgctcgcggc tcttaccagc ctaacttcga tcattggacc gctgatcgtc 540
acggcgattt atgccgcctc ggcgagcaca tggaacgggt tggcatggat tgtaggcgcc 600
gccctatacc ttgtctgcct ccccgcgttg cgtcgcggtg catggagccg ggccacctcg 660
acctgaatgg aagccggcgg cacctcgcta acggattcac cactccaaga attggagcca 720
atcaattctt gcggagaact gtgaatgcgc aaaccaaccc ttggcagaac atatccatcg 780
cgtccgccat ctccagcagc cgcacgcggc gcatctcggg cagcgttggg tcctggccac 840
gggtgcgcat gatcgtgctc ctgtcgttga ggacccggct aggctggcgg ggttgcctta 900
ctggttagca gaatgaatca ccgatacgcg agcgaacgtg aagcgactgc tgctgcaaaa 960
cgtctgcgac ctgagcaaca acatgaatgg tcttcggttt ccgtgtttcg taaagtctgg 1020
aaacgcggaa gtcagcgccc tgcaccatta tgttccggat ctgcatcgca ggatgctgct 1080
ggctaccctg tggaacacct acatctgtat taacgaagcg ctggcattga ccctgagtga 1140
tttttctctg gtcccgccgc atccataccg ccagttgttt accctcacaa cgttccagta 1200
accgggcatg ttcatcatca gtaacccgta tcgtgagcat cctctctcgt ttcatcggta 1260
tcattacccc catgaacaga aatccccctt acacggaggc atcagtgacc aaacaggaaa 1320
aaaccgccct taacatggcc cgctttatca gaagccagac attaacgctt ctggagaaac 1380
tcaacgagct ggacgcggat gaacaggcag acatctgtga atcgcttcac gaccacgctg 1440
atgagcttta ccgcagctgc ctcgcgcgtt tcggtgatga cggtgaaaac ctctgacaca 1500
tgcagctccc ggagacggtc acagcttgtc tgtaagcgga tgccgggagc agacaagccc 1560

```
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
```

```
catatgtgag agctaaactg atgaacgcct acccaagtta catcagtcca atcggatgtc  6360
tcccagctca cctccttggc gacatgtggg gaaagttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tgggaccttg ggaaaggtga ctttcgaatc ttgatgtgta  6660
ccaaggtgac aatggatgac tttcttacag cccatcatga aatgggtcac atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag ggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaaggggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct tttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
```

```
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact aggggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggtgggggg cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc ctttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgcccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
```

-continued

```
aggcgcgcgc aatcgttgac gctctagcgt gcaaaaggag agcctgtaag cgggcactct 15840
tccgtggtct ggtggataaa ttcgcaaggg tatcatggcg gacgaccggg gttcgagccc 15900
cgtatccggc cgtccgccgt gatccatgcg gttaccgccc gcgtgtcgaa cccaggtgtg 15960
cgacgtcaga caacgggggga gtgctccttt tggcttcctt ccaggcgcgg cggctgctgc 16020
gctagctttt ttggccactg gccgcgcgca gcgtaagcgg ttaggctgga aagcgaaagc 16080
attaagtggc tcgctccctg tagccggagg gttattttcc aagggttgag tcgcgggacc 16140
cccggttcga gtctcggacc ggccggactg cggcgaacgg gggtttgcct ccccgtcatg 16200
caagaccccg cttgcaaatt cctccggaaa cagggacgag cccctttttt gcttttccca 16260
gatgcatccg gtgctgcggc agatgcgccc ccctcctcag cagcggcaag agcaagagca 16320
gcggcagaca tgcagggcac cctcccctcc tcctaccgcg tcaggagggg cgacatccgc 16380
ggttgacgcg gcagcagatg gtgattacga accccccgcgg cgccgggccc ggcactacct 16440
ggacttggag gagggcgagg gcctggcgcg gctaggagcg ccctctcctg agcggcaccc 16500
aagggtgcag ctgaagcgtg atacgcgtga ggcgtacgtg ccgcggcaga acctgtttcg 16560
cgaccgcgag ggagaggagc ccgaggagat gcgggatcga aagttccacg cagggcgcga 16620
gctgcggcat ggcctgaatc gcgagcggtt gctgcgcgag gaggactttg agcccgacgc 16680
gcgaaccggg attagtcccg cgcgcgcaca cgtggcggcc gccgacctgg taaccgcata 16740
cgagcagacg gtgaaccagg agattaactt tcaaaaaagc tttaacaacc acgtgcgtac 16800
gcttgtggcg cgcgaggagg tggctatagg actgatgcat ctgtgggact ttgtaagcgc 16860
gctggagcaa aacccaaata gcaagccgct catggcgcag ctgttcctta tagtgcagca 16920
cagcagggac aacgaggcat tcagggatgc gctgctaaac atagtagagc ccgagggccg 16980
ctggctgctc gatttgataa acatcctgca gagcatagtg gtgcaggagc gcagcttgag 17040
cctggctgac aaggtggccg ccatcaacta ttccatgctt agcctgggca agttttacgc 17100
ccgcaagata taccataccc cttacgttcc catagacaag gaggtaaaga tcgaggggtt 17160
ctacatgcgc atggcgctga aggtgcttac cttgagcgac gacctgggcg tttatcgcaa 17220
cgagcgcatc cacaaggccg tgagcgtgag ccggcggcgc gagctcagcg accgcgagct 17280
gatgcacagc ctgcaaaggg ccctggctgg cacgggcagc ggcgatagag aggccgagtc 17340
ctactttgac gcgggcgctg acctgcgctg ggccccaagc cgacgcgccc tggaggcagc 17400
tggggccgga cctgggctgg cggtggcacc cgcgcgcgct ggcaacgtcg gcggcgtgga 17460
ggaatatgac gaggacgatg agtacgagcc agaggacggc gagtactaag cggtgatgtt 17520
tctgatcaga tgatgcaaga cgcaacggac ccggcggtgc gggcggcgct gcagagccag 17580
ccgtccggcc ttaactccac ggacgactgg cgccaggtca tggaccgcat catgtcgctg 17640
actgcgcgca atcctgacgc gttccggcag cagccgcagg ccaaccggct ctccgcaatt 17700
ctggaagcgg tggtcccggc gcgcgcaaac cccacgcacg agaaggtgct ggcgatcgta 17760
aacgcgctgg ccgaaaacag ggccatccgg cccgacgagg ccggcctggt ctacgacgcg 17820
ctgcttcagc gcgtggctcg ttacaacagc ggcaacgtgc agaccaacct ggaccggctg 17880
gtgggggatg tgcgcgaggc cgtggcgcag cgtgagcgcg cgcagcagca gggcaacctg 17940
ggctccatgg ttgcactaaa cgccttcctg agtacacagc ccgccaacgt gccgcgggga 18000
caggaggact acaccaactt tgtgagcgca ctgcggctaa tggtgactga gacaccgcaa 18060
agtgaggtgt accagtctgg gccagactat tttttccaga ccagtagaca aggcctgcag 18120
accgtaaacc tgagccaggc tttcaaaaac ttgcaggggc tgtggggggt gcgggctccc 18180
acaggcgacc gcgcgaccgt gtctagcttg ctgacgccca actcgcgcct gttgctgctg 18240
ctaatagcgc ccttcacgga cagtggcagc gtgtcccggg acacatacct aggtcacttg 18300
ctgacactgt accgcgaggc cataggtcag gcgcatgtgg acgagcatac tttccaggag 18360
attacaagtg tcagccgcgc gctggggcag gaggacacgg gcagcctgga ggcaacccta 18420
aactacctgc tgaccaaccg gcggcagaag atcccctcgt tgcacagttt aaacagcgag 18480
gaggagcgca ttttgcgcta cgtgcagcag agcgtgagcc ttaacctgat gcgcgacggg 18540
gtaacgccca gcgtggcgct ggacatgacc gcgcgcaaca tggaaccggg catgtatgcc 18600
tcaaaccggc cgtttatcaa ccgcctaatg gactacttgc atcgcgcggc cgccgtgaac 18660
cccgagtatt tcaccaatgc catcttgaac ccgcactggc taccgccccc tggtttctac 18720
accgggggat tcgaggtgcc cgagggtaac gatggattcc tctgggacga catagacgac 18780
agcgtgtttt ccccgcaacc gcagaccctg ctagagttgc aacagcgcga gcaggcagag 18840
gcggcgctgc gaaaggaaag cttccgcagg ccaagcagct tgtccgatct aggcgctgcg 18900
gccccgcggt cagatgctag tagcccattt ccaagcttga tagggtctct taccagcact 18960
cgcaccaccc gcccgcgcct gctgggcgag gaggagtacc taaacaactc gctgctgcag 19020
ccgcagcgcg aaaaaaacct gcctccggca tttcccaaca acgggataga gagcctagtg 19080
gacaagatga gtagatggaa gacgtacgcg caggagcaca gggacgtgcc aggcccgcgc 19140
ccgcccaccc gtcgtcaaag gcacgaccgt cagcggggtc tggtgtggga ggacgatgac 19200
tcggcagacg acagcagcgt cctggatttg ggagggagtg gcaacccgtt tgcgcacctt 19260
cgccccaggc tggggagaat gttttaaaaa aaaaaaagca tgatgcaaaa taaaaaactc 19320
accaaggcca tggcaccgag cgttggtttt cttgtattcc ccttagtatg cggcgcgcgg 19380
cgatgtatga ggaaggtcct cctccctcct acgagagtgt ggtgagcgcg gcgccagtgg 19440
cggcggcgct gggttctccc ttcgatgctc ccctggaccc gccgtttgtg cctccgcggt 19500
acctgcggcc taccgggggg agaaacagca tccgttactc tgagttggca cccctattcg 19560
acaccacccg tgtgtacctg gtggacaaca agtcaacgga tgtggcatcc ctgaactacc 19620
agaacgacca cagcaacttt ctgaccacgg tcattcaaaa caatgactac agcccggggg 19680
aggcaagcac acagaccatc aatcttgacg accggtcgca ctggggcggc gacctgaaaa 19740
ccatcctgca taccaacatg ccaaatgtga acgagttcat gtttaccaat aagtttaagg 19800
cgcgggtgat ggtgtcgcgc ttgcctacta aggacaatca ggtggagctg aaatacgagt 19860
gggtggagtt cacgctgccc gagggcaact actccgagac catgaccata gaccttatga 19920
acaacgcgat cgtggagcac tacttgaaag tgggcagaca gaacggggtt ctggaaagcg 19980
acatcggggt aaagtttgac acccgcaact tcagactggg gtttgacccc gtcactggtc 20040
ttgtcatgcc tggggtatat acaaacgaag ccttccatcc agacatcatt ttgctgccag 20100
gatgcggggt ggacttcacc cacagccgcc tgagcaactt gttgggcatc cgcaagcggc 20160
aacccttcca ggagggcttt aggatcacct acgatgatct ggagggtggt aacattcccg 20220
cactgttgga tgtggacgcc taccaggcga gcttgaaaga tgacaccgaa cagggcgggg 20280
gtggcgcagg cggcagcaac agcagtggca gcggcgcgga agagaactcc aacgcggcag 20340
ccgcggcaat gcagccggtg gaggacatga acgatcatgc cattcgcggc gacacctttg 20400
ccacacgggc tgaggagaag cgcgctgagg ccgaagcagc ggccgaagct gccgcccccg 20460
ctgcgcaacc cgaggtcgag aagcctcaga agaaaccggt gatcaaaccc ctgacagagg 20520
```

```
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg ccccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gccccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgcccgcg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaacccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
```

```
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc caccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tattttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttctttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttggggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
```

```
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atccccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg cacccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
```

```
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt tttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                            38496
```

```
SEQ ID NO: 221          moltype = DNA  length = 9701
FEATURE                 Location/Qualifiers
misc_feature            1..9701
                        note = vector for IgG1 against T27Y H34A R273K ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 221
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
```

```
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggaaa gttctggacc aatctgtatt ccctcacagt ccctttcggg  4560
caaaagccta atatagacgt gacagacgca atggttgatc aggcttggga tgctcaaagg  4620
atttttaagg aagctgagaa gtttttttgtg tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca tcatgaaatg ggtcacatcc agtatgatat ggcttatgca  4860
gctcaacctt tcctcttgag aaatggtgca aatgaaggtt ttcatgaagc tgtaggggaa  4920
```

-continued

```
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggacccctc acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc ccctttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac ccctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccctggc  8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat cccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
```

```
aggctttttt ggaggcctag gcttttgcaa aaagctaatt c                    9701

SEQ ID NO: 222          moltype = DNA  length = 38496
FEATURE                 Location/Qualifiers
misc_feature            1..38496
                        note = vector for IgA against T27Y H34A R273L ACE2 mutant
source                  1..38496
                        mol_type = other DNA
                        organism = synthetic construct
SEQUENCE: 222
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
```

```
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gactgttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tggaccttg ggaaaggtga ctttcgaatc ttgatgtgta  6660
ccaaggtgac aatggatgac tttcttacag cccatcatga aatgggtcac atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag gggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaaggggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
```

```
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct tttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact agggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggtgggggg cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
```

-continued

```
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacgggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
caagaccccg cttgcaaatt cctccggaaa cagggacgag cccctttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga accccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
```

```
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca cccctattcg  19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg cccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gcccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
```

```
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct ggggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaaccccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaaccttttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tatttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttctttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
```

-continued

```
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atccccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
```

-continued

```
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat ggggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt tttttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
```

```
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                            38496

SEQ ID NO: 223         moltype = DNA  length = 9701
FEATURE                Location/Qualifiers
misc_feature           1..9701
                       note = vector for IgG1 against T27Y H34A R273L ACE2 mutant
misc_difference        2929..2930
                       note = n is a, c, g, or t
misc_difference        2934
                       note = n is a, c, g, or t
source                 1..9701
                       mol_type = other DNA
                       organism = synthetic construct
SEQUENCE: 223
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
```

-continued

```
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggact gttctggacc aatctgtatt ccctcacagt ccctttcggg  4560
caaaagccta atatagacgt gacagacgca atggttgatc aggcttggga tgctcaaagg  4620
atttttaagg aagctgagaa gttttttgtg tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca tcatgaaatg ggtcacatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggaccccttc acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc cccttttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac cctccccag tgcctctcct ggtcgtggaa  6660
ggtgctactc cagtgcccac cagccttgtc ctaataaaat taagttgcat catttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
```

-continued

```
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccccctggc  8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                     9701
```

```
SEQ ID NO: 224          moltype = DNA  length = 38496
FEATURE                 Location/Qualifiers
misc_feature            1..38496
                        note = vector for IgA against T27Y H34A H505L ACE2 mutant
source                  1..38496
                        mol_type = other DNA
                        organism = synthetic construct
SEQUENCE: 224
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
```

```
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gacgtttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tggaccttgg ggaaaggtga ctttcgaatc ttgatgtgta  6660
ccaaggtgac aatggatgac tttcttacag cccatcatga aatgggtcac atccagtatg  6720
```

-continued

```
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcct ggttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag ggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaagggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct tttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
```

```
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact aggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggggtgggg cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacggggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
```

```
caagaccccg cttgcaaatt cctccggaaa cagggacgag cccctttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga acccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca cccctattcg  19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
```

```
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg ccccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gcccccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaaccccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
```

```
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tatttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttctttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
```

```
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atcccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccoctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gcccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
```

-continued

```
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc ccccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt tttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                           38496
```

```
SEQ ID NO: 225          moltype = DNA  length = 9701
FEATURE                 Location/Qualifiers
misc_feature            1..9701
                        note = vector for IgG1 against T27Y H34A H505L ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 225
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
```

```
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactcctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggacg tttctggacc aatctgtatt ccctcacagt ccctttcggg  4560
caaaagccta atatagacgt gacagacgca atggttgatc aggcttggga tgctcaaagg  4620
atttttaagg aagctgagaa gttttttgtg tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca tcatgaaatg ggtcacatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttcctggtt  5220
agcaatgact attcatttat acgttattac actcgcactc tttaccagtt tcaatttcag  5280
gaggctctgt gtcaggctgc caagcatgag ggaccccttc acaagtgtga tattagtaac  5340
```

```
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc cccttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac ccctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccccctggc  8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                      9701
```

```
SEQ ID NO: 226          moltype = DNA  length = 38496
FEATURE                 Location/Qualifiers
misc_feature            1..38496
                        note = vector for IgA against T27Y H34A H374N ACE2 mutant
source                  1..38496
```

```
                         mol_type = other DNA
                         organism = synthetic construct
SEQUENCE: 226
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat ttttaaccca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
```

-continued

```
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gacgtttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tgggaccttg ggaaaggtga ctttcgaatc ttgatgtgta  6660
ccaaggtgac aatggatgac tttcttacag cccataatga aatgggtcac atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagcccottt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag gggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaaggggata  8040
cattttcttg catggtaggg catgaggccc ttccccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct ttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
```

```
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact agggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag ggggtggggg cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
```

```
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agccccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgcccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacggggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
caagaccccg cttgcaaatt cctccggaaa cagggacgag ccccttttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga acccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
```

-continued

```
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca cccctattcg  19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg cccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gccccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
```

```
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaacccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tattttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttcttttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
```

```
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgcgcc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atccccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
```

```
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gcccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt catttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt ttttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
```

```
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                            38496
```

```
SEQ ID NO: 227          moltype = DNA  length = 9701
FEATURE                 Location/Qualifiers
misc_feature            1..9701
                        note = vector for IgG1 against T27Y H34A H374N ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 227
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac accccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
```

-continued

```
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggacg tttctggacc aatctgtatt ccctcacagt ccctttcggg  4560
caaaagccta atatagacgt gacagacgca atggttgatc aggcttggga tgctcaaagg  4620
atttttaagg aagctgagaa gtttttgtg tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca taatgaaatg ggtcacatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggacccctt c acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc cccttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattcttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac ccctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
```

```
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgaccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccctggc  8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                      9701

SEQ ID NO: 228         moltype = DNA  length = 38496
FEATURE                Location/Qualifiers
misc_feature           1..38496
                       note = vector for IgA against T27Y H34A H378N ACE2 mutant
source                 1..38496
                       mol_type = other DNA
                       organism = synthetic construct
SEQUENCE: 228
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatcccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
```

-continued

```
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gacgtttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tgggaccttg ggaaaggtga ctttcgaatc ttgatgtgta  6660
ccaaggtgac aatggatgac tttcttacag cccatcatga aatgggtaat atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
```

```
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag gggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaaggggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct ttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg ggagtaggc atccgcgccg caggccccgc agacggtctc  11880
```

```
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact agggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggggtgggg cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacggggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
caagaccccg cttgcaaatt cctccggaaa cagggacgag ccccttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga acccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
```

```
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca cccctattcg  19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
```

```
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg ccccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gccccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaacccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
```

-continued

```
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tatttttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttctttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
```

-continued

```
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atcccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gcccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
```

```
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt tttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                           38496

SEQ ID NO: 229          moltype = DNA  length = 9701
FEATURE                 Location/Qualifiers
misc_feature            1..9701
                        note = vector for IgG1 against T27Y H34A H378N ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 229
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
```

```
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac cccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggcccettt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggacg tttctggacc aatctgtatt ccctcacagt ccctttcggg  4560
caaaagccta atatagacgt gacagacgca atggttgatc aggcttggga tgctcaaagg  4620
atttttaagg aagctgagaa gtttttgtg tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca tcatgaaatg ggtaatatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggaccccttc acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc ccctttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
```

```
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac ccctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccctggc  8580
tctttcacgt cctctacccc ggcggcctcc actacctcct cgacccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                     9701
```

```
SEQ ID NO: 230          moltype = DNA  length = 38496
FEATURE                 Location/Qualifiers
misc_feature            1..38496
                        note = vector for IgA against T27Y H34A H345A ACE2 mutant
source                  1..38496
                        mol_type = other DNA
                        organism = synthetic construct
SEQUENCE: 230
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
```

-continued

```
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
```

```
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gacgtttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtgc ccctaccgct tggaccttg ggaaaggtga ctttcgaatc ttgatgtgta  6660
ccaaggtgac aatggatgac tttcttacag cccatcatga aatgggtcac atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag ggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaaggggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct tttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
```

```
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact agggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggtgggggc cgcgttcgtc  12300
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
```

```
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgcccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacgggggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
caagaccccg cttgcaaatt cctccggaaa cagggacgag ccccttttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga acccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
```

-continued

```
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca cccctattcg  19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg cccccgcgc aactagattg caagaaaaaa ctacttagac tcgtactgtt  21720
gtatgtatcc agcggcggcg gcgcgcaacg aagctatgtc caagcgcaaa atcaaagaag  21780
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gcccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
```

```
tccctgaagc gccgacgatg cttctgatag ctaacgtgtc gtatgtgtgt catgtatgcg  24000
tccatgtcgc cgccagagga gctgctgagc cgcccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaacccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tatttttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttcttttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
```

```
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
caagccatca acaaagcccg ccaagagttt ctgctacgaa agggacgggg ggtttacttg  31320
gacccccagt ccggcgagga gctcaaccca atccccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga cagggga ccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
```

```
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acacttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt ttttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
```

```
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                            38496

SEQ ID NO: 231          moltype = DNA  length = 9701
FEATURE                 Location/Qualifiers
misc_feature            1..9701
                        note = vector for IgG1 against T27Y H34A H345A ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 231
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct gaagccagtt accagtggct gctgccagtg gcgataagtc  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
```

-continued

```
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggacg tttctggacc aatctgtatt ccctcacagt ccctttcggg  4560
caaaagccta atatagacgt gacagacgca atggttgatc aggcttggga tgctcaaagg  4620
atttttaagg aagctgagaa gtttttttgtg tcagtcggtt tgccaaatat gacacaaggc  4680
ttctgggaaa atagcatgtt gactgatccc ggtaatgttc aaaaggctgt gtgtgcccct  4740
accgcttggg accttgggaa aggtgacttt cgaatcttga tgtgtaccaa ggtgacaatg  4800
gatgactttc ttacagccca tcatgaaatg ggtcacatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggaccccttc acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc ccctttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac cctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
```

```
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccctggc   8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                      9701
```

```
SEQ ID NO: 232          moltype = DNA  length = 38496
FEATURE                 Location/Qualifiers
misc_feature            1..38496
                        note = vector for IgA against T27Y H34A R273Q ACE2 mutant
source                  1..38496
                        mol_type = other DNA
                        organism = synthetic construct
SEQUENCE: 232
tattattgat gatgttaatt aacatgcatg gatcctacgt ctcgaccgat gcccttgaga  60
gccttcaacc cagtcagctc cttccggtgg gcgcggggca tgactatcgt cgccgcactt  120
atgactgtct tctttatcat gcaactcgta ggacaggtgc cggcagcgct ctgggtcatt  180
ttcggcgagg accgctttcg ctggagcgcg acgatgatcg gcctgtcgct tgcggtattc  240
ggaatcttgc acgccctcgc tcaagccttc gtcactggtc ccgccaccaa acgtttcggc  300
gagaagcagg ccattatcgc cggcatggcg gccgacgcgc tgggctacgt cttgctggcg  360
ttcgcgacgc gaggctggat ggccttcccc attatgattc ttctcgcttc cggcggcatc  420
gggatgcccg cgttgcaggc catgctgtcc aggcaggtag atgacgacca tcagggacag  480
cttcaaggat cgctcgcggc tcttaccagc ctaacttcga tcattggacc gctgatcgtc  540
acggcgattt atgccgcctc ggcgagcaca tggaacgggt tggcatggat tgtaggcgcc  600
gccctatacc ttgtctgcct ccccgcgttg cgtcgcggtg catggagccg ggccacctcg  660
acctgaatgg aagccggcgg cacctcgcta acggattcac cactccaaga attggagcca  720
atcaattctt gcggagaact gtgaatgcgc aaaccaaccc ttggcagaac atatccatcg  780
cgtccgccat ctccagcagc cgcacgcggc gcatctcggg cagcgttggg tcctggccac  840
gggtgcgcat gatcgtgctc ctgtcgttga ggacccggct aggctggcgg ggttgcctta  900
ctggttagca gaatgaatca ccgatacgcg agcgaacgtg aagcgactgc tgctgcaaaa  960
cgtctgcgac ctgagcaaca acatgaatgg tcttcggttt ccgtgtttcg taaagtctgg  1020
aaacgcggaa gtcagcgccc tgcaccatta tgttccggat ctgcatcgca ggatgctgct  1080
ggctaccctg tggaacacct acatctgtat taacgaagcg ctggcattga ccctgagtga  1140
tttttctctg gtcccgccgc atccataccg ccagttgttt accctcacaa cgttccagta  1200
accgggcatg ttcatcatca gtaacccgta tcgtgagcat cctctctcgt ttcatcggta  1260
tcattacccc catgaacaga aatccccctt acacggaggc atcagtgacc aaacaggaaa  1320
aaaccgccct taacatggcc cgctttatca gaagccagac attaacgctt ctggagaaac  1380
tcaacgagct ggacgcggat gaacaggcag acatctgtga atcgcttcac gaccacgctg  1440
atgagcttta ccgcagctgc ctcgcgcgtt tcggtgatga cggtgaaaac ctctgacaca  1500
tgcagctccc ggagacggtc acagcttgtc tgtaagcgga tgccgggagc agacaagccc  1560
gtcagggcgc gtcagcgggt gttggcgggt gtcggggcgc agccatgacc cagtcacgta  1620
gcgatagcgg agtgtatact ggcttaacta tgcggcatca gagcagattg tactgagagt  1680
gcaccatatg cggtgtgaaa taccgcacag atgcgtaagg agaaaatacc gcatcaggcg  1740
ctcttccgct tcctcgctca ctgactcgct gcgctcggtc gttcggctgc ggcgagcggt  1800
atcagctcac tcaaaggcgg taatacggtt atccacagaa tcaggggata acgcaggaaa  1860
gaacatgtga gcaaaaggcc agcaaaaggc caggaaccgt aaaaaggccg cgttgctggc  1920
gtttttccat aggctccgcc cccctgacga gcatcacaaa aatcgacgct caagtcagag  1980
gtggcgaaac ccgacaggac tataaagata ccaggcgttt ccccctggaa gctccctcgt  2040
gcgctctcct gttccgaccc tgccgcttac cggatacctg tccgcctttc tcccttcggg  2100
aagcgtggcg ctttctcata gctcacgctg taggtatctc agttcggtgt aggtcgttcg  2160
ctccaagctg ggctgtgtgc acgaaccccc cgttcagccc gaccgctgcg ccttatccgg  2220
taactatcgt cttgagtcca acccggtaag acacgactta tcgccactgg cagcagccac  2280
tggtaacagg attagcagag cgaggtatgt aggcggtgct acagagttct tgaagtggtg  2340
gcctaactac ggctacacta gaaggacagt atttggtatc tgcgctctgc tgaagccagt  2400
taccttcgga aaaagagttg gtagctcttg atccggcaaa caaaccaccg ctggtagcgg  2460
tggttttttt gtttgcaagc agcagattac gcgcagaaaa aaaggatctc aagaagatcc  2520
tttgatcttt tctacggggt ctgacgctca gtggaacgaa aactcacgtt aagggatttt  2580
ggtcatgaga ttatcaaaaa ggatcttcac ctagatcctt ttaaattaaa aatgaagttt  2640
taaatcaatc taaagtatat atgagtaaac ttggtctgac agttaccaat gcttaatcag  2700
tgaggcacct atctcagcga tctgtctatt tcgttcatcc atagttgcct gactccccgt  2760
cgtgtagata actacgatac gggagggctt accatctggc cccagtgctg caatgatacc  2820
```

```
gcgagaccca cgctcaccgg ctccagattt atcagcaata aaccagccag ccggaagggc  2880
cgagcgcaga agtggtcctg caactttatc cgcctccatc cagtctatta attgttgccg  2940
ggaagctaga gtaagtagtt cgccagttaa tagtttgcgc aacgttgttg ccattgctgc  3000
agccatgaga ttatcaaaaa ggatcttcac ctagatcctt ttcacgtaga aagccagtcc  3060
gcagaaacgg tgctgacccc ggatgaatgt cagctactgg gctatctgga caagggaaaa  3120
cgcaagcgca aagagaaagc aggtagcttg cagtgggctt acatggcgat agctagactg  3180
ggcggtttta tggacagcaa gcgaaccgga attgccagct ggggcgccct ctggtaaggt  3240
tgggaagccc tgcaaagtaa actggatggc tttcttgccg ccaaggatct gatggcgcag  3300
gggatcaagc tctgatcaag agacaggatg aggatcgttt cgcatgattg aacaagatgg  3360
attgcacgca ggttctccgg ccgcttgggt ggagaggcta ttcggctatg actgggcaca  3420
acagacaatc ggctgctctg atgccgccgt gttccggctg tcagcgcagg ggcgcccggt  3480
tctttttgtc aagaccgacc tgtccggtgc cctgaatgaa ctgcaagacg aggcagcgcg  3540
gctatcgtgg ctggccacga cgggcgttcc ttgcgcagct gtgctcgacg ttgtcactga  3600
agcgggaagg gactggctgc tattgggcga agtgccgggg caggatctcc tgtcatctca  3660
ccttgctcct gccgagaaag tatccatcat ggctgatgca atgcggcggc tgcatacgct  3720
tgatccggct acctgcccat tcgaccacca agcgaaacat cgcatcgagc gagcacgtac  3780
tcggatggaa gccggtcttg tcgatcagga tgatctggac gaagagcatc aggggctcgc  3840
gccagccgaa ctgttcgcca ggctcaaggc gagcatgccc gacggcgagg atctcgtcgt  3900
gacccatggc gatgcctgct tgccgaatat catggtggaa aatggccgct tttctggatt  3960
catcgactgt ggccggctgg gtgtggcgga ccgctatcag gacatagcgt tggctacccg  4020
tgatattgct gaagagcttg gcggcgaatg ggctgaccgc ttcctcgtgc tttacggtat  4080
cgccgctccc gattcgcagc gcatcgcctt ctatcgcctt cttgacgagt tcttctgaat  4140
tttgttaaaa tttttgttaa atcagctcat tttttaacca ataggccgaa atcggcaaaa  4200
tcccttataa atcaaaagaa tagaccgaga tagggttgag tgttgttcca gtttggaaca  4260
agagtccact attaaagaac gtggactcca acgtcaaagg gcgaaaaacc gtctatcagg  4320
gcgatggccc actacgtgaa ccatcaccct aatcaagttt tttggggtcg aggtgccgta  4380
aagcactaaa tcggaaccct aaagggagcc cccgatttag agcttgacgg ggaaagccgg  4440
cgaacgtggc gagaaaggaa gggaagaaag cgaaaggagc gggcgctagg gcgctggcaa  4500
gtgtagcggt cacgctgcgc gtaaccacca cacccgccgc gcttaatgcg ccgctacagg  4560
gcgcgtccat tcgccattca ggatcgaatt aattcttaat taacatcatc aataatatac  4620
cttattttgg attgaagcca atatgataat gagggggtgg agtttgtgac gtggcgcggg  4680
gcgtgggaac ggggcgggtg acgtagtagt gtggcggaag tgtgatgttg caagtgtggc  4740
ggaacacatg taagcgacgg atgtggcaaa agtgacgttt ttggtgtgcg ccggtgtaca  4800
caggaagtga caattttcgc gcggttttag gcggatgttg tagtaaattt gggcgtaacc  4860
gagtaagatt tggccatttt cgcgggaaaa ctgaataaga ggaagtgaaa tctgaataat  4920
tttgtgttac tcatagcgcg taatactgta atagtaatca attacggggt cattagttca  4980
tagcccatat atggagttcc gcgttacata acttacggta aatggcccgc ctggctgacc  5040
gcccaacgac ccccgcccat tgacgtcaat aatgacgtat gttcccatag taacgccaat  5100
agggactttc cattgacgtc aatgggtgga gtatttacgg taaactgccc acttggcagt  5160
acatcaagtg tatcatatgc caagtacgcc ccctattgac gtcaatgacg gtaaatggcc  5220
cgcctggcat tatgcccagt acatgacctt atgggacttt cctacttggc agtacatcta  5280
cgtattagtc atcgctatta ccatggtgat gcggttttgg cagtacatca atgggcgtgg  5340
atagcggttt gactcacggg gatttccaag tctccacccc attgacgtca atgggagttt  5400
gttttggcac caaaatcaac gggactttcc aaaatgtcgt aacaactccg ccccattgac  5460
gcaaatgggc ggtaggcgtg tacggtggga ggtctatata agcagagctg gtttagtgaa  5520
ccgtcagatc cgctagagat ctggtaccgt cgacgcggcc gctcgagcct aagcttatga  5580
gcagcagtag ttggcttctc ttgagtttgg tggcagtgac agcagcccag agtactatcg  5640
aggagcaggc taaatacttt ctggataagt ttaacgccga ggccgaagac ttgttctatc  5700
aatcttctct cgcttcatgg aattacaata ctaacatcac tgaggagaac gtccagaata  5760
tgaacaatgc tggcgacaaa tggagcgcct tcttgaagga gcagtctacc cttgcacaaa  5820
tgtatccact gcaggagata cagaacctta cagtaaagtt gcagctccag gctctccagc  5880
agaacggatc tagcgtgctt tcagaggata aaagcaaaag gctgaacacc atacttaata  5940
ccatgtccac aatttactct actggtaaag tatgtaaccc cgacaaccct caagaatgcc  6000
tccttcttga gccaggcctc aatgagatca tggctaatag tctggactat aatgaaagac  6060
tgtgggcatg ggagtcctgg agatctgaag tagggaagca actgaggccc ctttatgaag  6120
agtacgtcgt acttaagaat gaaatggccc gcgctaacca ctacgaggat tacggcgatt  6180
actggcgtgg ggactatgaa gtaaatggtg tagatggata cgactatagt cgtgggcaat  6240
tgattgagga tgtggagcac acttttgagg agataaaacc actctatgag catcttcacg  6300
catatgtgag agctaaactg atgaacgcct acccaagtta catcagtcca atcggatgtc  6360
tcccagctca cctccttggc gacatgtggg gacagttctg gaccaatctg tattccctca  6420
cagtcccttt cgggcaaaag cctaatatag acgtgacaga cgcaatggtt gatcaggctt  6480
gggatgctca aaggattttt aaggaagctg agaagttttt tgtgtcagtc ggtttgccaa  6540
atatgacaca aggcttctgg gaaaatagca tgttgactga tcccggtaat gttcaaaagg  6600
ctgtgtgtca ccctaccgct tgggaccttg ggaaaggtga ctttcgaatc ttgatgtgta  6660
ccaaggtgac aatggatgac tttcttacag cccatcatga aatgggtcac atccagtatg  6720
atatggctta tgcagctcaa cctttcctct tgagaaatgg tgcaaatgaa ggttttcatg  6780
aagctgtagg ggaaataatg tccctgagtg ctgcaacccc aaagcatctc aagagtatcg  6840
gattgttgag cccagatttt caagaagata acgagaccga aatcaacttc cttctgaaac  6900
aagccctcac aatagttggt actcttccat tcacatacat gctggagaaa tggcgttgga  6960
tggtttttaa gggggagata cctaaagatc agtggatgaa aaagtggtgg gagatgaagc  7020
gtgagatcgt aggggtcgtg gagccagtgc ctcatgatga gacttactgt gacccagcat  7080
cactcttcca cgttagcaat gactattcat ttatacgtta ttacactcgc actctttacc  7140
agtttcaatt tcaggaggct ctgtgtcagg ctgccaagca tgagggaccc cttcacaagt  7200
gtgatattag taacagtact gaggcaggcc aaaaactgtt caatatgttg aggcttggca  7260
aaagcgagcc atggactctc gccttggaaa atgttgtcgg ggctaaaaac atgaatgtac  7320
gccctctgct taactatttt gagccccttt ttacatggct caaggaccag aataagaact  7380
cctttgtcgg ctggtcaaca gactggtctc cctatgcaga ccctagtact cctcctactc  7440
cttctccatc aaccccacca actccatccc ctagctgctg tcacccaagg ctgtctctgc  7500
accgacctgc actcgaagac cttctgttgg gctctgaagc taacctgacc tgtactctta  7560
```

```
ctggcttgcg cgatgctagc ggcgtgactt tcacctggac acctagtagc ggtaaaagtg  7620
ctgtacaagg acctcctgaa cgcgacctgt gtggttgcta ctctgtgtct tctgtacttc  7680
ccggctgtgc cgagccctgg aatcacggga aaacctttac ctgcaccgcc gcttaccctg  7740
agtcaaaaac tcccctcact gccacattga gtaagtcagg gaatacattc aggccagagg  7800
ttcatttgtt gcctcctcca tctgaagaac ttgctttgaa cgagctggtc actctgacct  7860
gcttggctag gggtttctcc cccaaagatg tacttgtacg gtggttgcag ggcagccaag  7920
agttgccccg cgaaaagtat ttgacctggg cctcaagaca agaacccagc caggggacta  7980
ccacatttgc cgtgaccagt attctgcgtg tagccgctga agattggaag aaagggggata  8040
cattttcttg catggtaggg catgaggccc ttcccctcgc tttcactcag aagacaatag  8100
acagactcgc cggaaagcct actcacgtga atgttagcgt agtcatggct gaggttgacg  8160
gaacttgcta ctgagatatc cgatccaccg gatctagata actgatcata atcagccata  8220
ccacatttgt agaggtttta cttgctttaa aaaacctccc acacctcccc ctgaacctga  8280
aacataaaat gaatgcaatt gttgttgtta acttgtttat tgcagcttat aatggttaca  8340
aataaagcaa tagcatcaca aatttcacaa ataaagcatt tttttcactg cattctagtt  8400
gtggtttgtc caaactcatc aatgtatctt aggtttagtg aaccgtcaga tccgctagcg  8460
ttacataact tacggtaaat ggcccgcctg gctgaccgcc caacgacccc cgcccattga  8520
cgtcaataat gacgtatgtt cccatagtaa cgccaatagg gactttccat tgacgtcaat  8580
gggtggagta tttacggtaa actgcccact tggcagtaca tcaagtgtat catatgccaa  8640
gtacgccccc tattgacgtc aatgacggta aatggcccgc ctggcattat gcccagtaca  8700
tgaccttatg ggactttcct acttggcagt acatctacgt attagtcatc gctattacca  8760
tggtgatgcg gttttggcag tacatcaatg ggcgtggata gcggtttgac tcacggggat  8820
ttccaagtct ccaccccatt gacgtcaatg ggagtttgtt ttggcaccaa aatcaacggg  8880
actttccaaa atgtcgtaac aactccgccc cattgacgca aatgggcggt aggcgtgtac  8940
ggtgggaggt ctatataagc agagctggtt tagtgaaccg tcagatccgc tagagatctg  9000
gtaccgtcga cgcggccgct cgagcctaag cttatgaaga accatctgct tttctgggga  9060
gtacttgccg ttttcataaa agccgtacat gttaaagcac aagaggacga acgcattgtg  9120
ttggttgata ataaatgcaa atgtgctcgg ataacatctc ggatcattcg tagctcagag  9180
gaccccaatg aggatatagt agagcgaaac atcagaatta tagtacccct gaacaacaga  9240
gagaacataa gtgatcccac aagtccattg cggacacgct ttgtttacca tttgtctgat  9300
ctgtgtaaaa aatgtgatcc aacagaggtg gaactcgaca atcagatcgt caccgccacc  9360
cagtctaaca tctgcgatga agattcagct acagagacat gctacacata cgaccggaac  9420
aagtgctata ctgccgttgt gccactcgtt tacggtggag aaacaaagat ggttgaaact  9480
gcacttacac cagatgcctg ctatccagat tgagatatcc gatccaccgg atctagataa  9540
ctgatcataa tcagccatac cacatttgta gaggttttac ttgctttaaa aaacctccca  9600
cacctccccc tgaacctgaa acataaaatg aatgcaattg ttgttgttaa cttgtttatt  9660
gcagcttata atggttacaa ataaagcaat agcatcacaa atttcacaaa taaagcattt  9720
ttttcactgc attctagttg tggtttgtcc aaactcatca atgtatctta acgcggatct  9780
gggcgtggtt aagggtggga aagaatatat aaggtggggg tcttatgtag ttttgtatct  9840
gttttgcagc agccgccgcc gccatgagca ccaactcgtt tgatggaagc attgtgagct  9900
catatttgac aacgcgcatg cccccatggg ccggggtgcg tcagaatgtg atgggctcca  9960
gcattgatgg tcgccccgtc ctgcccgcaa actctactac cttgacctac gagaccgtgt  10020
ctggaacgcc gttggagact gcagcctccg ccgccgcttc agccgctgca gccaccgccc  10080
gcgggattgt gactgacttt gctttcctga gcccgcttgc aagcagtgca gcttcccgtt  10140
catccgcccg cgatgacaag ttgacggctc ttttggcaca attggattct ttgacccggg  10200
aacttaatgt cgtttctcag cagctgttgg atctgcgcca gcaggtttct gccctgaagg  10260
cttcctcccc tcccaatgcg gtttaaaaca taaataaaaa accagactct gtttggattt  10320
ggatcaagca agtgtcttgc tgtctttatt taggggtttt gcgcgcgcgg taggcccggg  10380
accagcggtc tcggtcgttg agggtcctgt gtattttttc caggacgtgg taaaggtgac  10440
tctggatgtt cagatacatg ggcataagcc cgtctctggg gtggaggtag caccactgca  10500
gagcttcatg ctgcggggtg gtgttgtaga tgatccagtc gtagcaggag cgctgggcgt  10560
ggtgcctaaa aatgtctttc agtagcaagc tgattgccag gggcaggccc ttggtgtaag  10620
tgtttacaaa gcggttaagc tgggatgggt gcatacgtgg ggatatgaga tgcatcttgg  10680
actgtatttt taggttggct atgttcccag ccatatccct ccggggattc atgttgtgca  10740
gaaccaccag cacagtgtat ccggtgcact tgggaaattt gtcatgtagc ttagaaggaa  10800
atgcgtggaa gaacttggag acgcccttgt gacctccaag attttccatg cattcgtcca  10860
taatgatggc aatgggccca cgggcggcgg cctgggcgaa gatatttctg ggatcactaa  10920
cgtcatagtt gtgttccagg atgagatcgt cataggccat ttttacaaag cgcgggcgga  10980
gggtgccaga ctgcggtata atggttccat ccggcccagg ggcgtagtta ccctcacaga  11040
tttgcatttc ccacgctttg agttcagatg gggggatcat gtctacctgc ggggcgatga  11100
agaaaacggt ttccggggta ggggagatca gctgggaaga aagcaggttc ctgagcagct  11160
gcgacttacc gcagccggtg ggcccgtaaa tcacacctat taccggctgc aactggtagt  11220
taagagagct gcagctgccg tcatccctga gcaggggggc cacttcgtta agcatgtccc  11280
tgactcgcat gttttccctg accaaatccg ccagaaggcg ctcgccgccc agcgatagca  11340
gttcttgcaa ggaagcaaag tttttcaacg gtttgagacc gtccgccgta ggcatgcttt  11400
tgagcgtttg accaagcagt tccaggcggt cccacagctc ggtcacctgc tctacggcat  11460
ctcgatccag catatctcct cgtttcgcgg gttggggcgg ctttcgctgt acggcagtag  11520
tcggtgctcg tccagacggg ccagggtcat gtctttccac gggcgcaggg tcctcgtcag  11580
cgtagtctgg gtcacggtga aggggtgcgc tccgggctgc gcgctggcca gggtgcgctt  11640
gaggctggtc ctgctggtgc tgaagcgctg ccggtcttcg ccctgcgcgt cggccaggta  11700
gcatttgacc atggtgtcat agtccagccc ctccgcggcg tggcccttgg cgcgcagctt  11760
gcccttggag gaggcgccgc acgaggggca gtgcagactt ttgagggcgt agagcttggg  11820
cgcgagaaat accgattccg gggagtaggc atccgcgccg caggccccgc agacggtctc  11880
gcattccacg agccaggtga gctctggccg ttcggggtca aaaaccaggt ttcccccatg  11940
ctttttgatg cgtttcttac ctctggtttc catgagccgg tgtccacgct cggtgacgaa  12000
aaggctgtcc gtgtccccgt atacagactt gagaggcctg tcctcgagcg gtgttccgcg  12060
gtcctcctcg tatagaaact cggaccactc tgagacaaag gctcgcgtcc aggccagcac  12120
gaaggaggct aagtgggagg ggtagcggtc gttgtccact agggggtcca ctcgctccag  12180
ggtgtgaaga cacatgtcgc cctcttcggc atcaaggaag gtgattggtt tgtaggtgta  12240
ggccacgtga ccgggtgttc ctgaaggggg gctataaaag gggtgggggg cgcgttcgtc  12300
```

-continued

```
ctcactctct tccgcatcgc tgtctgcgag ggccagctgt tggggtgagt actccctctg  12360
aaaagcgggc atgacttctg cgctaagatt gtcagtttcc aaaaacgagg aggatttgat  12420
attcacctgg cccgcggtga tgcctttgag ggtggccgca tccatctggt cagaaaagac  12480
aatctttttg ttgtcaagct tggtggcaaa cgacccgtag agggcgttgg acagcaactt  12540
ggcgatggag cgcagggttt ggtttttgtc gcgatcggcg cgctccttgg ccgcgatgtt  12600
tagctgcacg tattcgcgcg caacgcaccg ccattcggga aagacggtgg tgcgctcgtc  12660
gggcaccagg tgcacgcgcc aaccgcggtt gtgcagggtg acaaggtcaa cgctggtggc  12720
tacctctccg cgtaggcgct cgttggtcca gcagaggcgg ccgcccttgc gcgagcagaa  12780
tggcggtagg gggtctagct gcgtctcgtc cggggggtct gcgtccacgg taaagacccc  12840
gggcagcagg cgcgcgtcga agtagtctat cttgcatcct tgcaagtcta gcgcctgctg  12900
ccatgcgcgg gcggcaagcg cgcgctcgta tgggttgagt gggggacccc atggcatggg  12960
gtgggtgagc gcggaggcgt acatgccgca aatgtcgtaa acgtagaggg gctctctgag  13020
tattccaaga tatgtagggt agcatcttcc accgcggatg ctggcgcgca cgtaatcgta  13080
tagttcgtgc gagggagcga ggaggtcggg accgaggttg ctacgggcgg gctgctctgc  13140
tcggaagact atctgcctga agatggcatg tgagttggat gatatggttg gacgctggaa  13200
gacgttgaag ctggcgtctg tgagacctac cgcgtcacgc acgaaggagg cgtaggagtc  13260
gcgcagcttg ttgaccagct cggcggtgac ctgcacgtct agggcgcagt agtccagggt  13320
ttccttgatg atgtcatact tatcctgtcc cttttttttc cacagctcgc ggttgaggac  13380
aaactcttcg cggtctttcc agtactcttg gatcggaaac ccgtcggcct ccgaacggta  13440
agagcctagc atgtagaact ggttgacggc ctggtaggcg cagcatccct tttctacggg  13500
tagcgcgtat gcctgcgcgg ccttccggca tgaccagcat gaagggcacg agctgcttcc  13560
caaaggcccc catccaagta taggtctcta catcgtaggt gacaaagaga cgctcggtgc  13620
gaggatgcga gccgatcggg aagaactgga tctcccgcca ccaattggag gagtggctat  13680
tgatgtggtg aaagtagaag tccctgcgac gggccgaaca ctcgtgctgg cttttgtaaa  13740
aacgtgcgca gtactggcag cggtgcacgg gctgtacatc ctgcacgagg ttgacctgac  13800
gaccgcgcac aaggaagcag agtgggaatt tgagcccctc gcctggcggg tttggctggt  13860
ggtcttctac ttcggctgct tgtccttgac cgtctggctg ctcgagggga gttacggtgg  13920
atcggaccac cacgccgcgc gagcccaaag tccagatgtc cgcgcgcggc ggtcggagct  13980
tgatgacaac atcgcgcaga tgggagctgt ccatggtctg gagctcccgc ggcgtcaggt  14040
caggcgggag ctcctgcagg tttacctcgc atagacgggt cagggcgcgg gctagatcca  14100
ggtgatacct aatttccagg ggctggttgg tggcggcgtc gatggcttgc aagaggccgc  14160
atccccgcgg cgcgactacg gtaccgcgcg gcgggcggtg ggccgcgggg gtgtccttgg  14220
atgatgcatc taaaagcggt gacgcgggcg agcccccgga ggtagggggg gctccggacc  14280
cgccgggaga gggggcaggg gcacgtcggc gccgcgcgcg ggcaggagct ggtgctgcgc  14340
gcgtaggttg ctggcgaacg cgacgacgcg gcggttgatc tcctgaatct ggcgcctctg  14400
cgtgaagacg acgggcccgg tgagcttgaa cctgaaagag agttcgacag aatcaatttc  14460
ggtgtcgttg acggcggcct ggcgcaaaat ctcctgcacg tctcctgagt tgtcttgata  14520
ggcgatctcg gccatgaact gctcgatctc ttcctcctgg agatctccgc gtccggctcg  14580
ctccacggtg gcggcgaggt cgttggaaat gcgggccatg agctgcgaga aggcgttgag  14640
gcctccctcg ttccagacgc ggctgtagac cacgcccccct tcggcatcgc gggcgcgcat  14700
gaccacctgc gcgagattga gctccacgtg ccgggcgaag acggcgtagt ttcgcaggcg  14760
ctgaaagagg tagttgaggg tggtggcggt gtgttctgcc acgaagaagt acataaccca  14820
gcgtcgcaac gtggattcgt tgataattgt tgtgtaggta ctccgccgcc gagggacctg  14880
agcgagtccg catcgaccgg atcggaaaac ctctcgagaa aggcgtctaa ccagtcacag  14940
tcgcaaggta ggctgagcac cgtggcgggc ggcagcgggc ggcggtcggg gttgtttctg  15000
gcggaggtgc tgctgatgat gtaattaaag taggcggtct tgagacggcg gatggtcgac  15060
agaagcacca tgtccttggg tccggcctgc tgaatgcgca ggcggtcggc catgccccag  15120
gcttcgtttt gacatcggcg caggtctttg tagtagtctt gcatgagcct ttctaccggc  15180
acttcttctt ctccttcctc ttgtcctgca tctcttgcat ctatcgctgc ggcggcggcg  15240
gagtttggcc gtaggtggcg ccctcttcct cccatgcgtg tgaccccgaa gcccctcatc  15300
ggctgaagca gggctaggtc ggcgacaacg cgctcggcta atatggcctg ctgcacctgc  15360
gtgagggtag actggaagtc atccatgtcc acaaagcggt ggtatgcgcc cgtgttgatg  15420
gtgtaagtgc agttggccat aacggaccag ttaacggtct ggtgacccgg ctgcgagagc  15480
tcggtgtacc tgagacgcga gtaagccctc gagtcaaata cgtagtcgtt gcaagtccgc  15540
accaggtact ggtatcccac caaaaagtgc ggcggcggct ggcggtagag gggccagcgt  15600
agggtggccg gggctccggg ggcgagatct tccaacataa ggcgatgata tccgtagatg  15660
tacctggaca tccaggtgat gccggcggcg gtggtggagg cgcgcggaaa gtcgcggacg  15720
cggttccaga tgttgcgcag cggcaaaaag tgctccatgg tcgggacgct ctggccggtc  15780
aggcgcgcgc aatcgttgac gctctagcgt gcaaaaggag agcctgtaag cgggcactct  15840
tccgtggtct ggtggataaa ttcgcaaggg tatcatggcg gacgaccggg gttcgagccc  15900
cgtatccggc cgtccgccgt gatccatgcg gttaccgccc gcgtgtcgaa cccaggtgtg  15960
cgacgtcaga caacgggggga gtgctccttt tggcttcctt ccaggcgcgg cggctgctgc  16020
gctagctttt ttggccactg gccgcgcgca gcgtaagcgg ttaggctgga aagcgaaagc  16080
attaagtggc tcgctccctg tagccggagg gttattttcc aagggttgag tcgcgggacc  16140
cccggttcga gtctcggacc ggccggactg cggcgaacgg gggtttgcct ccccgtcatg  16200
caagaccccg cttgcaaatt cctccggaaa cagggacgag ccccttttttt gcttttccca  16260
gatgcatccg gtgctgcggc agatgcgccc ccctcctcag cagcggcaag agcaagagca  16320
gcggcagaca tgcagggcac cctcccctcc tcctaccgcg tcaggagggg cgacatccgc  16380
ggttgacgcg gcagcagatg gtgattacga acccccgcgg cgccgggccc ggcactacct  16440
ggacttggag gagggcgagg gcctggcgcg gctaggagcg ccctctcctg agcggcaccc  16500
aagggtgcag ctgaagcgtg atacgcgtga ggcgtacgtg ccgcggcaga acctgtttcg  16560
cgaccgcgag ggagaggagc ccgaggagat gcgggatcga aagttccacg cagggcgcga  16620
gctgcggcat ggcctgaatc gcgagcggtt gctgcgcgag gaggactttg agcccgacgc  16680
gcgaaccggg attagtcccg cgcgcgcaca cgtggcggcc gccgacctgg taaccgcata  16740
cgagcagacg gtgaaccagg agattaactt tcaaaaaagc tttaacaacc acgtgcgtac  16800
gcttgtggcg cgcgaggagg tggctatagg actgatgcat ctgtgggact ttgtaagcgc  16860
gctggagcaa aacccaaata gcaagccgct catggcgcag ctgttcctta tagtgcagca  16920
cagcagggac aacgaggcat tcagggatgc gctgctaaac atagtagagc ccgagggccg  16980
ctggctgctc gatttgataa acatcctgca gagcatagtg gtgcaggagc gcagcttgag  17040
```

```
cctggctgac aaggtggccg ccatcaacta ttccatgctt agcctgggca agttttacgc  17100
ccgcaagata taccataccc cttacgttcc catagacaag gaggtaaaga tcgaggggtt  17160
ctacatgcgc atggcgctga aggtgcttac cttgagcgac gacctgggcg tttatcgcaa  17220
cgagcgcatc cacaaggccg tgagcgtgag ccggcggcgc gagctcagcg accgcgagct  17280
gatgcacagc ctgcaaaggg ccctggctgg cacgggcagc ggcgatagag aggccgagtc  17340
ctactttgac gcgggcgctg acctgcgctg ggccccaagc cgacgcgccc tggaggcagc  17400
tggggccgga cctgggctgg cggtggcacc cgcgcgcgct ggcaacgtcg gcggcgtgga  17460
ggaatatgac gaggacgatg agtacgagcc agaggacggc gagtactaag cggtgatgtt  17520
tctgatcaga tgatgcaaga cgcaacggac ccggcggtgc gggcggcgct gcagagccag  17580
ccgtccggcc ttaactccac ggacgactgg cgccaggtca tggaccgcat catgtcgctg  17640
actgcgcgca atcctgacgc gttccggcag cagccgcagg ccaaccggct ctccgcaatt  17700
ctggaagcgg tggtcccggc gcgcgcaaac cccacgcacg agaaggtgct ggcgatcgta  17760
aacgcgctgg ccgaaaacag ggccatccgg cccgacgagg ccggcctggt ctacgacgcg  17820
ctgcttcagc gcgtggctcg ttacaacagc ggcaacgtgc agaccaacct ggaccggctg  17880
gtgggggatg tgcgcgaggc cgtggcgcag cgtgagcgcg cgcagcagca gggcaacctg  17940
ggctccatgg ttgcactaaa cgccttcctg agtacacagc ccgccaacgt gccgcgggga  18000
caggaggact acaccaactt tgtgagcgca ctgcggctaa tggtgactga gacaccgcaa  18060
agtgaggtgt accagtctgg gccagactat tttttccaga ccagtagaca aggcctgcag  18120
accgtaaacc tgagccaggc tttcaaaaac ttgcaggggc tgtggggggt gcgggctccc  18180
acaggcgacc gcgcgaccgt gtctagcttg ctgacgccca actcgcgcct gttgctgctg  18240
ctaatagcgc ccttcacgga cagtggcagc gtgtcccggg acacatacct aggtcacttg  18300
ctgacactgt accgcgaggc cataggtcag gcgcatgtgg acgagcatac tttccaggag  18360
attacaagtg tcagccgcgc gctggggcag gaggacacgg gcagcctgga ggcaacccta  18420
aactacctgc tgaccaaccg gcggcagaag atcccctcgt tgcacagttt aaacagcgag  18480
gaggagcgca ttttgcgcta cgtgcagcag agcgtgagcc ttaacctgat gcgcgacggg  18540
gtaacgccca gcgtggcgct ggacatgacc gcgcgcaaca tggaaccggg catgtatgcc  18600
tcaaaccggc cgtttatcaa ccgcctaatg gactacttgc atcgcgcggc cgccgtgaac  18660
cccgagtatt tcaccaatgc catcttgaac ccgcactggc taccgccccc tggtttctac  18720
accgggggat tcgaggtgcc cgagggtaac gatggattcc tctgggacga catagacgac  18780
agcgtgtttt ccccgcaacc gcagaccctg ctagagttgc aacagcgcga gcaggcagag  18840
gcggcgctgc gaaaggaaag cttccgcagg ccaagcagct tgtccgatct aggcgctgcg  18900
gccccgcggt cagatgctag tagcccattt ccaagcttga tagggtctct taccagcact  18960
cgcaccaccc gcccgcgcct gctgggcgag gaggagtacc taaacaactc gctgctgcag  19020
ccgcagcgcg aaaaaaacct gcctccggca tttcccaaca acgggataga gagcctagtg  19080
gacaagatga gtagatggaa gacgtacgcg caggagcaca gggacgtgcc aggcccgcgc  19140
ccgcccaccc gtcgtcaaag gcacgaccgt cagcggggtc tggtgtggga ggacgatgac  19200
tcggcagacg acagcagcgt cctggatttg ggagggagtg gcaacccgtt tgcgcacctt  19260
cgccccaggc tggggagaat gttttaaaaa aaaaaaagca tgatgcaaaa taaaaaactc  19320
accaaggcca tggcaccgag cgttggtttt cttgtattcc ccttagtatg cggcgcgcgg  19380
cgatgtatga ggaaggtcct cctccctcct acgagagtgt ggtgagcgcg gcgccagtgg  19440
cggcggcgct gggttctccc ttcgatgctc ccctggaccc gccgtttgtg cctccgcggt  19500
acctgcggcc taccgggggg agaaacagca tccgttactc tgagttggca ccccctattcg 19560
acaccacccg tgtgtacctg gtggacaaca agtcaacgga tgtggcatcc ctgaactacc  19620
agaacgacca cagcaacttt ctgaccacgg tcattcaaaa caatgactac agcccggggg  19680
aggcaagcac acagaccatc aatcttgacg accggtcgca ctggggcggc gacctgaaaa  19740
ccatcctgca taccaacatg ccaaatgtga acgagttcat gtttaccaat aagtttaagg  19800
cgcgggtgat ggtgtcgcgc ttgcctacta aggacaatca ggtggagctg aaatacgagt  19860
gggtggagtt cacgctgccc gagggcaact actccgagac catgaccata gaccttatga  19920
acaacgcgat cgtggagcac tacttgaaag tgggcagaca gaacggggtt ctggaaagcg  19980
acatcggggt aaagtttgac acccgcaact tcagactggg gtttgacccc gtcactggtc  20040
ttgtcatgcc tggggtatat acaaacgaag ccttccatcc agacatcatt ttgctgccag  20100
gatgcggggt ggacttcacc cacagccgcc tgagcaactt gttgggcatc cgcaagcggc  20160
aacccttcca ggagggcttt aggatcacct acgatgatct ggagggtggt aacattcccg  20220
cactgttgga tgtggacgcc taccaggcga gcttgaaaga tgacaccgaa cagggcgggg  20280
gtggcgcagg cggcagcaac agcagtggca gcggcgcgga agagaactcc aacgcggcag  20340
ccgcggcaat gcagccggtg gaggacatga acgatcatgc cattcgcggc gacacctttg  20400
ccacacgggc tgaggagaag cgcgctgagg ccgaagcagc ggccgaagct gccgcccccg  20460
ctgcgcaacc cgaggtcgag aagcctcaga agaaaccggt gatcaaaccc ctgacagagg  20520
acagcaagaa acgcagttac aacctaataa gcaatgacag caccttcacc cagtaccgca  20580
gctggtacct tgcatacaac tacggcgacc ctcagaccgg aatccgctca tggaccctgc  20640
tttgcactcc tgacgtaacc tgcggctcgg agcaggtcta ctggtcgttg ccagacatga  20700
tgcaagaccc cgtgaccttc cgctccacgc gccagatcag caactttccg gtggtgggcg  20760
ccgagctgtt gcccgtgcac tccaagagct tctacaacga ccaggccgtc tactcccaac  20820
tcatccgcca gtttacctct ctgacccacg tgttcaatcg ctttcccgag aaccagattt  20880
tggcgcgccc gccagccccc accatcacca ccgtcagtga aaacgttcct gctctcacag  20940
atcacgggac gctaccgctg cgcaacagca tcggaggagt ccagcgagtg accattactg  21000
acgccagacg ccgcacctgc ccctacgttt acaaggccct gggcatagtc tcgccgcgcg  21060
tcctatcgag ccgcactttt tgagcaagca tgtccatcct tatatcgccc agcaataaca  21120
caggctgggg cctgcgcttc ccaagcaaga tgtttggcgg ggccaagaag cgctccgacc  21180
aacacccagt gcgcgtgcgc gggcactacc gcgcgccctg gggcgcgcac aaacgcggcc  21240
gcactgggcg caccaccgtc gatgacgcca tcgacgcggt ggtggaggag gcgcgcaact  21300
acacgcccac gccgccacca gtgtccacag tggacgcggc cattcagacc gtggtgcgcg  21360
gagcccggcg ctatgctaaa atgaagagac ggcggaggcg cgtagcacgt cgccaccgcc  21420
gccgacccgg cactgccgcc caacgcgcgg cggcggccct gcttaaccgc gcacgtcgca  21480
ccggccgacg ggcggccatg cgggccgctc gaaggctggc cgcgggtatt gtcactgtgc  21540
cccccaggtc caggcgacga gcggccgccg cagcagccgc ggccattagt gctatgactc  21600
agggtcgcag gggcaacgtg tattgggtgc gcgactcggt tagcggcctg cgcgtgcccg  21660
tgcgcacccg cccccgcgc aactagattg caagaaaaaa ctacttagac tcgtactgtt  21720
gtatgtatcc agcggcggcg gcgcgcaacg aagctatgtc caagcgcaaa atcaaagaag  21780
```

```
agatgctcca ggtcatcgcg ccggagatct atggcccccc gaagaaggaa gagcaggatt  21840
acaagccccg aaagctaaag cgggtcaaaa agaaaaagaa agatgatgat gatgaacttg  21900
acgacgaggt ggaactgctg cacgctaccg cgcccaggcg acgggtacag tggaaaggtc  21960
gacgcgtaaa acgtgttttg cgacccggca ccaccgtagt ctttacgccc ggtgagcgct  22020
ccacccgcac ctacaagcgc gtgtatgatg aggtgtacgg cgacgaggac ctgcttgagc  22080
aggccaacga gcgcctcggg gagtttgcct acggaaagcg gcataaggac atgctggcgt  22140
tgccgctgga cgagggcaac ccaacaccta gcctaaagcc cgtaacactg cagcaggtgc  22200
tgcccgcgct tgcaccgtcc gaagaaaagc gcggcctaaa gcgcgagtct ggtgacttgg  22260
cacccaccgt gcagctgatg gtacccaagc gccagcgact ggaagatgtc ttggaaaaaa  22320
tgaccgtgga acctgggctg gagcccgagg tccgcgtgcg gccaatcaag caggtggcgc  22380
cgggactggg cgtgcagacc gtggacgttc agatacccac taccagtagc accagtattg  22440
ccaccgccac agagggcatg gagacacaaa cgtccccggt tgcctcagcg gtggcggatg  22500
ccgcggtgca ggcggtcgct gcggccgcgt ccaagacctc tacggaggtg caaacggacc  22560
cgtggatgtt tcgcgtttca gcccccccggc gcccgcgccg ttcgaggaag tacggcgccg  22620
ccagcgcgct actgcccgaa tatgccctac atccttccat tgcgcctacc cccggctatc  22680
gtggctacac ctaccgcccc agaagacgag caactacccg acgccgaacc accactggaa  22740
cccgccgccg ccgtcgccgt cgccagcccg tgctggcccc gatttccgtg cgcagggtgg  22800
ctcgcgaagg aggcaggacc ctggtgctgc caacagcgcg ctaccacccc agcatcgttt  22860
aaaagccggt ctttgtggtt cttgcagata tggccctcac ctgccgcctc cgtttcccgg  22920
tgccgggatt ccgaggaaga atgcaccgta ggaggggcat ggccggccac ggcctgacgg  22980
gcggcatgcg tcgtgcgcac caccggcggc ggcgcgcgtc gcaccgtcgc atgcgcggcg  23040
gtatcctgcc cctccttatt ccactgatcg ccgcggcgat tggcgccgtg cccggaattg  23100
catccgtggc cttgcaggcg cagagacact gattaaaaac aagttgcatg tggaaaaatc  23160
aaaataaaaa gtctggactc tcacgctcgc ttggtcctgt aactattttg tagaatggaa  23220
gacatcaact ttgcgtctct ggccccgcga cacggctcgc gcccgttcat gggaaactgg  23280
caagatatcg gcaccagcaa tatgagcggt ggcgccttca gctggggctc gctgtggagc  23340
ggcattaaaa atttcggttc caccgttaag aactatggca gcaaggcctg gaacagcagc  23400
acaggccaga tgctgaggga taagttgaaa gagcaaaatt tccaacaaaa ggtggtagat  23460
ggcctggcct ctggcattag cggggtggtg gacctggcca accaggcagt gcaaaataag  23520
attaacagta agcttgatcc ccgccctccc gtagaggagc ctccaccggc cgtggagaca  23580
gtgtctccag aggggcgtgg cgaaaagcgt ccgcgccccg acagggaaga aactctggtg  23640
acgcaaatag acgagcctcc ctcgtacgag gaggcactaa agcaaggcct gcccaccacc  23700
cgtcccatcg cgcccatggc taccggagtg ctgggccagc acacacccgt aacgctggac  23760
ctgcctcccc ccgccgacac ccagcagaaa cctgtgctgc caggcccgac cgccgttgtt  23820
gtaacccgtc ctagccgcgc gtccctgcgc cgcgccgcca gcggtccgcg atcgttgcgg  23880
cccgtagcca gtggcaactg gcaaagcaca ctgaacagca tcgtgggtct gggggtgcaa  23940
tccctgaagc gccgacgatg cttctgatag ctaacgtgtc gtatgtgtgt catgtatgcg  24000
tccatgtcgc cgccagagga gctgctgagc cgccgcgcgc ccgctttcca agatggctac  24060
cccttcgatg atgccgcagt ggtcttacat gcacatctcg ggccaggacg cctcggagta  24120
cctgagcccc gggctggtgc agtttgcccg cgccaccgag acgtacttca gcctgaataa  24180
caagtttaga aaccccacgg tggcgcctac gcacgacgtg accacagacc ggtcccagcg  24240
tttgacgctg cggttcatcc ctgtggaccg tgaggatact gcgtactcgt acaaggcgcg  24300
gttcacccta gctgtgggtg ataaccgtgt gctggacatg gcttccacgt actttgacat  24360
ccgcggcgtg ctggacaggg gccctacttt taagccctac tctggcactg cctacaacgc  24420
cctggctccc aagggtgccc caaatccttg cgaatgggat gaagctgcta ctgctcttga  24480
aataaaccta gaagaagagg acgatgacaa cgaagacgaa gtagacgagc aagctgagca  24540
gcaaaaaact cacgtatttg ggcaggcgcc ttattctggt ataaatatta caaaggaggg  24600
tattcaaata ggtgtcgaag gtcaaacacc taaatatgcc gataaaacat ttcaacctga  24660
acctcaaata ggagaatctc agtggtacga aacagaaatt aatcatgcag ctgggagagt  24720
cctaaaaaag actaccccaa tgaaaccatg ttacggttca tatgcaaaac ccacaaatga  24780
aaatggaggg caaggcattc ttgtaaagca acaaaatgga aagctagaaa gtcaagtgga  24840
aatgcaattt ttctcaacta ctgaggcagc cgcaggcaat ggtgataact tgactcctaa  24900
agtggtattg tacagtgaag atgtagatat agaaacccca gacactcata tttcttacat  24960
gcccactatt aaggaaggta actcacgaga actaatgggc caacaatcta tgcccaacag  25020
gcctaattac attgctttta gggacaattt tattggtcta atgtattaca acagcacggg  25080
taatatgggt gttctggcgg gccaagcatc gcagttgaat gctgttgtag atttgcaaga  25140
cagaaacaca gagctttcat accagctttt gcttgattcc attggtgata gaaccaggta  25200
cttttctatg tggaatcagg ctgttgacag ctatgatcca gatgttagaa ttattgaaaa  25260
tcatggaact gaagatgaac ttccaaatta ctgctttcca ctgggaggtg tgattaatac  25320
agagactctt accaaggtaa aacctaaaac aggtcaggaa aatggatggg aaaaagatgc  25380
tacagaattt tcagataaaa atgaaataag agttggaaat aattttgcca tggaaatcaa  25440
tctaaatgcc aacctgtgga gaaatttcct gtactccaac atagcgctgt atttgcccga  25500
caagctaaag tacagtcctt ccaacgtaaa aatttctgat aacccaaaca cctacgacta  25560
catgaacaag cgagtggtgg ctcccgggct agtggactgc tacattaacc ttggagcacg  25620
ctggtccctt gactatatgg acaacgtcaa cccatttaac caccaccgca atgctggcct  25680
gcgctaccgc tcaatgttgc tgggcaatgg tcgctatgtg cccttccaca tccaggtgcc  25740
tcagaagttc tttgccatta aaaacctcct tctcctgccg ggctcataca cctacgagtg  25800
gaacttcagg aaggatgtta acatggttct gcagagctcc ctaggaaatg acctaagggt  25860
tgacggagcc agcattaagt ttgatagcat ttgcctttac gccaccttct tccccatggc  25920
ccacaacacc gcctccacgc ttgaggccat gcttagaaac gacaccaacg accagtcctt  25980
taacgactat ctctccgccg ccaacatgct ctaccctata cccgccaacg ctaccaacgt  26040
gcccatatcc atcccctccc gcaactgggc ggctttccgc ggctgggcct tcacgcgcct  26100
taagactaag gaaaccccat cactgggctc gggctacgac ccttattaca cctactctgg  26160
ctctataccc tacctagatg gaacctttta cctcaaccac acctttaaga aggtggccat  26220
tacctttgac tcttctgtca gctggcctgg caatgaccgc ctgcttaccc ccaacgagtt  26280
tgaaattaag cgctcagttg acggggaggg ttacaacgtt gcccagtgta acatgaccaa  26340
agactggttc ctggtacaaa tgctagctaa ctataacatt ggctaccagg gcttctatat  26400
cccagagagc tacaaggacc gcatgtactc cttctttaga aacttccagc ccatgagccg  26460
tcaggtggtg gatgatacta aatacaagga ctaccaacag gtgggcatcc tacaccaaca  26520
```

```
caacaactct ggatttgttg gctaccttgc ccccaccatg cgcgaaggac aggcctaccc  26580
tgctaacttc ccctatccgc ttataggcaa gaccgcagtt gacagcatta cccagaaaaa  26640
gtttctttgc gatcgcaccc tttggcgcat cccattctcc agtaacttta tgtccatggg  26700
cgcactcaca gacctgggcc aaaaccttct ctacgccaac tccgcccacg cgctagacat  26760
gacttttgag gtggatccca tggacgagcc cacccttctt tatgttttgt ttgaagtctt  26820
tgacgtggtc cgtgtgcacc agccgcaccg cggcgtcatc gaaaccgtgt acctgcgcac  26880
gcccttctcg gccggcaacg ccacaacata aagaagcaag caacatcaac aacagctgcc  26940
gccatgggct ccagtgagca ggaactgaaa gccattgtca aagatcttgg ttgtgggcca  27000
tattttttgg gcacctatga caagcgcttt ccaggctttg tttctccaca caagctcgcc  27060
tgcgccatag tcaatacggc cggtcgcgag actgggggcg tacactggat ggcctttgcc  27120
tggaacccgc actcaaaaac atgctacctc tttgagccct ttggcttttc tgaccagcga  27180
ctcaagcagg tttaccagtt tgagtacgag tcactcctgc gccgtagcgc cattgcttct  27240
tcccccgacc gctgtataac gctggaaaag tccacccaaa gcgtacaggg gcccaactcg  27300
gccgcctgtg gactattctg ctgcatgttt ctccacgcct ttgccaactg gccccaaact  27360
cccatggatc acaaccccac catgaacctt attaccgggg tacccaactc catgctcaac  27420
agtccccagg tacagcccac cctgcgtcgc aaccaggaac agctctacag cttcctggag  27480
cgccactcgc cctacttccg cagccacagt gcgcagatta ggagcgccac ttctttttgt  27540
cacttgaaaa acatgtaaaa ataatgtact agagacactt tcaataaagg caaatgcttt  27600
tatttgtaca ctctcgggtg attatttacc cccacccttg ccgtctgcgc cgtttaaaaa  27660
tcaaaggggt tctgccgcgc atcgctatgc gccactggca gggacacgtt gcgatactgg  27720
tgtttagtgc tccacttaaa ctcaggcaca accatccgcg gcagctcggt gaagttttca  27780
ctccacaggc tgcgcaccat caccaacgcg tttagcaggt cgggcgccga tatcttgaag  27840
tcgcagttgg ggcctccgcc ctgcgcgcgc gagttgcgat acacagggtt gcagcactgg  27900
aacactatca gcgccgggtg gtgcacgctg gccagcacgc tcttgtcgga gatcagatcc  27960
gcgtccaggt cctccgcgtt gctcagggcg aacggagtca actttggtag ctgccttccc  28020
aaaaagggcg cgtgcccagg ctttgagttg cactcgcacc gtagtggcat caaaaggtga  28080
ccgtgcccgg tctgggcgtt aggatacagc gcctgcataa aagccttgat ctgcttaaaa  28140
gccacctgag cctttgcgcc ttcagagaag aacatgccgc aagacttgcc ggaaaactga  28200
ttggccggac aggccgcgtc gtgcacgcag caccttgcgt cggtgttgga gatctgcacc  28260
acatttcggc cccaccggtt cttcacgatc ttggccttgc tagactgctc cttcagcgcg  28320
cgctgcccgt tttcgctcgt cacatccatt tcaatcacgt gctccttatt tatcataatg  28380
cttccgtgta gacacttaag ctcgccttcg atctcagcgc agcggtgcag ccacaacgcg  28440
cagcccgtgg gctcgtgatg cttgtaggtc acctctgcaa acgactgcag gtacgcctgc  28500
aggaatcgcc ccatcatcgt cacaaaggtc ttgttgctgg tgaaggtcag ctgcaacccg  28560
cggtgctcct cgttcagcca ggtcttgcat acggccgcca gagcttccac ttggtcaggc  28620
agtagtttga agttcgcctt tagatcgtta tccacgtggt acttgtccat cagcgcgcgc  28680
gcagcctcca tgcccttctc ccacgcagac acgatcggca cactcagcgg gttcatcacc  28740
gtaatttcac tttccgcttc gctgggctct tcctcttcct cttgcgtccg cataccacgc  28800
gccactgggt cgtcttcatt cagccgccgc actgtgcgct tacctccttt gccatgcttg  28860
attagcaccg gtgggttgct gaaacccacc atttgtagcg ccacatcttc tctttcttcc  28920
tcgctgtcca cgattacctc tggtgatggc gggcgctcgg gcttgggaga agggcgcttc  28980
tttttcttct tgggcgcaat ggccaaatcc gccgccgagg tcgatggccg cgggctgggt  29040
gtgcgcggca ccagcgcgtc ttgtgatgag tcttcctcgt cctcggactc gatacgccgc  29100
ctcatccgct tttttggggg cgcccgggga ggcggcggcg acggggacgg ggacgacacg  29160
tcctccatgg ttgggggacg tcgcgccgca ccgcgtccgc gctcgggggt ggtttcgcgc  29220
tgctcctctt cccgactggc catttccttc tcctataggc agaaaaagat catggagtca  29280
gtcgagaaga aggacagcct aaccgccccc tctgagttcg ccaccaccgc ctccaccgat  29340
gccgccaacg cgcctaccac cttccccgtc gaggcacccc cgcttgagga ggaggaagtg  29400
attatcgagc aggacccagg ttttgtaagc gaagacgacg aggaccgctc agtaccaaca  29460
gaggataaaa agcaagacca ggacaacgca gaggcaaacg aggaacaagt cgggcggggg  29520
gacgaaaggc atggcgacta cctagatgtg ggagacgacg tgctgttgaa gcatctgcag  29580
cgccagtgcg ccattatctg cgacgcgttg caagagcgca gcgatgtgcc cctcgccata  29640
gcggatgtca gccttgccta cgaacgccac ctattctcac cgcgcgtacc ccccaaacgc  29700
caagaaaacg gcacatgcga gcccaacccg cgcctcaact tctaccccgt atttgccgtg  29760
ccagaggtgc ttgccaccta tcacatcttt ttccaaaact gcaagatacc cctatcctgc  29820
cgtgccaacc gcagccgagc ggacaagcag ctggccttgc ggcagggcgc tgtcatacct  29880
gatatcgcct cgctcaacga agtgccaaaa atctttgagg gtcttggacg cgacgagaag  29940
cgcgcggcaa acgctctgca acaggaaaac agcgaaaatg aaagtcactc tggagtgttg  30000
gtggaactcg agggtgacaa cgcgcgccta gccgtactaa aacgcagcat cgaggtcacc  30060
cactttgcct acccggcact taacctaccc cccaaggtca tgagcacagt catgagtgag  30120
ctgatcgtgc gccgtgcgca gcccctggag agggatgcaa atttgcaaga acaaacagag  30180
gagggcctac ccgcagttgg cgacgagcag ctagcgcgct ggcttcaaac gcgcgagcct  30240
gccgacttgg aggagcgacg caaactaatg atggccgcag tgctcgttac cgtggagctt  30300
gagtgcatgc agcggttctt tgctgacccg gagatgcagc gcaagctaga ggaaacattg  30360
cactacacct ttcgacaggg ctacgtacgc caggcctgca agatctccaa cgtggagctc  30420
tgcaacctgg tctcctacct tggaattttg cacgaaaacc gccttgggca aaacgtgctt  30480
cattccacgc tcaagggcga ggcgcgccgc gactacgtcc gcgactgcgt ttacttattt  30540
ctatgctaca cctggcagac ggccatgggc gtttggcagc agtgcttgga ggagtgcaac  30600
ctcaaggagc tgcagaaact gctaaagcaa aacttgaagg acctatggac ggccttcaac  30660
gagcgctccg tggccgcgca cctggcggac atcattttcc ccgaacgcct gcttaaaacc  30720
ctgcaacagg gtctgccaga cttcaccagt caaagcatgt tgcagaactt taggaacttt  30780
atcctagagc gctcaggaat cttgcccgcc acctgctgtg cacttcctag cgactttgtg  30840
cccattaagt accgcgaatg ccctccgccg ctttggggcc actgctacct tctgcagcta  30900
gccaactacc ttgcctacca ctctgacata atggaagacg tgagcggtga cggtctactg  30960
gagtgtcact gtcgctgcaa cctatgcacc ccgcaccgct ccctggtttg caattcgcag  31020
ctgcttaacg aaagtcaaat tatcggtacc tttgagctgc agggtccctc gcctgacgaa  31080
aagtccgcgg ctccggggtt gaaactcact ccggggctgt ggacgtcggc ttaccttcgc  31140
aaatttgtac ctgaggacta ccacgcccac gagattaggt tctacgaaga ccaatcccgc  31200
ccgcctaatg cggagcttac cgcctgcgtc attacccagg gccacattct tggccaattg  31260
```

-continued

```
caagccatca acaaagcccg ccaagagttt ctgctacgaa agggacgggg ggtttacttg  31320
gacccccagt ccggcgagga gctcaaccca atccccccgc cgccgcagcc ctatcagcag  31380
cagccgcggg cccttgcttc ccaggatggc acccaaaaag aagctgcagc tgccgccgcc  31440
acccacggac gaggaggaat actgggacag tcaggcagag gaggttttgg acgaggagga  31500
ggaggacatg atggaagact gggagagcct agacgaggaa gcttccgagg tcgaagaggt  31560
gtcagacgaa acaccgtcac cctcggtcgc attcccctcg ccggcgcccc agaaatcggc  31620
aaccggttcc agcatggcta caacctccgc tcctcaggcg ccgccggcac tgcccgttcg  31680
ccgacccaac cgtagatggg acaccactgg aaccagggcc ggtaagtcca agcagccgcc  31740
gccgttagcc caagagcaac aacagcgcca aggctaccgc tcatggcgcg ggcacaagaa  31800
cgccatagtt gcttgcttgc aagactgtgg gggcaacatc tccttcgccc gccgctttct  31860
tctctaccat cacggcgtgg ccttcccccg taacatcctg cattactacc gtcatctcta  31920
cagcccatac tgcaccggcg gcagcggcag caacagcagc ggccacacag aagcaaaggc  31980
gaccggatag caagactctg acaaagccca agaaatccac agcggcggca gcagcaggag  32040
gaggagcgct gcgtctggcg cccaacgaac ccgtatcgac ccgcgagctt agaaacagga  32100
tttttcccac tctgtatgct atatttcaac agagcagggg ccaagaacaa gagctgaaaa  32160
taaaaaacag gtctctgcga tccctcaccc gcagctgcct gtatcacaaa agcgaagatc  32220
agcttcggcg cacgctggaa gacgcggagg ctctcttcag taaatactgc gcgctgactc  32280
ttaaggacta gtttcgcgcc ctttctcaaa tttaagcgcg aaaactacgt catctccagc  32340
ggccacaccc ggcgccagca cctgttgtca gcgccattat gagcaaggaa attcccacgc  32400
cctacatgtg gagttaccag ccacaaatgg gacttgcggc tggagctgcc caagactact  32460
caacccgaat aaactacatg agcgcgggac cccacatgat atcccgggtc aacggaatac  32520
gcgcccaccg aaaccgaatt ctcctggaac aggcggctat taccaccaca cctcgtaata  32580
accttaatcc ccgtagttgg cccgctgccc tggtgtacca ggaaagtccc gctcccacca  32640
ctgtggtact tcccagagac gcccaggccg aagttcagat gactaactca ggggcgcagc  32700
ttgcgggcgg ctttcgtcac agggtgcggt cgcccgggca gggtataact cacctgacaa  32760
tcagagggcg aggtattcag ctcaacgacg agtcggtgag ctcctcgctt ggtctccgtc  32820
cggacgggac atttcagatc ggcggcgccg gccgctcttc attcacgcct cgtcaggcaa  32880
tcctaactct gcagacctcg tcctctgagc cgcgctctgg aggcattgga actctgcaat  32940
ttattgagga gtttgtgcca tcggtctact ttaacccctt ctcgggacct cccggccact  33000
atccggatca atttattcct aactttgacg cggtaaagga ctcggcggac ggctacgact  33060
gaatgttaag tggagaggca gagcaactgc gcctgaaaca cctggtccac tgtcgccgcc  33120
acaagtgctt tgcccgcgac tccggtgagt tttgctactt tgaattgccc gaggatcata  33180
tcgagggccc ggcgcacggc gtccggctta ccgcccaggg agagcttgcc cgtagcctga  33240
ttcgggagtt tacccagcgc cccctgctag ttgagcggga caggggaccc tgtgttctca  33300
ctgtgatttg caactgtcct aaccctggat tacatcaaga tcctctagtt aatgtcaggt  33360
cgcctaagtc gattaactag agtacccggg gatcttattc cctttaacta ataaaaaaaa  33420
ataataaagc atcacttact taaaatcagt tagcaaattt ctgtccagtt tattcagcag  33480
cacctccttg ccctcctccc agctctggta ttgcagcttc ctcctggctg caaactttct  33540
ccacaatcta aatggaatgt cagtttcctc ctgttcctgt ccatccgcac ccactatctt  33600
catgttgttg cagatgaagc gcgcaagacc gtctgaagat accttcaacc ccgtgtatcc  33660
atatgacacg gaaaccggtc ctccaactgt gccttttctt actcctccct ttgtatcccc  33720
caatgggttt caagagagtc cccctggggt actctctttg cgcctatccg aacctctagt  33780
tacctccaat ggcatgcttg cgctcaaaat gggcaacggc ctctctctgg acgaggccgg  33840
caaccttacc tcccaaaatg taaccactgt gagcccacct ctcaaaaaaa ccaagtcaaa  33900
cataaacctg gaaatatctg caccccctcac agttacctca gaagccctaa ctgtggctgc  33960
cgccgcacct ctaatggtcg cgggcaacac actcaccatg caatcacagg ccccgctaac  34020
cgtgcacgac tccaaactta gcattgccac ccaaggaccc ctcacagtgt cagaaggaaa  34080
gctagccctg caaacatcag gcccccctcac caccaccgat agcagtaccc ttactatcac  34140
tgcctcaccc cctctaacta ctgccactgg tagcttgggc attgacttga aagagcccat  34200
ttatacacaa aatggaaaac taggactaaa gtacggggct cctttgcatg taacagacga  34260
cctaaacact ttgaccgtag caactggtcc aggtgtgact attaataata cttccttgca  34320
aactaaagtt actggagcct tgggttttga ttcacaaggc aatatgcaac ttaatgtagc  34380
aggaggacta aggattgatt ctcaaaacag acgccttata cttgatgtta gttatccgtt  34440
tgatgctcaa aaccaactaa atctaagact aggacagggc cctcttttta taaactcagc  34500
ccacaacttg gatattaact acaacaaagg cctttacttg tttacagctt caaacaattc  34560
caaaaagctt gaggttaacc taagcactgc caaggggttg atgtttgacg ctacagccat  34620
agccattaat gcaggagatg ggcttgaatt tggttcacct aatgcaccaa acacaaatcc  34680
cctcaaaaca aaaattggcc atggcctaga atttgattca aacaaggcta tggttcctaa  34740
actaggaact ggccttagtt ttgacagcac aggtgccatt acagtaggaa acaaaaataa  34800
tgataagcta actttgtgga ccacaccagc tccatctcct aactgtagac taaatgcaga  34860
gaaagatgct aaactcactt tggtcttaac aaaatgtggc agtcaaatac ttgctacagt  34920
ttcagttttg gctgttaaag gcagtttggc tccaatatct ggaacagttc aaagtgctca  34980
tcttattata agatttgacg aaaatggagt gctactaaac aattccttcc tggacccaga  35040
atattggaac tttagaaatg gagatcttac tgaaggcaca gcctatacaa acgctgttgg  35100
atttatgcct aacctatcag cttatccaaa atctcacggt aaaactgcca aaagtaacat  35160
tgtcagtcaa gtttacttaa acggagacaa aactaaacct gtaacactaa ccattacact  35220
aaacggtaca caggaaacag gagacacaac tccaagtgca tactctatgt cattttcatg  35280
ggactggtct ggccacaact acattaatga aatatttgcc acatcctctt acactttttc  35340
atacattgcc caagaataaa gaatcgtttg tgttatgttt caacgtgttt atttttcaat  35400
tgcagaaaat ttcaagtcat ttttcattca gtagtatagc cccaccacca catagcttat  35460
acagatcacc gtaccttaat caaactcaca gaaccctagt attcaacctg ccacctccct  35520
cccaacacac agagtacaca gtcctttctc cccggctggc cttaaaaagc atcatatcat  35580
gggtaacaga catattctta ggtgttatat tccacacggt ttcctgtcga gccaaacgct  35640
catcagtgat attaataaac tccccgggca gctcacttaa gttcatgtcg ctgtccagct  35700
gctgagccac aggctgctgt ccaacttgcg gttgcttaac gggcggcgaa ggagaagtcc  35760
acgcctacat gggggtagag tcataatcgt gcatcaggat agggcggtgg tgctgcagca  35820
gcgcgcgaat aaactgctgc cgccgccgct ccgtcctgca ggaatacaac atggcagtgg  35880
tctcctcagc gatgattcgc accgcccgca gcataaggcg ccttgtcctc cgggcacagc  35940
agcgcaccct gatctcactt aaatcagcac agtaactgca gcacagcacc acaatattgt  36000
```

```
tcaaaatccc acagtgcaag gcgctgtatc caaagctcat ggcggggacc acagaaccca  36060
cgtggccatc ataccacaag cgcaggtaga ttaagtggcg acccctcata aacacgctgg  36120
acataaacat tacctctttt ggcatgttgt aattcaccac ctcccggtac catataaacc  36180
tctgattaaa catggcgcca tccaccacca tcctaaacca gctggccaaa acctgcccgc  36240
cggctataca ctgcagggaa ccgggactgg aacaatgaca gtggagagcc caggactcgt  36300
aaccatggat catcatgctc gtcatgatat caatgttggc acaacacagg cacacgtgca  36360
tacacttcct caggattaca agctcctccc gcgttagaac catatcccag ggaacaaccc  36420
attcctgaat cagcgtaaat cccacactgc agggaagacc tcgcacgtaa ctcacgttgt  36480
gcattgtcaa agtgttacat tcgggcagca gcggatgatc ctccagtatg gtagcgcggg  36540
tttctgtctc aaaaggaggt agacgatccc tactgtacgg agtgcgccga gacaaccgag  36600
atcgtgttgg tcgtagtgtc atgccaaatg gaacgccgga cgtagtcata tttcctgaag  36660
caaaaccagg tgcgggcgtg acaaacagat ctgcgtctcc ggtctcgccg cttagatcgc  36720
tctgtgtagt agttgtagta tatccactct ctcaaagcat ccaggcgccc cctggcttcg  36780
ggttctatgt aaactccttc atgcgccgct gccctgataa catccaccac cgcagaataa  36840
gccacaccca gccaacctac acattcgttc tgcgagtcac acacgggagg agcgggaaga  36900
gctggaagaa ccatgttttt ttttttattc caaaagatta tccaaaacct caaaatgaag  36960
atctattaag tgaacgcgct cccctccggt ggcgtggtca aactctacag ccaaagaaca  37020
gataatggca tttgtaagat gttgcacaat ggcttccaaa aggcaaacgg ccctcacgtc  37080
caagtggacg taaaggctaa acccttcagg gtgaatctcc tctataaaca ttccagcacc  37140
ttcaaccatg cccaaataat tctcatctcg ccaccttctc aatatatctc taagcaaatc  37200
ccgaatatta agtccggcca ttgtaaaaat ctgctccaga gcgccctcca ccttcagcct  37260
caagcagcga atcatgattg caaaaattca ggttcctcac agacctgtat aagattcaaa  37320
agcggaacat taacaaaaat accgcgatcc cgtaggtccc ttcgcagggc cagctgaaca  37380
taatcgtgca ggtctgcacg gaccagcgcg gccacttccc cgccaggaac catgacaaaa  37440
gaacccacac tgattatgac acgcatactc ggagctatgc taaccagcgt agccccgatg  37500
taagcttgtt gcatgggcgg cgatataaaa tgcaaggtgc tgctcaaaaa atcaggcaaa  37560
gcctcgcgca aaaaagaaag cacatcgtag tcatgctcat gcagataaag gcaggtaagc  37620
tccggaacca ccacagaaaa agacaccatt tttctctcaa acatgtctgc gggtttctgc  37680
ataaacacaa aataaaataa caaaaaaaca tttaaacatt agaagcctgt cttacaacag  37740
gaaaaacaac ccttataagc ataagacgga ctacggccat gccggcgtga ccgtaaaaaa  37800
actggtcacc gtgattaaaa agcaccaccg acagctcctc ggtcatgtcc ggagtcataa  37860
tgtaagactc ggtaaacaca tcaggttgat tcacatcggt cagtgctaaa aagcgaccga  37920
aatagcccgg gggaatacat acccgcaggc gtagagacaa cattacagcc cccataggag  37980
gtataacaaa attaatagga gagaaaaaca cataaacacc tgaaaaaccc tcctgcctag  38040
gcaaaatagc accctcccgc tccagaacaa catacagcgc ttccacagcg gcagccataa  38100
cagtcagcct taccagtaaa aaagaaaacc tattaaaaaa acaccactcg acacggcacc  38160
agctcaatca gtcacagtgt aaaaaagggc caagtgcaga gcgagtatat ataggactaa  38220
aaaatgacgt aacggttaaa gtccacaaaa aacacccaga aaaccgcacg cgaacctacg  38280
cccagaaacg aaagccaaaa aacccacaac ttcctcaaat cgtcacttcc gttttcccac  38340
gttacgtcac ttcccatttt aagaaaacta caattcccaa cacatacaag ttactccgcc  38400
ctaaaaccta cgtcacccgc cccgttccca cgccccgcgc cacgtcacaa actccacccc  38460
ctcattatca tattggcttc aatccaaaat aaggta                           38496
```

```
SEQ ID NO: 233          moltype = DNA  length = 9701
FEATURE                 Location/Qualifiers
misc_feature            1..9701
                        note = vector for IgG1 against T27Y H34A R273Q ACE2 mutant
misc_difference         2929..2930
                        note = n is a, c, g, or t
misc_difference         2934
                        note = n is a, c, g, or t
source                  1..9701
                        mol_type = other DNA
                        organism = synthetic construct
SEQUENCE: 233
ggcgtaatct gctgcttgca aacaaaaaaa ccaccgctac cagcggtggt ttgtttgccg  60
gatcaagagc taccaactct ttttccgaag gtaactggct tcagcagagc gcagatacca  120
aatactgtcc ttctagtgta gccgtagtta ggccaccact tcaagaactc tgtagcaccg  180
cctacatacc tcgctctgct aatcctgtta ccagtggctg ctgccagtgg cgataagtcg  240
gtgtcttacc gggttggact caagagatag ttaccggata aggcgcagcg gtcgggctga  300
acggggggtt cgtgcacaca gcccagcttg gagcgaacga cctacaccga actgagatac  360
ctacagcgtg agctatgaga aagcgccacg cttcccgaag ggagaaaggc ggacaggtat  420
ccggtaagcg gcagggtcgg aacaggagag cgcacgaggg agcttccagg gggaaacgcc  480
tggtatcttt atagtcctgt cgggtttcgc cacctctgac ttgagcgtcg atttttgtga  540
tgctcgtcag gggggcggag cctatggaaa aacgccagca acgcaagcta gagtttaaac  600
ttgacagatg agacaataac cctgataaat gcttcaataa tattgaaaaa ggaaaagtat  660
gagtattcaa catttccgtg tcgcccttat tccctttttt gcggcatttt gccttcctgt  720
ttttgctcac ccagaaacgc tggtgaaagt aaaagatgca gaagatcact tgggtgcgcg  780
agtgggttac atcgaactgg atctcaacag cggtaagatc cttgagagtt ttcgccccga  840
agaacgtttc ccaatgatga gcacttttaa agttctgcta tgtggcgcgg tattatcccg  900
tattgatgcc gggcaagagc aactcggtcg ccgcatacac tattctcaga atgacttggt  960
tgaatactca ccagtcacag aaaagcatct tacggatggc atgacagtaa gagaattatg  1020
cagtgctgcc ataaccatga gtgataacac tgcggccaac ttacttctga caactatcgg  1080
aggaccgaag gagctaaccg cttttttgca caacatgggg gatcatgtaa ctcgccttga  1140
tcgttgggaa ccggagctga atgaagccat accaaacgac gagcgtgaca ccacgatgcc  1200
tgtagcaatg gcaacaacgt tgcgaaaact attaactggc gaactactta ctctagcttc  1260
ccggcaacaa ctaatagact ggatggaggc ggataaagtt gcaggaccac ttctgcgctc  1320
ggcacttccg gctggctggt ttattgctga taaatcagga gccggtgagc gtgggtcacg  1380
cggtatcatt gcagcactgg ggccggatgg taagccctcc cgtatcgtag ttatctacac  1440
```

-continued

```
tacggggagt caggcaacta tggatgaacg aaatagacag atcgctgaga taggtgcctc  1500
actgattaag cattggtaag gataaatttc tggtaaggag gacacgtatg gaagtgggca  1560
agttggggaa gccgtatccg ttgctgaatc tggcatatgt gggagtataa gacgcgcagc  1620
gtcgcatcag gcattttttt ctgcgccaat gcaaaaaggc catccgtcag gatggccttt  1680
cggcataact agggccgccg atatttgaaa atatggcata ttgaaaatgt cgccgatgtg  1740
agtttctgtg taactgatat cgccattttt ccaaaagtga tttttgggca tacgcgatat  1800
ctggcgatag cgcttatatc gtttacgggg gatggcgata gacgactttg gtgacttggg  1860
cgattctgtg tgtcgcaaat atcgcagttt cgatataggt gacagacgat atgaggctat  1920
atcgccgata gaggcgacat caagctggca catggccaat gcatatcgat ctatacattg  1980
aatcaatatt ggccattagc catattattc attggttata tagcataaat caatattggc  2040
tattggccat tgcatacgtt gtatccatat cataatatgt acatttatat tggctcatgt  2100
ccaacattac cgccatgttg acattgatta ttgactagtt attaatagta atcaattacg  2160
gggtcattag ttcatagccc atatatggag ttccgcgtta cataacttac ggtaaatggc  2220
ccgcctggct gaccgcccaa cgacccccgc ccattgacgt caataatgac gtatgttccc  2280
atagtaacgc caatagggac tttccattga cgtcaatggg tggagtattt acggtaaact  2340
gcccacttgg cagtacatca agtgtatcat atgccaagta cgccccctat tgacgtcaat  2400
gacggtaaat ggcccgcctg gcattatgcc cagtacatga ccttatggga ctttcctact  2460
tggcagtaca tctacgtatt agtcatcgct attaccatgg tgatgcggtt ttggcagtac  2520
atcaatgggc gtggatagcg gtttgactca cggggatttc caagtctcca ccccattgac  2580
gtcaatggga gtttgttttg gcaccaaaat caacgggact ttccaaaatg tcgtaacaac  2640
tccgccccat tgacgcaaat gggcggtagg cgtgtacggt gggaggtcta tataagcaga  2700
gctcgtttag tgaaccgtca gatcgcctgg agacgccatc cacgctgttt tgacctccat  2760
agaagacacc gggaccgatc cagcctccgc ggccgggaac ggtgcattgg aacgcggatt  2820
ccccgtgcca agagtgacgt aagtaccgcc tatagagtct ataggcccac ccccttggct  2880
tcttatgcat gctatactgt ttttggcttg gggtctatac acccccccgnn ttcntcatgt  2940
tataggtgat ggtatagctt agcctatagg tgtgggttat tgaccattat tgaccactcc  3000
ccctattggt gacgatactt tccattacta atccataaca tggctctttg ccacaactct  3060
ctttattggc tatatgccaa tacactgtcc ttcagagact gacacggact ctgtattttt  3120
acaggatggg gtctcattta ttatttacaa attcacatat acaacaccac cgtccccagt  3180
gcccgcagtt tttattaaac ataacgtggg atctccacgc gaatctcggg tacgtgttcc  3240
ggacatgggc tcttctccgg tagcggcgga gcttctacat ccgagccctg ctcccatgcc  3300
tccagcgact catggtcgct cggcagctcc ttgctcctaa cagtggaggc cagacttagg  3360
cacagcacga tgcccaccac caccagtgtg ccgcacaagg ccgtggcggt agggtatgtg  3420
tctgaaaatg agctcgggga gcgggcttgc accgctgacg catttggaag acttaaggca  3480
gcggcagaag aagatgcagg cagctgagtt gttgtgttct gataagagtc agaggtaact  3540
cccgttgcgg tgctgttaac ggtggagggc agtgtagtct gagcagtact cgttgctgcc  3600
gcgcgcgcca ccagacataa tagctgacag actaacagac tgttcctttc catgggtctt  3660
ttctgcagtc accgtccttg acacgaagct gctagcgcca ccatgagcag cagtagttgg  3720
cttctcttga gtttggtggc agtgacagca gcccagagta ctatcgagga gcaggctaaa  3780
tactttctgg ataagtttaa cgccgaggcc gaagacttgt tctatcaatc ttctctcgct  3840
tcatggaatt acaatactaa catcactgag gagaacgtcc agaatatgaa caatgctggc  3900
gacaaatgga gcgccttctt gaaggagcag tctacccttg cacaaatgta tccactgcag  3960
gagatacaga accttacagt aaagttgcag ctccaggctc tccagcagaa cggatctagc  4020
gtgctttcag aggataaaag caaaaggctg aacaccatac ttaataccat gtccacaatt  4080
tactctactg gtaaagtatg taaccccgac aaccctcaag aatgcctcct tcttgagcca  4140
ggcctcaatg agatcatggc taatagtctg gactataatg aaagactgtg ggcatgggag  4200
tcctggagat ctgaagtagg gaagcaactg aggccccttt atgaagagta cgtcgtactt  4260
aagaatgaaa tggcccgcgc taaccactac gaggattacg gcgattactg gcgtggggac  4320
tatgaagtaa atggtgtaga tggatacgac tatagtcgtg ggcaattgat tgaggatgtg  4380
gagcacactt ttgaggagat aaaaccactc tatgagcatc ttcacgcata tgtgagagct  4440
aaactgatga acgcctaccc aagttacatc agtccaatcg gatgtctccc agctcacctc  4500
cttggcgaca tgtggggaca gttctggacc aatctgtatt ccctcacagt ccctttcggg  4560
caaaagccta atatagacgt gacagacgca atggttgatc aggcttggga tgctcaaagg  4620
atttttaagg aagctgagaa gtttttgtg  tcagtcggtt tgccaaatat gacacaaggc  4680
ttctgggaaa atagcatgtt gactgatccc ggtaatgttc aaaaggctgt gtgtcaccct  4740
accgcttggg accttgggaa aggtgacttt cgaatcttga tgtgtaccaa ggtgacaatg  4800
gatgactttc ttacagccca tcatgaaatg ggtcacatcc agtatgatat ggcttatgca  4860
gctcaacctt tcctcttgag aaatggtgca aatgaaggtt ttcatgaagc tgtaggggaa  4920
ataatgtccc tgagtgctgc aaccccaaag catctcaaga gtatcggatt gttgagccca  4980
gattttcaag aagataacga gaccgaaatc aacttccttc tgaaacaagc cctcacaata  5040
gttggtactc ttccattcac atacatgctg gagaaatggc gttggatggt ttttaagggg  5100
gagataccta aagatcagtg gatgaaaaag tggtgggaga tgaagcgtga gatcgtaggg  5160
gtcgtggagc cagtgcctca tgatgagact tactgtgacc cagcatcact cttccacgtt  5220
agcaatgact attcatttat acgttattac actcgcactc tttaccagtt tcaatttcag  5280
gaggctctgt gtcaggctgc caagcatgag ggacccctto acaagtgtga tattagtaac  5340
agtactgagg caggccaaaa actgttcaat atgttgaggc ttggcaaaag cgagccatgg  5400
actctcgcct tggaaaatgt tgtcggggct aaaaacatga atgtacgccc tctgcttaac  5460
tattttgagc cccttttttac atggctcaag gaccagaata agaactcctt tgtcggctgg  5520
tcaacagact ggtctcccta tgcagacaaa acacatactt gcccaccttg tcctgcacca  5580
gagctgctgg gaggtccaag cgtgttcctg tttccaccca agcccaaaga cacactgatg  5640
atttctcgaa ctccagaagt gacctgcgtg gtcgtggacg tgagccacga ggatcccgaa  5700
gtgaagttca actggtacgt ggatggcgtg gaggtccata atgctaagac taaaccccgg  5760
gaggaacagt acaacagcac ttatagggtc gtgtccgtgc tgaccgtcct gcatcaggat  5820
tggctgaacg ggaaggaata taagtgcaaa gtgtctaata aggcactgcc cgcccctatc  5880
gagaaaacaa ttagcaaggc taagggtcag cctagagaac cacaggtgta cactctgcct  5940
ccaagtcgcg acgagctgac caagaaccag gtgtcactga catgtctggt caaaggcttt  6000
tatccctcag atatcgcagt ggagtgggaa agcaatggac agcctgagaa caattacaag  6060
accacacccc ctgtgctgga cagtgatggc tcattctttc tgtattctaa gctgacagtg  6120
gacaaaagta ggtggcagca gggaaacgtg ttctcctgct ctgtcatgca cgaagcactg  6180
```

```
cacaatcatt atacccagaa gagtctgtca ctgagccctg gcaaatgagc gataccgatt  6240
ctagaactag atcataatca gccataccac atttgtagag gttttacttg ctttaaaaaa  6300
cctcccacac ctccccctga acctgaaaca taaaatgaat gcaattgttg ttgttaactt  6360
gtttattgca gcttataatg gttacaaata aagcaatagc atcacaaatt tcacaaataa  6420
agcatttttt tcactgcatt ctagttgtgg tttgtccaaa ctcatcaatg tatcttaagg  6480
ccgcaggtaa gccagcccag gcctcgccct ccagctcaag gcgggacagg tgccctagag  6540
tagcctgcat ccagggacag gccccagccg ggtgctgaca cgtccacctc catctcttcc  6600
tcaggtctgc ccgggtggca tccctgtgac ccctccccag tgcctctcct ggtcgtggaa  6660
ggtgctactc cagtgcccac cagccttgtc ctaataaaat taagttgcat cattttgttt  6720
gactaggtgt ccttgtataa tattatgggg tggaggcggg tggtatggag caaggggccc  6780
aagttaactt gtttattgca gcttataatg gttacaaata aagcaatagc atcacaaatt  6840
tcacaaataa agcatttttt tcactgcatt ctagttgtgg tttgtccaaa ctcatcaatg  6900
tatcttatca tgtctggatc cgcttcaggc accgggcttg cgggtcatgc accaggtgcg  6960
cggtccttcg ggcacctcga cgtcggcggt gacggtgaag ccgagccgct cgtagaaggg  7020
gaggttgcgg ggcgcggagg tctccaggaa ggcgggcacc ccggcgcgct cggccgcctc  7080
cactccgggg agcacgacgg cgctgcccag acccttgccc tggtggtcgg gcgagacgcc  7140
gacggtggcc aggaaccacg cgggctcctt gggccggtgc ggcgccagga ggccttccat  7200
ctgttgctgc gcggccagcc tggaaccgct caactcggcc atgcgcgggc cgatctcggc  7260
gaacaccgcc cccgcttcga cgctctccgg cgtggtccag accgccaccg cggcgccgtc  7320
gtccgcgacc cacaccttgc cgatgtcgag cccgacgcgc gtgaggaaga gttcttgcag  7380
ctcggtgacc cgctcgatgt ggcggtccgg gtcgacggtg tggcgcgtgg cggggtagtc  7440
ggcgaacgcg gcggcgaggg tgcgtacggc ccgggggacg tcgtcgcggg tggcgaggcg  7500
caccgtgggc ttgtactcgg tcatggtggc ctgcagagtc gctctgtgtt cgaggccaca  7560
cgcgtcacct taatatgcga agtggacctg ggaccgcgcc gccccgactg catctgcgtg  7620
ttttcgccaa tgacaagacg ctgggcgggg tttgtgtcat catagaacta aagacatgca  7680
aatatatttc ttccggggac accgccagca aacgcgagca acgggccacg gggatgaagc  7740
agctgcgcca ctccctgaag atccatcgtc tcctaacaag ttacatcact cctgcccttc  7800
ctcaccctca tctccatcac ctccttcatc tccgtcatct ccgtcatcac cctccgcggc  7860
agccccttcc accataggtg gaaaccaggg aggcaaatct actccatcgt caaagctgca  7920
cacagtcacc ctgatattgc aggtaggagc gggctttgtc ataacaaggt ccttaatcgc  7980
atccttcaaa acctcagcaa atatatgagt ttgtaaaaag accatgaaat aacagacaat  8040
ggactccctt agcgggccag gttgtgggcc gggtccaggg gccattccaa aggggagacg  8100
actcaatggt gtaagacgac attgtggaat agcaagggca gttcctcgcc ttaggttgta  8160
aagggaggtc ttactacctc catatacgaa cacaccggcg acccaagttc cttcgtcggt  8220
agtcctttct acgtgactcc tagccaggag agctcttaaa ccttctgcaa tgttctcaaa  8280
tttcgggttg gaacctcctt gaccacgatg ctttccaaac caccctcctt ttttgcgcct  8340
gcctccatca ccctgacccc cgctgcgcgg gggcacgtca ggctcaccat ctgggccgcc  8400
ttcttggtgg tattcaaaat aatcggcttc ccctacaggg tggaaaaatg gccttctacc  8460
tggagggggc ctgcgcggtg gagacccgga tgatgatgac tgactactgg gactcctggg  8520
cctcttttct ccacgtccac gacctctccc cctggctctt tcacgacttc ccccccctggc  8580
tctttcacgt cctctacccc ggcggcctcc actacctcct cgaccccggc ctccactacc  8640
tcctcgaccc cggcctccac tgcctcctcg accccggcct ccacctcctg ctcctgcccc  8700
tcccgctcct gctcctgctc ctgttccacc gtgggtccct ttgcagccaa tgcaacttgg  8760
acgtttttgg ggtctccgga caccatctct atgtcttggc cctgatcctg agccgcccgg  8820
ggctcctggt cttccgcctc ctcgtcctcg tcctcttccc cgtcctcgtc catgtgccat  8880
gatggcggcc tgcagctgtg ttcgaggccg cgcgtgtcac cttaatatgc gaagtggacc  8940
tgggaccgcg ccgccccgac tgcatctgcg tgttcgagtt cgccaatgac aagacgctgg  9000
gcggggagat ccccccttatt aaccctaaac gggtagcata tgcttcccgg gtagtagtat  9060
atactatcca gactaaccct aattcaatag catatgttac ccaacgggaa gcatatgcta  9120
tcgaattagg gttagtaaaa gggtcctaag gaacagcgat ctggatagca tatgctatcc  9180
taatctatat ctgggtagca tatgctatcc taatctatat ctgggtagca taggctatcc  9240
taatctatat ctgggtagca tatgctatcc taatctatat ctgggtagta tatgctatcc  9300
taatttatat ctgggtagca taggctatcc taatctatat ctgggtagca tatgctatcc  9360
taatctatat ctgggtagta tatgctatcc taatctgtat ccgggtagca tatgctatcc  9420
tcatgcatat acagtcagca tatgataccc agtagtagag tgggagtgct atcctttgca  9480
tatgccgcca cctcccaagg agatctgtcg acatcgatgg gcgcgggtgt acactccgcc  9540
catcccgccc ctaactccgc ccagttccgc ccattctccg cctcatggct gactaatttt  9600
ttttatttat gcagaggccg aggccgcctc ggcctctgag ctattccaga agtagtgagg  9660
aggctttttt ggaggcctag gcttttgcaa aaagctaatt c                     9701
```

```
SEQ ID NO: 234         moltype = AA  length = 841
FEATURE                Location/Qualifiers
REGION                 1..841
                       note = ACE2-Fc IgG Hybrid Protein
REGION                 1..776
                       note = misc_feature - ACE2 Portion
REGION                 777..841
                       note = misc_feature - IgG Fc Portion
source                 1..841
                       mol_type = protein
                       organism = synthetic construct
SEQUENCE: 234
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
```

```
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADKTHTC PPCPAPELLG GPSVFLFPPK PKDTLMISRT PEVTCVVVDV  660
SHEDPEVKFN WYVDGVEVHN AKTKPREEQY NSTYRVVSVL TVLHQDWLNG KEYKCKVSNK  720
ALPAPIEKTI SKAKGQPREP QVYTLPPSRD ELTKNQVSLT CLVKGFYPSD IAVEWESNGQ  780
PENNYKTTPP VLDSDGSFFL YSKLTVDKSR WQQGNVFSCS VMHEALHNHY TQKSLSLSPG  840
K                                                                841

SEQ ID NO: 235         moltype = AA  length = 841
FEATURE                Location/Qualifiers
REGION                 1..841
                       note = ACE2-Fc IgG R273Q Hybrid Protein
REGION                 1..776
                       note = misc_feature - ACE2 Portion with R273Q mutation
REGION                 777..841
                       note = misc_feature - IgG Fc Portion
source                 1..841
                       mol_type = protein
                       organism = synthetic construct
SEQUENCE: 235
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGQFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADKTHTC PPCPAPELLG GPSVFLFPPK PKDTLMISRT PEVTCVVVDV  660
SHEDPEVKFN WYVDGVEVHN AKTKPREEQY NSTYRVVSVL TVLHQDWLNG KEYKCKVSNK  720
ALPAPIEKTI SKAKGQPREP QVYTLPPSRD ELTKNQVSLT CLVKGFYPSD IAVEWESNGQ  780
PENNYKTTPP VLDSDGSFFL YSKLTVDKSR WQQGNVFSCS VMHEALHNHY TQKSLSLSPG  840
K                                                                841

SEQ ID NO: 236         moltype = AA  length = 865
FEATURE                Location/Qualifiers
REGION                 1..865
                       note = ACE2-Fc IgA Hybrid Protein
REGION                 1..776
                       note = misc_feature - ACE2 Portion
REGION                 777..865
                       note = misc_feature - IgA Fc Portion
source                 1..865
                       mol_type = protein
                       organism = synthetic construct
SEQUENCE: 236
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGRFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADPSTPP TPSPSTPPTP SPSCCHPRLS LHRPALEDLL LGSEANLTCT  660
LTGLRDASGV TFTWTPSSGK SAVQGPPERD LCGCYSVSSV LPGCAEPWNH GKTFTCTAAY  720
PESKTPLTAT LSKSGNTFRP EVHLLPPPSE ELALNELVTL TCLARGFSPK DVLVRWLQGS  780
QELPREKYLT WASRQEPSQG TTTFAVTSIL RVAAEDWKKG DTFSCMVGHE ALPLAFTQKT  840
IDRLAGKPTH VNVSVVMAEV DGTCY                                      865

SEQ ID NO: 237         moltype = AA  length = 865
FEATURE                Location/Qualifiers
REGION                 1..865
                       note = ACE2-Fc IgA R273Q Hybrid Protein
REGION                 1..776
                       note = misc_feature - ACE2 Portion with R273Q mutation
REGION                 777..865
                       note = misc_feature - IgA Fc Portion
source                 1..865
                       mol_type = protein
                       organism = synthetic construct
SEQUENCE: 237
MSSSSWLLLS LVAVTAAQST IEEQAKTFLD KFNHEAEDLF YQSSLASWNY NTNITEENVQ  60
NMNNAGDKWS AFLKEQSTLA QMYPLQEIQN LTVKLQLQAL QQNGSSVLSE DKSKRLNTIL  120
```

```
NTMSTIYSTG KVCNPDNPQE CLLLEPGLNE IMANSLDYNE RLWAWESWRS EVGKQLRPLY  180
EEYVVLKNEM ARANHYEDYG DYWRGDYEVN GVDGYDYSRG QLIEDVEHTF EEIKPLYEHL  240
HAYVRAKLMN AYPSYISPIG CLPAHLLGDM WGQFWTNLYS LTVPFGQKPN IDVTDAMVDQ  300
AWDAQRIFKE AEKFFVSVGL PNMTQGFWEN SMLTDPGNVQ KAVCHPTAWD LGKGDFRILM  360
CTKVTMDDFL TAHHEMGHIQ YDMAYAAQPF LLRNGANEGF HEAVGEIMSL SAATPKHLKS  420
IGLLSPDFQE DNETEINFLL KQALTIVGTL PFTYMLEKWR WMVFKGEIPK DQWMKKWWEM  480
KREIVGVVEP VPHDETYCDP ASLFHVSNDY SFIRYYTRTL YQFQFQEALC QAAKHEGPLH  540
KCDISNSTEA GQKLFNMLRL GKSEPWTLAL ENVVGAKNMN VRPLLNYFEP LFTWLKDQNK  600
NSFVGWSTDW SPYADPSTPP TPSPSTPPTP SPSCCHPRLS LHRPALEDLL LGSEANLTCT  660
LTGLRDASGV TFTWTPSSGK SAVQGPPERD LCGCYSVSSV LPGCAEPWNH GKTFTCTAAY  720
PESKTPLTAT LSKSGNTFRP EVHLLPPPSE ELALNELVTL TCLARGFSPK DVLVRWLQGS  780
QELPREKYLT WASRQEPSQG TTTFAVTSIL RVAAEDWKKG DTFSCMVGHE ALPLAFTQKT  840
IDRLAGKPTH VNVSVVMAEV DGTCY                                        865

SEQ ID NO: 238         moltype = AA  length = 6
FEATURE                Location/Qualifiers
source                 1..6
                       mol_type = protein
                       organism = synthetic construct
SEQUENCE: 238
SPYVMH                                                             6

SEQ ID NO: 239         moltype = AA  length = 6
FEATURE                Location/Qualifiers
source                 1..6
                       mol_type = protein
                       organism = synthetic construct
SEQUENCE: 239
SSYVMH                                                             6

SEQ ID NO: 240         moltype = AA  length = 9
FEATURE                Location/Qualifiers
source                 1..9
                       mol_type = protein
                       organism = synthetic construct
SEQUENCE: 240
AIWGWTNTY                                                          9

SEQ ID NO: 241         moltype = AA  length = 11
FEATURE                Location/Qualifiers
source                 1..11
                       mol_type = protein
                       organism = synthetic construct
SEQUENCE: 241
GRELAAFTKT A                                                       11

SEQ ID NO: 242         moltype = AA  length = 11
FEATURE                Location/Qualifiers
source                 1..11
                       mol_type = protein
                       organism = synthetic construct
SEQUENCE: 242
GEELAAFTKT A                                                       11

SEQ ID NO: 243         moltype = AA  length = 9
FEATURE                Location/Qualifiers
source                 1..9
                       mol_type = protein
                       organism = synthetic construct
SEQUENCE: 243
DLWGPGFFA                                                          9

SEQ ID NO: 244         moltype = AA  length = 39
FEATURE                Location/Qualifiers
source                 1..39
                       mol_type = protein
                       organism = synthetic construct
SEQUENCE: 244
YADSVKGRFT ISSDNSKNTL YLQMNSLRAE DTAVYYCAR                         39

SEQ ID NO: 245         moltype = AA  length = 39
FEATURE                Location/Qualifiers
source                 1..39
                       mol_type = protein
                       organism = synthetic construct
SEQUENCE: 245
YADSVKGRFT ISVDNSKNTL YLQMNSLRAE DTAVYYCAR                         39
```

PEPTIDE THERAPEUTICS AGAINST SARS-COV-2 SPIKE PROTEIN

CROSS-REFERENCE TO RELATED APPLICATIONS

This patent application claims the benefit under 35 U.S.C. § 120 to International Application No. PCT/US2021/021819 filed on 11 Mar. 2021. The PCT application claims the benefit under 35 U.S.C. § 120 to U.S. application Ser. No. 16/880,804 filed on 21 May 2020. The PCT application also claims the benefit under 35 U.S.C. § 119 (e) to U.S. Provisional Application Nos. 62/988,328 filed on 11 Mar. 2020, 62/991,504 filed on 18 Mar. 2020, 63/016,048 filed on 27 Apr. 2020, 63/016,241 filed on 27 Apr. 2020, 63/022,146 filed on 8 May 2020, 63/036,445 filed on 9 Jun. 2020, 63/080,887 filed on 21 Sep. 2020, 63/082,145 filed on 23 Sep. 2020, and 63/121,102 filed on 3 Dec. 2020. The entire contents of PCT/US2021/021819, U.S. Ser. No. 16/880,804, U.S. 62/988,328, U.S. 62/991,504, U.S. 63/016,048, U.S. 63/016,241, U.S. 63/022,146, U.S. 63/036,445, U.S. 63/080,887, U.S. 63/082,145, and U.S. 63/082,145 are hereby incorporated by reference.

STATEMENT OF A SEQUENCE LISTING

The present disclosure contains references to amino acid sequences and nucleic acid sequences which have been submitted concurrently herewith as the sequence listing text file entitled "ST26_SL_1_Mar_2023," file size 692 KiloBytes (KB), created on 1 Mar. 2023. The aforementioned sequence listing is hereby incorporated by reference in its entirety pursuant to 37 C.F.R. § 1.52 (e) (5).

FIELD

The present disclosure relates to proteins that can be administered to subjects for the prevention and/or treatment of COVID-19 and other such virally induced diseases.

BACKGROUND

Angiotensin-converting enzyme 2 (ACE2) is a regulatory carboxypeptidase of the renin-angiotensin hormone system and functions as regulator of cardiovascular homeostasis. ACE2 is expressed in numerous tissues, including lung alveolar epithelial cells, enterocytes of the small intestine, Leydig cells and Sertoli cells, the renal proximal tubule, and testis. ACE2 is also a receptor for human coronaviruses such as severe acute respiratory syndrome coronavirus (SARS-CoV) and severe acute respiratory syndrome coronavirus 2 (SARS-CoV-2). The widespread expression of ACE2 in various human tissues makes it possible for human coronaviruses to infect effectively and massively.

Currently, there are no known effective treatment options that can reduce or even entirely avoid the pathogenic effects of a coronavirus infection and its sequelae. While several drugs (e.g., remdesivir, hydroxychloroquine, azithromycin, immune suppressive steroids, etc.), have been proposed for treatment of COVID-19, efficacy is presently unknown. Moreover, most of the known proposed drugs will not directly affect the virus or prevent its entry into the host cells but will often reduce an overstimulated immune response to the virus. Likewise, there are no known effective vaccine compositions that would help treat or avoid coronavirus disease.

Batlle & al. (2020) *Clin. Sci.* 134:543-45 hypothesize that a soluble angiotensin converting enzyme 2 (ACE2) extracellular domain, conjugated to a gamma globulin (IgG1) crystallizable fragment (Fc) domain, can serve as a therapeutic against COVID-19 infection.

Batlle & Wysocki describe chimeric ACE2-Fc constructs in International Patent Application Publication No. WO 2018/140456.

Esvelt (2020, "Designing virus-specific sACE2 mimics for competitive inhibition of SARS-CoV-2," available at covid19-hpc-consortium.org/projects/5e90e0ca836090007f1ddb39) hypothesizes that ACE2 constructs can be mutated to achieve varieties that have a higher binding affinity to the severe acute respiratory syndrome coronavirus 2 (SARS-CoV-2) Spike protein's receptor-binding domain (Spike-RBD). Hypothetically, such mutants would outcompete natural ACE2 for Spike-RBD, thus blocking the ability of the Spike-RBD to bind ACE2 on human cells.

Jiang & al. (2020) *Trends Immunol.* 41 (5): 355-59 report neutralizing monoclonal antibodies (mAbs) against SARS-CoV-2.

SUMMARY

Disclosed herein are various proteinaceous therapeutics that can be used to treat and/or prevent COVID-19 infection. In certain embodiments, ACE2 decoy peptides and fragments of ACE2 decoy peptides—optionally conjugated to an Fc domain—are disclosed that have a higher affinity for SARS CoV-2 Spike RBD than does human, wild-type ACE2. These ACE2 decoy peptides and fragments thereof can be used to prevent or inhibit viral entry in an individual not actively infected with SARS CoV-2. They can also be used in an individual already infected with SARS-CoV-2 to prevent spread of virus from infected to non-infected cells, thus slowing and containing the disease. Also disclosed herein are nucleotides and nucleotide vectors (including viral vectors) suitable for inducing a subject's own cells to produce these therapeutically effective ACE2 decoy peptides, fragments, and/or chimeras.

Additionally or alternatively, also disclosed herein are various mAbs that specifically bind SARS CoV-2 spike, as well as Fab and scFv fragments of these mAbs. These mAbs and fragments can be used to prevent viral entry in an individual not actively infected with SARS CoV-2. They can also be used in an individual already infected with SARS-CoV-2 to prevent spread of virus from infected to non-infected cells, thus slowing and containing the disease. Also disclosed herein are nucleotides and nucleotide vectors (including viral vectors) suitable for inducing a subject's own cells to produce these therapeutically effective mAbs and/or fragments.

Various objects, features, aspects, and advantages will become more apparent from the following detailed description of preferred embodiments, along with the accompanying drawings.

DETAILED DESCRIPTION

I. Definitions

Figure 1:
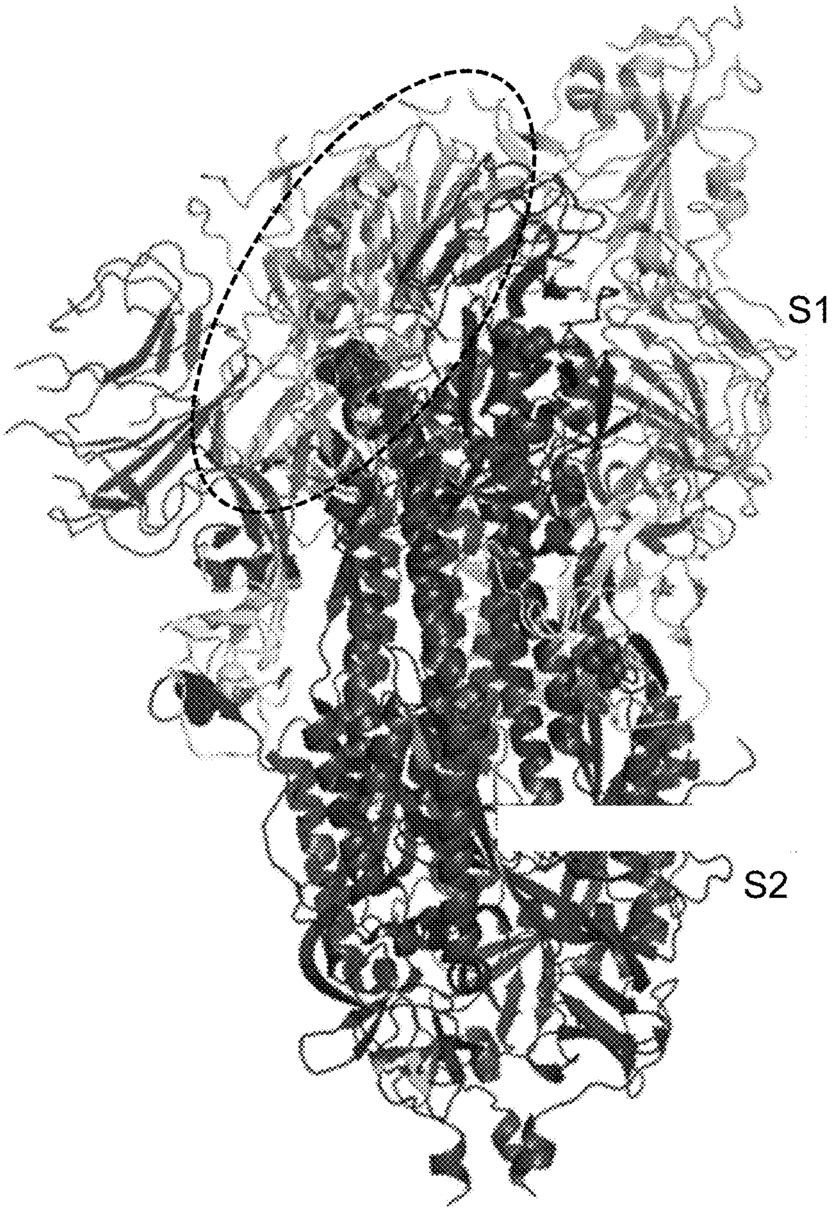
FIG. 1 depicts a crystal structure of the SARS-CoV-2 Spike protein trimer. The trimer's S1 and S2 domains are indicated. Broken lines delineate the portion of the trimer enlarged in FIG. 2.

The following definitions refer to the various terms used above and throughout the disclosure.

"Concomitant" or "concomitantly" includes administering an agent (e.g., IL-15 agonist) in the presence of a further agent (e.g., an ACE2 mutant). Concomitant administration in a therapeutic treatment method includes methods in which a first, second, third, or additional agents are co-administered. Concomitant administration also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent (e.g., an ACE2 mutant) and a second actor may administer to the subject a second agent (e.g., IL-15 agonist), and the administering steps may be executed at the same time, or nearly the same time. The actor and the subject may be the same entity (e.g., human). Thus, the term embraces both simultaneous administration and substantially simultaneous administration, i.e., at about the same time.

As used herein, a mutation position in an ACE2 mutant is designated relative to the corresponding position in SEQ ID NO:135.

"Encoding"—when used to describe a polynucleotide—conveys that when transcription is initiated from the polynucleotide in a wild-type human cell, the transcript produced would be translated into a given protein. That is to say, a polynucleotide "encodes" a polypeptide when the codon triplets of wild-type human tRNA would produce the polypeptide from the polynucleotide according to the ordinary workings of transcription and translation in the wild-type human cell.

"Effective amount" or "therapeutically effective amount" refers to the amount and/or dosage, and/or dosage regime of one or more agent(s) necessary to bring about the desired result e.g., an amount sufficient to prevent an infection in a subject, an amount sufficient to reduce the occurrence of an infection in a subject, and/or an amount sufficient to treat an infection in a subject.

"IL-15 agonist" refers to a compound or molecule that binds to and activates the IL-15 receptor ("IL-15Rα"). The type of compound or molecule of the IL-15 agonist is not particularly limited so long as it binds to and activates the IL-15Rα. The IL-15 agonist may be a peptide, protein, small molecule (e.g., a pharmaceutical drug), or oligonucleotide. The peptide or proteins may be a single amino acid sequence or two or more sequences bound via covalent attachments (e.g., disulfide bonds) or non-covalent attachments (e.g., hydrophilic or hydrophobic interactions, hydrogen bonds). In a particular embodiment, the IL-15 agonist is an antibody, modified antibody, chimeric antibody, or a derivative thereof. In a further embodiment, the IL-15 agonist is a superagonist complex, such as an IL-15 derivative bound to an IL-15Rα/IgG1 Fc fusion protein, also known as nogapendekin alfa-imbakicept (NAI). NAI is also known in the literature as N-803, ALT-803, or IL-$15_{N72D}$: IL-15RαSu/$IgG_1$. U.S. Pat. No. 9,328,159, which describes NAI, is incorporated herein by reference in its entirety. Clinical trials involving N-803 are described in NCT04385849, which is incorporated herein by reference in its entirety. In some embodiments, the IL-15 agonist is administered alone, and/or as the sole therapeutic agent for the treatment of a disease, disorder, condition, or infection as described herein. In another embodiment, the IL-15 agonist is administered in combination with another compound or molecule, for example in combination with: an antibody or Fab fragment that binds to a Spike protein or modified variant thereof; an ACE decoy peptide or variant thereof; and/or an agent that modulates ACE or ACE2 signaling (e.g., an ACE inhibitor or an angiotensin receptor antagonist).

Binding of the IL-15 agonist to the IL-15Rα induces a signal to downstream elements to activate the IL-15 signaling pathway and activate the cell. Cells expressing IL-15Rα include, but are not limited to, T cells, NK cells, monocytes, macrophages, dendritic cells, keratinocytes, fibroblasts, myocytes, and nerve cells. Guo, et al. *Cytokine Growth Factor Rev.,* 2017. Binding of the IL-15 agonist to the IL-15Rα propagates a signal through the IL-15Rα (e.g., via a conformational change) that initiates the IL-15 signaling pathway to activate an immune response, such as an antiviral response.

"Subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In certain embodiments, the subject can be human (e.g., adult male, adult female, adolescent male, adolescent female, male child, female child) under the care of a physician or other health worker. In certain embodiments the subject may not be under the care of a physician or other health worker.

"SARS-CoV-2" refers to severe acute respiratory syndrome coronavirus 2. It is a highly infectious, positive sense, single-stranded RNA virus that causes the respiratory illness known as COVID-19. The sequence of the wildtype virus can be found at ncbi.nlm.nih.gov/nuccore/NC_045512.2 (RefSeq NC_045512.2). As used herein, SARS-CoV-2 also includes mutations and variants of the canonical virus, including but not limited to SARS-CoV-2 mutants and variants that can induce COVID-19 symptoms in the global human population. In some embodiments, the SARS-CoV-2 mutants and variants induce any two or more COVID-19 symptoms in at least 10% of the global human population.

COVID-19 is the respiratory illness in humans caused by infection of a subject with SARS-CoV-2, which includes the wildtype virus and mutants and variants thereof. Symptoms of COVID-19 include, but are not limited to headache, confusion, loss of smell and taste, nasal congestion and rhinorrhea, cough, muscle aches and/or pain, sore throat, fever, chills, diarrhea, breathing difficulties, pneumonia, vomiting, dyspnea, hypoxia, respiratory failure, shock, multiorgan dysfunction, and combinations thereof. In some subjects, the symptoms will occur in clusters, e.g., cough, sputum, shortness of breath and fever; or muscle pain, joint pain, headache, and fatigue.

An "agent that modulates at least one of ACE and ACE2 signaling" refers to a compound or molecule that modulates (e.g., increases or decreases) the expression and/or activity of angiotensin converting enzyme (ACE) or ACE2 in particular. In some embodiments, The agent that modulates at least one of ACE or ACE2 signaling may be an ACE inhibitor or a compound that increases ACE2 expression. In some embodiments, the compound may be an ACE inhibitor selected from, but not limited to, the group consisting of Benazepril, Captopril, Fosinopril, Lisinopril, Enalapril, Perindopril, Moexipril, Quinapril, Ramipril, and Trandolapril. In some embodiments, the compound is an angiotensin receptor antagonist selected from, but not limited to, Candesartan, Olmesartan, Valsartan, and Losartan. Additionally or alternatively, the additional agent may be an inhibitor of BDKRB1/2, AGTR1, MAS1, or renin.

"Treat" and "treatment" each refer to a method for reducing, inhibiting, or otherwise ameliorating an infection by administering a therapeutic to a subject in need of treatment. In some embodiments, the subject in need of treatment may include a subject having, diagnosed as having, or suspected to have an infection. In a particular embodiment, treat or treatment include administering a therapeutic to a subject having, diagnosed as having, or suspected of having COVID-19. Additionally or alternatively, the subject may be infected with SARS-CoV-2, diagnosed with being infected with SARS-CoV-2, or suspected of being infected with SARS-CoV-2. In some embodiments, the subject may be asymptomatic. Treatment includes administration of any of an ACE2 decoy peptide or variant thereof optionally fused to an Fc domain, Fab fragment or antibody that binds to the Spike protein, an IL-15 agonist, IL-2, or an agent that modulates at least one of ACE and ACE2 signaling, alone, or any combination thereof.

II. ACE2 Decoy Peptide and Variants Thereof

The natural cell-surface receptor for SARS CoV-2 is the extracellular domain of ACE2. By mutating the portion of ACE2 that interacts with the SARS-CoV-2 Spike-RBD, one can make ACE2 decoy peptides (or peptide fragments thereof) that bind to the RBD with higher affinity than does the wild-type ACE2 extracellular domain. The modified forms of ACE2 decoy peptide may be changed to preserve at least three domains known to interact with the SARS-COV Spike glycoprotein. Likewise, ACE2 portions preferably include a leader peptide to allow secretion from a recombinant cell producing ACE2-Fc constructs (discussed herein). Thus, where a truncation is present on the C terminus, the truncation may remove the sequence motif needed for cleavage by ADAM17 and/or the sequence motif needed for cleavage by TMPRSS11D and/or TMPRSS2. These high-affinity ACE2-Fc constructs can effectively "chelate" the virus away from the wild-type ACE2 on the surfaces of a subject's cells.

The ACE2 protein is 805 amino acids long, but in certain preferred embodiments the ACE2 decoy will not include the entire 805 amino acid ACE2 sequence, but will rather consist of a truncation, for example the ACE2 decoy peptide may lack a transmembrane domain. In certain embodiments, the therapeutic protein will contain no more than 700 amino acids, for example no more than 600 amino acids, no more than 500 amino acids, no more than 400 amino acids, no more than 300 amino acids, no more than 200 amino acids, no more than 100 amino acids, or even 50 or fewer amino acids. For example, certain preferred embodiments will consist of amino acid residues 1-740, or 1-615, or 10-400, or 20-100, or 21-614, or 20-50, or 320-360. Wildtype ACE2 is illustrated as SEQ ID NO:135.

Suitable mutations that improve the ACE2 binding affinity for Spike-RBD include mutations to the glutamine at ACE2 position 24 (SEQ ID NO:136), to the threonine at position 27 (SEQ ID NO:137), to the aspartic acid at position 30 (SEQ ID NO:138), to the histidine at position 34 (SEQ ID NO:139), to the glutamic acid at position 35 (SEQ ID NO:140), to the aspartic acid at position 38 (SEQ ID NO:141), to the tyrosine at position 41 (SEQ ID NO:142), to the arginine at position 273 (SEQ ID NO:201), to the histidine at position 345 (SEQ ID NO:202), to the aspartic acid at position 355 (SEQ ID NO:143), to the histidine at position 374 (SEQ ID NO:203), to the histidine at position 378 (SEQ ID NO:204), to the histidine at position 505 (SEQ ID NO:205). Various combinations of these individual point mutations (e.g., position 24 & position 27, 24 & 30, 24 & 34, 24 & 35, 24 & 38, 24 & 41, 24 & 355, 27 & 30, 27 & 34, 37 & 35, 27 & 38, 27 & 41, 27 & 355, 30 & 34, 30 & 35, 30 & 38, 30 & 41, 30 & 355, 34 & 35, 34 & 38, 34 & 41, 34 & 355, 35 & 38, 35 & 41, 35 & 355, 38 & 41, 38 & 355, 41 & 355, 24 & 27 & 30, 24 & 27 & 34, 24 & 27 & 35, 24 & 27 & 38, 24 & 27 & 41, 24 & 27 & 355, 24 & 30 & 34, 24 & 30 & 35, 24 & 30 & 38, 24 & 30 & 41, 24 & 30 & 355, 24 & 34 & 35, 24 & 34 & 38, 24 & 34 & 41, 24 & 34 & 355, 24 & 35 & 38, 24 & 35 & 41, 24 & 35 & 355, 24 & 38 & 41, 24 & 38 & 355, 24 & 41 & 355, 27 & 30 & 34, 27 & 30 & 35, 27 & 30 & 38, 27 & 30 & 41, 27 & 30 & 355, 27 & 34 & 35, 27 & 34 & 38, 27 & 34 & 41, 27 & 34 & 273, 27 & 34 & 345, 27 & 34 & 355, 27 & 34 & 374, 27 & 34 & 505, 27 & 35 & 38, 27 & 35 & 41, 27 & 35 & 355, 27 & 38 & 41, 27 & 38 & 355, 27 & 41 & 355, 30 & 34 & 35, 30 & 34 & 38, 30 & 34 & 41, 30 & 34 & 355, 30 & 35 & 38, 30 & 35 & 41, 30 & 35 & 355, 30 & 38 & 41, 30 & 38 & 355, 30 & 41 & 355, 34 & 35 & 38, 34 & 35 & 41, 34 & 35 & 355, 34 & 38 & 41, 34 & 38 & 355, 34 & 41 & 355, 35 & 38 & 41, 35 & 38 & 355, 35 & 41 & 355, 38 & 41 & 355, 24 & 27 & 30 & 35, 24 & 27 & 30 & 38, 24 & 27 & 30 & 41, 24 & 27 & 30 & 355, 24 & 30 & 35 & 38, 24 & 30 & 35 & 41, 24 & 30 & 35 & 355, 24 & 35 & 38 & 41, 24 & 35 & 38 & 355, 24 & 38 & 41 & 355, 27 & 30 & 35 & 38, 27 & 30 & 35 & 41, 27 & 30 & 35 & 355, 27 & 35 & 38 & 41, 27 & 35 & 38 & 355, 27 & 38 & 41 & 355, 30 & 35 & 38 & 41, 30 & 35 & 38 & 355, 30 & 38 & 41 & 355, 35 & 38 & 41 & 355, 24 & 27 & 30 & 35 & 38, 24 & 27 & 30 & 35 & 41, 24 & 27 & 30 & 35 & 355, 27 & 30 & 34 & 35 & 41, 27 & 30 & 34 & 35 & 355, 30 & 34 & 35 & 38 & 41, 30 & 34 & 35 & 38 & 355, 30 & 34 & 38 & 41 & 355, 30 & 35 & 38 & 41 & 355, 34 & 35 & 38 & 41 & 355, 24 & 27 & 30 & 34 & 35 & 41, 24 & 27 & 30 & 34 & 35 & 355, 24 & 27 & 34 & 35 & 41 & 355, 24 & 27 & 30 & 34 & 41 & 355, 24 & 27 & 30 & 34 & 35 & 355, 24 & 30 & 34 & 35 & 38 & 41, 24 & 30 & 34 & 35 & 38 & 355, 27 & 30 & 34 & 35 & 38 & 41, 27 & 30 & 34 & 35 & 38 & 355, 27 & 30 & 34 & 35 & 41 & 355, 30 & 34 & 35 & 38 & 41 & 355, 24 & 27 & 30 & 34 & 35 & 38 & 41, 24 & 27 & 30 & 35 & 38 & 355, 24 & 27 & 30 & 34 & 35 & 41 & 355, 24 & 27 & 30 & 34 & 38 & 41 & 355, 24 & 27 & 30 & 35 & 38 & 41 & 355, 24 & 27 & 34 & 35 & 38 & 41 & 355, 24 & 30 & 34 & 35 & 38 & 41 & 355, 27 & 30 & 34 & 35 & 38 & 41 & 355, and 24 & 27 & 30 & 34 & 35 & 38 & 41 & 355) are also useful for improving affinity for RBD, and all such mutations are illustrated in SEQ ID NO:144.

SEQ ID NOs: 136-144, 147-159, and 201-212 are offered only as examples of suitable ACE2 decoy peptides, but many variations on these sequences are also useful for anti-COVID19 therapeutic purposes. For example, polypeptides having at least 70% sequence identity (i.e., at least 75% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity) to any one of SEQ ID NOs: 136-144, 147-159, and 201-212 are also useful for therapeutic purposes, provided that the molecule retains—broadly—the overall binding site structure and orientation of the individual SEQ ID NOs: 136-144, 147-159, and 201-212 molecules. SEQ ID NOs: 136-144 disclose ACE2 decoy peptide mutants with a potential single mutation within the protein. SEQ ID NOs: 147-159 and 201-205 disclose ACE2 decoy peptide mutants with a specific single mutation within the protein. SEQ ID NOs: 206-212 describe ACE2 decoy peptide mutants with three point mutations (e.g., a triple mutant).

In one embodiment, a double mutant of ACE2 decoy peptide having the mutations T27Y and H34A is contemplated. An essential mechanism for SARS-CoV-1 and -2 infection begins with the viral spike protein binding to the human receptor protein ACE2. A double mutated ACE2 decoy peptide, or peptide of the binding domain, can bind to the viral spike protein with a very high binding affinity and thus outcompete, reduce, or even entirely avoid viral docking. In one embodiment, the α-helix of ACE2 decoy peptide has the mutations T27Y and H34A. This mutated ACE2 decoy peptide may be generated by introducing the T27Y and H34A mutations into the α-helix of ACE2, wherein the α-helix is proximal to the RBD when the RBD and the ACE2 form a binding complex. The mutated α-helix is shown to have a higher binding affinity to the RBD as compared to a wild type α-helix of ACE2. This double mutated ACE2 decoy peptide may be used for treating or preventing COVID-19.

Additionally or alternatively, the ACE2 decoy peptide moiety can be fused to an Fc domain to create a therapeutic protein chimera (also referred to as a hybrid polypeptide, hybrid construct, fusion polypeptide and/or fusion construct). While any Fc domain (e.g., an Fc domain from IgA, IgD, IgE, IgG, IgM, etc.) can be used, in preferred embodiments the chimera will comprise an Fc domain from an IgA or IgG. In additional embodiments, the IgGFc is selected from the group consisting of $IgG_1Fc$, $IgG_2Fc$, $IgG_3Fc$, and $IgG_4Fc$. For example, the Fc domain can have at least 70% identity (e.g., at least 75%, at least 80%, at least 85%, at least 90%, at least 95%, at least 96%, at least 97%, at least 98%, at least 99%, or even 100% identity) to SEQ ID NO: 145 or 146. In some embodiments, the ACE2 decoy peptide mutants comprising multiple mutations, such as three mutations, for example T27Y and H34A and an additional mutation (e.g., at R273K, R273L, R273Q, H345A, H374N, H378N, and H505L) may be transferred onto an IgA scaffold. In a preferred embodiment, the triple mutation is the T27Y, H34A, and H374N mutation. Fusing the ACE2 moiety to the IgFc domain can be accomplished by incorporating nucleotide sequences encoding the ACE2 mutants and an IgFc scaffold (e.g., an IgAFc scaffold) into a vector, such as an adenoviral vector. The vector is then formulated in a pharmaceutical composition suitable for administration, such as by subcutaneous, intramuscular, or oral delivery. Alternatively, The ACE2 decoy peptide and Fc may be coupled via a linker, e.g., a flexible peptide linker. Typically, peptide linkers may have between 5 and 25 amino acids and all known flexible linkers are deemed appropriate for use herein. Particularly suitable linkers include a run of glycines interspersed with serines (e.g., GGGS). Additionally or alternatively, the ACE2-Fc hybrid construct may be immobilized on a carrier. All manners of modifications to permit immobilization are suitable, e.g., biotinylation, cellulose binding domain, etc. A detectable label may also be added to the ACE2-Fc hybrid construct to enable in situ detection and/or quantification in a quantitative assay. Suitable labels include luminescent labels, radioisotope labels, enzymatic labels, etc.

III. Antigen Binding Fragments and Antibodies

Antigen binding fragments (Fab fragments) and antibodies that bind to the SARS-CoV-2 Spike protein—and particularly antibodies that bind to the Spike RBD—can interfere with SARS-CoV-2 entry into a host cell. The antibodies and Fab fragments disclosed herein can bind SARS-CoV-2 Spike, including several that can bind the Spike RBD.

To illustrate the anti-Spike antibodies and Fab fragments disclosed herein, exemplary Fab fragments are described having a heavy chain variable region ($V_H$) with a structure A-$V_H$CDR1-B-$V_H$CDR2-C-$V_H$CDR3-D. These exemplary anti-Spike Fab fragments also have a light chain variable region ($V_L$) with a structure SEQ ID NO:131-$V_L$ CDR3-E. Amino acid sequences for the $V_H$ & $V_L$ of various such Fab fragments are set forth in Table 1 below. The binding affinities of certain of these Fab fragments have been confirmed by surface plasmon resonance (SPR).

TABLE 1

Exemplary anti-Spike Fab sequences (CDR numbers = SEQ ID NOs)

| | | $V_H$ | | | | | | $V_L$ | | | |
|---|---|---|---|---|---|---|---|---|---|---|---|
| Fab # | | CDR1 | | CDR2 | | CDR3 | | | CDR3 | | SPR |
| N-612-002 | SEQ ID NO: 127 | 3 | SEQ ID NO: 128 | 4 | SEQ ID NO: 129 | 5 | SEQ ID NO: 130 | SEQ ID NO: 131 | 6 | SEQ ID NO: 132 | + |
| N-612-007 | | 7 | | 8 | | 9 | | | 10 | | + |
| N-612-012 | | 11 | | 12 | | 13 | | | 14 | | |
| N-612-034 | | 15 | | 16 | | 17 | | | 18 | | |
| N-612-003 | | 19 | | 20 | | 21 | | | 22 | | |
| N-612-052 | | 23 | | 24 | | 25 | | | 26 | | |
| N-612-004 | | 27 | | 28 | | 29 | | | 30 | | + |
| N-612-006 | | 31 | | 32 | | 33 | | | 34 | | + |
| N-612-014 | | 35 | | 36 | | 37 | | | 38 | | + |
| N-612-032 | | 39 | | 40 | | 41 | | | 42 | | + |
| N-612-056 | | 43 | | 44 | | 45 | | | 46 | | + |
| N-612-054 | | 47 | | 48 | | 49 | | | 50 | | |
| N-612-060 | | 51 | | 52 | | 53 | | | 54 | | |
| N-612-013 | | 55 | | 56 | | 57 | | | 58 | | + |
| N-612-038 | | 59 | | 60 | | 61 | | | 62 | | |
| N-612-041 | | 63 | | 64 | | 65 | | | 66 | | |
| N-612-017 | | 67 | | 68 | | 69 | | | 70 | | + |
| N-612-057 | | 71 | | 72 | | 73 | | | 74 | | |
| N-612-044 | | 75 | | 76 | | 77 | | | 78 | | |
| N-612-005 | | 79 | | 80 | | 81 | | | 82 | | |
| N-612-087 | | 173 | | 174 | | 175 | | | 176 | | + |
| N-612-072 | | 177 | | 178 | | 179 | | | 180 | | + |
| N-612-085 | | 181 | | 182 | | 183 | | | 184 | | + |
| N-612-086 | | 185 | | 186 | | 187 | | | 188 | | + |
| N-612-181 | | 189 | | 190 | | 191 | | | 192 | | |
| N-612-074 | | 193 | | 194 | | 195 | | | 196 | | + |
| N-612-194 | | 197 | | 198 | | 199 | | | 200 | | + |
| N-612-17-01 | | 67 | | 68 | | 69 | | | 70 | | |
| N-612-17-03 | | 67 | | 68 | | 241 | | | 70 | | |
| N-612-017-5B02 | | 63 | | 240 | | 69 | | | 70 | | |
| N-612-017-5B05 | | 238 | | 68 | | 242 | | | 70 | | |
| N-612-017-5B05SV | | 239 | | 68 | 245 | 242 | | | 70 | | |
| N-612-056-21 | | 43 | | 44 | 129 | 243 | | | 46 | | |

Certain of the anti-Spike Fab fragments bind specifically to the Spike RBD. Amino acid sequences for the $V_H$ & $V_L$ of various such Fab fragments are set forth in Table 2 below. The binding affinities of certain of these Fab fragments for the Spike protein trimer and/or for an RBD peptide have been confirmed by surface plasmon resonance (SPR).

TABLE 2

Exemplary anti-RBD Fab sequences (CDR numbers = SEQ ID NOs)

| | V$_H$ | | | | | | | | V$_L$ | | | SPR | |
|---|---|---|---|---|---|---|---|---|---|---|---|---|---|
| Fab # | | CDR1 | | CDR2 | | CDR3 | | | | CDR3 | | Trimer | Peptide |
| N-612-123 | SEQ ID | 83 | SEQ ID | 84 | SEQ ID | 85 | SEQ ID | SEQ ID | | 86 | SEQ ID | | |
| N-612-142 | NO: 127 | 87 | NO: 128 | 88 | NO: 129 | 89 | NO: 130 | NO: 131 | | 90 | NO: 132 | + | |
| N-612-149 | | 91 | | 92 | | 93 | | | | 94 | | | |
| N-612-168 | | 95 | | 96 | | 97 | | | | 98 | | | |
| N-612-107 | | 99 | | 100 | | 101 | | | | 102 | | + | + |
| N-612-111 | | 103 | | 104 | | 105 | | | | 106 | | + | + |
| N-612-159 | | 107 | | 108 | | 109 | | | | 110 | | | |
| N-612-131 | | 111 | | 112 | | 113 | | | | 114 | | + | |
| N-612-102 | | 115 | | 116 | | 117 | | | | 118 | | + | + |
| N-612-115 | | 119 | | 120 | | 121 | | | | 122 | | + | |
| N-612-143 | | 123 | | 124 | | 125 | | | | 126 | | + | |

Notwithstanding the particular embodiments set out in Tables 1 and 2, the skilled person understands that the affinity of an antibody or Fab fragment is determined by the complementarity determining regions (CDRs), and that a great deal of change and adjustment can be made to the non-CDR portions of the variable domains without materially altering the usefulness of these antibodies or Fab fragments in neutralizing SARS-CoV-2 infectivity. Therefore, many sequences beyond those exemplified above are equally useful for treating COVID-19 disease. Particularly suitable sequences will retain at least 70% identity (e.g., at least 75%, at least 80%, at least 85%, at least 90%, at least 95%, at least 96%, at least 97%, at least 98%, or at least 99%) to SEQ ID NO: 127, at least 70% identity (e.g., at least 75%, at least 80%, at least 85%, at least 90%, at least 95%, at least 96%, at least 97%, at least 98%, or at least 99%) to SEQ ID NO:128, at least 70% identity (e.g., at least 75%, at least 80%, at least 85%, at least 90%, at least 95%, at least 96%, at least 97%, at least 98%, or at least 99%) to SEQ ID NO:129, at least 70% identity (e.g., at least 75%, at least 80%, at least 85%, at least 90%, at least 95%, at least 96%, at least 97%, at least 98%, or at least 99%) to SEQ ID NO:130, and at least 70% identity (e.g., at least 75%, at least 80%, at least 85%, at least 90%, at least 95%, at least 96%, at least 97%, at least 98%, or at least 99%) to SEQ ID NO:132. Similarly, particular suitable sequences will retain at least 70% identity (e.g., at least 75%, at least 80%, at least 85%, at least 90%, at least 95%, at least 96%, at least 97%, at least 98%, or at least 99%) to SEQ ID NO:131, except that such sequences will retain 100% identity to the light chain CDR1 and CDR2 within the SEQ ID NO:131 sequence.

In some embodiments, Fab fragments and antibodies that bind to the Spike protein (e.g., the Spike RBD) may additionally or alternatively bind to a modified and/or mutated Spike protein. The modified and/or mutated Spike protein may be found on Sars-Cov-2 variants. The modified Spike protein may differ from wild-type or naturally occurring Spike protein by containing point mutations, insertions, deletions, and/or inversions. In an embodiment, the one or more point mutations are selected from the group consisting S13I, L18F, T19R, T20N, P26S, A67V, ΔH69, ΔV70, G75V, T76I, D80A, T95I, D138Y, ΔL141, G142D, ΔG142, ΔV143, ΔY144, ΔY145, W152C, E154K, E156G, ΔF157, ΔR158, R190S, N211I, ΔL212, R214ins, D215G, ΔL241, ΔL242, L242H, ΔA243, ΔL244, R246N, ΔS247, ΔY248, ΔL249, ΔT250, ΔP251, ΔG252, ΔD253, G339D, S371L, S373P, S375F, K417N, K417T, N440K, G446S, S447N, L452Q, L452R, T478K, E484A, E484K, E484Q, F490S, Q493R, G496S, Q498R, N501Y, Y505H, T547K, A570D, D614G, H655Y, N679K, P681H, P681R, A701V, T716I, D796Y, N858K, T859N, D950N, Q954H, S982A, N969K, L981F, Q1071H, E1095K, H1101Y, D1118H, T1027I, V1176F and combinations thereof. Particular multiple mutations include, but are not limited to those listed in Table 3 below:

TABLE 3

| WHO Label | Pango lineage | Alternate Name | Mutations |
|---|---|---|---|
| Alpha | B.1.1.7 | UK variant | ΔH69, ΔV70, ΔY144, N501Y, A570D, P681H, T716I, S982A, D1118H |
| Beta | B.1.351 (501.V2) | South Africa variant | D80A, D215G, ΔL241, ΔL242, L242H, ΔA243, K417N, E484K, N501Y, D614G, A701V |
| Gamma | B.1.1.248 (P.1) | Brazil Variant | L18F, T20N, P26S, D138Y, R190S, K417T, E484K, N501Y, D614G, H655Y, T1027I, V1176F |
| Delta | B.617.2 | | T19R, G142D, E156G, ΔF157, ΔR158, L452R, T478K, D614G, P681R, D950N |
| Epsilon | B.1.427/ B.1.429 | CAL.20C or California variant | S13I, W152C, L452R, D614G |
| Zeta, Eta, or Iota | P.2 | | E484K, D614G, V1176F |
| Theta | P.3 | | ΔL141, ΔG142, ΔV143, ΔA243, ΔL244, E484K, N501Y, D614G, P681H, E1095K, H1101Y, V1176F |
| Kappa | B.1.617.1 | | G142D, E154K, L452R, E484Q, D614G, P681R, Q1071H |

TABLE 3-continued

| WHO Label | Pango lineage | Alternate Name | Mutations |
|---|---|---|---|
| Lambda | C.37 | | G75V, T76I, R246N, ΔS247, ΔY248, ΔL249, ΔT250, ΔP251, ΔG252, ΔD253, L452Q, F490S, D614G, T859N |
| Omicron | BA.1 | | A67V, ΔH69, ΔV70, T95I, G142D, ΔV143, ΔY144, ΔY145, N211I, ΔL212, R214ins, G339D, S371L, S373P, S375F, K417N, N440K, G446S, S447N, T478K, E484A, Q493R, G496S, Q498R, N501Y, Y505H, T547K, D614G, H655Y, N679K, P681H, N764K, D796Y, N858K, Q954H, N969K, L981F |

IV. Polynucleotides and Vectors

Contemporary molecular biologists know how to make nucleotides that express the proteins described herein, and how to express such nucleotides in cells to obtain the relevant proteins. Further embodiments provided herein include polynucleotides that encode a polypeptide comprising an ACE2 decoy peptide, wherein the ACE2 decoy peptide is a polypeptide of SEQ ID NO: 135 or a variant thereof. For example, a polynucleotide encoding wild-type human ACE2 is presented herein as SEQ ID NO:168. The ordinary molecular biologist knows how to alter the sequence of SEQ ID NO:168 to encode SEQ ID NOs: 136-144, 147-159, and 201-212 and appropriate variants thereof (e.g., variants having at least 70% identity (e.g., at least 75%, at least 80%, at least 85%, at least 90%, at least 95%, at least 96%, at least 97%, at least 98%, or at least 99% to any one of SEQ ID NOs: 136-144). Non-limiting examples of polynucleotides encoding SEQ ID NOs: 206-212 are provided herein as SEQ ID NOs: 213-219, respectively. Non-limiting examples of polynucleotides encoding suitable Fc domains are provided herein as SEQ ID NOs: 169 & 170. In a particular embodiment, the polynucleotide encodes an ACE2 decoy polypeptide wherein the threonine at position 27 is replaced with tyrosine (T27Y), the histidine at position 34 is replaced with alanine (H34A), and the histidine at position 374 is replaced with asparagine (H374N). In a particular embodiment, the polynucleotide is characterized by SEQ ID NO: 216. In a further embodiment, the ACE2 decoy peptide or variant thereof is fused or otherwise linked to an IgFc to form a fusion polypeptide. In a particular embodiment, the IgFc is selected from the group consisting of IgAFc, IgDFc, IgEFc, IgGFc, and IgMFc. Where the IgFc is an IgGFc, the Fc may be an $IgG_1Fc$, $IgG_2Fc$, $IgG_3Fc$, or $IgG_4Fc$.

Similarly, examples of suitable polynucleotides encoding Fab heavy and light chains are presented herein as SEQ ID NOs: 171 & 172. The ordinary molecular biologist knows how to alter the sequences of SEQ ID NOs: 171 & 172 to encode Fab fragments with the relevant CDRs of the anti-Spike and anti-RBD antibodies disclosed herein. Similarly, the ordinary molecular biologist knows how to alter SEQ ID NOs: 171 & 172 further to encode an Fc domain or other such extended structure, if the user wishes to express these Fab fragments in the context of whole immunoglobulins. In an embodiment, the polynucleotide encodes a Fab fragment comprising a heavy variable ($V_H$) chain having at least 85% sequence identity to each of SEQ ID NOs: 127-130 and a light variable ($V_L$) chain having at least 85% identity to each of SEQ ID NOs: 131 & 132, wherein each of the $V_H$ chain and the $V_L$ chain have three complementarity determining regions (CDRs). Examples of CDRs for the $V_H$ chain include SEQ ID NOs: 3-5, 7-9, 11-13, 15-17, 19-21, 23-25, 27-29, 31-33, 35-37, 39-41, 43-45, 47-49, 51-53, 55-57, 59-61, 63-65, 67-69, 71-73, 75-77, 79-81, 83-85, 87-89, 91-93, 95-97, 99-101, 103-105, 107-109, 111-113, 115-117, 119-121, 123-125, 173-175, 177-179, 181-183, 185-187, 189-191, 193-195, 197-199, 238, and 240-243. Examples of CDRs for the $V_L$ chain include SEQ ID NOs: 6, 10, 14, 18, 22, 26, 30, 34, 38, 42, 46, 50, 54, 58, 62, 66, 70, 74, 78, 82, 86, 90, 94, 98, 102, 106, 110, 114, 118, 122, 126, 176, 180, 184, 188, 192, 196, and 200. In a further embodiment, the polynucleotide encodes a Fab fragment and a crystallizable fragment (Fc) domain.

In certain embodiments, the polynucleotides described above can be expressed in a supporter cell line. Mammalian cell lines such as Chinese hamster ovary (CHO) cells or 293T cells are particularly suitable for these purposes. The proteins described above are generally soluble, and will therefore be excreted from a producing cell unless they are modified for intracellular retention. Proteins produced in this manner can be purified from the culture medium. Where desired, the proteins may be tagged with (e.g.) a poly-histidine tag or other such commercially common tags to facilitate purification. Proteins produced and purified in this manner can then be administered to a subject in need thereof as described below.

Additionally or alternatively, the polynucleotides described above can be incorporated into a vector (e.g., a transfection vector or a viral transduction vector). Such vectors can then be transfected or transduced into the subject's own cells. In this way, the subject's own cells (e.g., the subject's respiratory mucosa) will produce ACE2 chimeras and/or anti-Spike antibodies to defend these tissues against SARS-CoV-2 infection. Non-limiting examples of vectors comprising the polynucleotides described above are provided herein as SEQ ID NOs: 220-233.

V. Methods of Treatment

The proteins, polynucleotides, and vectors described above can be used to treat and/or prevent COVID-19 disease and/or infection with SARS-CoV-2 or variant thereof. To treat and/or prevent this infection and disease, the proteins, polynucleotides, and vectors described above may be administered to the subject in need thereof in a therapeutically effective amount. The subject may be symptomatic or asymptomatic.

Where a protein is to be administered, any suitable route of administration may be used, including but not limited to intravenous injection, intramuscular injection, subcutaneous injection, and inhalation (e.g. aerosol inhalation). In a particular embodiment, the Fab fragment or polypeptide comprising an ACE2 decoy peptide is administered by inhalation (e.g. aerosol inhalation) to the respiratory mucosa of the subject. In some embodiments, the Fab fragment or polypeptide comprising an ACE2 decoy peptide is supplied to the respiratory mucosa of the subject. Therapeutically effective amounts of these proteins include but are not limited to 1 μg of protein per kg of subject body weight, 5 μg/kg, 10 μg/kg, 50 μg/kg, 100 μg/kg, 500 μg/kg, 1 mg/kg, 5 mg/kg, 10 mg/kg, 50 mg/kg, 100 mg/kg, 500 mg/kg, and 1 mg/kg or more.

Where a polynucleotide is to be transfected, any suitable amount can be administered, including (but not limited to) 10 ng, 50 ng, 100 ng, 500 ng, 1 μg, 5 μg, 10 μg, 50 μg, 100 μg, 500 μg, 1 mg, 5 mg, 10 mg, 50 mg, 100 mg, and 500 mg or more. To transfect subject cells with polynucleotides as described herein, it will be useful to extract cells from the subject, transfect them according to known techniques, and then transfuse the transfected cells back into the subject. Particularly suitable cells circulate throughout the body, such as circulating lymphocytes.

Where a polynucleotide is to be transduced, the viral vector can be administered directly to the subject, or cells can be extracted for transduction and re-transfusion. The viral vector can be administered to the subject by any suitable route of administration, including but not limited to intravenous injection, intramuscular injection, subcutaneous injection, and inhalation (e.g. aerosol inhalation). In a particular embodiment, the viral vector is administered by inhalation (e.g. aerosol inhalation). In another embodiment, the viral vector is supplied to the subject's respiratory mucosa.

Therapeutically effective virus amounts include but are not limited to $1\times10^7$ viral particles (VPs), $5\times10^7$ VPs, $1\times10^8$ VPs, $5\times10^8$ VPs, $1\times10^9$ VPs, $5\times10^9$ VPs, $1\times10^{10}$ VPs, or more than $1\times10^{10}$ VPs. Adenoviral vectors are particularly suitable for this purpose because of the large cargo capacity of the adenovirus. Suitable adenoviral vectors include those disclosed in WO 98/17783, WO 02/27007, WO 09/6479, & WO 14/31178, each of which is incorporated herein by reference in its entirety. Suitable methods for administering these adenoviral vectors are disclosed in WO 16/112188, which is herein incorporated by reference in its entirety.

Alternatively and/or additionally, administration of a protein or polypeptide (e.g. an ACE2 decoy peptide or a Fab fragment that binds to the SARS-CoV-2 Spike protein) may be combined with a protein or a polynucleotide that encodes a protein that stimulates an immune response to the viral infection (e.g. a SARS-CoV-2 infection). Where appropriate, such treatments include administration of an "IL-15 agonist" (e.g., NAI), an immune stimulatory cytokine or analog thereof (e.g., IL-2), a checkpoint inhibitor, an OX40 ligand, and/or cell lysate to provide a source of DAMPS and PAMPS. The polynucleotides may be a viral vector, such as from a non-pathogenic virus. In some embodiments, the NAI is administered at a dose of about 5 μg/kg/day to about 15 μg/kg/day. In a particular embodiment, the NAI is administered at a dose of about 5 μg/kg/day, about 6 μg/kg/day, about 7 μg/kg/day, about 8 μg/kg/day, about 9 μg/kg/day, about 10 μg/kg/day, about 11 μg/kg/day, about 12 μg/kg/day, about 13 μg/kg/day, about 14 μg/kg/day, or about 15 μg/kg/day. In a specific embodiment, the NAI is administered at about 10 μg/kg/day.

In a still further embodiment, an additional agent that modulates at least one of ACE and ACE2 signaling is administered. The agent that modulates at least one of ACE or ACE2 signaling may be an ACE inhibitor or a compound that increases ACE2 expression. In some embodiments, the compound may be an ACE inhibitor selected from, but not limited to, the group consisting of Benazepril, Captopril, Fosinopril, Lisinopril, Enalapril, Perindopril, Moexipril, Quinapril, Ramipril, and Trandolapril. In some embodiments, the compound is an angiotensin receptor antagonist selected from, but not limited to, Candesartan, Olmesartan, Valsartan, and Losartan. Additionally or alternatively, the additional agent may be an inhibitor of BDKRB1/2, AGTR1, MAS1, or renin.

In another embodiment, treatment of a subject having, diagnosed with having, or suspected of having SARS-CoV-2 comprises administering an IL-15 agonist or IL-2 as the sole therapeutic agent. Alternatively, the IL-15 agonist is administered in combination with another active agent, such as an agent that modulates at least one of ACE or ACE2 signaling. In another embodiment, treatment of a subject infected with, diagnosed as being infected with, or suspected of being infected with COVID-19 comprises an IL-15 agonist or IL-2 as the sole therapeutic agent or in combination with another active agent, such as an agent that modulates at least one of ACE or ACE2 signaling. In a further embodiment, the IL-15 agonist for treating SARS-CoV-2 and/or COVID-19 infection is NAI. In some embodiments, the NAI is administered at a dose of about 5 μg/kg/day to about 15 μg/kg/day. In a particular embodiment, the NAI is administered at a dose of about 5 μg/kg/day, about 6 μg/kg/day, about 7 μg/kg/day, about 8 μg/kg/day, about 9 μg/kg/day, about 10 μg/kg/day, about 11 μg/kg/day, about 12 μg/kg/day, about 13 μg/kg/day, about 14 μg/kg/day, and about 15 μg/kg/day. In a specific embodiment, the NAI is administered at about 10 μg/kg/day.

With respect to the non-pathogenic virus it should be appreciated that all viruses suitable for gene therapy are deemed suitable for use herein. However, especially preferred viruses are those already established in therapy, including adenoviruses, adeno-associated viruses, alphaviruses, herpes viruses, lentiviruses, etc. Among other appropriate choices, adenoviruses are particularly preferred. It should be particularly appreciated that these viruses are suitable for delivery of both payloads, the nucleic acid sequence for the host protein that is critical to viral entry/replication and the nucleic acid sequence for the antigenic viral proteins.

Moreover, it is further generally preferred that the virus is a replication deficient and non-immunogenic virus. For example, suitable viruses include genetically modified alphaviruses, adenoviruses, adeno-associated viruses, herpes viruses, lentiviruses, etc. However, adenoviruses are particularly preferred. For example, genetically modified replication defective adenoviruses are preferred that are suitable not only for multiple vaccinations but also vaccinations in individuals with preexisting immunity to the adenovirus (see e.g., WO 2009/006479 and WO 2014/031178, which are incorporated by reference in its entirety).

In some embodiments, the replication defective adenovirus vector comprises a replication defective adenovirus 5 vector. In some embodiments, the replication defective adenovirus vector comprises a deletion in the E2b region. In some embodiments, the replication defective adenovirus vector further comprises a deletion in the E1 and/or E3 region. In that regard, it should be noted that deletion of the E2b gene and other late proteins in the genetically modified replication defective adenovirus to reduce immunogenicity. Moreover, due to these specific deletions, such genetically modified viruses were replication deficient and allowed for relatively large recombinant cargo.

EXAMPLES

The following example is provided to further illustrate the invention disclosed herein but, of course, should not be construed as in any way limiting its scope.

Example 1: Selected exemplary constructs presented herein were expressed in CHO-S using Maxcyte electroporation. $3.2\times10^8$ cells were electroporated in Maxcyte electroporation buffer and cultured in CD Opti CHO media with CD CHO efficient feed for 14 days at 32° C. and 3% $CO_2$. ACE2-Fc hybrid constructs were isolated following known isolation procedures. The ACE2-Fc IgG Hybrid Protein had an amino acid sequence of SEQ ID NO:234, while the ACE2-Fc IgG R273Q Hybrid Protein (lacking ACE2 activity) had an amino acid sequence SEQ ID NO: 235. The ACE2-Fc IgA Hybrid Protein had an amino acid sequence of SEQ ID NO:236, while the ACE2-Fc IgA R273Q Hybrid Protein (lacking ACE2 activity) had an amino acid sequence SEQ ID NO:237.

Yield and relative purity for a small-scale Maxcyte production of IgG-Fc hybrid constructs were in a desirable range. Table 4 provides numerical results for the size exclusion chromatography.

TABLE 4

| ID | Production Culture Volume (mL) | Yield | % Main on SEC-HPLC |
|---|---|---|---|
| ACE2-IgG1Fc | 30 | 5.2 | 90.9 |
| ACE2(R273Q)-IgG1Fc | 30 | 8.4 | 91.7 |
| ACE2-IgG1Fc-Avi-tag | 40 | 6.2 | 94.5 |

ACE2-IgAFc expression was as efficient as ACE2-$IgG_1Fc$ expression, with no apparent differences in the mutated form (R273Q) vs. non-mutated form. Traditional IgG purification processes are often not effective for IgA, so the hybrid constructs were isolated using ion exchange chromatographic and affinity media selective for IgA. The purified ACE2-Fc hybrid constructs were tested for binding and avidity against 2019-n-COV Spike protein. Table 5 lists exemplary test results.

TABLE 5

| Method | Ligand | Analyte | $k_{on}$ (1/Ms) | $k_{off}$ (1/s) | KD (nM) |
|---|---|---|---|---|---|
| Octet-SA sensor | Spike-RBD | ACE2-$IgG_1Fc$ | 1.03E+05 | 7.89E−05 | 0.76 |
| Octet-SA sensor | Spike-RBD | ACE2(R273Q)-$IgG_1Fc$ | 1.04E+05 | 9.86E−05 | 0.95 |
| Octet-SA sensor | Spike-RBD | rACE2(1-740aa) dimer | 5.37E+04 | 6.63E−05 | 1.2 |
| SPR | 2019-nCoV Spike | ACE2 (1-615aa) monomer | 1.88E+05* | 2.76E−03* | 14.7* |

Where modified ACE2-Fc hybrid constructs are used for diagnostic tests, multiple test formats can be chosen. One exemplary system uses a biotin tagged ACE2-Fc hybrid construct immobilized to MSD streptavidin plate and another modified ACE2-Fc hybrid construct for detection (sulfo-tag MSD label). As shown, the ACE2-Fc hybrid constructs have high sensitivity and specificity.

Example 2: To confirm the affinities of various anti-Spike antibodies disclosed herein for the SARS-CoV-2 Spike, KD was determined by surface plasmon resonance (SPR). All SPR experiments were carried out on Pioneer FE (Sartorius Corporation) and the data were analyzed by Qdat analytical software. Antibodies were captured on the SPR sensor coated with anti-Human IgG Fc. OneStep kinetic assay was performed using 50 nM RBD-SD1 or 20 nM sc-S-PP-T4F samples. The mAbs whose ability to bind Spike trimer and/or RBD peptide are indicated in Tables 1 & 2 above.

Figure 2:
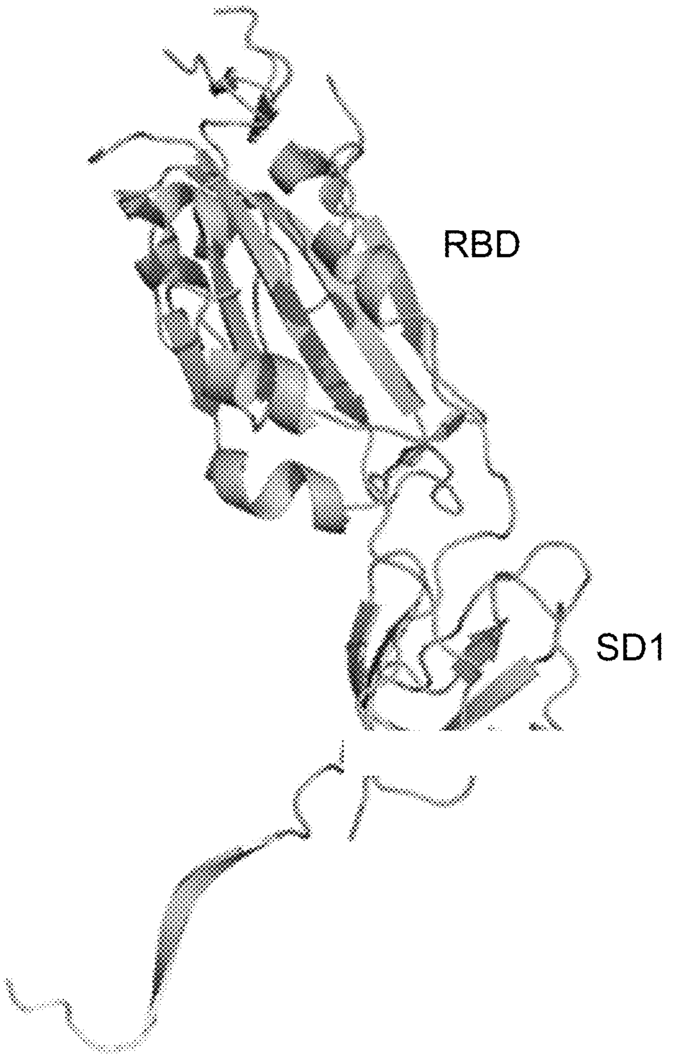
FIG. 2 depicts a crystal structure of the receptor binding domain (RBD) of the Spike trimer's S1 domain.
Figure 3A:
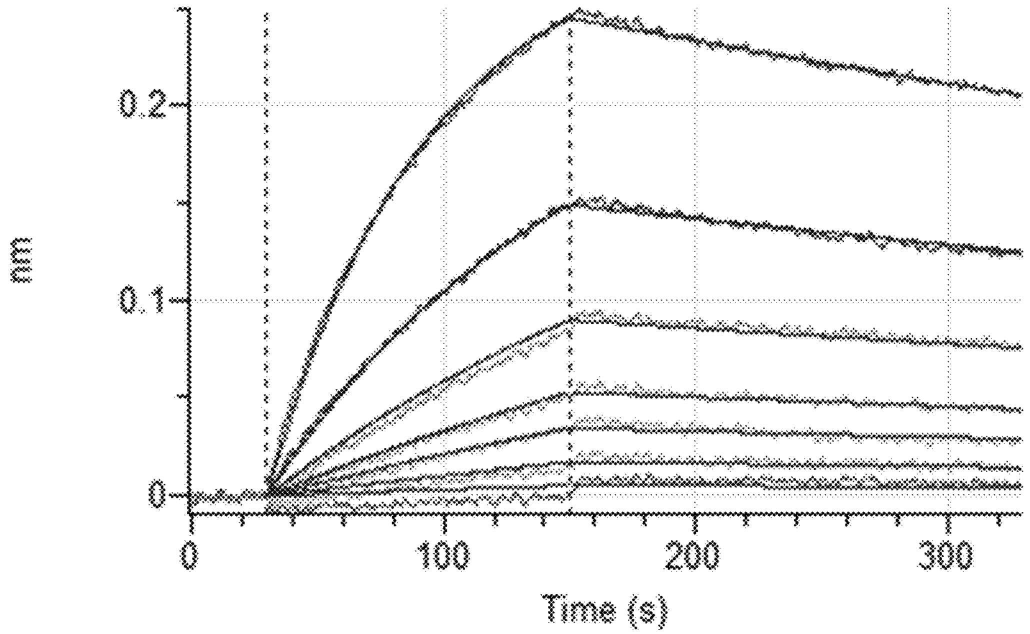
FIG. 3A depicts SPR results obtained with N-612-004 mAb. The plot shows the affinity results against a cleaved Spike peptide.
Figure 3B:
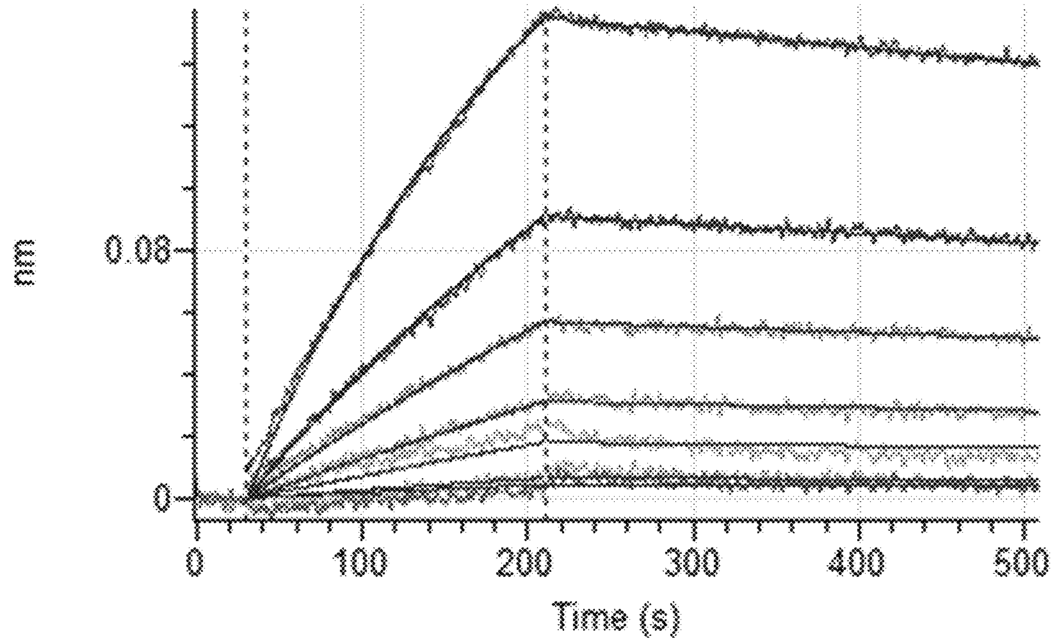
FIG. 3B depicts SPR results obtained with N-612-004 mAb. The plot shows the affinity results against the RBD-S1 peptide.
Figure 4A:
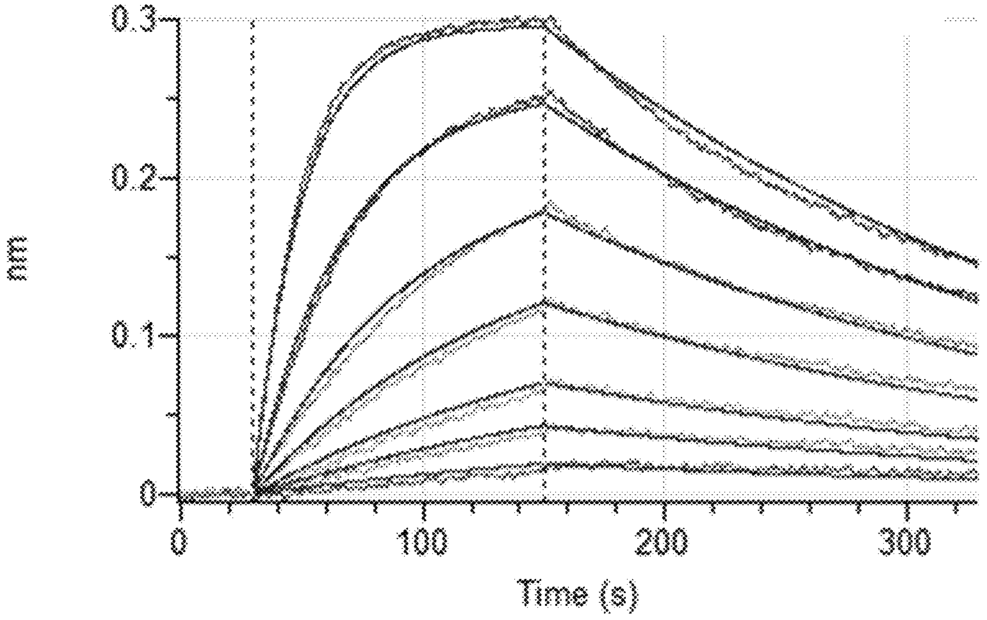
FIG. 4A depicts SPR results obtained with N-612-017 mAb. The plot shows the affinity results against a cleaved Spike peptide.
Figure 4B:
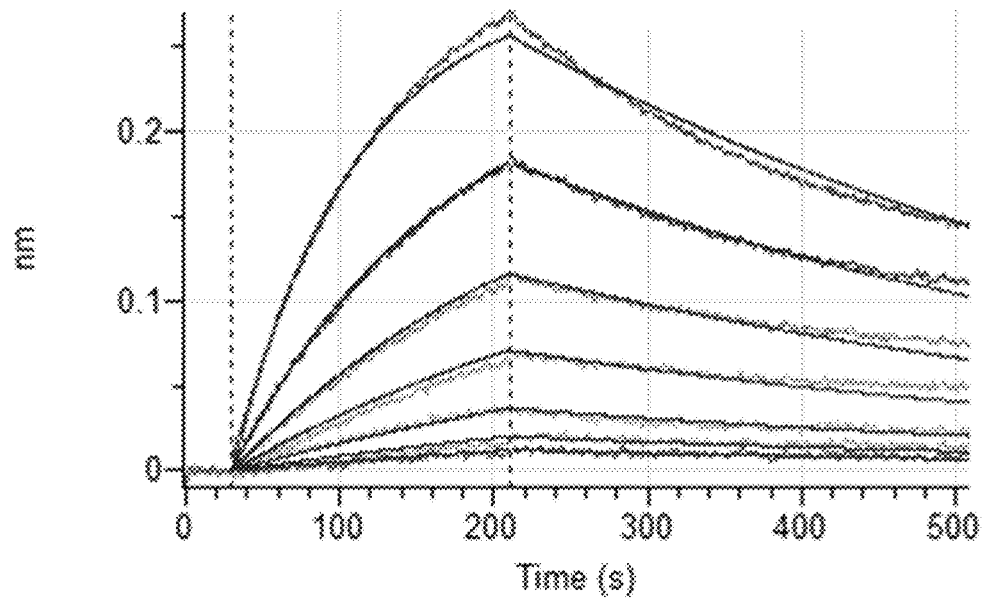
FIG. 4B depicts SPR results obtained with N-612-017 mAb. The plot shows the affinity results against the RBD-S1 peptide.

Example 3: To study epitope of antibodies, sc-S-PP-T4F, RBD-SD1, and RBD were used as analytes. These various constructs are illustrated in FIGS. 1 & 2. All epitope analyses were run on Octet Red96e (Sartorius Corp.). Antibodies were captured on anti-Human Capture (AHC) biosensors. A 2× dilution series starting at 20 nM sc-S-PP-T4F and another starting at 100 nM RBS-SD1 and RBD were used for kinetic assay cycle. Table 3 below summarizes these epitope determination trials with a select few mAbs. FIGS. 3A-3B & 4A-4B show SPR plots from some of these trials. N-612-004 and N-612-017 each bind cleaved Spike peptide with 1:1 binding mode, which was observed with binding RDB-SD1, indicating that cleaved Spike contains only S1 domain. The calculated $k_{off}$ for the N-612-004 against cleaved Spike is $9.8\times10^{-4}$, for N-612-004 against RBD-S1 is $3.4\times10^{-4}$, for N-612-017 against cleaved Spike is $3.9\times10^{-3}$, and for N-612-017 against RBD-S1 is $1.9\times10^{-3}$.

Figure 5:
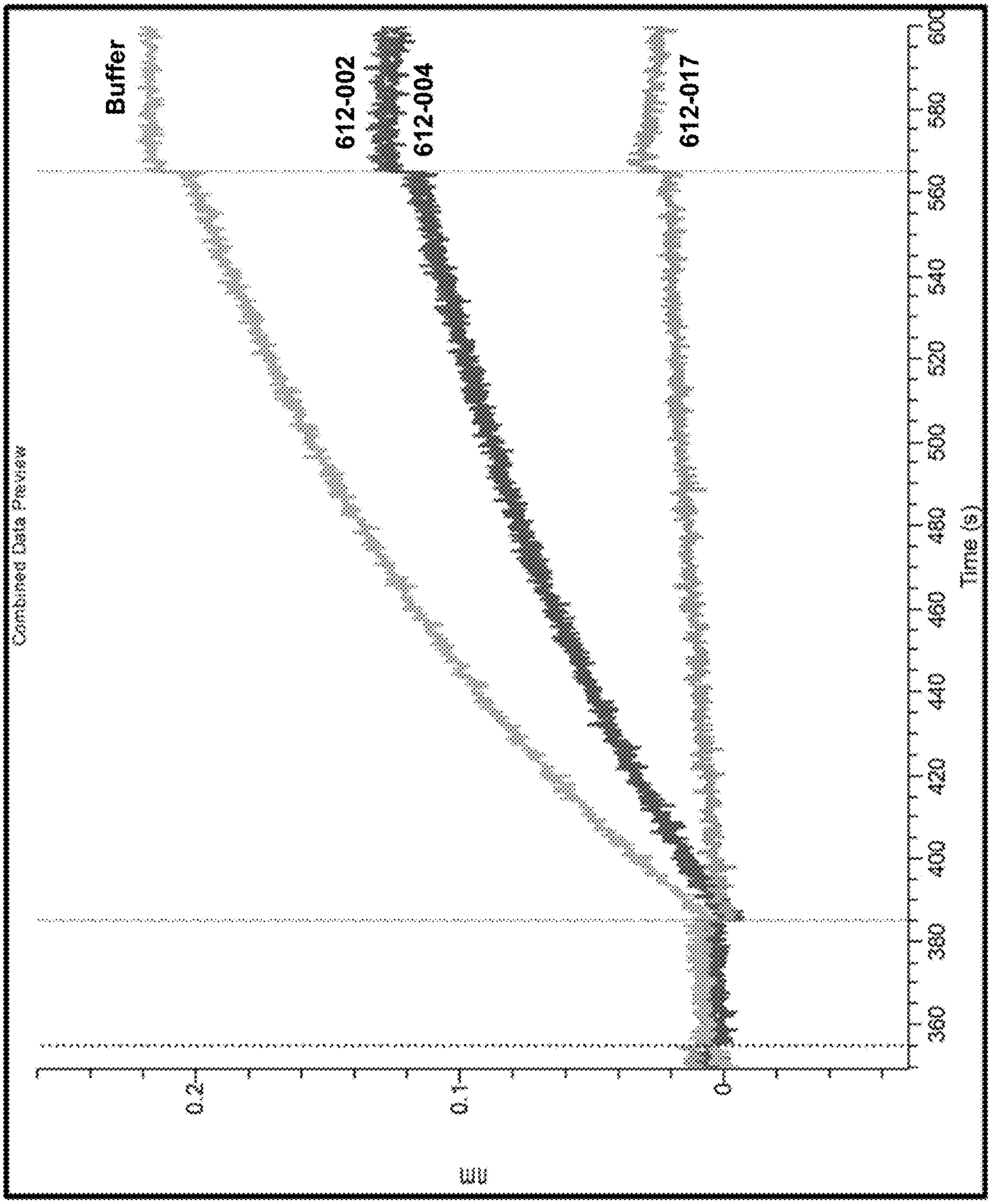
FIG. 5 depicts a bio-layer interferometry assays illustrating the ability of selected mAbs to block SARS-CoV-2 Spike to ACE2. The line labeled "buffer" shows ACE2 binding to RBD without obstruction. The lines for N-612-002 and N-612-004 substantially overlap across the whole time series. The N-612-017 line runs nearest the horizon.

Example 4: Ni-NTA biosensors were coated with His-tagged RBD-SD1 and quenched with anti-RBD-SD1 antibodies. Immediately after quenching, the sensors were incubated with ACE2-IgG1Fc solution to determine which antibody blocked ACE2-IgGFc binding to RBD-SD1 on sensors. In FIG. 5, N-612-004 binds both S and S-RBD-SD1, while N-612-002 only binds S. In other words, N-612-002 binds RBD or Spike but does not interfere with ACE2 binding. Steric hindrance likely explains the low N-612-002 binding. The overlapping N-612-002 and N-612-004 lines run discernibly underneath the line for buffer, showing some obstruction of ACE2/RBD binding. Notably, mAb N-612-017 is able to obstruct Spike binding to ACE2 almost completely in these in vitro conditions.

TABLE 6

| Anti-Spike IgG1 binding analysis summary (ND = not determined) | | | | | |
|---|---|---|---|---|---|
| IgG | Sc-S-PP-T4F (uncleaved S) | S-T4F (cleaved S) | RBD-S1 | RBD | ACE2 blocking |
| N-612-002 | Yes (Avidity) | No | No | No | No |
| N-612-004 | Yes (Avidity) | Yes (1:1 binding) | Yes (1:1 binding) | No | No |
| N-612-007 | Yes (Avidity) | Yes (Avidity) | No | No | No |
| N-612-014 | Yes (Avidity) | Yes (1:1 binding) | No | No | No |
| N-612-017 | Yes (Avidity) | Yes (1:1 binding) | Yes (1:1 binding) | Yes (1:1 binding) | Yes |
| N-612-041 | Yes (Avidity) | ND | Yes (1:1 binding) | No | No |
| N-612-044 | Yes (Avidity) | ND | No | No | No |
| N-612-074 | Yes (Avidity) | ND | Yes (1:1 binding) | Yes (1:1 binding) | ND |

Figure 6:
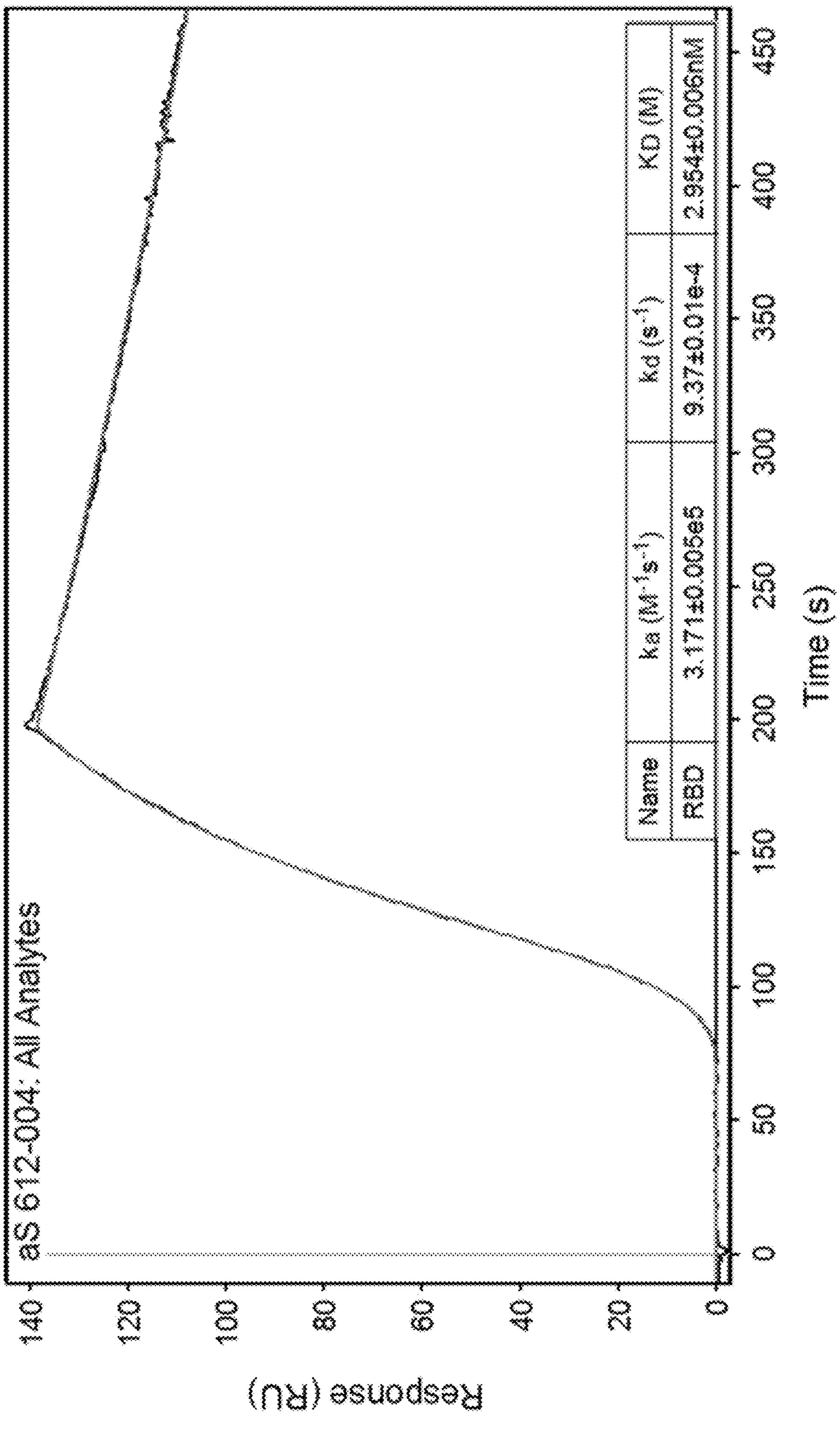
FIG. 6 depicts a $K_D$ determination by SPR for N-612-004 against RBD peptide.
Figure 7:
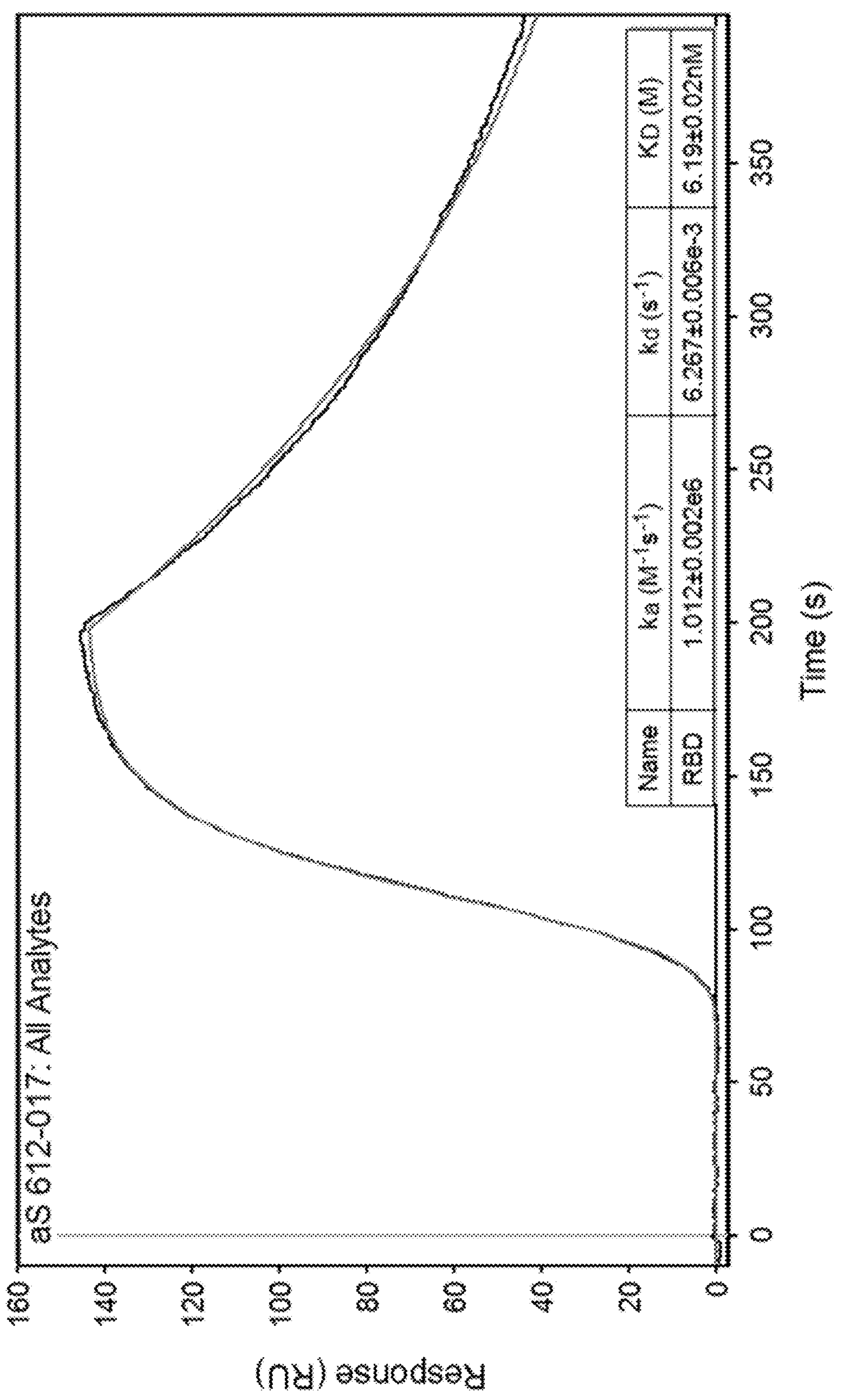
FIG. 7 depicts a $K_D$ determination by SPR for N-612-017 against RBD peptide.
Figure 8:
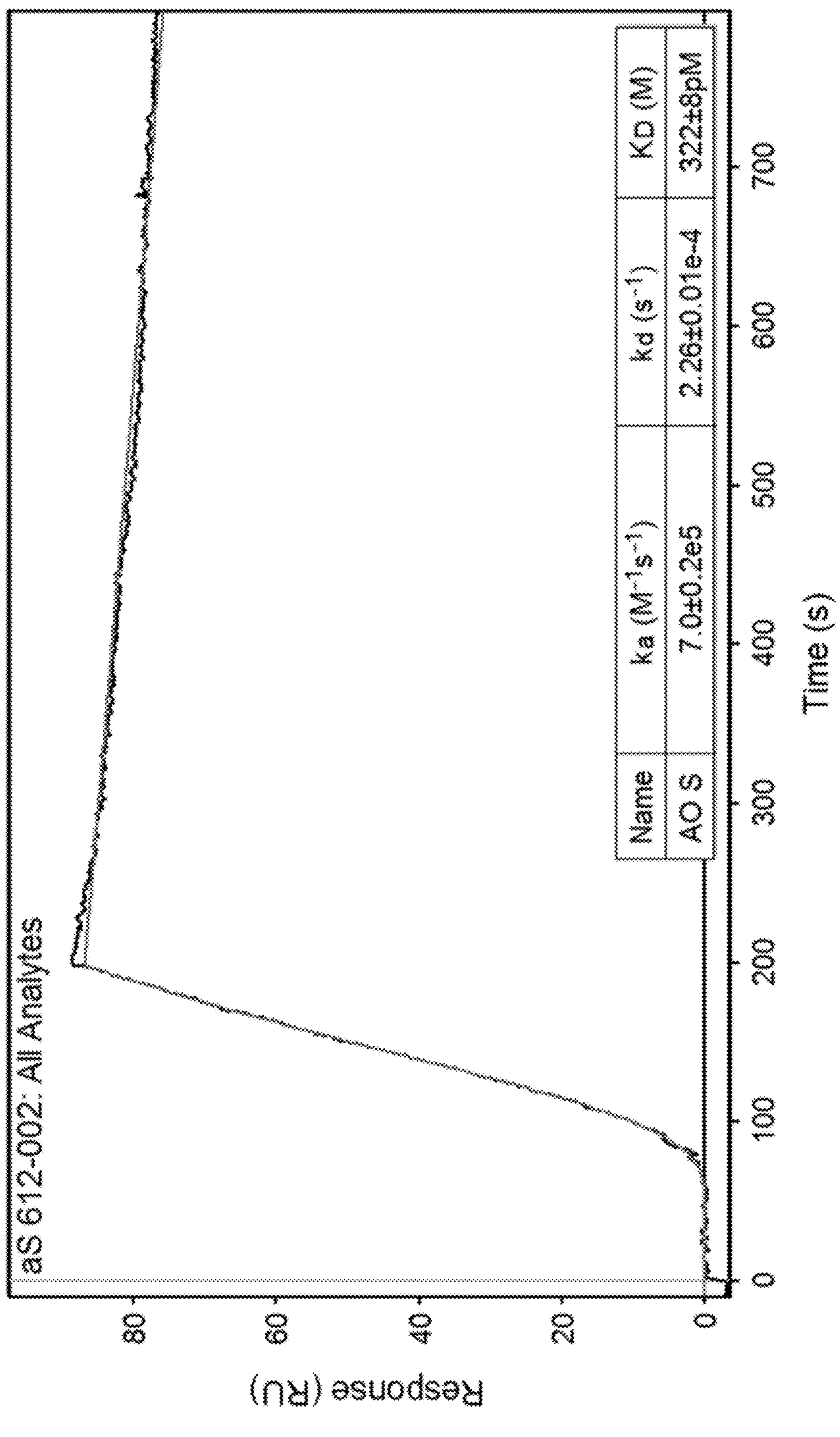
FIG. 8 depicts a $K_D$ determination by SPR for N-612-002 against SARS-CoV-2 Spike protein construct Sc-S-PP-T4F.
Figure 9:
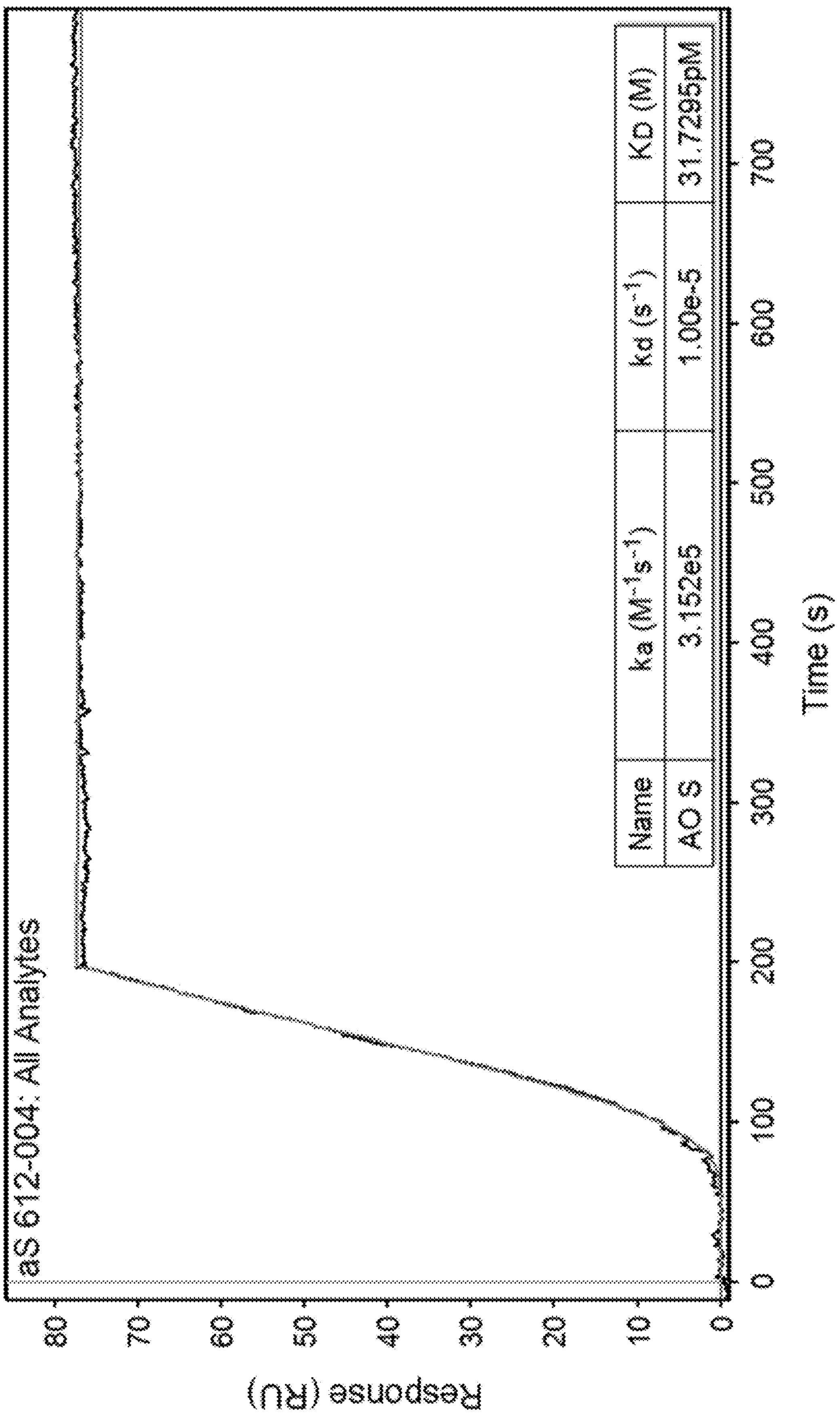
FIG. 9 depicts a $K_D$ determination by SPR for N-612-004 against SARS-CoV-2 Spike protein construct Sc-S-PP-T4F.
Figure 10:
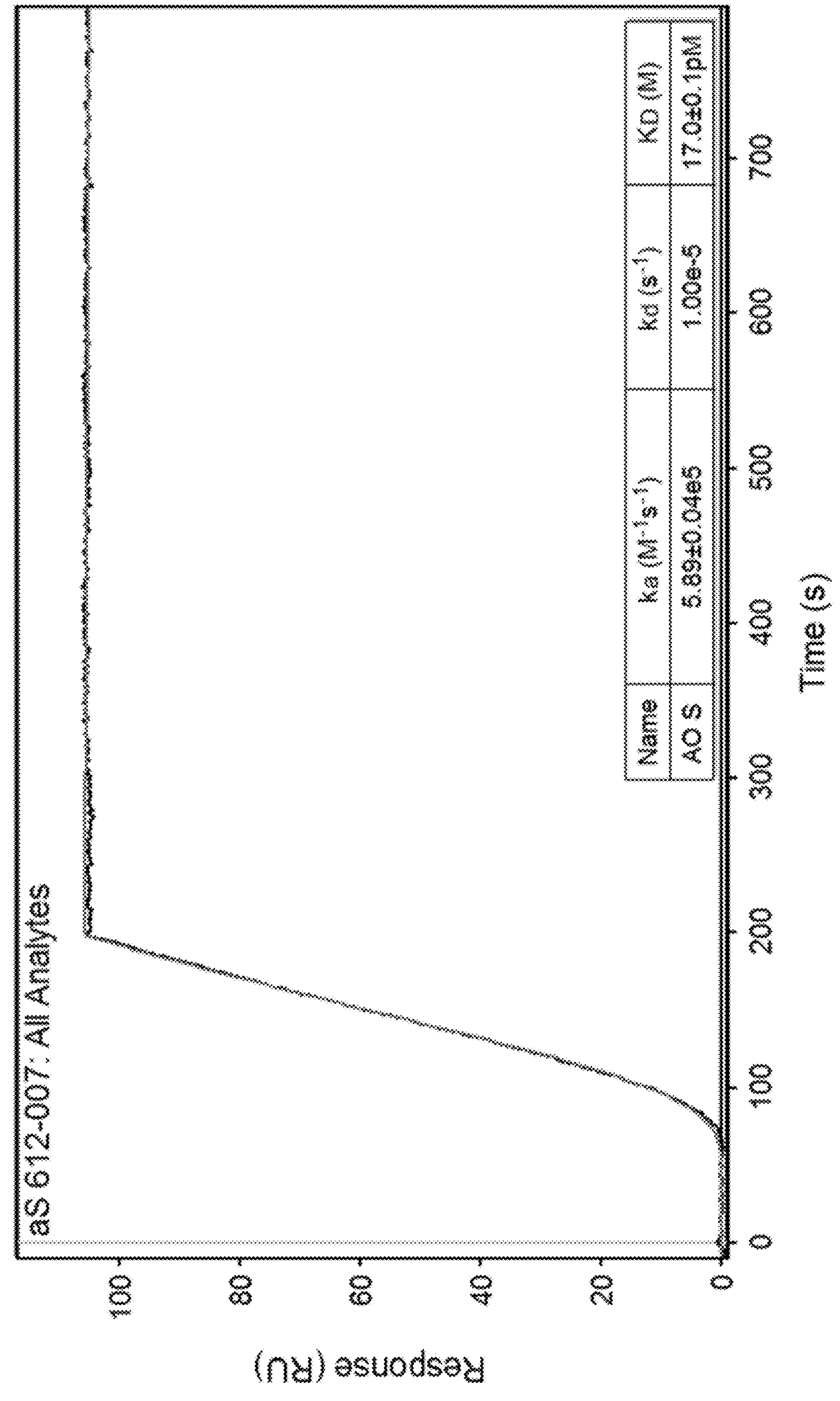
FIG. 10 depicts a $K_D$ determination by SPR for N-612-007 against SARS-CoV-2 Spike protein construct Sc-S-PP-T4F.
Figure 11:
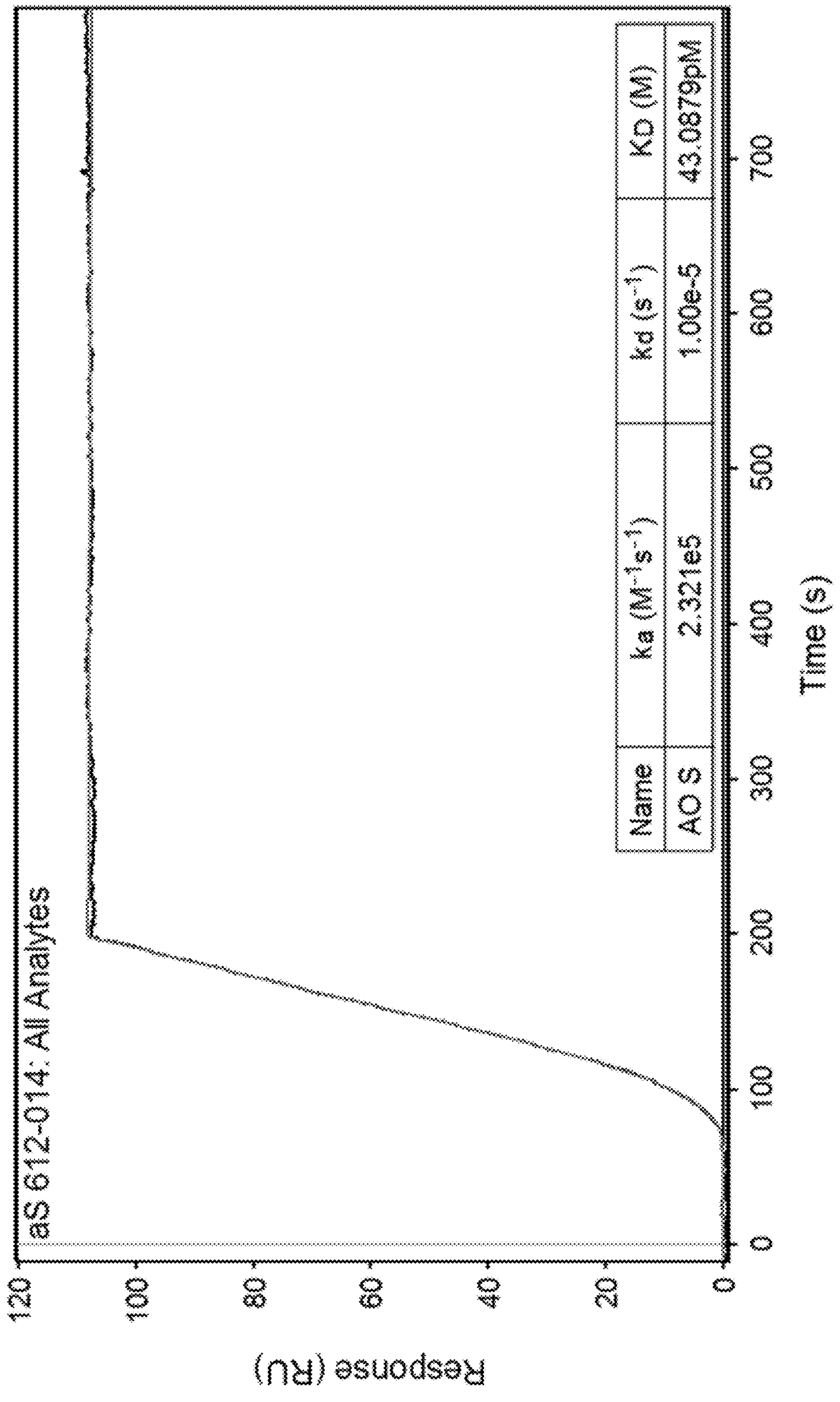
FIG. 11 depicts a $K_D$ determination by SPR for N-612-014 against SARS-CoV-2 S Spike protein construct Sc-S-PP-T4F.
Figure 12:
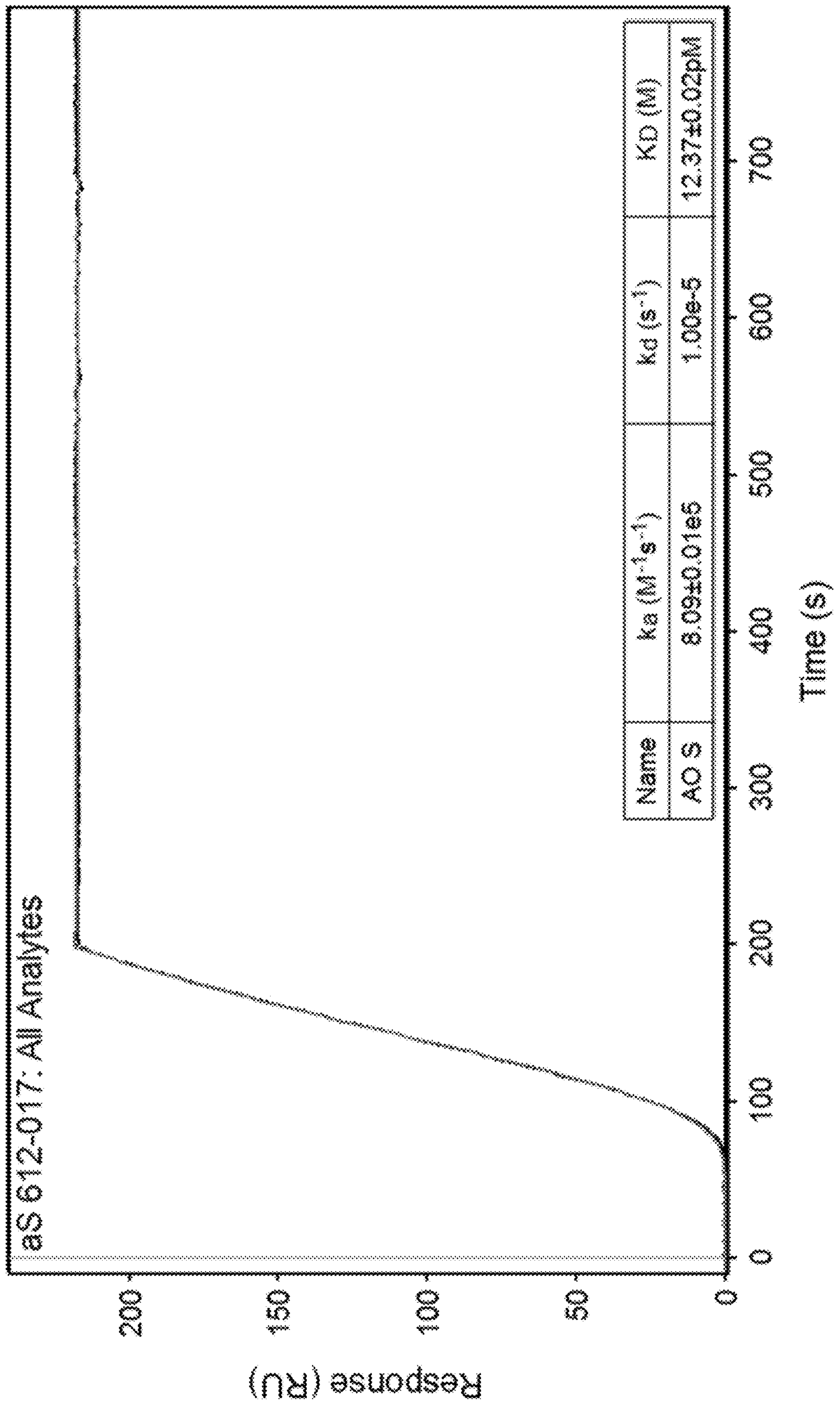
FIG. 12 depicts a $K_D$ determination by SPR for N-612-017 against SARS-CoV-2 Spike protein construct Sc-S-PP-T4F.

Example 5: A Pioneer FE instrument was used to measure the binding affinities between IgG1 and the recombinant spike trimer ectodomain or RBD-SD1 protein. SPR affinity curves for two anti-spike IgG1s against the RBD-SD1 peptide show $K_D$ determinations in FIGS. 6 and 7. SPR affinity curves for a selection of anti-spike IgG1s against Sc-S-PP-T4F show $K_D$ determinations in FIGS. 8-12. Spike binding data is avidity enhanced resulting in flat dissociation curves.

Figure 13:
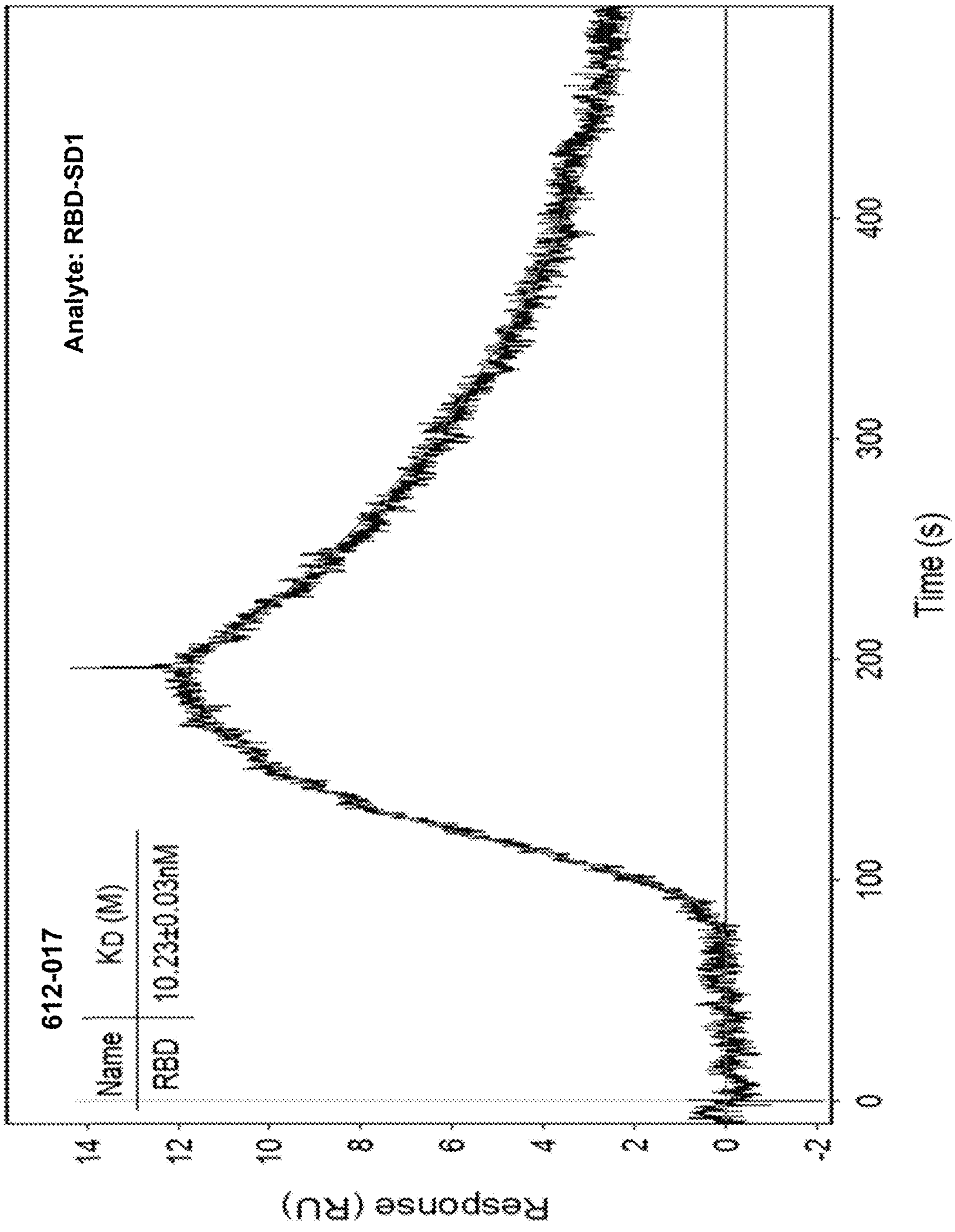
FIG. 13 depicts a $K_D$ determination by SPR for N-612-017 scFv against RBD peptide.
Figure 14:
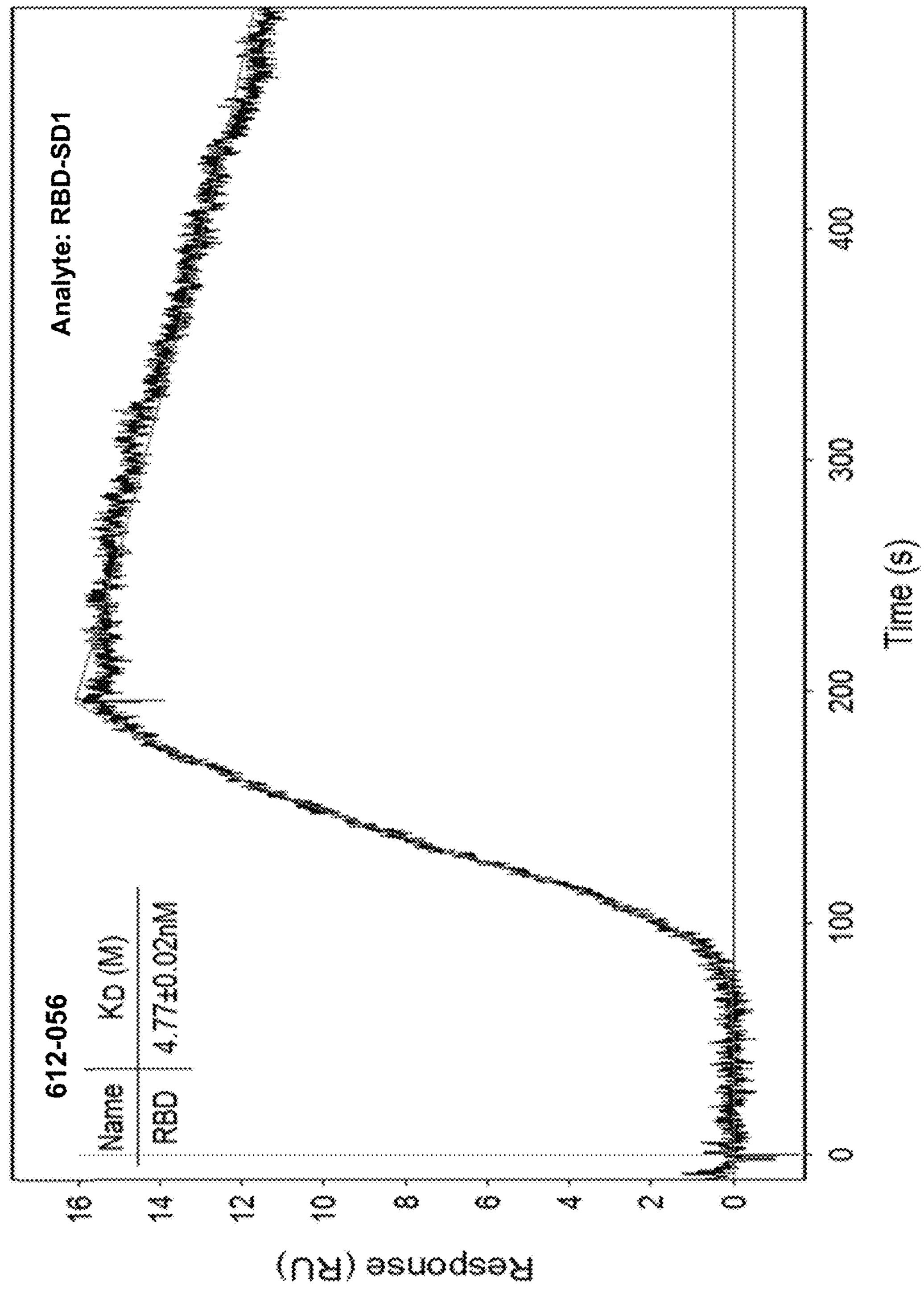
FIG. 14 depicts a $K_D$ determination by SPR for N-612-056 scFv against RBD peptide.
Figure 15:
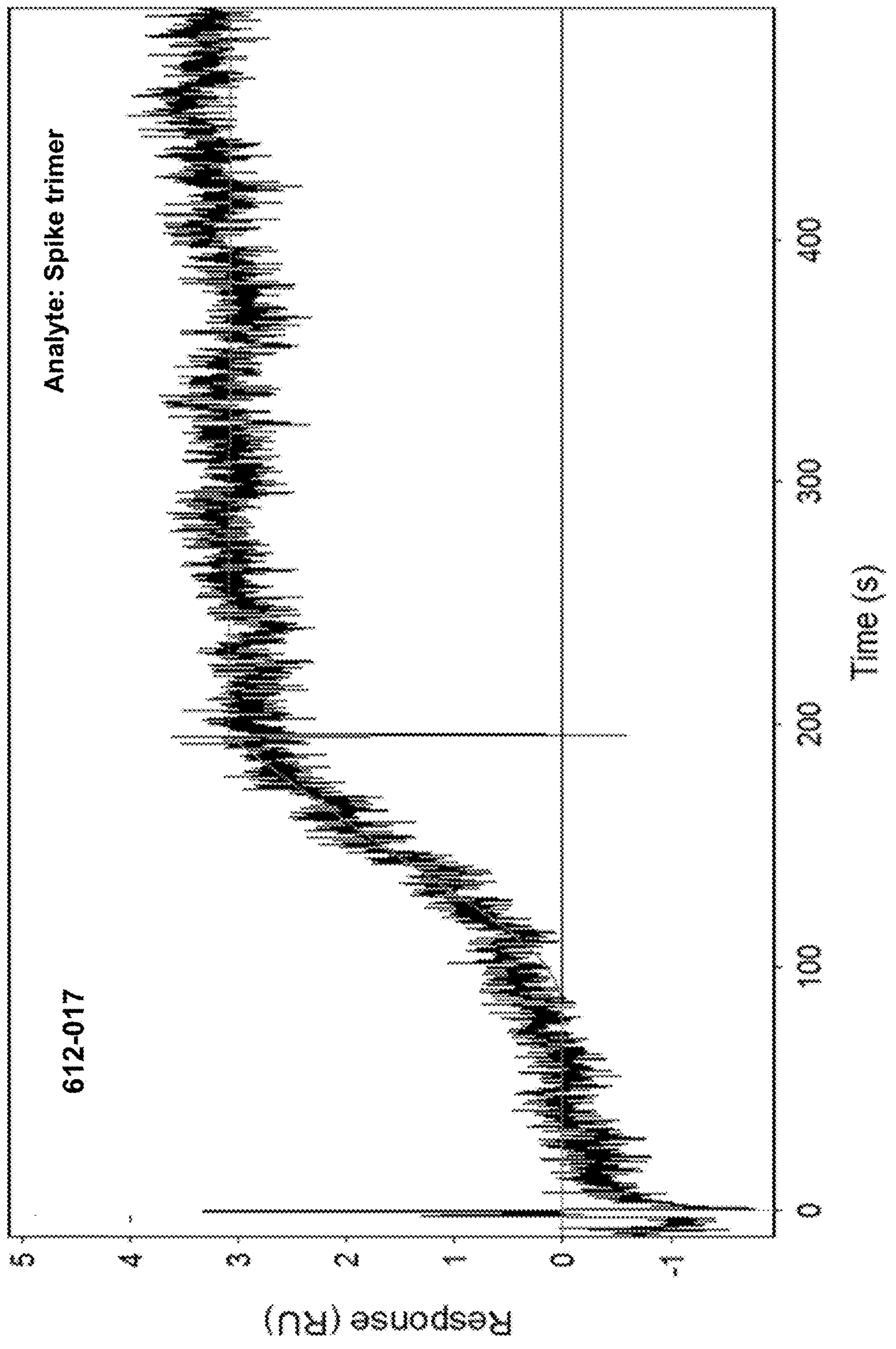
FIG. 15 depicts a $K_D$ determination by SPR for N-612-017 scFv against SARS-CoV-2 Spike trimer.
Figure 16:
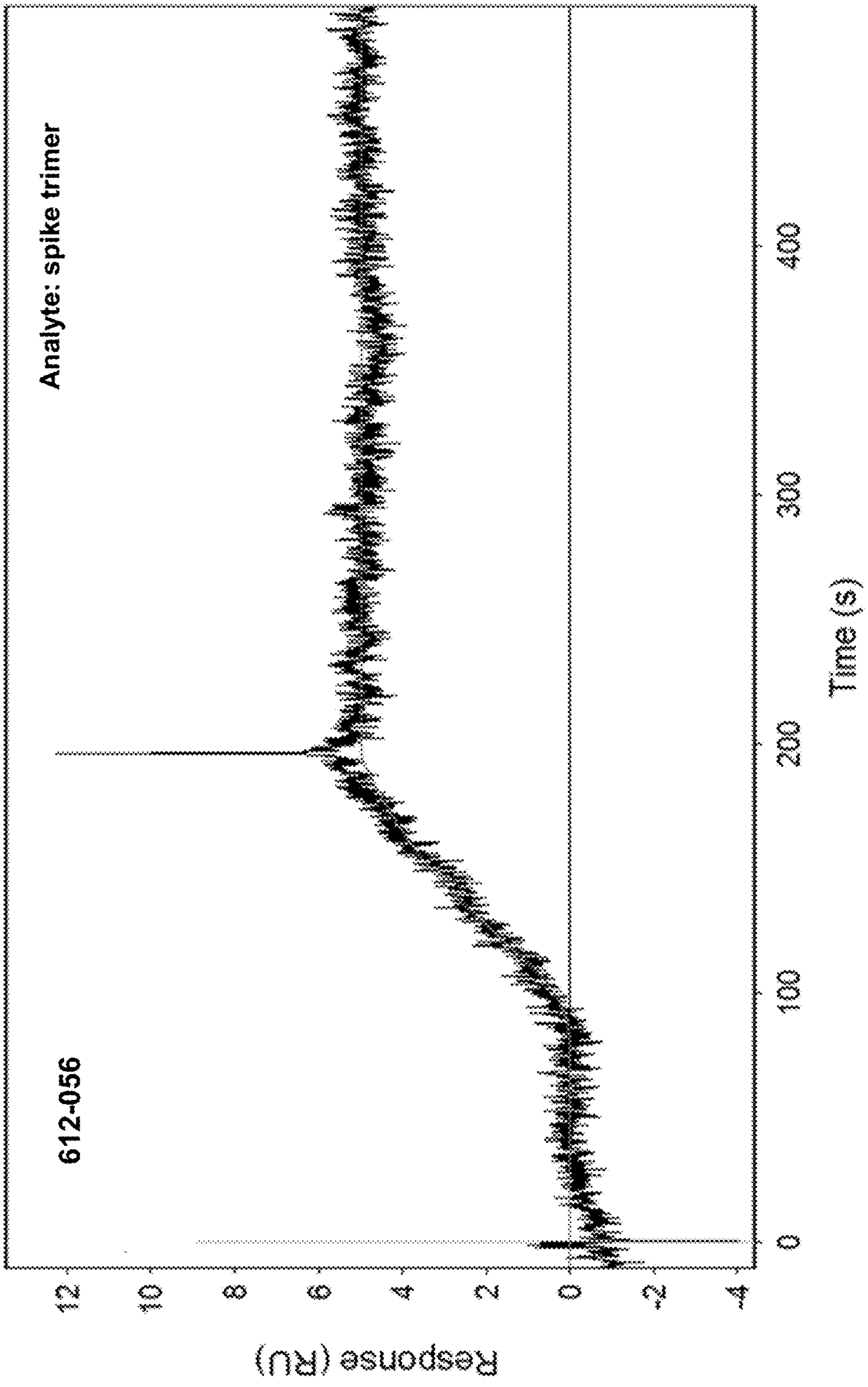
FIG. 16 depicts a $K_D$ determination by SPR for N-612-056 scFv against SARS-CoV-2 Spike trimer.

Example 6: Binding affinities between scFv and the recombinant spike trimer ectodomain or RBD-SD1 protein were measured on a Pioneer FE instrument. Briefly, biotinylated anti-FLAG M2 antibody was immobilized onto the PCH biosensor (Molecular Devices/ForteBio) coated with neutravidin. Triple-FLAG-tagged scFvs were captured with anti-FLAG M2 on the sensor and the binding affinities were measured using OneStep injection with the recombinant analyte protein. Avidity effects with the spike trimer result in a flat dissociation curve that was not fitted. SPR affinity curves for two anti-spike scFvs against the RBD-SD1 peptide show $K_D$ determinations in FIGS. 13 and 14. SPR affinity curves for the anti-spike scFvs against SARS-CoV-2 Spike trimers show $K_D$ determinations in FIGS. 15 and 16.

Figure 17:
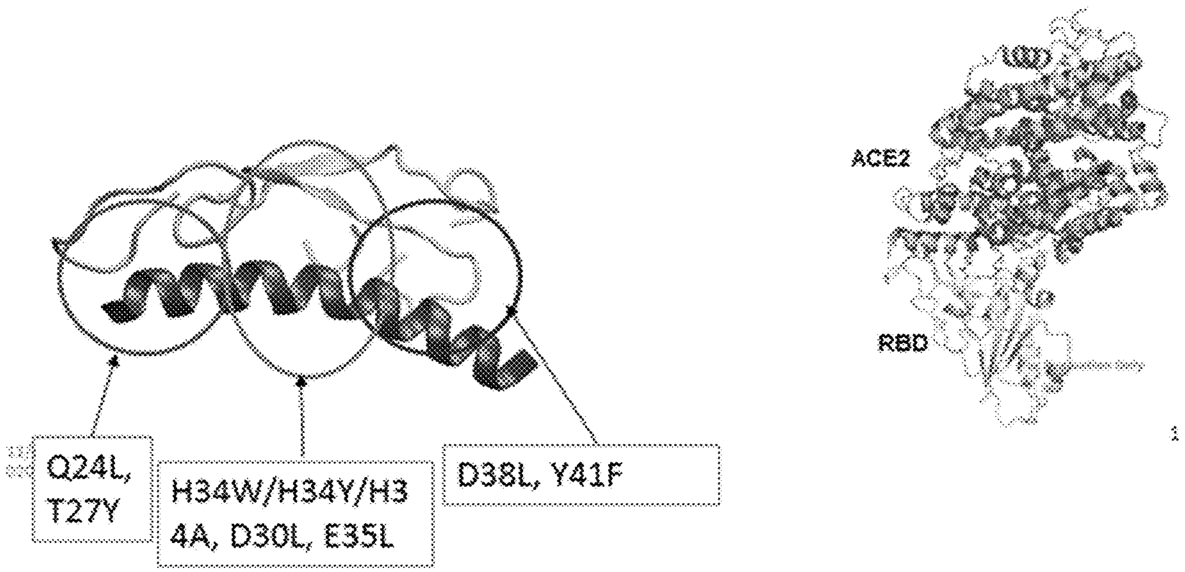
FIG. 17 depicts a conformational structure and a crystal structure of an ACE2-Ig$G_1$Fc.

Example 7: RBD structure can be likened to a human foot, with "heel," "arch," and "toe" regions. Close analysis of the binding interface reveals a pocket between the "arch" portion and the ACE2 α-helix. Water could be displaced from this pocket to increase binding strength between RBD and the ACE2 α-helix. Mutants of this α-helix could be used as competitive inhibitors of ACE2/RBD binding, or as a molecular trap to sequester RBD from cell-surface ACE2. FIG. 17 and Table 7 illustrate an ACE2-$IgG_1Fc$ mutation study confirming that the 'heel' is the most important element for binding affinity to RBD. While the H34A mutant ACE2 α-helix was shown to bind to the RBD with a Kd of 9.4 nM, and the T27Y mutant ACE2 α-helix was shown to bind to the RBD with a Kd of 3.8 nM, the presence of a double mutation, H34A and T27Y creates a synergistic effect and increases the binding affinity to about 1 nM.

TABLE 7

| Mutants | Plasmid | Target basis | Anticipated effect of mutation | kon (1/Ms) | koff (1/s) | KD (nM) |
|---|---|---|---|---|---|---|
| WT | | | | 3.10E+05 | 6.20E−03 | 19.6 |
| Q24L | SR1 | Q H-bonds with A and N on Spike | Predicted to not change binding kinetics | 5.70E+05 | 1.90E−02 | 32.6 |
| T27Y | SR3 | | Predicted to not change binding kinetics | 4.00E+05 | 3.70E−03 | 9.4 |
| H34W | SR5 | H34 important per MD but not EM | Predicted to further space fill & increase binding kinetics | 5.60E+05 | 2.20E−02 | 38.6 |
| H34Y | SR7 | H34 important per MD but not EM | Predicted to further space fill & increase binding kinetics | 4.60E+05 | 3.90E−02 | 84.7 |
| H34A | SR9 | H34 important per MD but not EM | Predicted to reduce binding kinetics | 2.30E+05 | 8.40E−04 | 3.6 |
| D30L | SR11 | 50% H-bond to K in Spike in MD, none in EM | Predicted to reduce binding kinetics | 2.80E+05 | 9.90E−03 | 34.9 |
| E35L | SR13 | E H-bonds | Predicted to reduce binding kinetics | 4.80E+05 | 1.10E−02 | 22.8 |
| H34InsAE35 | SR15 | | Predicted to further space fill & increase binding kinetics; distinguish importance of space fill vs H-bond as this insertion may impact H34 & E35 H-bonds | — | — | Very weak |
| D355L | SR17 | 64% H-bond to T in Spike | Predicted to reduce binding kinetics | 5.20E+05 | 4.10E−02 | 80 |

TABLE 7-continued

| Mutants | Plasmid | Target basis | Anticipated effect of mutation | kon (1/Ms) | koff (1/s) | KD (nM) |
|---|---|---|---|---|---|---|
| D38L | SR19 | 36% interaction with Y on Spike | Predicted to reduce binding kinetics | — | — | very weak |
| Y41F | SR21 | 19% H-bond | Predicted to reduce binding kinetics | — | — | No binding |

Figure 18A:
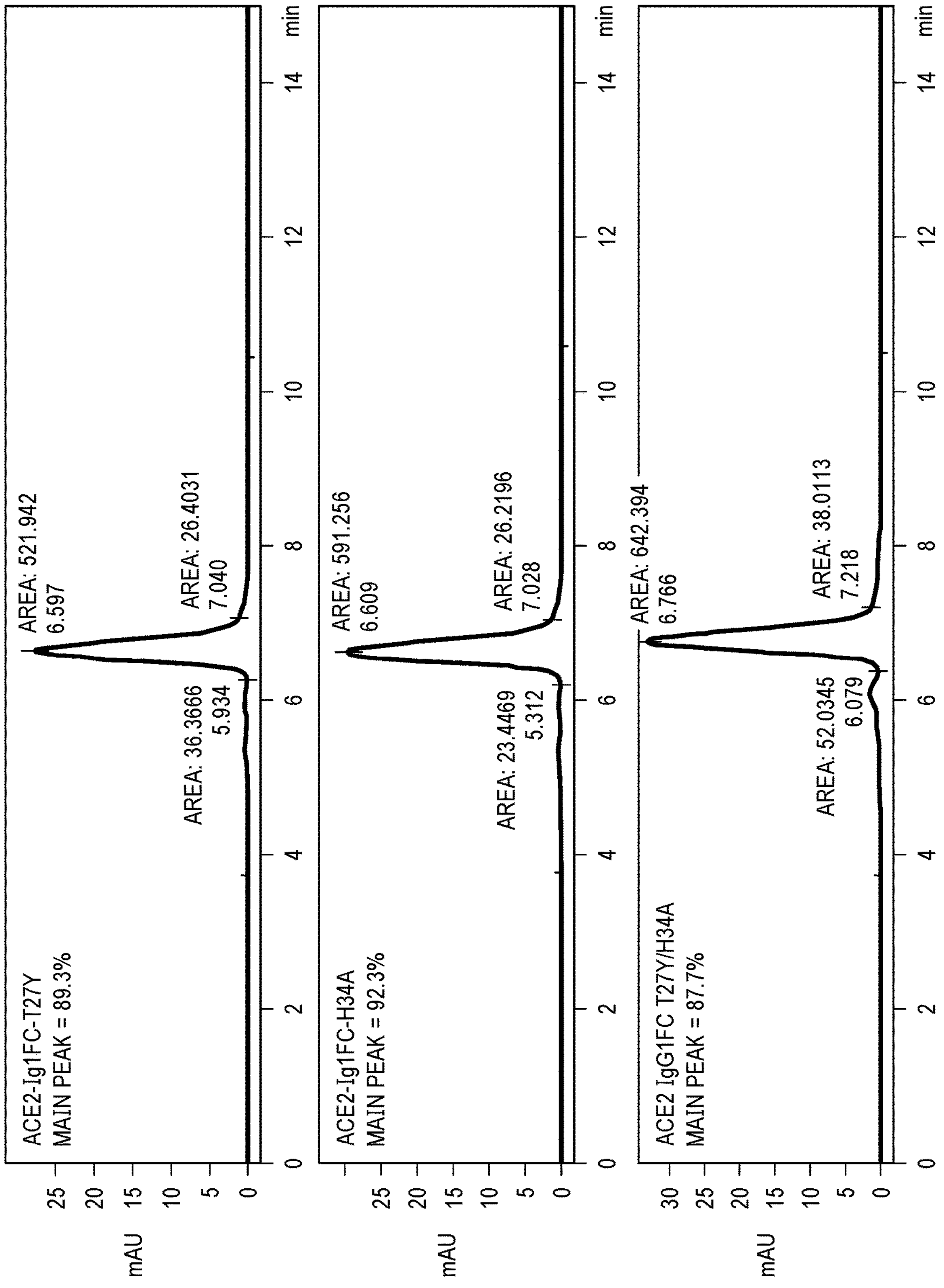
FIG. 18A illustrates purification of ACE2-Ig$G_1$Fc mutant decoy peptides and depicts HPLC purification.
Figure 18B:
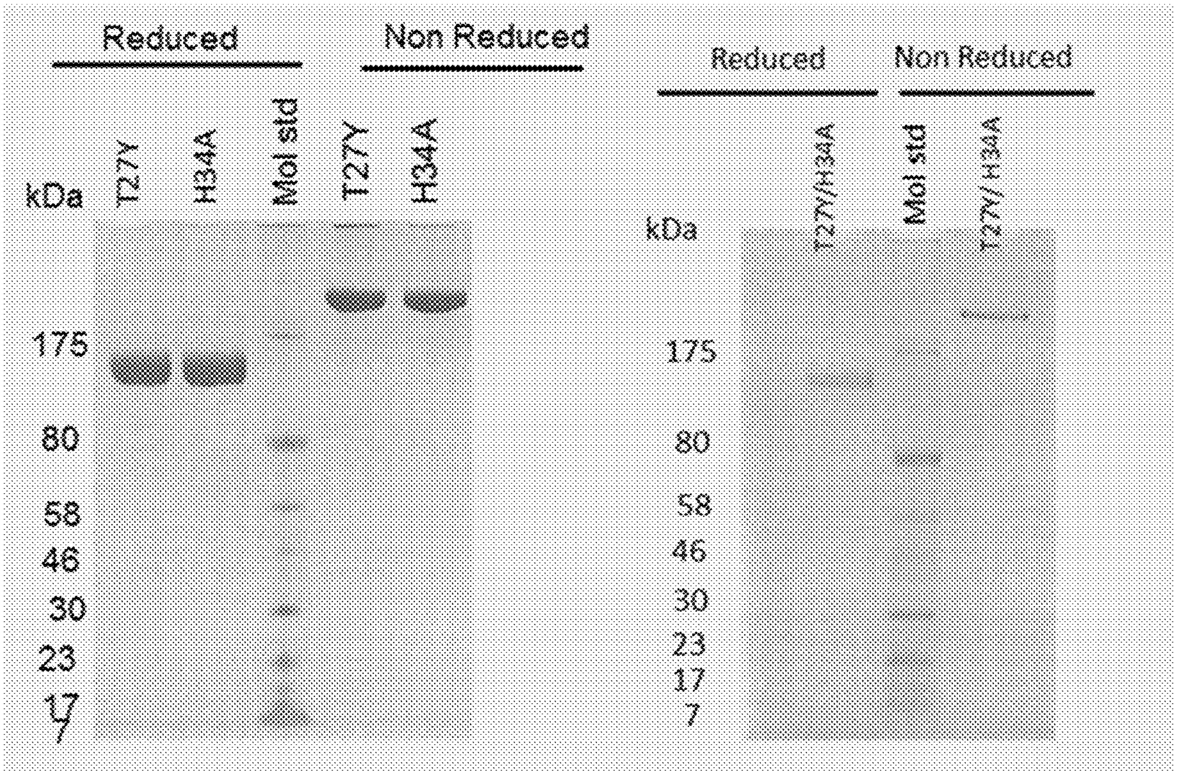
FIG. 18B illustrates purification of ACE2-Ig$G_1$Fc mutant decoy peptides and shows the purity of the recovered ACE2 Ig$G_1$Fc mutant decoy peptides under reducing and non-reducing conditions.

FIGS. 18A and 18B illustrate that ACE2-IgG1Fc mutants were successfully expressed and purified. The purification summary in Table 8 shows the purification of single point mutations H34A and T27Y as well as the double mutant (H34A and T27Y).

TABLE 8

| Sample | Final Titer (μg/mL) | Conc. (mg/mL) | Mass (mg) |
|---|---|---|---|
| T27Y | 39.0 | 0.94 | 0.9 |
| H34A | 39.1 | 1.1 | 0.9 |
| T27Y/H34A | 15.6 | 1.1 | 1.1 |

Figure 19:
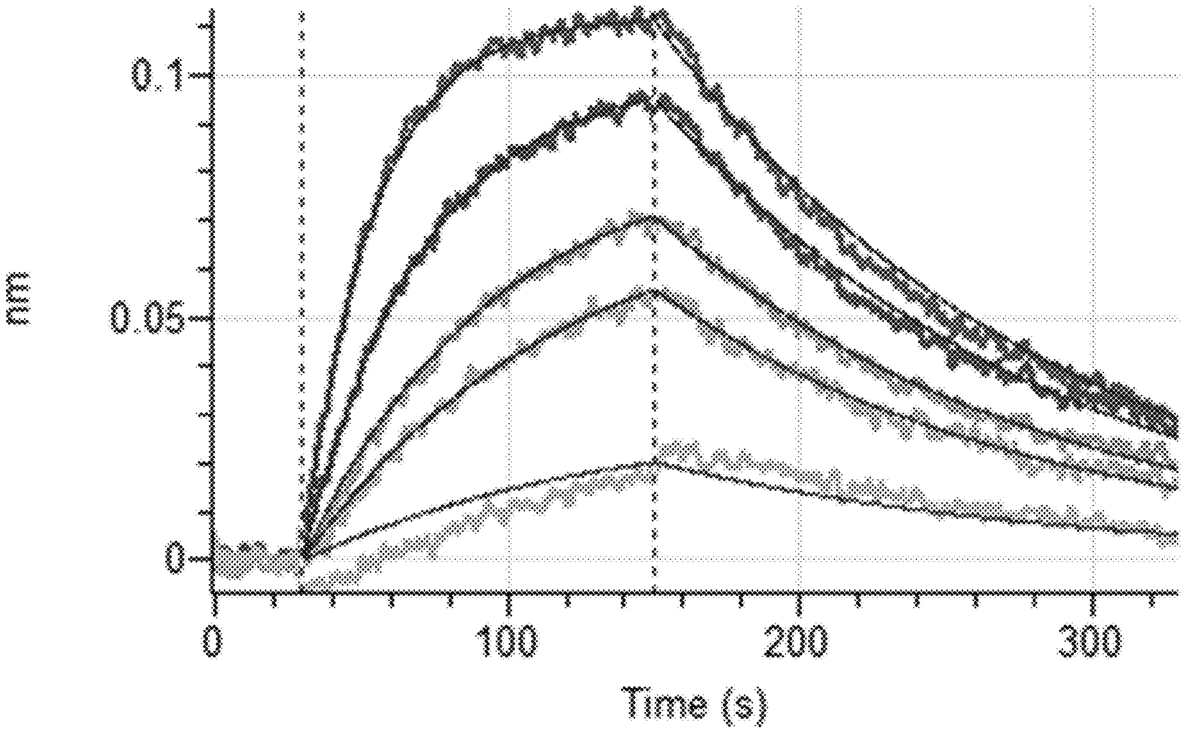
FIG. 19 depicts the binding affinity of wildtype ACE2 decoy against RBD-SD1.
Figure 20:
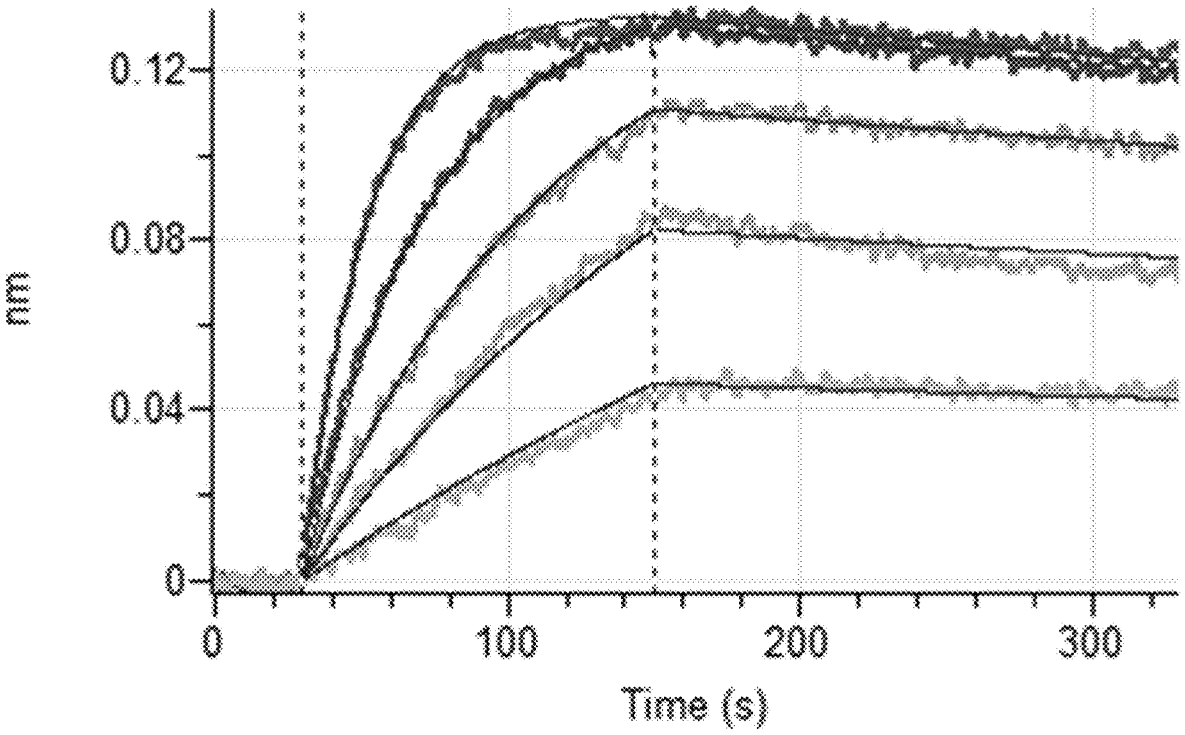
FIG. 20 depicts the binding affinity of the T27Y/H34A mutant ACE2 decoy against RBD-SD1.

Example 8: The binding affinities of wildtype ACE2-$IgG_1Fc$ antibody, the T27Y and H34A single mutants, and the T27Y/H34A double mutant ACE2-$IgG_1Fc$ antibody were measured. The antibodies were captured on AHC biosensors as in Example 3. A two-fold dilution series starting at 200 μM RBD-SP1 was used for kinetic assay cycle. FIGS. 19 and 20 show SPR plots from some of these trials. Table 9 below summarizes binding data for the two antibodies.

TABLE 9

Binding data for wildtype and ACE2 mutant antibodies

| Antibody | $k_{on}$ (1/Ms) | $k_{off}$ (1/s) | $k_D$ (nM) | Virus neutralization $IC_{50}$ (μg/mL) |
|---|---|---|---|---|
| ACE2(WT)-$IgG_1Fc$ | $3.5 \times 10^5$ | $7.4 \times 10^{-3}$ | 21.4 | 3.2 |
| ACE2(T27Y)-$IgG_1Fc$ | $2.9 \times 10^5$ | $1.2 \times 10^{-3}$ | 4.1 | ND |
| ACE2(H34A)-$IgG_1Fc$ | $5.1 \times 10^5$ | $4.1 \times 10^{-3}$ | 8.0 | ND |
| ACE2(T27Y/H34A)-$IgG_1Fc$ | $4.6 \times 10^5$ | $4.6 \times 10^{-4}$ | 1.0 | 0.24 |

Figure 21:
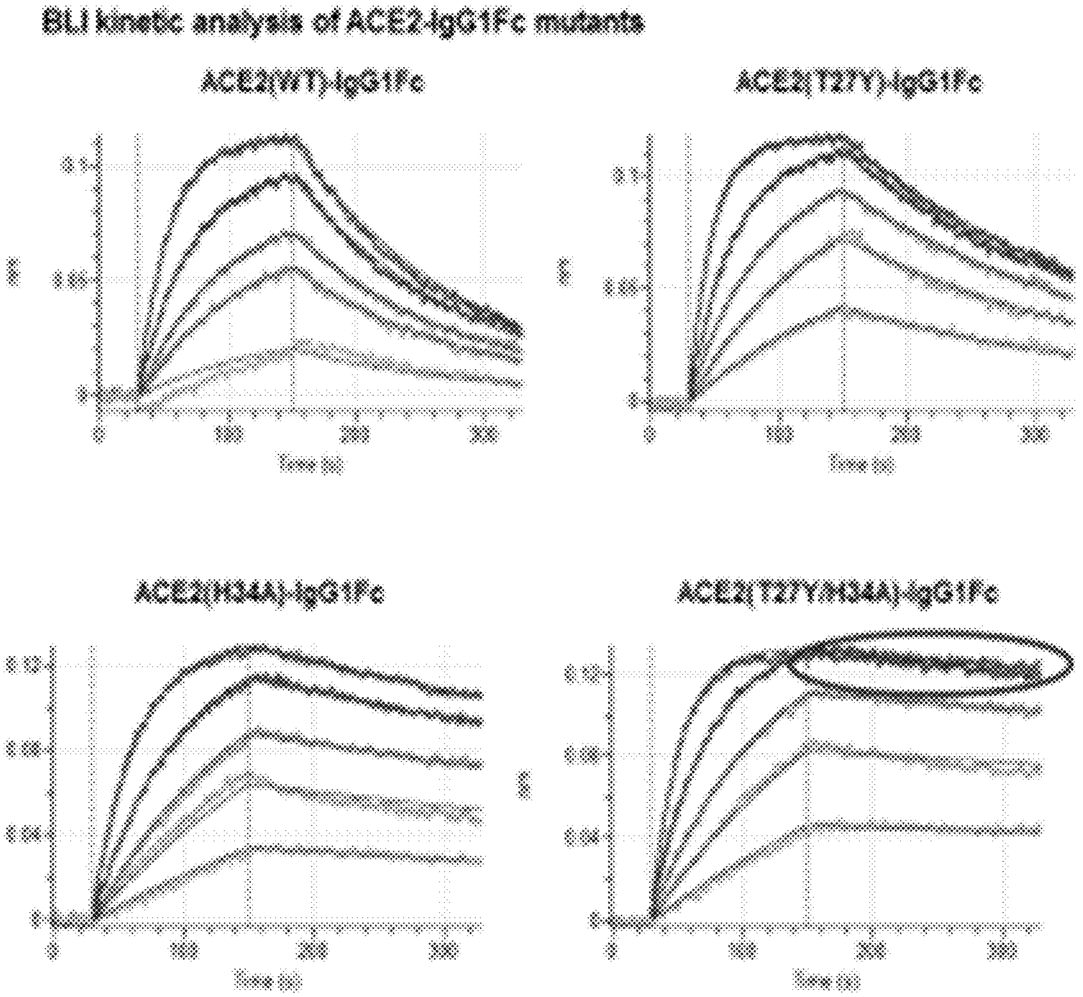
FIG. 21 depicts KD determination by SPR for ACE2 wildtype and ACE2 mutant decoy peptides fused to Ig$G_1$Fc.

FIG. 21 illustrates that ACE2-$IgG_1Fc$ double mutations (T27Y/H34A) has superior binding affinity for RBD as compared to wildtype ACE2-$IgG_1Fc$ and ACE2-$IgG_1Fc$ single mutants.

Figure 22:
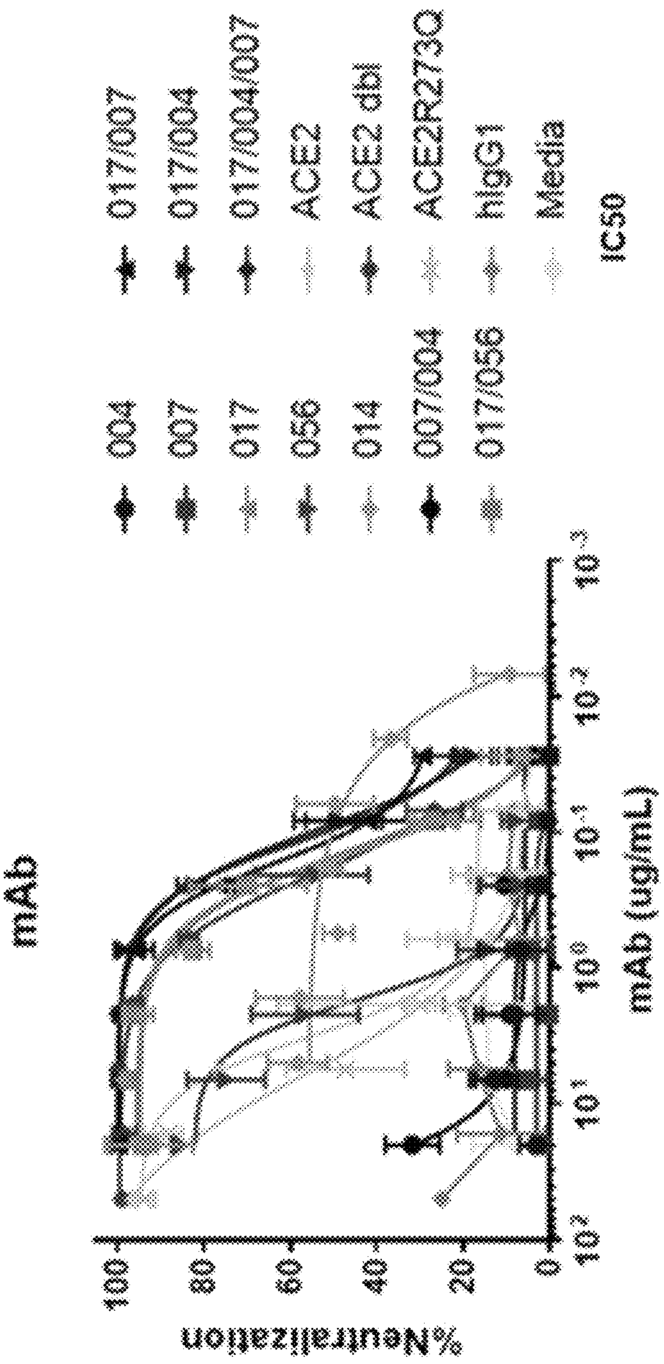
FIG. 22 illustrates live SARS-CoV-2 neutralization data.

Example 9: FIG. 22 illustrates live SARS-CoV-2 neutralization data. The neutralization of SARS-CoV-2 was tested against wild type and mutant ACE2-$IgG_1Fc$. Wild type ACE2-$IgG_1Fc$ as well as its enzyme inactivation mutation (R273Q) were fairly adequate in neutralizing SARS-CoV-2. ACE2-$IgG_1Fc$ with H34A and T27Y mutations (ACE2 dbl) was much better in neutralizing SARS-CoV-2 than the wild type variant. The ACE2 double mutant, having the H34A and T27Y mutations, was as good as antibody 017 in neutralizing SARS-CoV-2. Table 10 reports the $IC_{50}$ values of various neutralizing antibodies and ACE2 decoy peptides calculated from the neutralization experiment.

TABLE 10

| Antibody/Decoy | $IC_{50}$ (μg/mL) |
|---|---|
| N-612-004 | 0.1940 |
| N-612-007 | 0.04515 |
| N-612-017 | 0.07556 |
| N-612-017/N-612-004 | 0.094 |
| N-612-017/N-612-004/N-612-007 | 0.04563 |
| ACE2 decoy | 1.616 |
| N-612-056 | 0.8549 |
| N-612-014 | 0.007907 |
| N-612-017/N-612-056 | 0.06423 |
| N-612-017/N-612-007 | 0.04519 |
| ACE2 dbl decoy | 0.1076 |
| ACE2 R273Q decoy | 3.029 |
| $hIgG_1$ | no activity |
| Media | no activity |

The combination of ACE2-$IgG_1Fc$ or ACE2 IgA with H34A and T27Y expressed as an adenovirus vaccine with various antibodies was also tested for neutralization ability. It was found that combining antibodies N-612-017 with either N-612-007 (binds S2) or N-612-004 (binds SD1) or both together improves neutralization though neither N-612-004 nor N-612-007 had much neutralization activity. Finally, combining N-612-017 with N-612-014 and/or N-612-056 was found to significantly improve neutralization.

Figure 23:
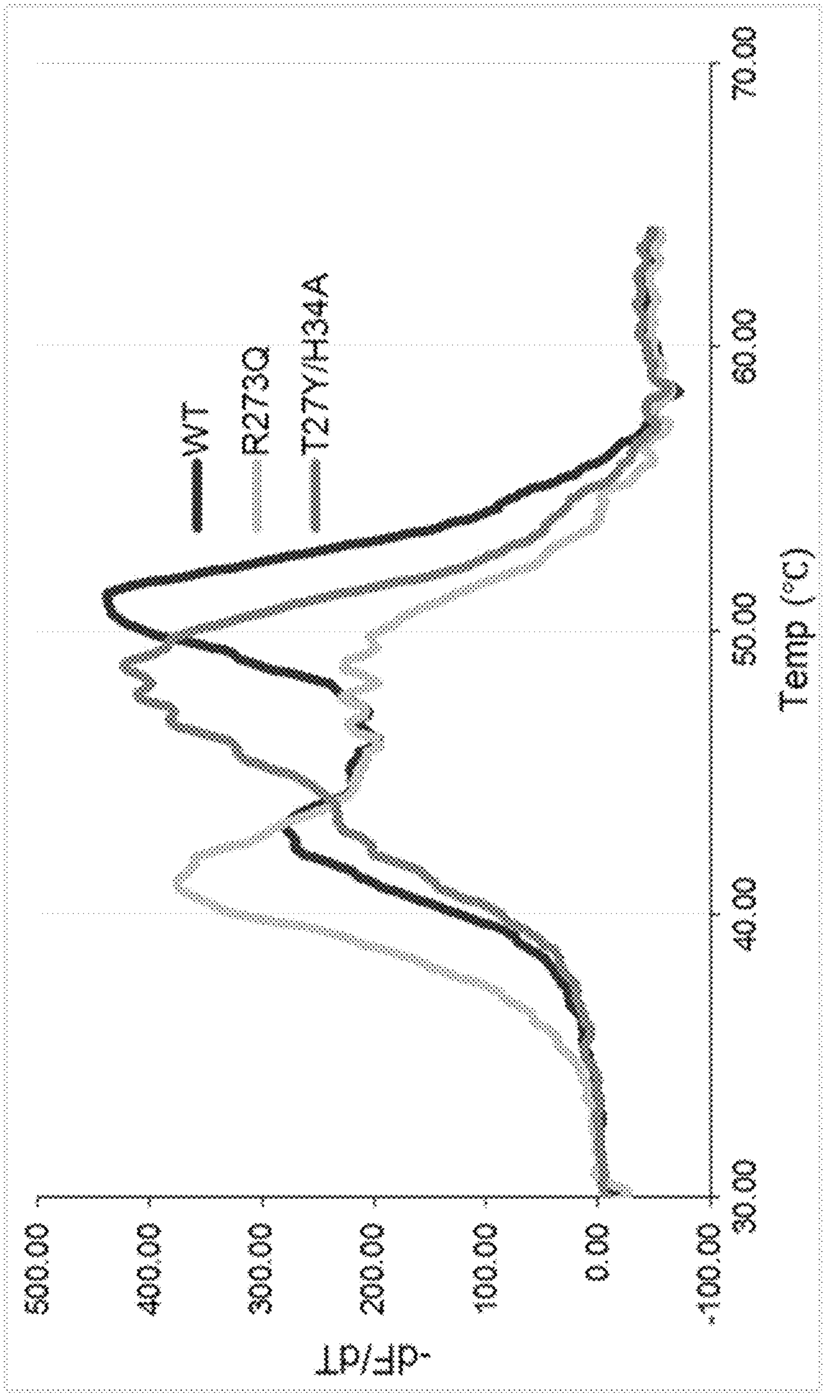
FIG. 23 depicts the stability of wildtype and mutant ACE2 decoy peptides.
Figure 24:
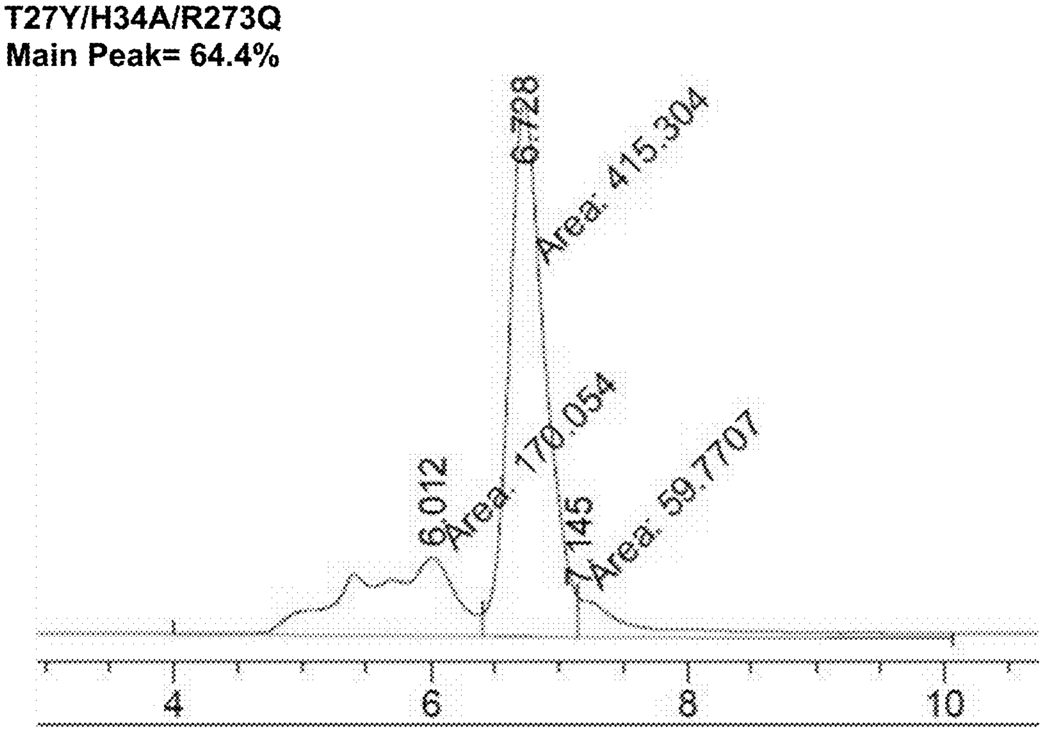
FIG. 24 depicts the size of the T27Y/H34A/R273Q triple mutant ACE2 decoy peptide by size exclusion chromatography.
Figure 25:
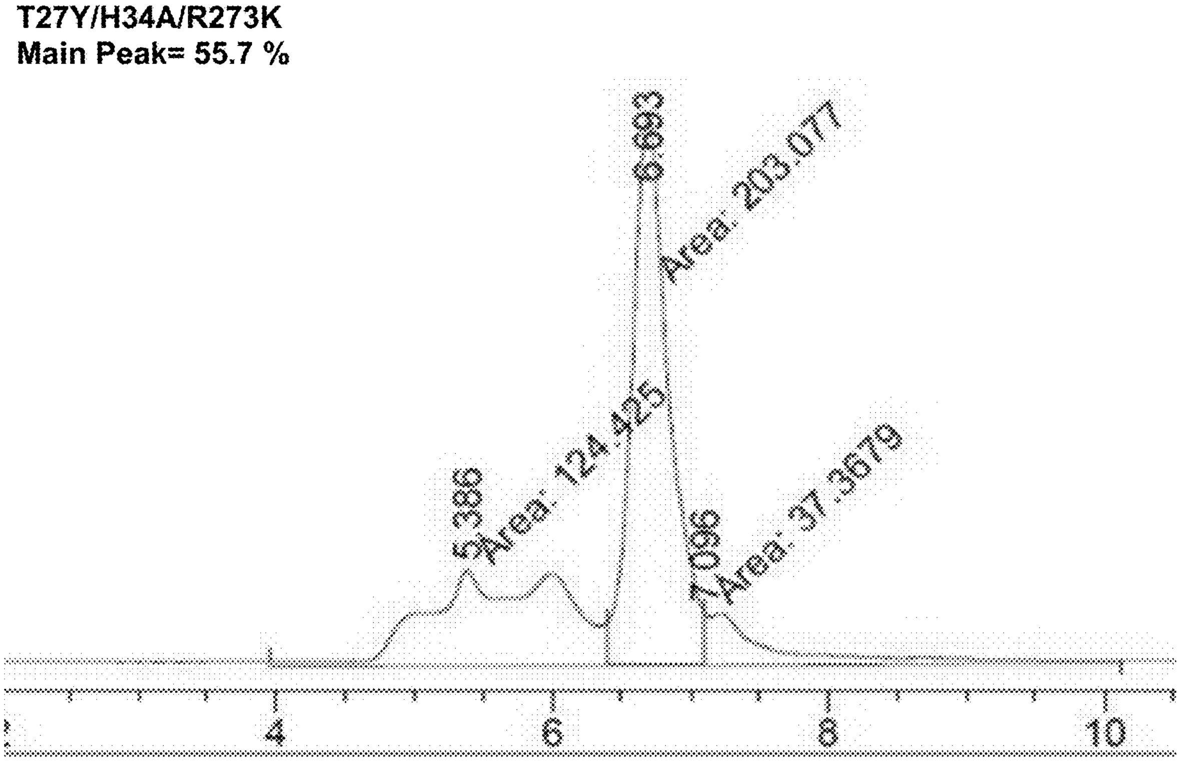
FIG. 25 depicts the size of the T27Y/H34A/R273K triple mutant ACE2 decoy peptide by size exclusion chromatography.
Figure 26:
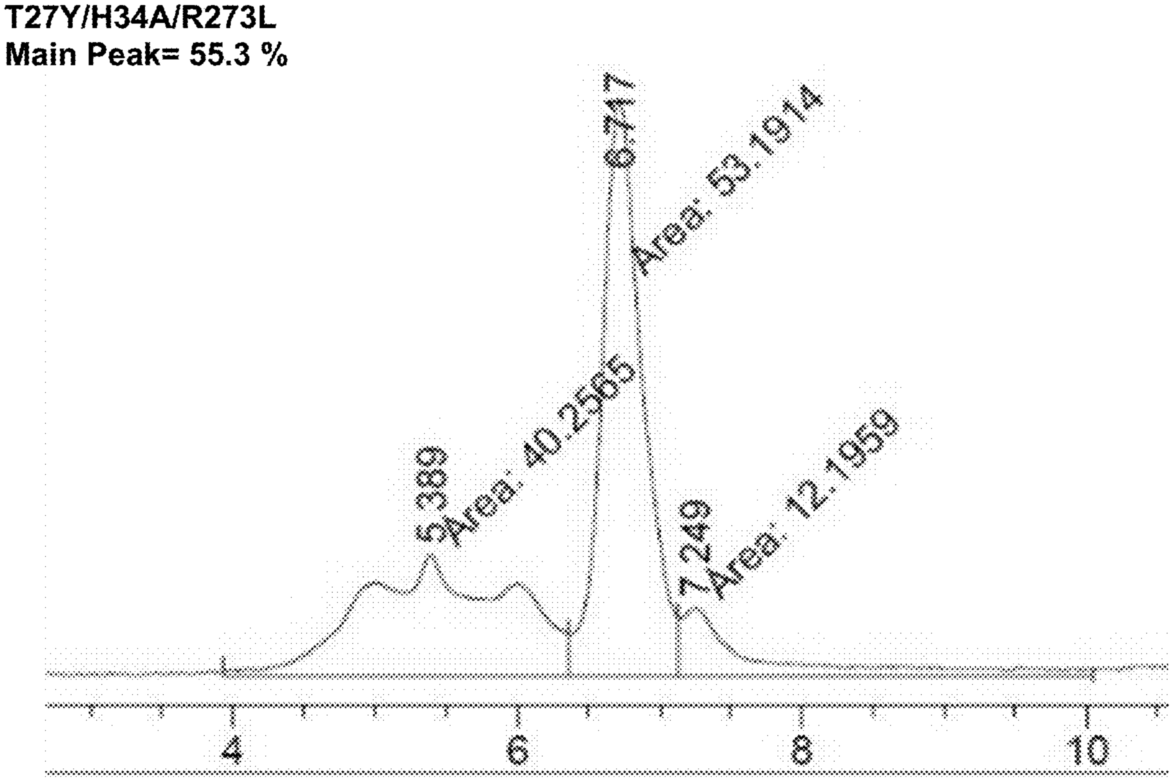
FIG. 26 depicts the size of the T27Y/H34A/R273L triple mutant ACE2 decoy peptide by size exclusion chromatography.
Figure 27:
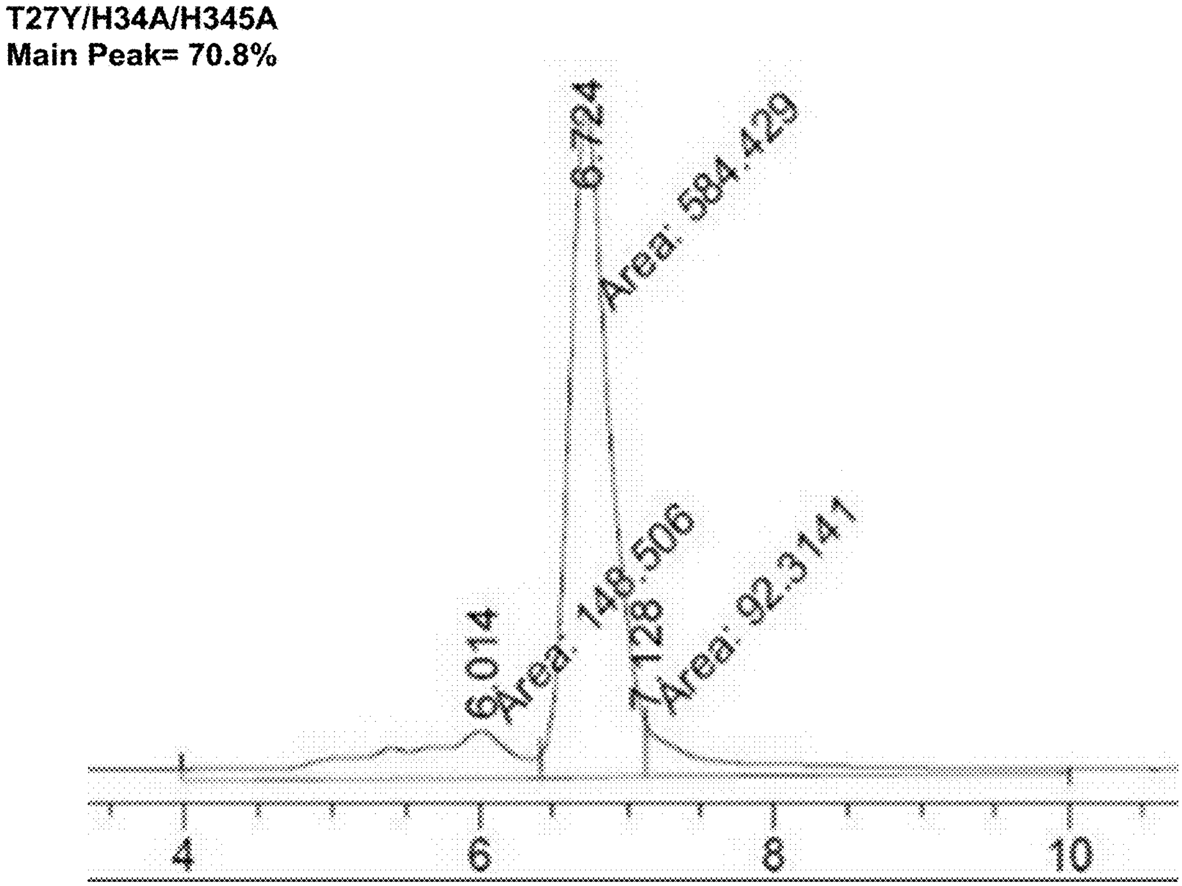
FIG. 27 depicts the size of the T27Y/H34A/H345A triple mutant ACE2 decoy peptide by size exclusion chromatography.
Figure 28:
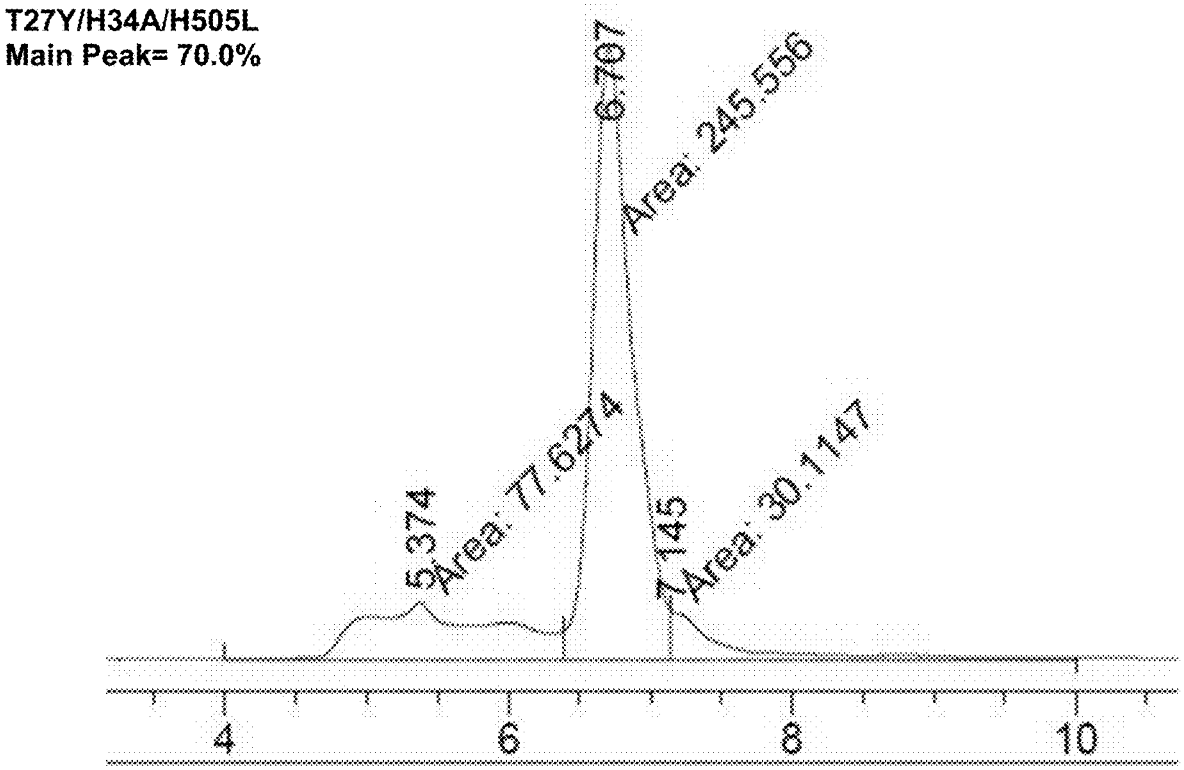
FIG. 28 depicts the size of the T27Y/H34A/H505L triple mutant ACE2 decoy peptide by size exclusion chromatography.
Figure 29:
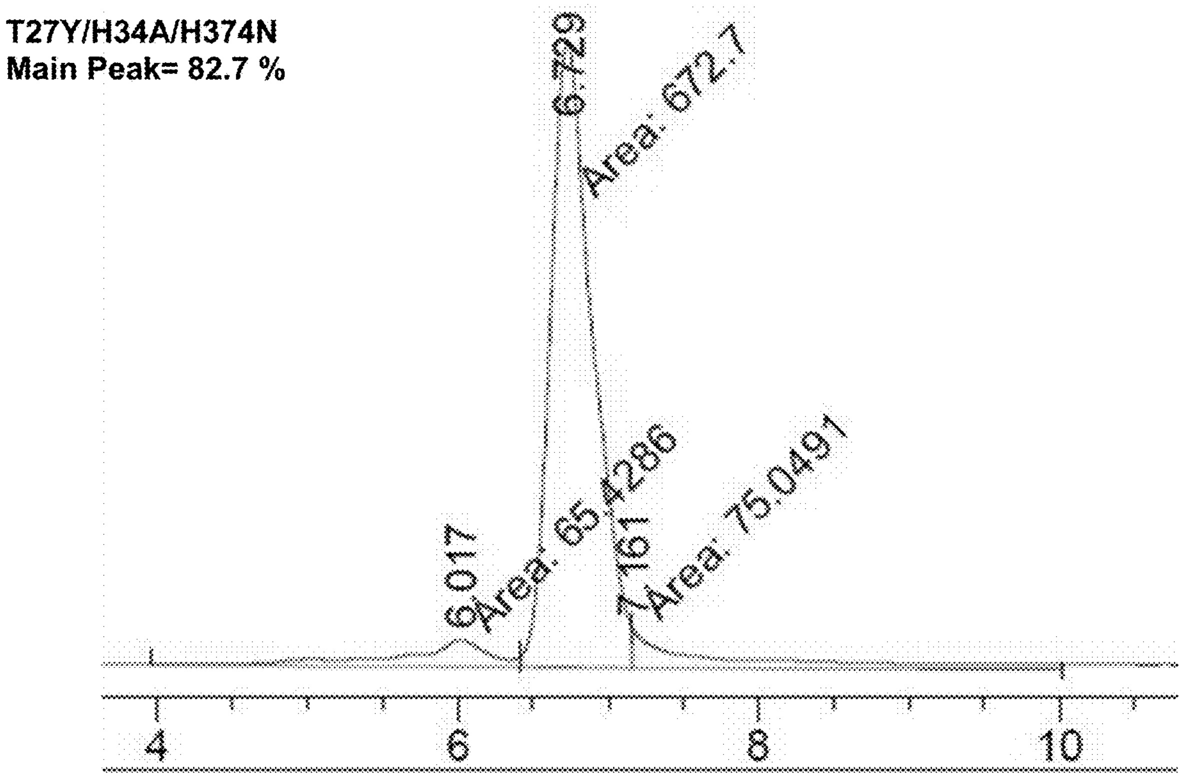
FIG. 29 depicts the size of the T27Y/H34A/H374N triple mutant ACE2 decoy peptide by size exclusion chromatography.
Figure 30:
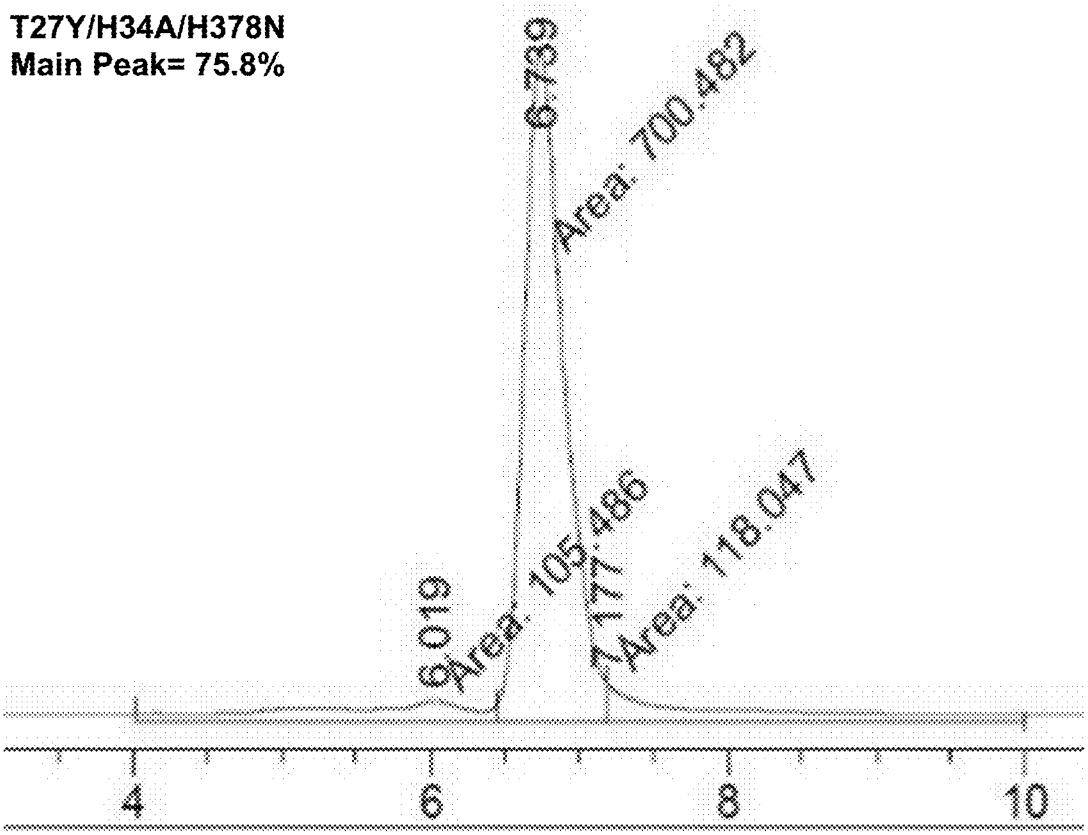
FIG. 30 depicts the size of the T27Y/H34A/H378N triple mutant ACE2 decoy peptide by size exclusion chromatography.

Example 10: The stabilities of wildtype, R273Q mutant, and T27Y/H34A double mutant ACE2 decoy peptides were measured by differential scanning fluorimetry (DSF). 20 μL of 1 mg/mL antibody was mixed with 10 μL of 20× SYPRO orange. The plate was scanned from 20° C. to 70° C. at 0.5° C. increment in a CFX96 Real-Time System (BioRad). The DSF results for the wildtype, R273Q mutant, and T27Y/H34A double mutant ACE2 decoy peptides are shown in FIG. 23.

Figure 31:
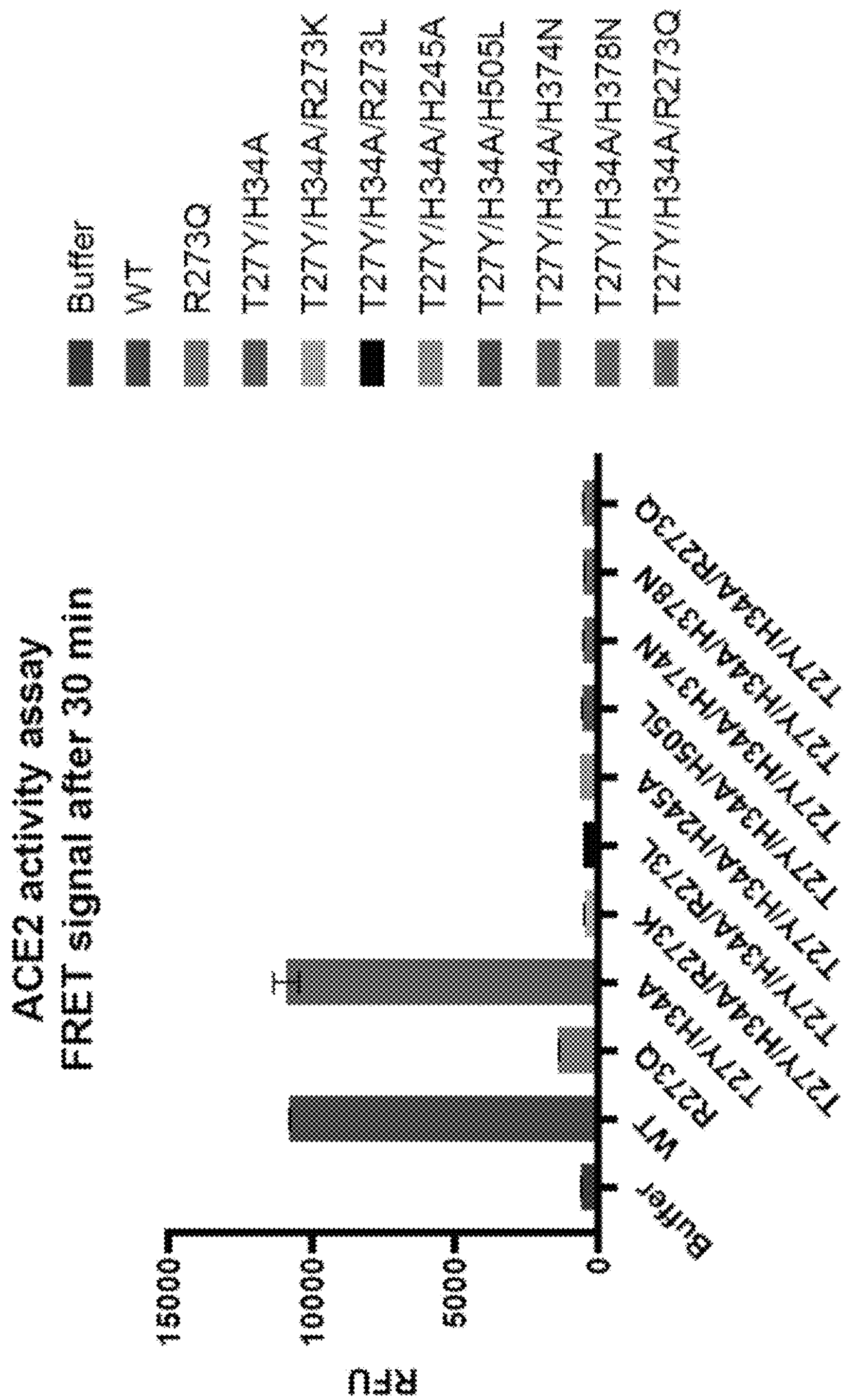
FIG. 31 depicts the ACE2 activity of triple mutant ACE2 decoy peptides.
Figure 32:
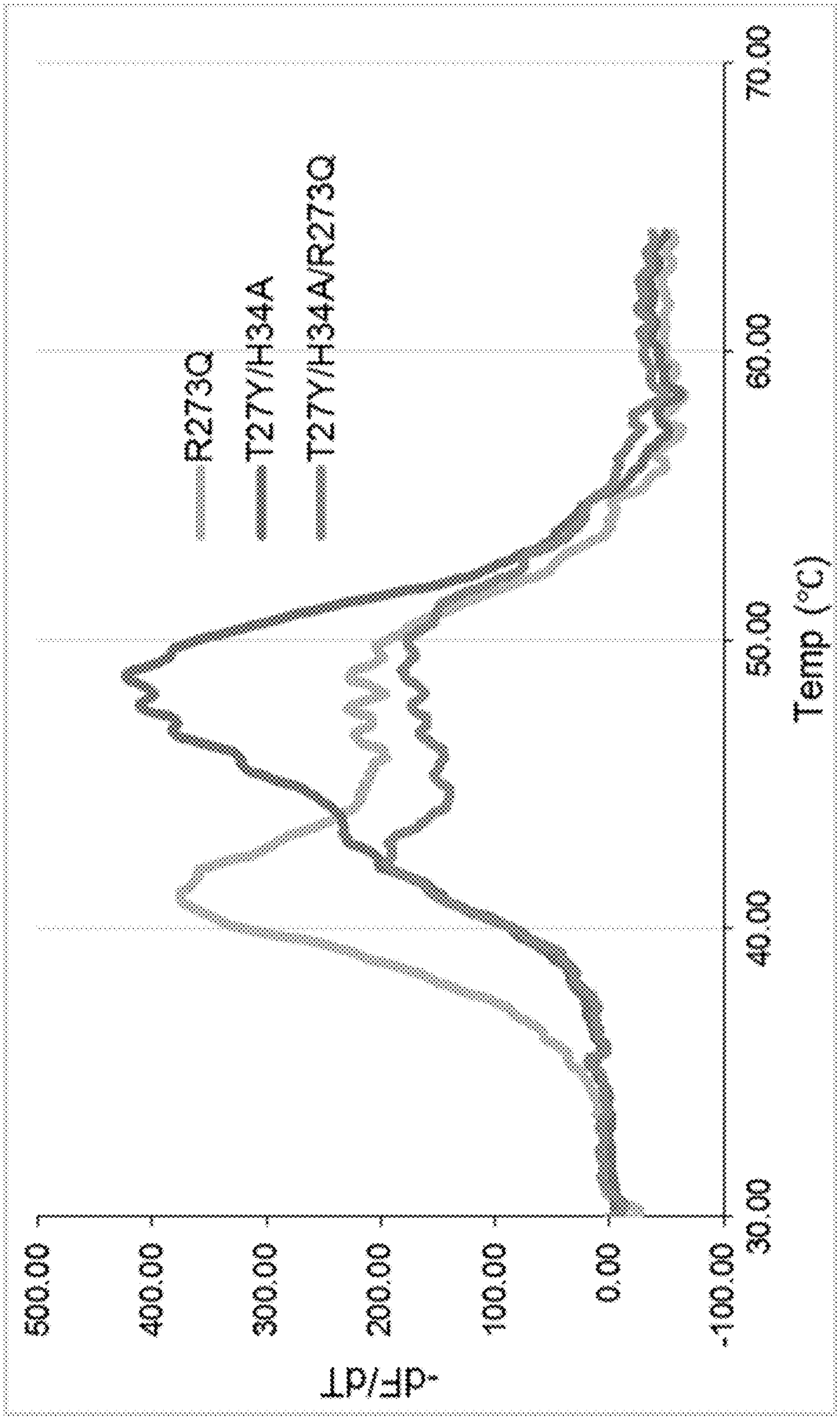
FIG. 32 depicts the stability of single, double, and triple mutant ACE2 decoy peptides.
Figure 33:
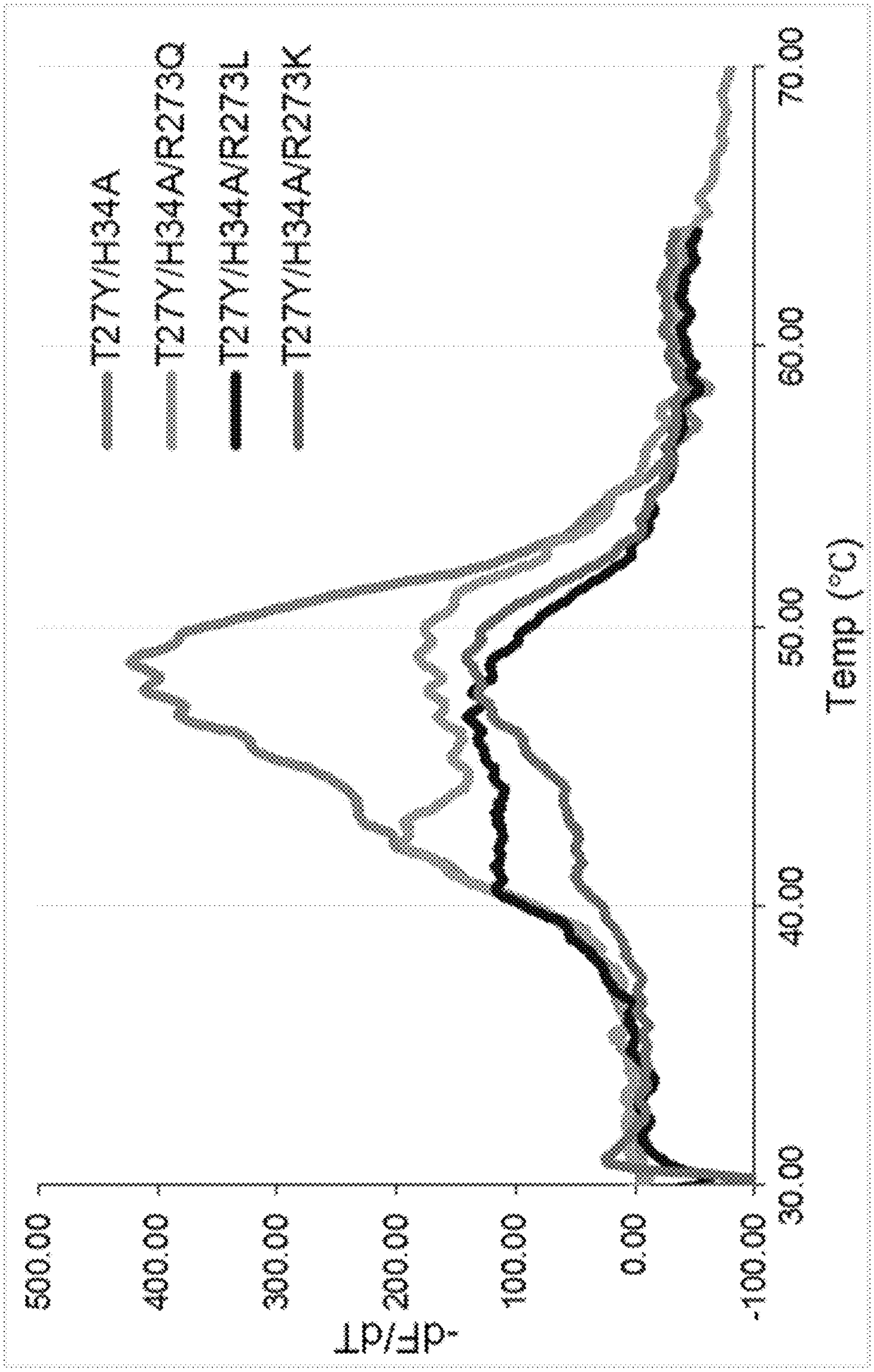
FIG. 33 depicts the stability of double and triple mutant ACE2 decoy peptides.
Figure 34:
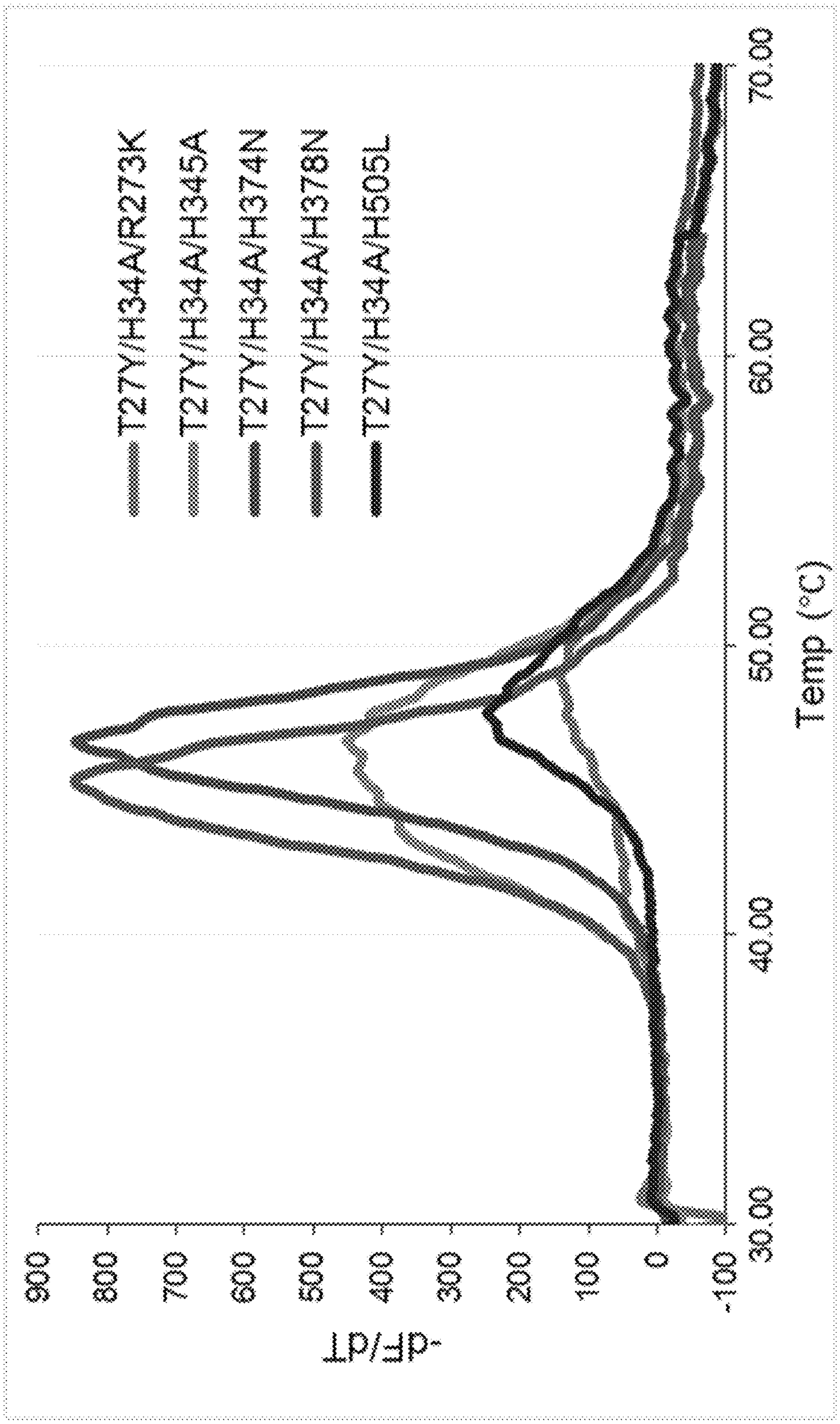
FIG. 34 depicts the stability of various triple mutant ACE2 decoy peptides.

Example 11: Seven triple mutant ACE2 decoy peptides were prepared. The size of each triple mutant ACE2 decoy peptides was measured by size exclusion chromatography. Briefly, purified triple mutant ACE2 decoy peptides were run on a Zenix-C SEC-300 (Sepax), 3 μm, 7.8×300 mm in a running buffer containing 50 mM sodium phosphate, 250 mM sodium chloride, and a pH of 6.8. FIGS. 24-30 show the sizes of each triple mutant ACE2 decoy peptide. The ACE2 activities of wildtype ACE2 decoy peptide, R273Q mutant ACE2 decoy peptide, T27Y/H34A double mutant ACE2 decoy peptide and each triple mutant ACE2 decoy peptide were also determined. 1 μg/mL of each sample was mixed with 20 μM substrate (MCA-Tyr-Val-Ala-Asp-Pro-Lys (DNP)-OH (R&D systems) in 75 mM HEPES, 1 M sodium chloride and pH 7.4. The samples were incubated with shaking (700 rpm) for 30 minutes at room temperature. The FRET signal was measured (top read) at excitation and emission wavelengths of 320 nm and 405 nm, respectively. FIG. 31 shows the ACE2 activity of the wildtype and mutant ACE2 decoy peptides. Table 11 summarizes the binding data for the triple mutant ACE2 decoy peptides. The stabilities of various triple mutant ACE2 decoy peptides was measured and compared to single and double ACE2 mutant decoy peptides. DSF was performed as described in Example 7 above. FIG. 32 shows the stabilities of the R273Q, T27Y/H34A, and T27Y/H34A/R273Q mutant ACE2 decoy peptides. FIG. 33 shows the stabilities of three triple mutant ACE2 decoy peptides as compared to the double mutant ACE2 decoy peptide. FIG. 34 shows the stabilities of five triple mutant ACE2 decoy peptides.

TABLE 11

Binding data for T27Y/H34A/XXX triple mutant ACE2 decoy peptides

| Antibody | $k_{on}$ (1/Ms) | $k_{off}$ (1/s) | $k_D$ (nM) |
|---|---|---|---|
| T27Y/H34A | $3.77 \times 10^5$ | $2.11 \times 10^{-4}$ | 0.56 |
| T27Y/H34A/R273K (206) | $4.04 \times 10^5$ | $1.79 \times 10^{-4}$ | 0.44 |
| T27Y/H34A/R273L (207) | $4.06 \times 10^5$ | $4.04 \times 10^{-4}$ | 1.00 |
| T27Y/H34A/H345A (211) | $4.15 \times 10^5$ | $3.95 \times 10^{-4}$ | 0.95 |
| T27Y/H34A/H505L (208) | $4.09 \times 10^5$ | $2.91 \times 10^{-4}$ | 0.71 |
| T27Y/H34A/H374N (209) | $3.88 \times 10^5$ | $2.44 \times 10^{-4}$ | 0.63 |
| T27Y/H34A/H378N (210) | $3.95 \times 10^5$ | $3.32 \times 10^{-4}$ | 0.84 |
| T27Y/H34A/R273Q (212) | $4.86 \times 10^5$ | $4.09 \times 10^{-4}$ | 0.84 |

Figure 35:
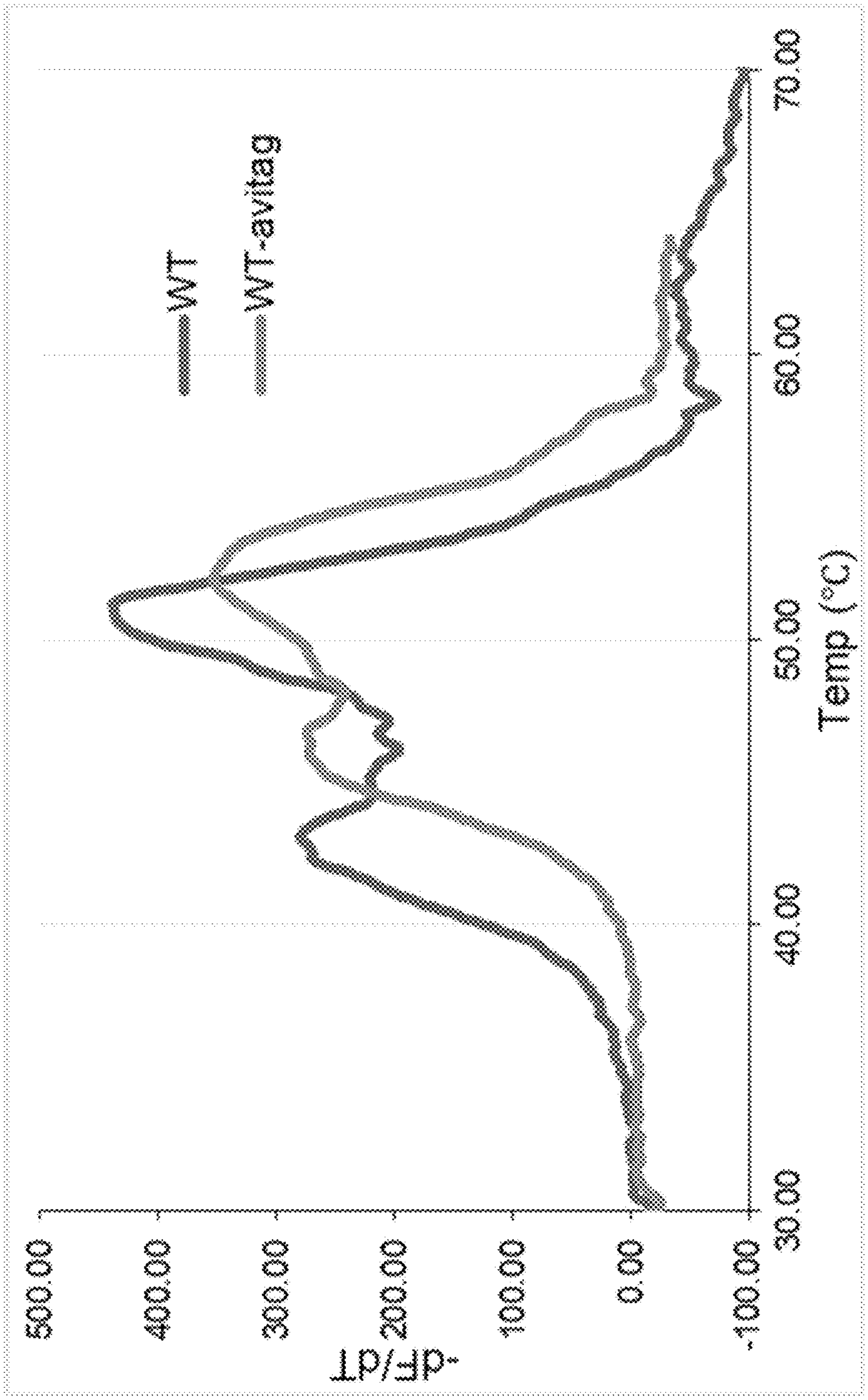
FIG. 35 depicts the stability of avidin-tagged and untagged wildtype ACE2-IgGFc.

Example 12: Wildtype ACE2 decoy peptide was fused to avidin at the C-terminal of the antibody. The stability of the avidin-tagged and untagged wildtype ACE2 decoy peptide was measured by DSF as described in Example 7. FIG. 35 shows the stability of the avidin-tagged and untagged wildtype ACE2 decoy peptide.

Figure 36:
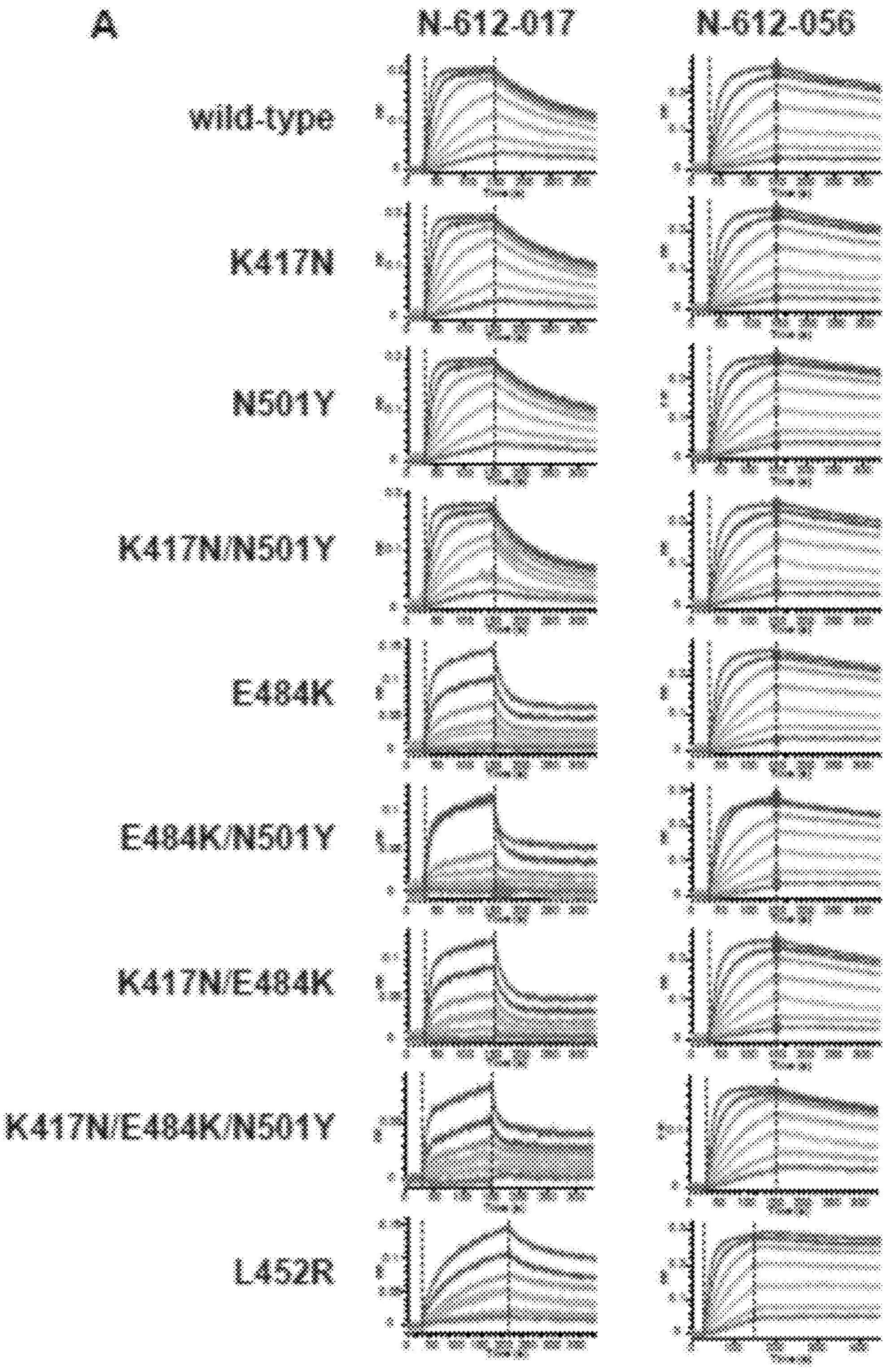
FIG. 36 depicts a $K_D$ determination by SPR for N-612-017 and N-612-056 against SARS-CoV-2 Spike protein and variants thereof.
Figure 37:
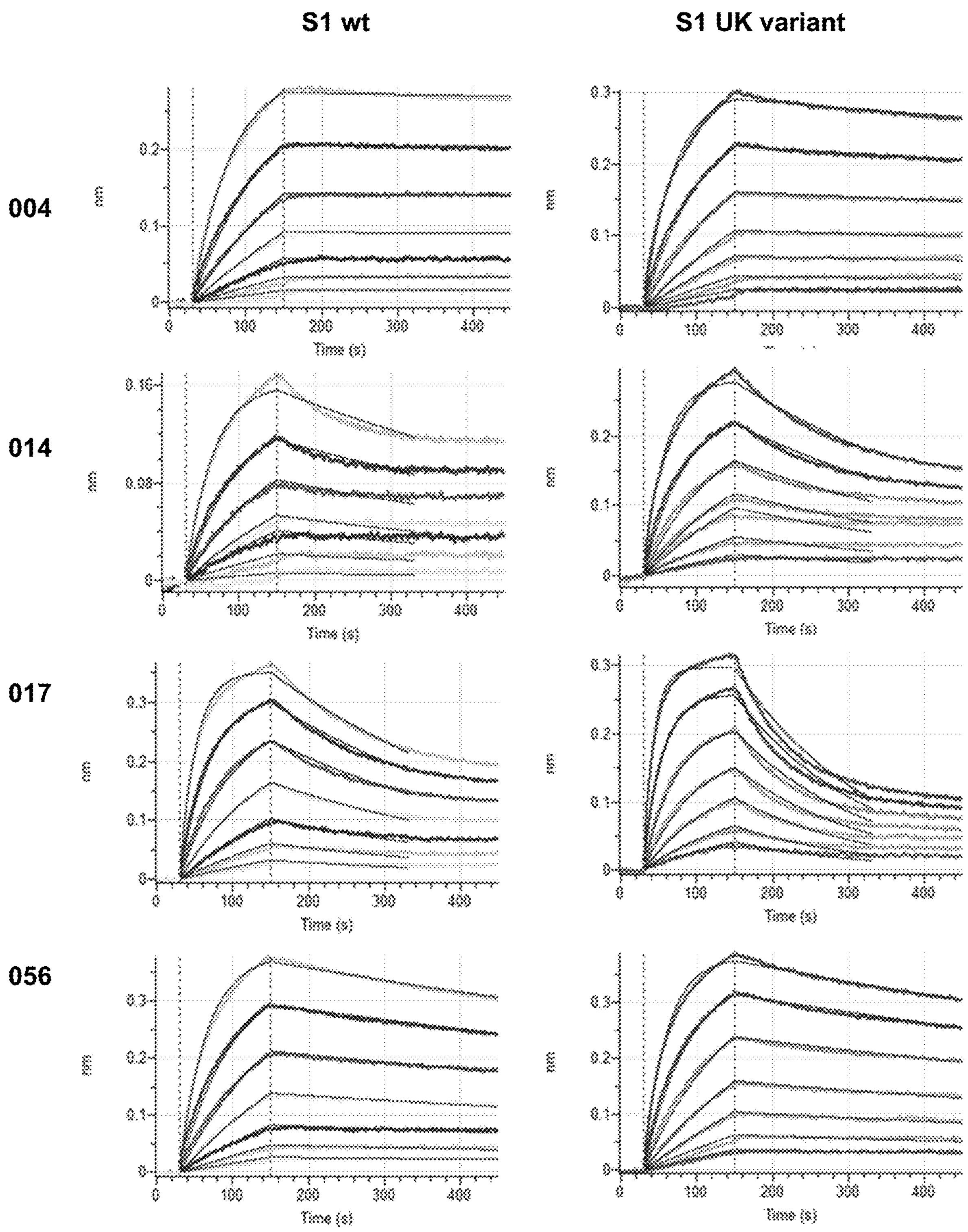
FIG. 37 depicts a $K_D$ determination by SPR for N-612-004, N-612-017, N-612-017, and N-612-056 against SARS-CoV-2 Spike protein and variants thereof.

Example 13: Anti-Spike antibodies were exposed to wildtype and mutant Spike proteins and the binding affinities of the antibodies for the Spike proteins were measured. All experiments used a running buffer composed of 10 mM HEPES, pH 7.4, 150 mM NaCl, 0.02% tween 20, 0.1% BSA unless indicated otherwise. For 1:1 binding affinity determination of mAbs against SARS-CoV-2 RBD wild-type and mutants and S1 variant, mAbs were immobilized onto AHC sensor (Sartorius Corporation), and the RBD (wild-type or mutants) and S1 concentration series of 200, 100, 50, 25, 12.5, 6.25, 3.125 nM were tested to determine $K_D$. The binding of N-612-017 or N-612-056 to wildtype or mutant Spike proteins is shown in FIG. 36. The binding of N-612-004, N-612-014, N-612-017, and N-612-056 to wildtype Spike or the UK variant Spike protein are shown in FIG. 37. Tables 12 and 13 present the $K_D$ of the various anti-Spike antibodies against the wildtype and mutant Spike proteins.

TABLE 12

($K_D$ (nM)):

| RBD Mutation | Pango Lineage | N-612-017 | N-612-017-01 | N-612-017-03 | N-612-017-05B02 | N-612-017-05B05 | N-612-017-5B05SV | N-612-056 | N-612-056-21 |
|---|---|---|---|---|---|---|---|---|---|
| Wildtype | | 5.29 | 0.64 | 0.25 | 0.11 | 3.28 | 6.62 | 2.98 | 0.41 |
| K417N | — | 5.4 | NT | NT | NT | NT | NT | 3.5 | NT |
| N501Y | Alpha | 7.25 | 1.36 | 0.50 | 0.21 | 4.93 | NT | 1.92 | 0.69 |
| K417N/N201Y | — | 7.5 | | | | | | 2.8 | |
| E484K | Zeta/Eta/Iota | 49.7 | 0.37 | 0.21 | 0.18 | 2.68 | NT | 2.52 | 0.62 |
| K417N/E484K | — | 56.5 | | | | | | 3.3 | |
| E484K/N501Y | Theta | 63.1 | 0.57 | 0.21 | 0.12 | 2.38 | NT | 1.92 | 0.45 |
| K417N/E484K/N501Y | Beta | 30.6 | 0.77 | 0.35 | 0.15 | 2.56 | 3.23 | 2.43 | 0.11 |
| L452R | — | 51.2 | NT | NT | NT | NT | NT | 0.45 | NT |
| K417T/E484K/N501Y | Gamma | 3.79 | 0.29 | 0.21 | 0.14 | 1.55 | NT | 1.32 | 0.13 |
| L452R/T478K | Delta | 40.0 | 25.6 | 20.3 | 2.21 | 1.13 | 1.28 | 0.75 | 0.11 |
| L452R | Epsilon | NB | 33.1 | 58.7 | 6.16 | 2.44 | NT | 1.44 | 0.11 |
| L452R/E484Q | Kappa | NB | 13.2 | 12.7 | 1.70 | 0.99 | NT | 0.78 | 0.29 |
| L452Q/F490S | Lambda | NB | NB | NB | Very weak | NB | NB | 5.82 | 0.61 |
| G339D/S371L/S373P/S375F/K417N/N440K/G446S/S447N/T478K/E484A/Q493R/G496S/Q498R/N501Y/Y505H | Omicron | 17.4 | | 0.32 | | | 2.18 | | 0.28 |

NT: Not tested;

NB: No binding

TABLE 13

| Mutation | N-612-004 $K_D$ (nM) | N-612-014 $K_D$ (nM) | N-612-017 $K_D$ (nM) | N-612-056 $K_D$ (nM) |
|---|---|---|---|---|
| Wildtype | 0.62 | 11.4 | 12.0 | 4.5 |
| ΔH69/ΔV70/ΔY144/N501Y/A570D/D614G/P681H (UK variant) | 2.4 | 14.8 | 15.9 | 4.2 |

Figure 38:
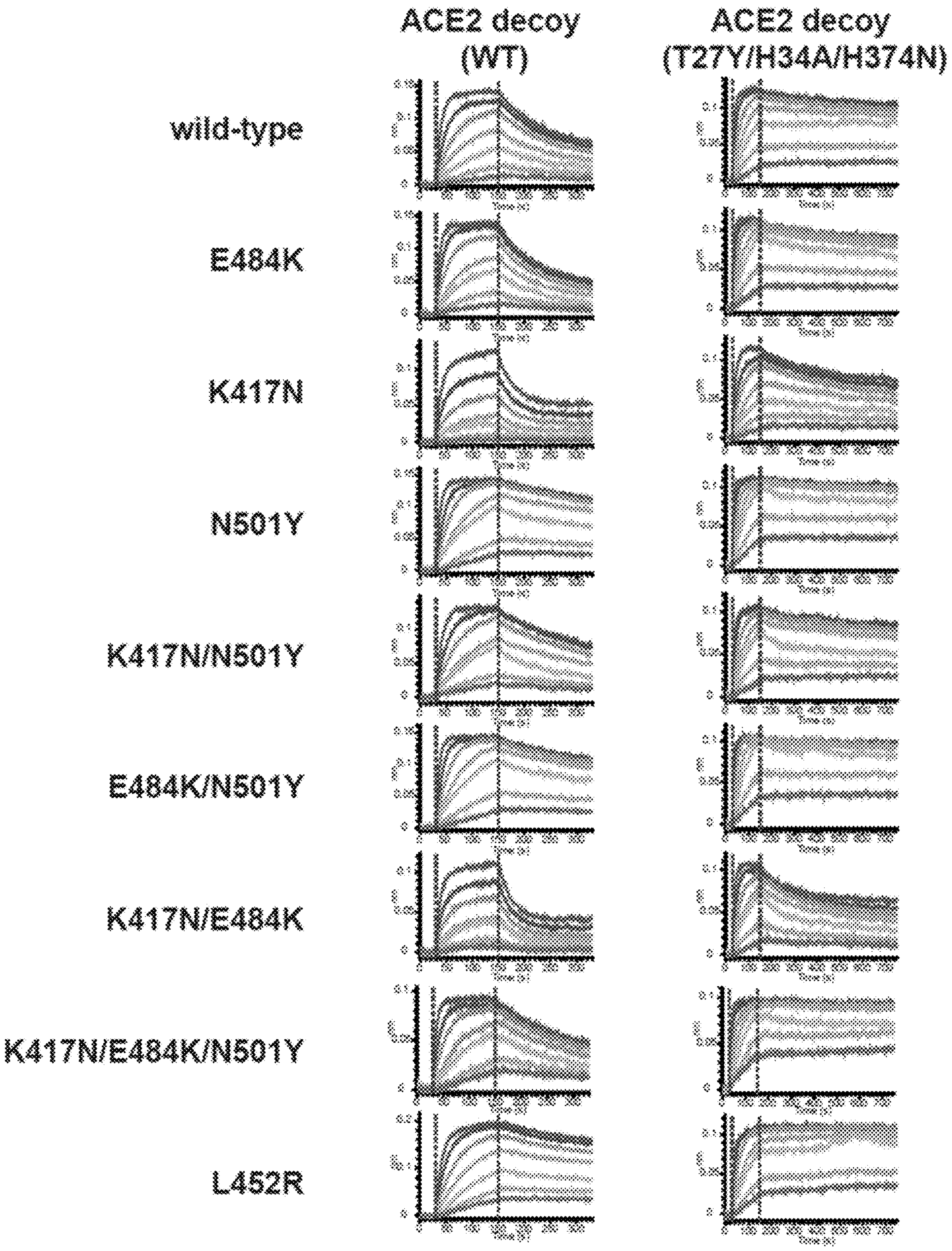
FIG. 38 depicts a $K_D$ determination by SPR for wildtype ACE2 and T27Y/H34A/H374N ACE2 decoy peptide against SARS-CoV-2 Spike protein and variants thereof.

Example 14: ACE2 decoy peptides were exposed to wildtype and mutant Spike proteins and the binding affinities of the ACE2 decoy peptides for the Spike proteins were measured. All experiments used a running buffer composed of 10 mM HEPES, pH 7.4, 150 mM NaCl, 0.02% tween 20, 0.1% BSA unless indicated otherwise. For 1:1 binding affinity determination of ACE2-decoy peptides against SARS-CoV-2 RBD wild-type and mutants, ACE2-decoy peptides were immobilized onto AHC sensor (Sartorius Corporation), and the RBD (wild-type or mutants) concentration series of 200, 100, 50, 25, 12.5, 6.25, 3.125 nM were used to determine $K_D$. The binding of wildtype ACE2-$IgG_1Fc$ and the T27Y/H34A/H374N triple mutant ACE2 decoy-$IgG_1Fc$ to wildtype or mutant Spike proteins is shown in FIG. 38. Table 14 present the $K_{on}$, $K_{off}$, and $K_D$ of the ACE2 decoy peptides against the wildtype and mutant Spike proteins.

TABLE 14

| | ACE2(WT)-$IgG_1Fc$ | | | ACE2(T27Y/H34A/H374N)-$IgG_1Fc$ | | |
|---|---|---|---|---|---|---|
| RBD mutants | $K_{on}$ (1/Ms) | $K_{off}$(1/s) | $K_D$ (nM) | $K_{on}$ (1/Ms) | $K_{off}$ | $K_D$ (nM) |
| Wild-type | $5.25 \times 10^5$ | $4.90 \times 10^{-3}$ | 9.33 | $6.91 \times 10^5$ | $2.17 \times 10^{-4}$ | 0.315 |
| E484K | $8.00 \times 10^5$ | $7.02 \times 10^{-3}$ | 8.77 | $1.00 \times 10^6$ | $3.95 \times 10^{-4}$ | 0.393 |
| K417N | $3.97 \times 10^5$ | $1.35 \times 10^{-2}$ | 34.0 | $4.46 \times 10^5$ | $9.33 \times 10^{-4}$ | 2.090 |
| K417N/E484K | $4.84 \times 10^5$ | $1.73 \times 10^{-2}$ | 35.7 | $8.03 \times 10^5$ | $1.10 \times 10^{-3}$ | 1.370 |
| N501Y | $6.38 \times 10^5$ | $1.45 \times 10^{-3}$ | 2.27 | $9.50 \times 10^5$ | $1.40 \times 10^{-4}$ | 0.148 |
| E484K/N501Y | $8.26 \times 10^5$ | $1.76 \times 10^{-3}$ | 2.13 | $1.22 \times 10^6$ | $1.16 \times 10^{-4}$ | 0.095 |
| K417N/N501Y | $4.57 \times 10^5$ | $3.47 \times 10^{-3}$ | 7.60 | $7.47 \times 10^5$ | $3.34 \times 10^{-4}$ | 0.447 |
| K417N/E484K/N501Y | $7.45 \times 10^5$ | $3.93 \times 10^{-3}$ | 5.28 | $7.56 \times 10^5$ | $3.51 \times 10^{-4}$ | 0.465 |
| L452R | $4.39 \times 10^5$ | $1.19 \times 10^{-3}$ | 2.71 | $4.62 \times 10^5$ | $1.02 \times 10^{-4}$ | 0.221 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A SARS-Co V-2 spike(S) protein antigen binding fragment (Fab fragment) comprising a heavy variable ($V_H$) chain having at least 90% sequence identity to each of SEQ ID NOs: 127-130 and a light variable ($V_L$) chain having 100% sequence identity to SEQ ID NO: 131 and having at least 90% sequence identity to SEQ ID NO: 132, wherein each of the $V_H$ chain and the $V_L$ chain have three complementarity determining regions (CDRs), and wherein the $V_H$ CDRs comprise SEQ ID NOs: 3-5 and the $V_L$ CDRs comprise SEQ ID NO: 6;

the $V_H$ CDRs comprise SEQ ID NOs: 7-9 and the $V_L$ CDRs comprise SEQ ID NO: 10;

the $V_H$ CDRs comprise SEQ ID NOs: 11-13 and the $V_L$ CDRs comprise SEQ ID NO: 14;

the $V_H$ CDRs comprise SEQ ID NOs: 15-17 and the $V_L$ CDRs comprise SEQ ID NO: 18;

the $V_H$ CDRs comprise SEQ ID NOs: 19-21 and the $V_L$ CDRs comprise SEQ ID NO: 22;

the $V_H$ CDRs comprise SEQ ID NOs: 23-25 and the $V_L$ CDRs comprise SEQ ID NO: 26;

the $V_H$ CDRs comprise SEQ ID NOs: 27-29 and the $V_L$ CDRs comprise SEQ ID NO: 30;

the $V_H$ CDRs comprise SEQ ID NOs: 31-33 and the $V_L$ CDRs comprise SEQ ID NO: 34;

the $V_H$ CDRs comprise SEQ ID NOs: 35-37 and the $V_L$ CDRs comprise SEQ ID NO: 38;

the $V_H$ CDRs comprise SEQ ID NOs: 39-41 and the $V_L$ CDRs comprise SEQ ID NO: 42;

the $V_H$ CDRs comprise SEQ ID NOs: 43-45 and the $V_L$ CDRs comprise SEQ ID NO: 46;

the $V_H$ CDRs comprise SEQ ID NOs: 47-49 and the $V_L$ CDRs comprise SEQ ID NO: 50;

the $V_H$ CDRs comprise SEQ ID NOs: 43, 44, and 243 and the $V_L$ CDRs comprise SEQ ID NO: 46; or the $V_H$ CDRs comprise SEQ ID NOs: 51-53 and the $V_L$ CDRs comprise SEQ ID NO: 54.

2. The Fab fragment of claim 1, wherein the $V_H$ CDRs comprise SEQ ID NOs: 43-45 and the $V_L$ CDRs comprise SEQ ID NO: 46.

3. The Fab fragment of claim 1, wherein the $V_H$ chain has an arrangement (SEQ ID NO:127)-$V_H$ CDR1-(SEQ ID NO:128)-$V_H$ CDR2-(SEQ ID NO:129)-$V_H$ CDR3-(SEQ ID NO:130).

4. The Fab fragment of claim 1, wherein the $V_L$ has an arrangement (SEQ ID NO:131)-$V_L$ CDR1-(SEQ ID NO:132).

5. The Fab fragment of claim 1, wherein the Fab fragment further comprises a crystallizable fragment (Fc) domain.

6. The Fab fragment of claim 1, wherein the Fab fragment is bound to a SARS-CoV-2 spike protein.

7. The Fab fragment of claim 6, wherein the spike protein has one or more point mutations selected from the group consisting of S13I, L18F, T19R, T20N, P26S, A67V, ΔH69, ΔV70, G75V, T76I, D80A, T95I, D138Y, G142D, ΔL141, ΔG142, ΔV143, ΔY144, ΔY145, W152C, E154K, E156G, ΔF157, ΔR158, R190S, N211I, ΔL212, R214ins, D215G, ΔL241, ΔL242, L242H, ΔA243, ΔL244, R246N, ΔS247, ΔY248, ΔL249, ΔT250, ΔP251, ΔG252, ΔD253, G339D, S371L, S373P, S375F, K417N, K417T, N440K, G446S, S447N, L452Q, L452R, T478K, E484A, E484K, E484Q, F490S, Q493R, G496S, Q498R, N501Y, Y505H, T547K, A570D, D614G, H655Y, N679K, P681H, P681R, A701V, T716I, D796Y, N858K, T859N, D950N, Q954H, S982A, N969K, L981F, Q1071H, E1095K, H1101Y, D1118H, T1027I, V1176F, and a combination thereof.

8. A method of treating COVID-19 in a subject in need thereof, the method comprising administering the Fab fragment of claim 1 to the respiratory mucosa of the subject.

9. The method of claim 8, further comprising administering IL-2, IL-15, or an IL-15 superagonist to the subject.

10. A SARS-Co V-2 spike(S) protein antigen binding fragment (Fab fragment) comprising a heavy variable ($V_H$) chain having at least 90% sequence identity to each of SEQ ID NOs: 127, 128, and 130, and one of SEQ ID NOs: 129, 244, and 245 and a light variable ($V_L$) chain having 100% sequence identity to SEQ ID NO: 131 and having at least 90% sequence identity to SEQ ID NO: 132, wherein each of the $V_H$ chain and the $V_L$ chain have three complementarity determining regions (CDRs), and wherein the $V_H$ CDRs comprise SEQ ID NOs: 67-69 and the $V_L$ CDRs comprise SEQ ID NO: 70;

the $V_H$ CDRs comprise SEQ ID NOs: 67, 68, and 241 and the $V_L$ CDRs comprise SEQ ID NO: 70;

the $V_H$ CDRs comprise SEQ ID NOs: 63, 240, and 69 and the $V_L$ CDRs comprise SEQ ID NO: 70;

the $V_H$ CDRs comprise SEQ ID NOs: 238, 68, and 242 and the $V_L$ CDRs comprise SEQ ID NO: 70;

the $V_H$ CDRs comprise SEQ ID NOs: 239, 68, and 242 and the $V_L$ CDRs comprise SEQ ID NO: 70; or the $V_H$ CDRs comprise SEQ ID NOs: 43, 44, and 243 and the $V_L$ CDRs comprise SEQ ID NO: 46.

11. The Fab fragment of claim 10, wherein the $V_H$ CDRs comprise SEQ ID NOs: 67-69, and 130 and the $V_L$ CDRs comprise SEQ ID NO: 70.

12. The Fab fragment of claim 10, wherein the $V_H$ CDRs comprise SEQ ID NOs: 67, 68, and 241 and the $V_L$ CDRs comprise SEQ ID NO: 70.

13. The Fab fragment of claim 10, wherein the $V_H$ CDRs comprise SEQ ID NOs: 63, 69, and 240 and the $V_L$ CDRs comprise SEQ ID NO: 70.

14. The Fab fragment of claim 10, wherein the $V_H$ CDRs comprise SEQ ID NOs: 68, 238, and 242 and the $V_L$ CDRs comprise SEQ ID NO: 70.

15. The Fab fragment of claim 10, wherein the $V_H$ CDRs comprise SEQ ID NOs: 68, 239, and 242 and the $V_L$ CDRs comprise SEQ ID NO: 70.

16. The Fab fragment of claim 10, wherein the $V_H$ CDRs comprise SEQ ID NOs: 43, 44, and 243 and the $V_L$ CDRs comprise SEQ ID NO: 46.

17. The Fab fragment of claim 10, wherein the $V_H$ chain has an arrangement (SEQ ID NO:127)-$V_H$ CDR1-(SEQ ID NO:128)-$V_H$ CDR2-(SEQ ID NO:129)-$V_H$ CDR3-(SEQ ID NO:130).

18. The Fab fragment of claim 10, wherein the $V_H$ chain has an arrangement (SEQ ID NO:127)-$V_H$ CDR1-(SEQ ID NO:128)-$V_H$ CDR2-(SEQ ID NO:244)-$V_H$ CDR3-(SEQ ID NO:130).

19. The Fab fragment of claim 10, wherein the $V_L$ has an arrangement (SEQ ID NO:131)-$V_L$ CDR1-(SEQ ID NO:132).

20. The Fab fragment of claim 10, wherein the Fab fragment further comprises a crystallizable fragment (Fc) domain.

21. The Fab fragment of claim 10, wherein the Fab fragment is bound to a SARS-CoV-2 spike protein.

22. The Fab fragment of claim 21, wherein the spike protein has one or more point mutations selected from the group consisting of S13I, L18F, T19R, T20N, P26S, A67V, ΔH69, ΔV70, G75V, T76I, D80A, T95I, D138Y, G142D, ΔL141, ΔG142, ΔV143, ΔY144, ΔY145, W152C, E154K, E156G, ΔF157, ΔR158, R190S, N211I, ΔL212, R214ins, D215G, ΔL241, ΔL242, L242H, ΔA243, ΔL244, R246N, ΔS247, ΔY248, ΔL249, ΔT250, ΔP251, ΔG252, ΔD253, G339D, S371L, S373P, S375F, K417N, K417T, N440K, G446S, S447N, L452Q, L452R, T478K, E484A, E484K, E484Q, F490S, Q493R, G496S, Q498R, N501Y, Y505H, T547K, A570D, D614G, H655Y, N679K, P681H, P681R, A701V, T716I, D796Y, N858K, T859N, D950N, Q954H, S982A, N969K, L981F, Q1071H, E1095K, H1101Y, D1118H, T1027I, V1176F, and a combination thereof.

23. A method of treating COVID-19 in a subject in need thereof, the method comprising administering the Fab fragment of claim 10 to the respiratory mucosa of the subject.

24. The method of claim 23, further comprising administering IL-2, IL-15, or an IL-15 superagonist to the subject.

* * * * *